(12) United States Patent
Wang et al.

(10) Patent No.: US 11,078,192 B2
(45) Date of Patent: Aug. 3, 2021

(54) AROMATIC ACETYLENE OR AROMATIC ETHYLENE COMPOUND, INTERMEDIATE, PREPARATION METHOD, PHARMACEUTICAL COMPOSITION AND USE THEREOF

(71) Applicant: GUANGZHOU MAXINOVEL PHARMACEUTICALS CO., LTD., Guangzhou (CN)

(72) Inventors: Yuguang Wang, Guangdong (CN); Zusheng Xu, Guangdong (CN); Tianzhi Wu, Guangdong (CN); Min He, Guangdong (CN); Nong Zhang, Guangdong (CN)

(73) Assignee: GUANGZHOU MAXINOVEL PHARMACEUTICALS CO., LTD.

( * ) Notice: Subject to any disclaimer, the term of this patent is extended or adjusted under 35 U.S.C. 154(b) by 92 days.

(21) Appl. No.: 16/315,307

(22) PCT Filed: Jul. 4, 2017

(86) PCT No.: PCT/CN2017/091643
§ 371 (c)(1),
(2) Date: Jan. 4, 2019

(87) PCT Pub. No.: WO2018/006795
PCT Pub. Date: Jan. 11, 2018

(65) Prior Publication Data
US 2019/0308957 A1 Oct. 10, 2019

(30) Foreign Application Priority Data
Jul. 5, 2016 (CN) .......................... 201610523836.9

(51) Int. Cl.
| | |
|---|---|
| *C07D 405/10* | (2006.01) |
| *C07D 405/04* | (2006.01) |
| *C07D 207/08* | (2006.01) |
| *C07D 211/60* | (2006.01) |
| *C07D 213/38* | (2006.01) |
| *C07D 213/48* | (2006.01) |
| *C07D 231/10* | (2006.01) |
| *C07D 231/12* | (2006.01) |
| *C07D 319/18* | (2006.01) |
| *A61P 35/00* | (2006.01) |

(Continued)

(52) U.S. Cl.
CPC ............ *C07D 405/10* (2013.01); *A61P 35/00* (2018.01); *C07C 22/04* (2013.01); *C07C 22/08* (2013.01); *C07C 25/24* (2013.01); *C07C 43/225* (2013.01); *C07C 47/548* (2013.01); *C07C 47/55* (2013.01); *C07C 47/575* (2013.01); *C07C 69/94* (2013.01); *C07C 215/10* (2013.01); *C07C 217/58* (2013.01); *C07C 229/22* (2013.01); *C07C 229/24* (2013.01); *C07C 229/64* (2013.01); *C07C 233/18* (2013.01); *C07C 235/84* (2013.01); *C07C 237/30* (2013.01); *C07C 255/56* (2013.01); *C07D 207/08* (2013.01); *C07D 211/60* (2013.01); *C07D 213/38* (2013.01); *C07D 213/48* (2013.01); *C07D 231/10* (2013.01); *C07D 231/12* (2013.01); *C07D 319/18* (2013.01); *C07D 405/04* (2013.01); *C07B 2200/07* (2013.01)

(58) Field of Classification Search
CPC .. C07D 405/10; C07D 405/04; C07D 207/08; C07D 211/60; C07D 213/38; C07D 213/48; C07D 231/10; C07D 231/12; C07D 319/18; A61P 35/00; C07C 22/04; C07C 22/08; C07C 25/24; C07C 43/225; C07C 47/548; C07C 47/55; C07C 47/575; C07C 69/94; C07C 215/10; C07C 217/58; C07C 229/22; C07C 229/24; C07C 229/64; C07C 233/18; C07C 235/84; C07C 237/30; C07C 255/56; C07B 220/07
See application file for complete search history.

(56) References Cited

U.S. PATENT DOCUMENTS

2010/0292227 A1 11/2010 Yoakim et al.

FOREIGN PATENT DOCUMENTS

| CA | 2304274 A1 | 4/1999 |
|---|---|---|
| CN | 101712604 A | 5/2010 |

(Continued)

OTHER PUBLICATIONS

Carter et al., "PD-1:PD-L inhibitory pathway affects both CD4+ and CD8+ T cells and is overcome by IL-2", Eur. J. Immunol., 2002, 32(3), p. 634-643.

(Continued)

*Primary Examiner* — Timothy R Rozof
(74) *Attorney, Agent, or Firm* — Dilworth IP, LLC

(57) ABSTRACT

Disclosed are an aromatic acetylene or aromatic ethylene compound, an intermediate, a preparation method, a pharmaceutical composition and a use thereof. The aromatic acetylene or aromatic ethylene compound has a significant inhibitory effect on PD-1 and PD-L1, and can effectively relieve or treat cancers and other related diseases.

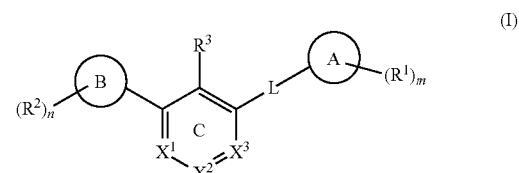

(I)

21 Claims, No Drawings

(51) Int. Cl.
| | |
|---|---|
| C07C 22/04 | (2006.01) |
| C07C 22/08 | (2006.01) |
| C07C 25/24 | (2006.01) |
| C07C 43/225 | (2006.01) |
| C07C 47/548 | (2006.01) |
| C07C 47/55 | (2006.01) |
| C07C 47/575 | (2006.01) |
| C07C 69/94 | (2006.01) |
| C07C 215/10 | (2006.01) |
| C07C 217/58 | (2006.01) |
| C07C 229/22 | (2006.01) |
| C07C 229/24 | (2006.01) |
| C07C 229/64 | (2006.01) |
| C07C 233/18 | (2006.01) |
| C07C 235/84 | (2006.01) |
| C07C 237/30 | (2006.01) |
| C07C 255/56 | (2006.01) |

(56) References Cited

FOREIGN PATENT DOCUMENTS

| | | |
|---|---|---|
| CN | 105705489 A | 6/2016 |
| EP | 2952503 A1 | 12/2015 |
| JP | 10195063 B | 7/1998 |
| JP | 2001517646 A | 10/2001 |
| JP | 2003502413 A | 1/2003 |
| JP | 2011505341 A | 2/2011 |
| JP | 2012526728 A | 11/2012 |
| WO | 9804528 A2 | 2/1998 |
| WO | WO98/04528 A2 * | 2/1998 |
| WO | 0078739 A1 | 12/2000 |
| WO | 0153268 A2 | 7/2001 |
| WO | 0162233 A2 | 8/2001 |
| WO | 2004014865 A1 | 2/2004 |
| WO | 2009067600 A | 5/2009 |
| WO | 2011045344 A1 | 4/2011 |
| WO | 2012168944 A1 | 12/2012 |
| WO | 2015033299 A1 | 3/2015 |
| WO | 2015033301 A1 | 3/2015 |
| WO | 2015034820 A1 | 3/2015 |
| WO | 2015036927 A1 | 3/2015 |
| WO | 2015044900 A1 | 4/2015 |
| WO | 2015160641 A2 | 10/2015 |
| WO | 2017066227 A1 | 4/2017 |

OTHER PUBLICATIONS

PCT International Search Report and Written Opinion dated Sep. 30, 2017 in corresponding Appl. No. PCT/CN2017/091643, 17 pages.
Liu et al., "Design and synthesis of 3'-(prop-2-yn-l-yloxy)-biphenyl substituted cyclic acylguanidine compounds as BACE1 inhibitors", Chinese Chemical Letters, vol. 27, No. 6, 2016, p. 961-963.
Liu et al., "Design and synthesis of cyclic acylguanidines as BACE1 inhibitors", Chinese Chemical Letters, vol. 26, No. 10, 2015, p. 1327-1330.
"RN1899005-22-1" Registry enter STN: Apr. 27, 2016.
"RN1646560-09-9" Registry enter STN: Feb. 11, 2015.
"RN1638536-50-1" Registry enter STN: Dec. 11, 2014.
"RN1225389-46-7" Registry enter STN: May 27, 2010.
"RN1225389-45-6" Registry enter STN: May 27, 2010.
"RN1098107-07-3" Registry enter STN: Jan. 30, 2009.
"RN1098106-07-0" Registry enter STN: Jan. 30, 2009.
"RN1098104-35-8" Registry enter STN: Jan. 30, 2009.
"RN263916-95-6" Registry enter STN: May 8, 2000.
"RN223654-82-8" Registry enter STN: May 28, 1999.
"RN1803418-36-1" Registry enter STN: Sep. 8, 2015.
"RN1581311-49-0" Registry enter STN: Apr. 7, 2014.
"RN1581311-48-9" Registry enter STN: Apr. 7, 2014.
"RN1269763-65-6" Registry enter STN: Mar. 24, 2011.
"RN1106005-31-5" Registry enter STN: Feb. 15, 2009.
"RN1106005-25-7" Registry enter STN: Feb. 15, 2009.
"RN1051472-23-1" Registry enter STN: Sep. 22, 2008.
"RN934537-51-6" Registry enter STN: May 10, 2007.
"RN638214-15-0" Registry enter STN: Jan. 16, 2004.
"RN1258410-97-7" Registry enter STN: Jan. 5, 2011.
"RN264912-33-6" Registry enter STN: May 16, 2000.
"RN52500-13-7" Registry enter STN: Nov. 16, 1984.
Extended European Search Report dated Apr. 1, 2019, in corresponding European Patent Application No. 17823607.1, 14 pages.
Bly et al., "Heterocyclic studies. XIII. The aldol condensation of 2,3-dihydro-5-methyl-6-phenyl-4H-1, 2 diazep in-4-one and reaarangement to a pyridazine", Journal of Organic Chemistry, vol. 29, No. 8, 1964, p. 2128-2135.
Malik et al., "Synthesis and photophysical properties of alkynylated pyrimidines by site-selective sonogashira reactions of 2,4,5,6-tetrachloropyrimidine; First synthesis of tetraalkynyl-pyrimidines", European Journal of Organic Chemisty, vol. 2011, No. 11, 2011, p. 2088-2093.
Nguyen et al. "Insulin-mimetic selaginellins from selaginella tamariscina with protein tyrosine phosphatase 1B (PTP1B) inhibitory activity", Journal of Natural Products, vol. 78, No. 1, 2015, p. 34-42.
Liu, Jia-Kuo et al., Design and synthesis of 3'-(prop-2-yn-1-yloxy)-biphenyl substituted cyclic acylguanidine compounds as BACE1 inhibitors, Chinese Chemical Society and Institute of Materia Medica, Chinese Academy of Medical Sciences, 2016, pp. 1-3.
Nguyen, Phi-Hung et al., Insulin-Mimetic Selaginellins from Selaginella tamariscina with Protein Tyrosine Phosphatase 1B (PTP1B) Inhibitory Activity, Journal of Natural Products, American Chemical Society and American Society of Pharmacognosy, 2015, pp. 34-42.
Liu, Jia-Kuo et al., Design and synthesis of cyclic acylguanidines as BACE1 inhibitors, Chinese Chemical Society and Institute of Materia Medica, Chinese Academy of Medical Sciences, 2015, pp. 1-4.
Malik, Imran et al., Synthesis and Photophysical Properties of Alkynylated Pyrimidines by Site-Selective Sonogashira Reactions of 2, 4, 5, 6-Tetrachloropyrimidine; First Synthesis of Tetraalkynyl-pyrimidines, Eur. J. Org. Chem., 2011, pp. 2088-2093.
Bly, Ruta K. et al., Heterocyclic Studies. XIII. The Aldo Condensation of 2,3-Dihydro-5-methyl-6-phenyl-4H-1,2-diazepin-4-one and Rearrangement to a Pyridazine, Department of Chemistry, University of Delaware, Newark, Delaware, 1963, pp. 2128-2135.
First Office Action in AU Patent Application No. 2017294231 dated Sep. 16, 2020.
Office Action issued in related European Patent Application No. 17823607.1, dated Dec. 17, 2020, 5 pages.
First Office Action issued in a corresponding Japanese Application No. 2019-500436, dated Mar. 22, 2021.

* cited by examiner

AROMATIC ACETYLENE OR AROMATIC ETHYLENE COMPOUND, INTERMEDIATE, PREPARATION METHOD, PHARMACEUTICAL COMPOSITION AND USE THEREOF

The present application claims priority of the Chinese Patent Application No. CN201610523836.9 filed on Jul. 5, 2016. The contents of the above Chinese Patent Application are incorporated herein by reference in their entireties.

FIELD OF INVENTION

The present invention relates to an aromatic acetylene or aromatic ethylene compound, an intermediate, a preparation method, a pharmaceutical composition and a use thereof.

PRIOR ARTS

PD-1 (programmed death 1) is an important immunosuppressive molecule. It is a member of CD28 superfamily and was originally cloned from the apoptotic mouse T-cell hybridoma 2B4.11. Immunomodulation targeting PD-1 is of great importance to anti-tumor, anti-infection, anti-autoimmune diseases and survival of organ transplantation. Its ligand PD-L1 can also be served as a target, and the corresponding antibodies can also play the same role.

PD-1/PD-L1 plays a role of a negative immunomodulatory effect. When PD-1 on the cell surface is coupled to PD-L1, it can cause the phosphorylation of Tyr of the Immunoreceptor Tyrosine-based Swith motifs (ITSM) domain in T-cell cytoplasmic region. Then the phosphorylated Tyr recruits tyrosine-protein phosphatase 2 and tyrosine-protein phosphatase 1 to block not only the activation of extracellular signal-regulated kinase but also the activation of phosphatidylinositol 3-kinase (PI3K) and serine/threonine protein kinase (Akt), finally inhibits T lymphocyte proliferation and related cytokines secretion. PD-1/PD-L1 signaling can inhibit T cell activation and proliferation, meanwhile cytokine interleukin 2 (IL2), interferon γ and IL-10 secretion is also reduced (*Eur. J. Immunol.*, 2002, 32(3), 634-643). In addition, the function of PD-1/PD-L1 signaling to the B cell immune is also similar to that of T cell. After PD-1 binds to B cell antigen receptor, PD-1 cytoplasmic domain interacts tyrosinase containing the site binding to protein tyrosinase 2, finally blocks B cell activation. The role of immunosuppressive molecule PD-1/PD-L1 in tumor immune escape has attracted more and more attention. A lot of studies have confirmed that PD-L1 on the surface of tumor cells in the tumor microenvironment increases, and binds to PD-1 of activated T cells, transmitting a negative regulatory signal and leading to apoptosis or immune incompetence of tumor antigen-specific T cells, thereby inhibiting the immune response and promoting the escape of tumor cells.

Currently PD-1/PD-L1 antibody inhibitors that have been approved for market include Nivolumab (2014) developed by BMS, Lambrolizumab (2014) developed by Merck and Atezolizumab (2016) developed by Roche. PD-1/PD-L1 antibody inhibitors under research include Pidilizumab of Cure Tech, AMP-224 of GSK and MEDI-4736 of AstraZeneca. These are all biomacromolecules, but small molecule PD-1/PD-L1 inhibitors are still in the early stage of development. The PD-L1 small molecule inhibitor AC-170 (WO2012168944, WO2015033299, WO2015033301, WO2015036927, WO2015044900) which is a polypeptide developed by Curis has just entered clinical stage I, a small molecule PD-1/PD-L1 inhibitor which is a benzyl phenyl ether developed by BMS (WO2015034820, WO2015160641) is still in the preclinical stage. Compared to biomacromolecules, small molecule compounds can act on intracellular targets across the cell membrane, so they are used in a wide range of applications. Secondly, small molecules can often have a good bioavailability and compliance after being chemically modified, thus effectively avoiding the decomposition and inactivation of enzymes in the digestive intestinal tract. Finally, the research of small molecule is quite mature in many aspects, e.g., manufacturing process, dosage form design and route of administration.

At present, there are no disclosure of aromatic acetylene or aromatic ethylene compounds as small molecule PD-1/PD-L1 inhibitors in the prior art, and this situation needs to be solved.

Content of the Present Invention

The technical problem to be solved in the present invention is to provide an aromatic acetylene or aromatic ethylene compound which is completely different from the prior art, an intermediate, a preparation method, a pharmaceutical composition and a use thereof. The aromatic acetylene or aromatic ethylene compound of the present invention has a significant inhibitory effect on PD-1 and/or PD-L1, and can effectively alleviate or treat cancer and other related diseases.

The present invention provides an aromatic acetylene or aromatic ethylene compound represented by formula I, a pharmaceutically acceptable salt, a tautomer, a mesomer, a racemate, a stereoisomer, a metabolite, a metabolic precursor or a prodrug thereof:

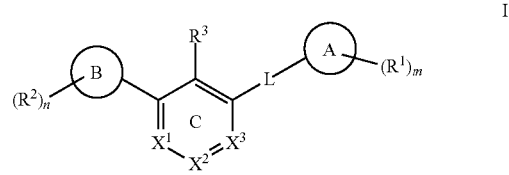

wherein, ring A and ring B are independently an aromatic ring or a heteroaromatic ring;

L is alkynyl or —C(R$^4$)=C(R$^5$)—;

X$^1$ is N or —CR$^6$;

X$^2$ is N or —CR$^7$;

X$^3$ is N or —CR$^8$;

X$^1$, X$^2$ and X$^3$ are not N simultaneously;

each of R$^1$ is independently hydrogen, deuterium, substituted or unsubstituted hydroxy, substituted or unsubstituted amino, halogen, substituted or unsubstituted alkyl or substituted or unsubstituted alkoxy;

each of R$^2$ is independently hydrogen, deuterium, substituted or unsubstituted hydroxy, substituted or unsubstituted amino, halogen, substituted or unsubstituted alkyl, or, substituted or unsubstituted alkoxy, or two adjacent R$^2$ together with the two atoms on the ring B to which they are attached form a 5-7 membered substituted or unsubstituted carbocycle, or substituted or unsubstituted heterocycle; in the heterocycle, the heteroatom is oxygen and/or nitrogen, the number of the heteroatom(s) is 1-4;

R$^3$ is hydrogen, deuterium, halogen, cyano, or, substituted or unsubstituted alkyl;

R$^4$ and R$^5$ are each independently hydrogen, deuterium, substituted or unsubstituted alkyl, or, substituted or unsubstituted cycloalkyl, or $R^4$ and $R^5$ together with the carbon-carbon double bond to which they are attached form a 5-7 membered substituted or unsubstituted carbocycle, or substituted or unsubstituted heterocycle; in the heterocycle, the heteroatom is selected from the group consisting of nitrogen, oxygen and sulfur, the number of the heteroatom(s) is 1-4;

$R^6$, $R^7$ and $R^8$ are each independently hydrogen, deuterium, substituted or unsubstituted hydroxy, halogen, substituted or unsubstituted amino, substituted or unsubstituted alkyl, or, substituted or unsubstituted alkoxy, or $R^6$ and $R^7$ together with the two atoms on the ring C to which they are attached form a 5-7 membered substituted or unsubstituted heterocycle; or $R^7$ and $R^8$ together with the two atoms on the ring C to which they are attached form a 5-7 membered substituted or unsubstituted heterocycle; in the heterocycle, the heteroatom is nitrogen and/or oxygen, the number of the heteroatom(s) is 1-4;

m is 1, 2 or 3;

n is 1 or 2;

in the definition of each $R^1$, the substituent in the substituted alkyl or the substituted alkoxy is selected from the group consisting of halogen, $C_1$-$C_4$ alkyl, hydroxy,

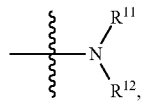

benzyl, benzyl substituted by cyano, $C_1$-$C_4$ alkoxy, $C_1$-$C_4$ carboxyl, $C_1$-$C_4$ ester group or $C_1$-$C_4$ acylamino; the substituent in the substituted hydroxy or the substituted amino is selected from the group consisting of $C_1$-$C_4$ alkyl, benzyl, benzyl substituted by cyano, $C_1$-$C_4$ alkoxy, $C_1$-$C_4$ carboxyl, $C_1$-$C_4$ ester group or $C_1$-$C_4$ acylamino; when there are more substituents than one, the substituents are the same or different;

in the definition of each $R^2$, the substituent in the substituted alkyl or the substituted alkoxy is selected from the group consisting of halogen, $C_1$-$C_4$ alkyl, hydroxy,

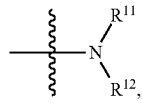

$C_1$-$C_4$ alkoxy, $C_1$-$C_4$ carboxyl, $C_1$-$C_4$ ester group or $C_1$-$C_4$ acylamino; the substituent in the substituted hydroxy or the substituted amino is selected from the group consisting of $C_1$-$C_4$ alkyl, benzyl, benzyl substituted by cyano, $C_1$-$C_4$ alkoxy, $C_1$-$C_4$ carboxyl, $C_1$-$C_4$ ester group or $C_1$-$C_4$ acylamino; when two adjacent $R^2$ together with the two atoms on the ring B to which they are attached form a 5-7 membered substituted carbocycle or substituted heterocycle, the substituent in the substituted carbocycle or the substituted heterocycle is selected from the group consisting of halogen, $C_1$-$C_4$ alkyl, hydroxy,

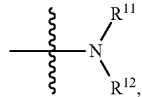

$C_1$-$C_4$ alkoxy, $C_1$-$C_4$ carboxyl, $C_1$-$C_4$ ester group or $C_1$-$C_4$ acylamino; when there are more substituents than one, the substituents are the same or different;

in the definition of $R^4$ or $R^5$, the substituent in the substituted alkyl or the substituted cycloalkyl is selected from the group consisting of halogen, $C_1$-$C_4$ alkyl, hydroxy, amino, $C_1$-$C_4$ alkoxy, $C_1$-$C_4$ carboxyl, $C_1$-$C_4$ ester group or $C_1$-$C_4$ acylamino; when $R^4$ and $R^5$ together with the carbon-carbon double bond to which they are attached form a 5-7 membered substituted carbocycle, or, substituted heterocycle, the substituent in the substituted carbocycle or the substituted heterocycle is selected from the group consisting of halogen, $C_1$-$C_4$ alkyl, hydroxy,

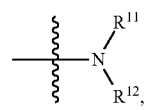

$C_1$-$C_4$ carboxyl, $C_1$-$C_4$ ester group or $C_1$-$C_4$ acylamino; when there are more substituents than one, the substituents are the same or different;

in the definition of $R^6$, $R^7$ or $R^8$, the substituent in the substituted alkyl or the substituted alkoxy is selected from the group consisting of halogen, $C_1$-$C_4$ alkyl, hydroxy,

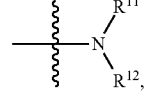

$C_1$-$C_4$ alkoxy, $C_1$-$C_4$ carboxyl, $C_1$-$C_4$ ester group or $C_1$-$C_4$ acylamino; the substituent in the substituted hydroxy or the substituted amino is selected from the group consisting of $C_1$-$C_4$ alkyl, benzyl, benzyl substituted by cyano, $C_1$-$C_4$ alkoxy, $C_1$-$C_4$ carboxyl, $C_1$-$C_4$ ester group or $C_1$-$C_4$ acylamino; when $R^6$ and $R^7$ together with the two atoms on the ring C to which they are attached form a 5-7 membered substituted heterocycle, or when $R^7$ and $R^8$ together with the two atoms on the ring C to which they are attached form a 5-7 membered substituted heterocycle, the substituent in the substituted heterocycle is selected from the group consisting of halogen, $C_1$-4 alkyl, hydroxy,

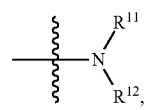

$C_1$-$C_4$ alkoxy, $C_1$-$C_4$ carboxyl, $C_1$-$C_4$ ester group or $C_1$-$C_4$ acylamino; when there are more substituents than one, the substituents are the same or different;

in

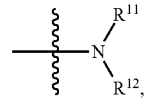

$R^{11}$ and $R^{12}$ are independently hydrogen, substituted or unsubstituted alkyl, alkoxy, hydroxyalkyl or aminoalkyl; or $R^{11}$ and $R^{12}$ together with the nitrogen atom to which they are attached form a 5-7 membered substituted or unsubstituted heterocycle; in the heterocycle, the heteroatom is nitrogen, or nitrogen and oxygen, the number of the heteroatom(s) is 1-4;

in the definition of $R^{11}$ or $R^{12}$, the substituent in the substituted alkyl is selected from the group consisting of halogen, $C_1$-$C_4$ alkyl, hydroxy,

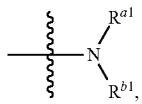

$C_1$-$C_4$ alkoxy, $C_1$-$C_4$ carboxyl, $C_1$-$C_4$ ester group or $C_1$-$C_4$ acylamino; when $R^{11}$ and $R^{12}$ together with the nitrogen atom to which they are attached form a 5-7 membered substituted or unsubstituted heterocycle, the substituent in the substituted heterocycle is selected from the group consisting of halogen, $C_1$-$C_4$ alkyl, hydroxy,

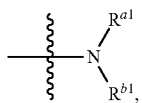

$C_1$-$C_4$ alkoxy, $C_1$-$C_4$ carboxyl, $C_1$-$C_4$ ester group or $C_1$-$C_4$ acylamino; when there are more substituents than one, the substituents are the same or different; in

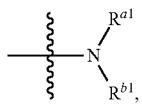

$R^{a1}$ and $R^{b1}$ are independently hydrogen or $C_1$-$C_4$ alkyl.

In a preferred embodiment of the present invention, L is $C_2$-$C_{10}$ heteroaryl having at least one N. Wherein, the heteroatom contained in the $C_2$-$C_{10}$ heteroaryl group is selected from N, O and S, the number of the heteroatom(s) is 1-4, when the number of the heteroatom is more than one, the heteroatoms are the same or different. More preferably, L is $C_2$-$C_6$ heteroaryl, wherein the heteroatom contained in the $C_2$-$C_6$ heteroaryl is selected from N, O and S, and the number of the heteroatoms is 2-4, wherein at least one heteroatom is N. Most preferably, L is pyrazolyl.

In a preferred embodiment of the present invention, when L is $C_2$-$C_{10}$ heteroaryl, the N atom thereof links to the ring A, and the C atom thereof links to the ring C.

In a preferred embodiment of the present invention, each of $R^2$ can also be independently

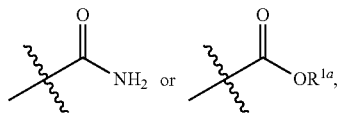

wherein $R^{1a}$ is $C_1$-$C_4$ alkyl.

In a preferred embodiment of the present invention, when $R^{11}$ and $R^{12}$ together with the nitrogen atom to which they are attached form a 5-7 membered substituted heterocycle, the substituent in the substituted heterocycle can also be substituted $C_1$-$C_4$ alkyl, the substituent in the substituted $C_1$-$C_4$ alkyl is selected from the group consisting of halogen, $C_1$-$C_4$ alkyl, hydroxy,

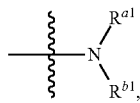

$C_1$-$C_4$ alkoxy, $C_1$-$C_4$ carboxyl, $C_1$-$C_4$ ester group or $C_1$-$C_4$ acylamino; when there are more substituents than one, the substituents are the same or different; in

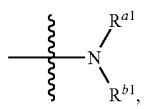

$R^{a1}$ and $R^{b1}$ are independently hydrogen, $C_1$-$C_4$ alkyl or

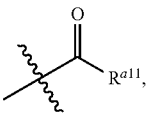

$R^{a11}$ is $C_1$-$C_4$ alkyl.

In a preferred embodiment of the present invention, in

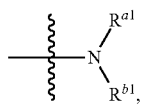

one of $R^{a1}$ and $R^{b1}$ is hydrogen and the other is

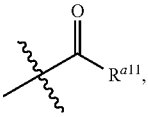

$R^{a11}$ is $C_1$-$C_4$ alkyl.

In a preferred embodiment of the present invention, in

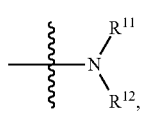

$R^{11}$ or $R^{12}$ can also be independently substituted or unsubstituted $C_6$-$C_{14}$ aryl, or substituted or unsubstituted $C_3$-$C_6$ cycloalkyl; in the definition of $R^{11}$ and $R^{12}$, the substituent in the substituted $C_6$-$C_{14}$ aryl or the substituted $C_3$-$C_6$ cycloalkyl is selected from the group consisting of halogen, $C_1$-$C_4$ alkyl, hydroxy,

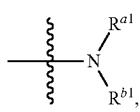

$C_1$-$C_4$ alkoxy, $C_1$-$C_4$ carboxyl, $C_1$-$C_4$ ester group or $C_1$-$C_4$ acylamino; when there are more substituents than one, the substituents are the same or different; in

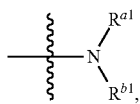

$R^{a1}$ and $R^{b1}$ are independently hydrogen, $C_1$-$C_4$ alkyl or

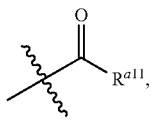

$R^{a11}$ is $C_1$-$C_4$ alkyl.

In the present invention, when the substituent in the substituted alkyl, the substituted alkoxy, the substituted cycloalkyl, the substituted carbocycle or the substituted heterocycle is halogen, the halogen is preferably fluorine, chlorine, bromine or iodine.

In the present invention, when the substituent in the substituted hydroxy, the substituted amino, the substituted alkyl, the substituted alkoxy, the substituted cycloalkyl, the substituted carbocycle or the substituted heterocycle is $C_1$-$C_4$ alkyl, the $C_1$-$C_4$ alkyl is preferably methyl, ethyl, n-propyl, isopropyl, n-butyl, isobutyl or tert-butyl.

In the present invention, when the substituent in the substituted alkyl, the substituted alkoxy, the substituted cycloalkyl, the substituted carbocycle or the substituted heterocycle is

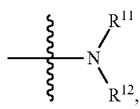

and $R^{11}$ and $R^{12}$ are independently substituted or unsubstituted alkyl, the substituted or unsubstituted alkyl is preferably substituted or unsubstituted $C_1$-$C_4$ alkyl. The substituted or unsubstituted $C_1$-$C_4$ alkyl is preferably substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl or substituted or unsubstituted tert-butyl.

In the present invention, when the substituent in the substituted hydroxy, the substituted amino, the substituted alkyl, the substituted alkoxy, the substituted cycloalkyl, the substituted carbocycle or the substituted heterocycle is $C_1$-$C_4$ alkoxy, the $C_1$-$C_4$ alkoxy is preferably methoxy, ethoxy, n-propoxy, isopropoxy, n-butoxy, isobutoxy or tert-butoxy.

In the present invention, when the substituent in the substituted hydroxy, the substituted amino, the substituted alkyl, the substituted alkoxy, the substituted cycloalkyl, the substituted carbocycle or the substituted heterocycle is $C_1$-$C_4$ carboxyl, the $C_1$-$C_4$ carboxyl is preferably

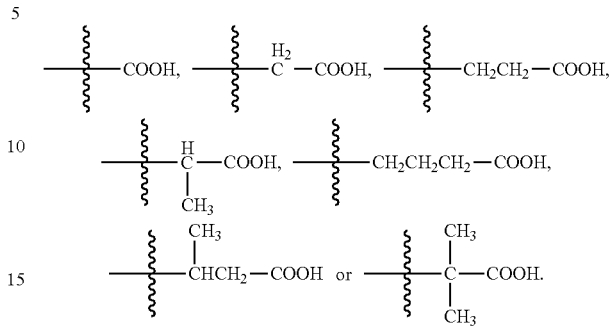

In the present invention, when the substituent in the substituted hydroxy, the substituted amino, the substituted alkyl, the substituted alkoxy, the substituted cycloalkyl, the substituted carbocycle or the substituted heterocycle is $C_1$-$C_4$ ester group, the $C_1$-$C_4$ ester group is preferably

wherein $R^a$ is $C_1$-$C_4$ alkyl; in the definition of $R^a$ the $C_1$-$C_4$ alkyl is preferably methyl, ethyl, n-propyl, isopropyl, n-butyl, isobutyl or tert-butyl.

In the present invention, when the substituent in the substituted hydroxy, the substituted amino, the substituted alkyl, the substituted alkoxy, the substituted cycloalkyl, the substituted carbocycle or the substituted heterocycle is $C_1$-$C_4$ acylamino, the $C_1$-$C_4$ acylamino is preferably

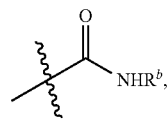

wherein $R^b$ is hydrogen or $C_1$-$C_4$ alkyl; in the definition of $R^b$, the $C_1$-$C_4$ alkyl is preferably methyl, ethyl, n-propyl, isopropyl, n-butyl, isobutyl or tert-butyl.

In the definition of ring A or ring B, the aromatic ring is preferably $C_6$-$C_{14}$ aromatic ring. The $C_6$-$C_{14}$ aromatic ring is preferably $C_6$-$C_{10}$ aromatic ring, more preferably benzene ring.

In the definition of ring A or ring B, the heteroaromatic ring is preferably $C_2$-$C_{10}$ heteroaromatic ring having 1-4 heteroatoms selected from nitrogen, oxygen and sulfur. The $C_2$-$C_{10}$ heteroaromatic ring is preferably $C_2$-$C_8$ heteroaromatic ring having 1-3 heteroatoms selected from nitrogen and oxygen. The $C_2$-$C_8$ heteroaromatic ring is preferably

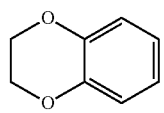

or pyridine ring

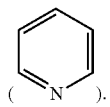

In a preferred embodiment of the present invention, in the definition of ring A or ring B, the $C_2$-$C_8$ heteroaromatic ring is more preferably pyrazole ring

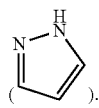

In a preferred embodiment of the present invention, when the ring A is $C_2$-$C_{10}$ heteroaromatic ring, the $C_2$-$C_{10}$ heteroaromatic ring refers to a stable monocyclic ring or bicyclic ring with up to 7 atoms in each ring, wherein at least one ring is an aromatic ring having 1-4 heteroatoms selected from O, N and S, e.g., pyridine ring.

In a preferred embodiment of the present invention, when the ring B is $C_2$-$C_{10}$ heteroaromatic ring, the $C_2$-$C_{10}$ heteroaromatic ring refers to a stable bicyclic ring with up to 7 atoms in each ring, wherein one ring is an aromatic ring without heteroatom, the other ring is $C_2$-$C_{10}$ heterocycloalkane or $C_2$-$C_{10}$ heteroaromatic ring. The heteroatom contained in the $C_2$-$C_{10}$ heterocycloalkane is selected from N, O and S, the number of the heteroatom(s) is 1-4, e.g.,

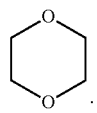

The $C_2$-$C_{10}$ heteroaryl refers to a stable monocyclic ring or bicyclic ring with up to 7 atoms in each ring, wherein at least one ring is an aromatic ring having 1-4 heteroatoms selected from O, N and S, e.g., pyridine ring.

In a preferred embodiment of the present invention, ring A is preferably benzene ring or pyridine ring.

In a preferred embodiment of the present invention, ring B is preferably benzene ring or

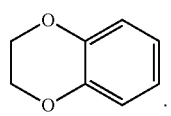

In a preferred embodiment of the present invention, each of $R^2$ is independently preferably hydrogen, D or

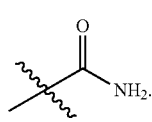

In a preferred embodiment of the present invention, in

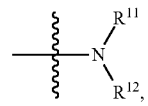

$R^{11}$ and $R^{12}$ are independently hydrogen, substituted or unsubstituted alkyl, alkoxy, hydroxyalkyl, aminoalkyl, or substituted or unsubstituted $C_3$-$C_6$ cycloalkyl; or $R^{11}$ and $R^{12}$ together with the nitrogen atom to which they are attached form a 5-7 membered substituted or unsubstituted heterocycle; in the heterocycle, the heteroatom is nitrogen, or nitrogen and oxygen, the number of the heteroatom(s) is 1-4.

In a preferred embodiment of the present invention, in

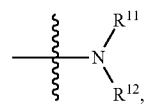

one of $R^{11}$ and $R^{12}$ is hydrogen, the other is substituted or unsubstituted alkyl, alkoxy, hydroxyalkyl, aminoalkyl, or substituted or unsubstituted $C_3$-$C_6$ cycloalkyl; or $R^{11}$ and $R^{12}$ together with the nitrogen atom to which they are attached form a 5-7 membered substituted or unsubstituted heterocycle; in the heterocycle, the heteroatom is nitrogen, or nitrogen and oxygen, the number of the heteroatom(s) is 1-4.

In a preferred embodiment of the present invention, in the definition of ring A, when m is 2 or 3, wherein one $R^1$ is substituted alkyl, the substituent in the substituted alkyl is

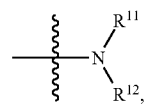

$R^{11}$ and $R^{12}$ together with the nitrogen atom to which they are attached form a 5-7 membered substituted heterocycle, when the substituent in the substituted heterocycle is $C_1$-$C_4$ acylamino, other $R^1$ is not halogen.

In the present invention, the halogen is preferably fluorine, chlorine, bromine or iodine.

In the present invention, the alkyl is preferably $C_1$-$C_4$ alkyl. The $C_1$-$C_4$ alkyl is preferably methyl, ethyl, n-propyl, isopropyl, n-butyl, isobutyl or tert-butyl.

In the present invention, the alkoxy is preferably $C_1$-$C_4$ alkoxy. The $C_1$-$C_4$ alkoxy is preferably methoxy, ethoxy, n-propoxy, isopropoxy or tert-butoxy.

In the present invention, the cycloalkyl is preferably $C_3$-$C_6$ cycloalkyl. The $C_3$-$C_6$ cycloalkyl is preferably cyclopropyl, cyclobutyl, cyclopentyl or cyclohexyl.

In the present invention, the hydroxyalkyl is preferably $C_1$-$C_4$ hydroxyalkyl. The $C_1$-$C_4$ hydroxyalkyl is preferably

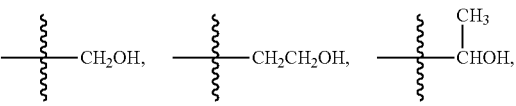

-continued

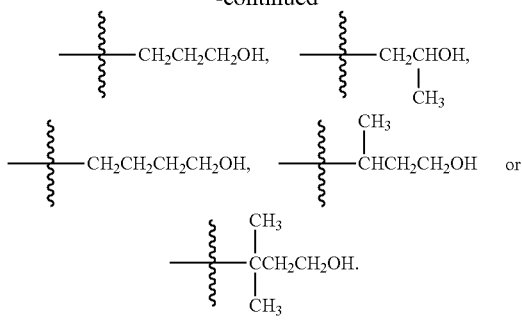

In the present invention, the aminoalkyl is preferably $C_1$-$C_4$ aminoalkyl. The $C_1$-$C_4$ aminoalkyl is preferably

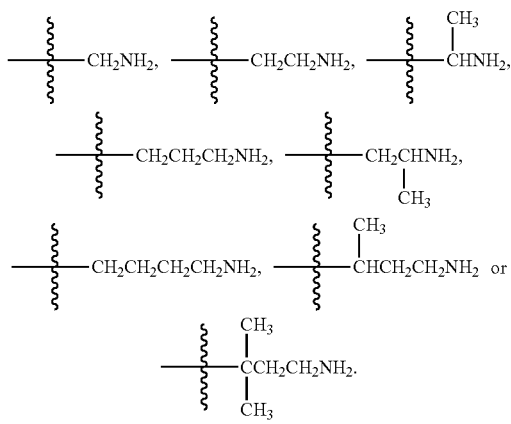

In the present invention, the carbocycle is preferably cyclopentane, cyclohexane or cycloheptane.

In the present invention, the heterocycle is preferably pyrrole ring or piperidine ring.

In a preferred embodiment of the present invention, in formula I, each of $R^1$ is independently preferably hydrogen, deuterium, halogen, substituted or unsubstituted hydroxy, substituted or unsubstituted alkyl, or, substituted or unsubstituted alkoxy. Wherein, the substituted hydroxy is preferably

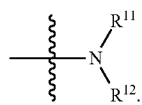

The substituent in the substituted alkyl is preferably substituted by one or more than one

The substituted alkyl is preferably

The

is preferably

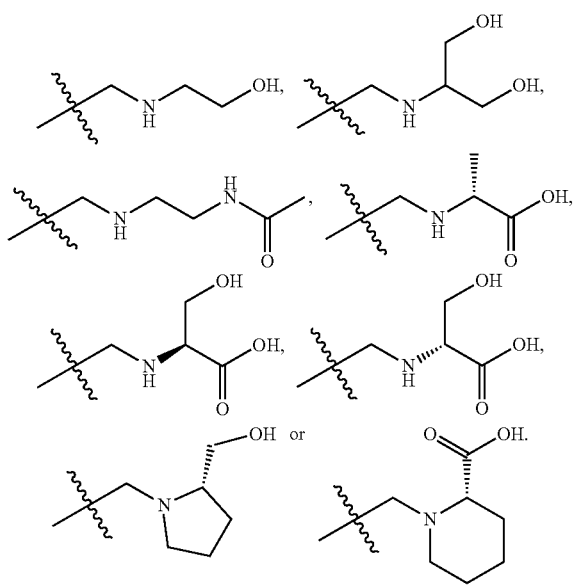

In a preferred embodiment of the present invention, the

is preferably

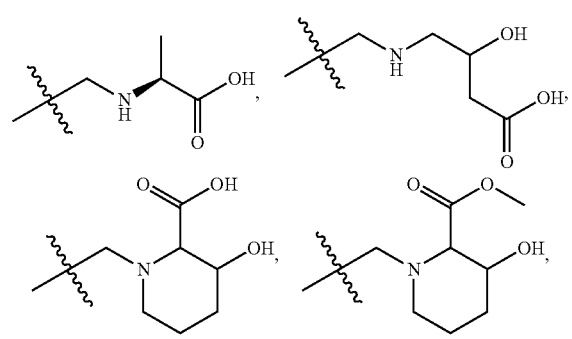

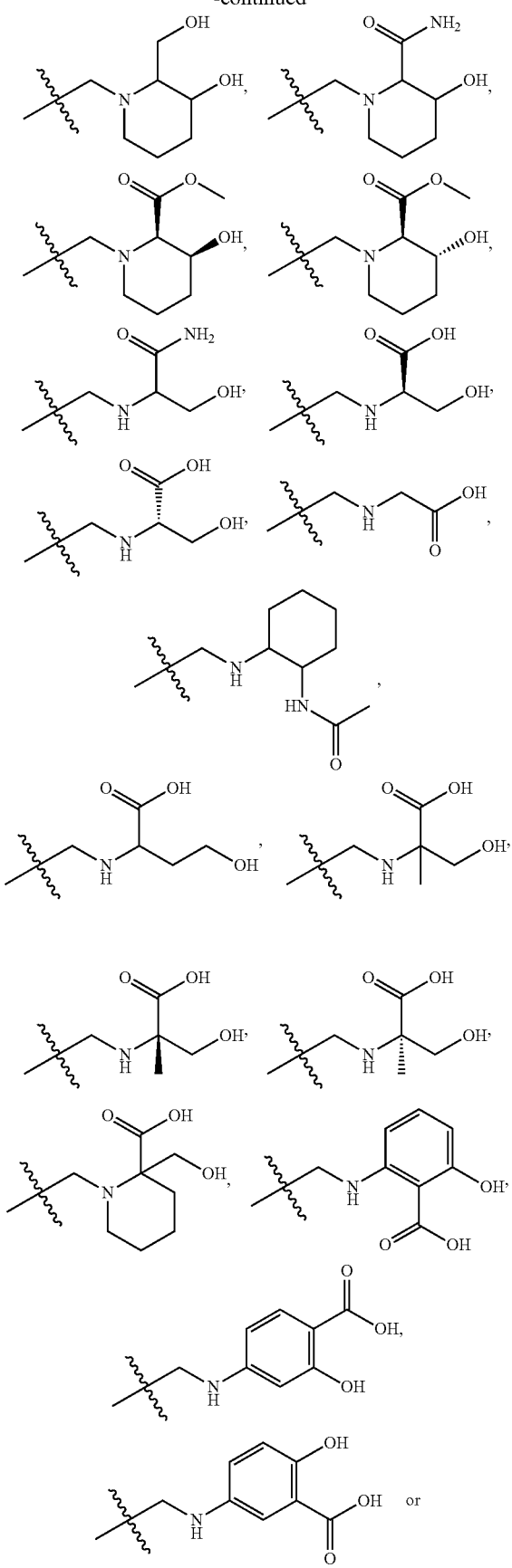

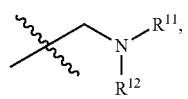

In a preferred embodiment of the present invention, when $R^1$ is

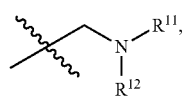

$R^1$ is located at the para-position of the atom on the ring A linking to L.

In a preferred embodiment of the present invention, when $R^1$ is

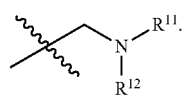

there can be additional 0, 1 or 2 substituents present on the ring A. When there is additional 1 substituent present on the ring A, the substituent is located at the ortho-position or the para-position of

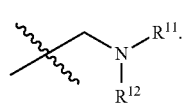

When there is additional 2 substituent present on the ring A, the 2 substituents are located at the ortho-position of

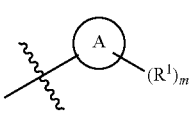

In a preferred embodiment of the present invention,

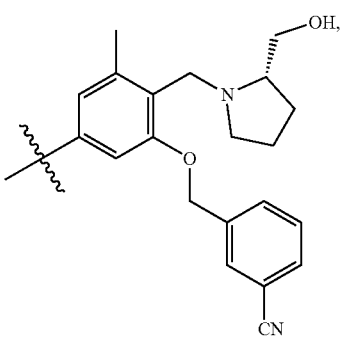

is preferably

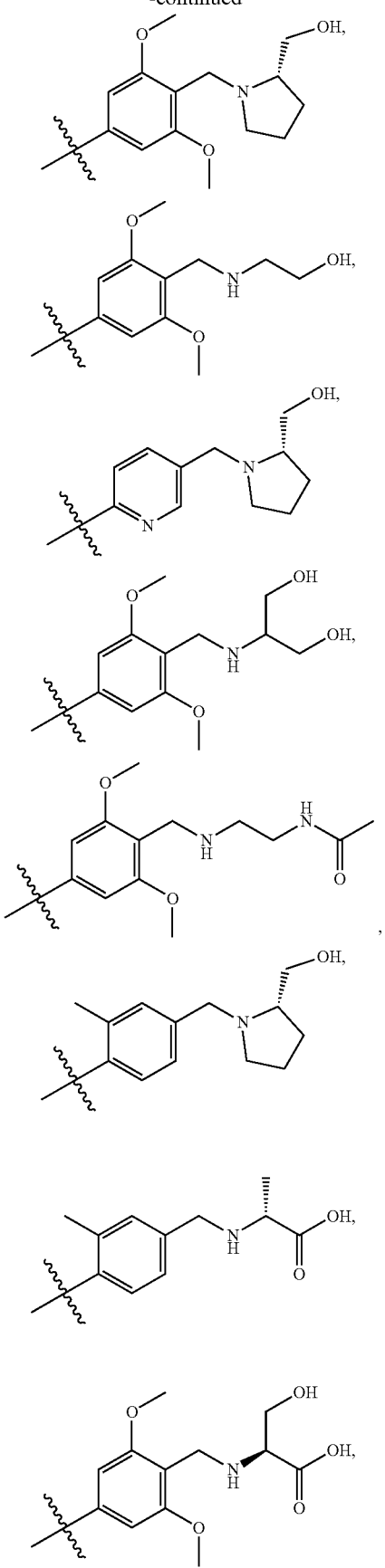
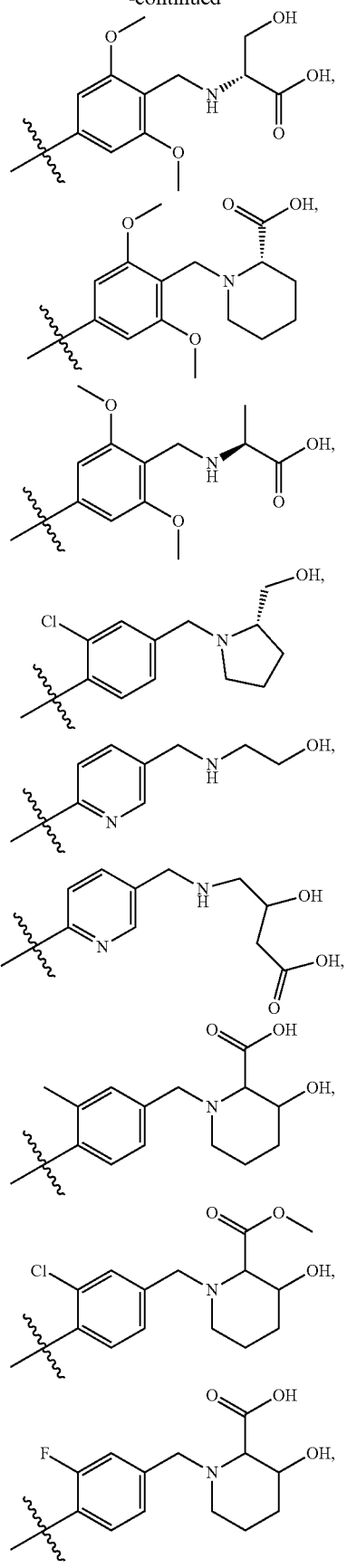

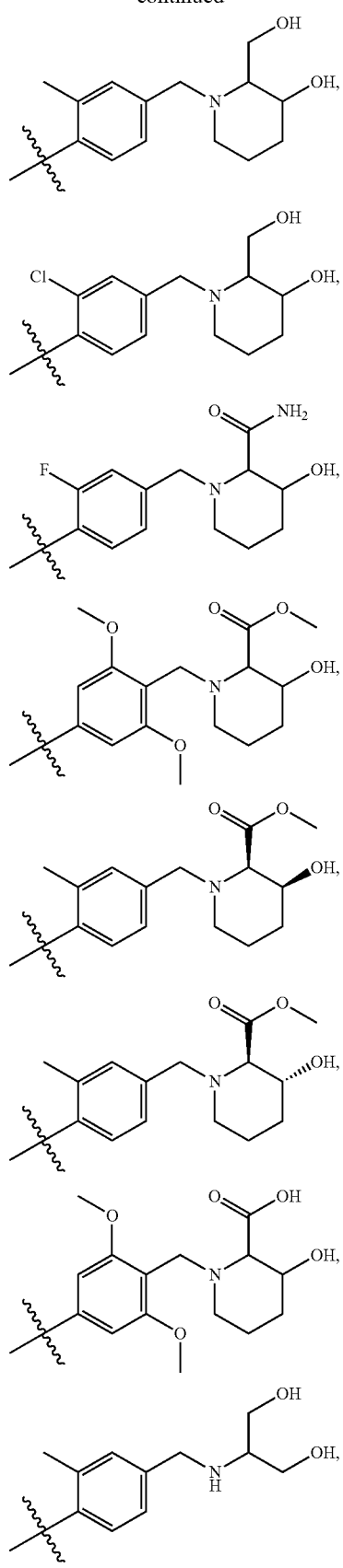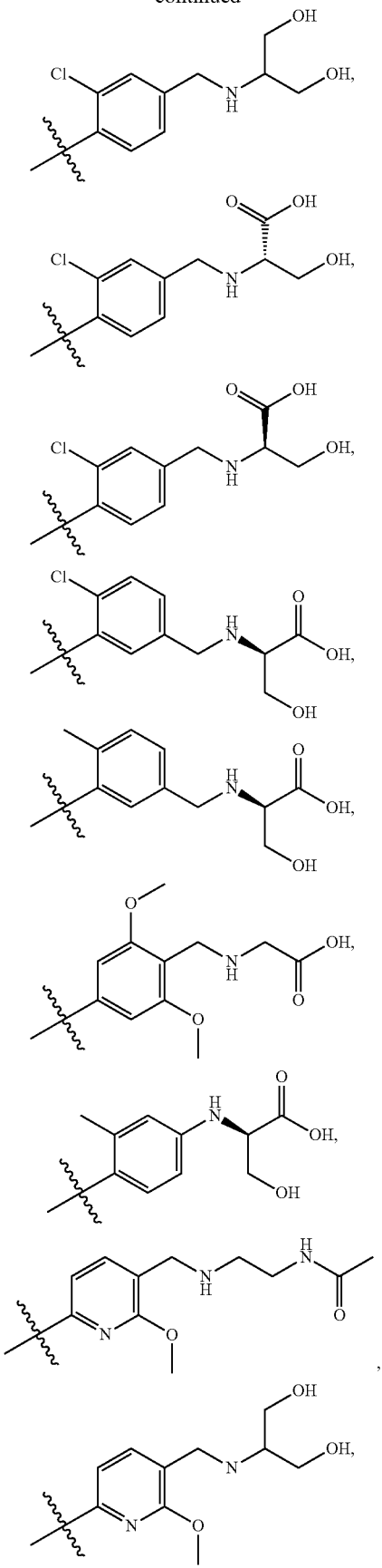

-continued
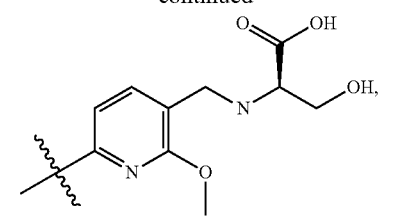
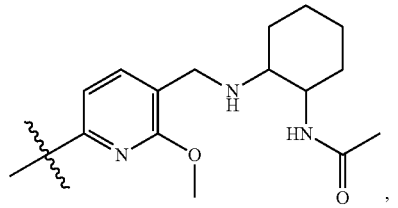
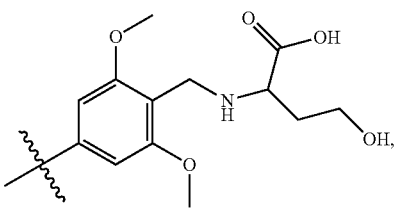
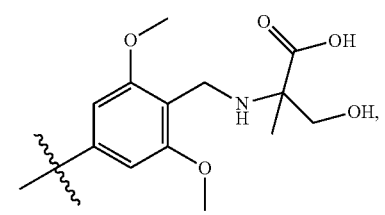
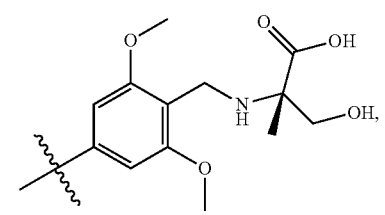
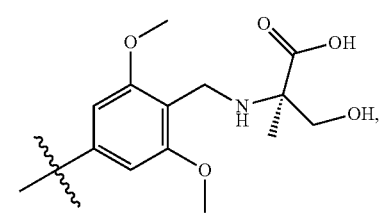
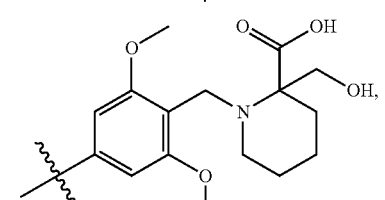
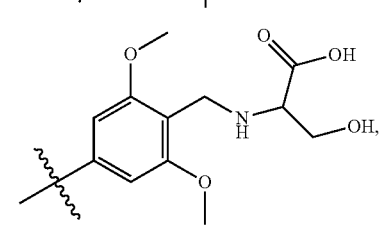
-continued
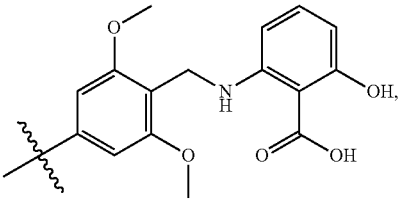
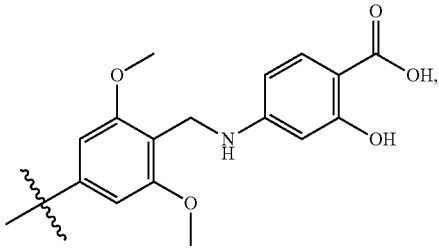
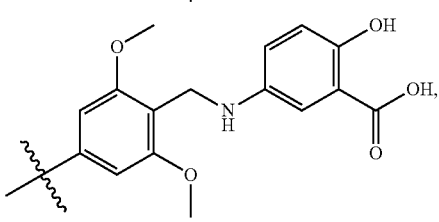
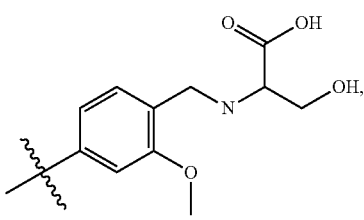
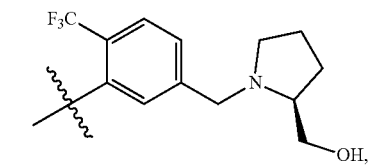
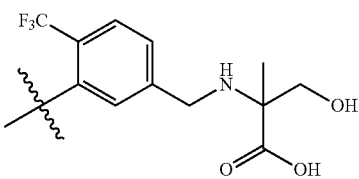
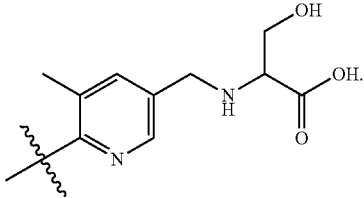
In a preferred embodiment of the present invention,
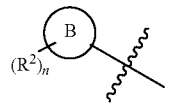

is preferably

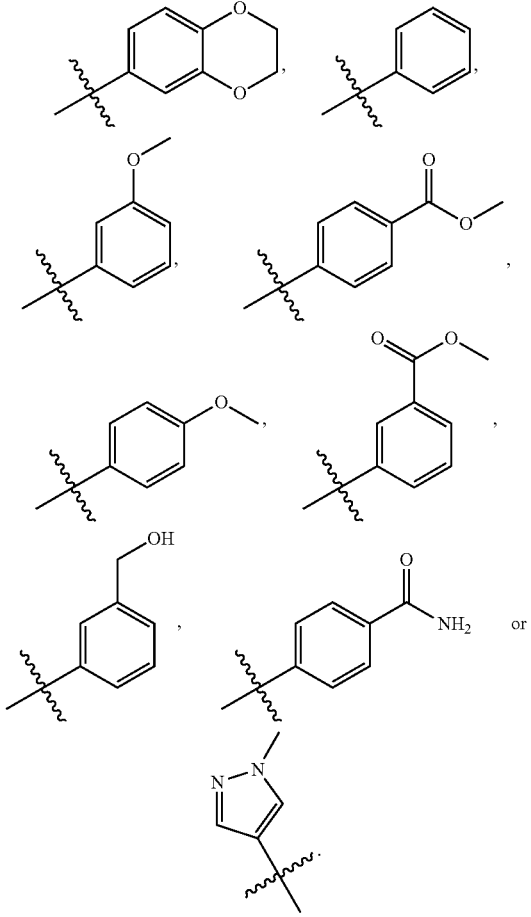

In a preferred embodiment of the present invention,

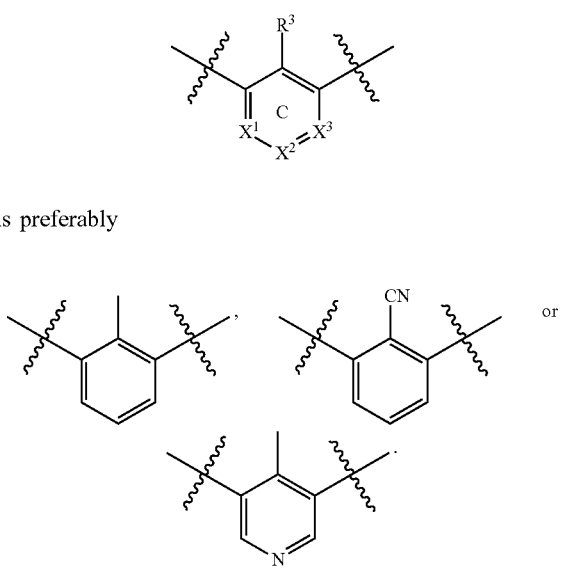

is preferably

In a preferred embodiment of the present invention, formula I is preferably represented by formula II-0, II-1 or II-2:

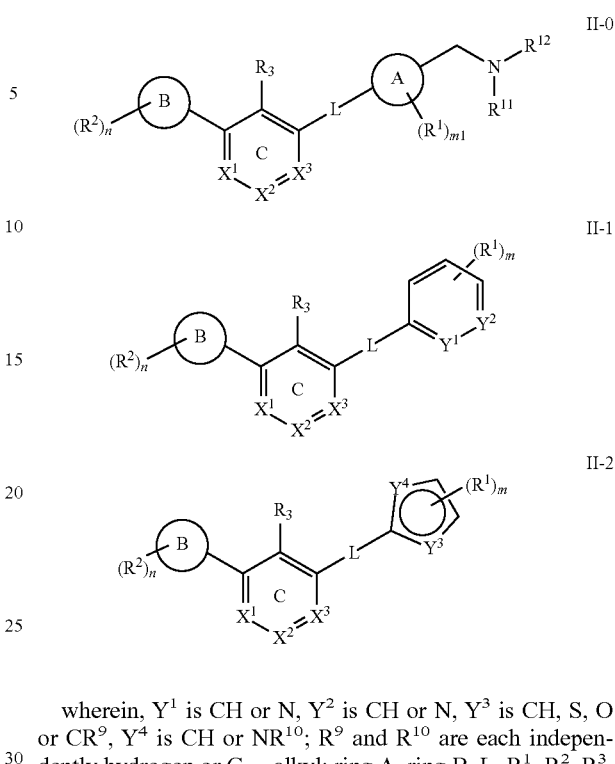

wherein, $Y^1$ is CH or N, $Y^2$ is CH or N, $Y^3$ is CH, S, O or $CR^9$, $Y^4$ is CH or $NR^{10}$; $R^9$ and $R^{10}$ are each independently hydrogen or $C_{1-4}$ alkyl; ring A, ring B, L, $R^1$, $R^2$, $R^3$, $R^{11}$, $R^{12}$, $X^1$, $X^2$, $X^3$, n and m are defined as above, m1 is 0, 1 or 2. In the definition of $R^9$ or $R^{10}$, the $C_1$-4 alkyl is preferably methyl, ethyl, n-propyl, isopropyl, n-butyl, isobutyl or tert-butyl.

In a preferred embodiment of the present invention, formula I is preferably represented by formula II-1-1 or II-1-2:

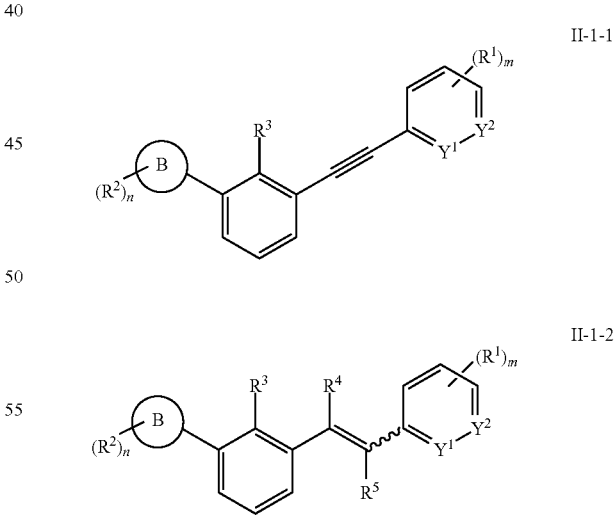

wherein, ring B, $R^1$, $R^2$, $R^3$, $R^4$, $R^5$, $Y^1$, $Y^2$, n and m are defined as above, in formula II-1-2, the wavy line means the olefin is cis or trans configuration.

In a preferred embodiment of the present invention, formula II-1-1 or II-1-2 is preferably represented by II-1-1A or II-1-2A:

II-1-1A

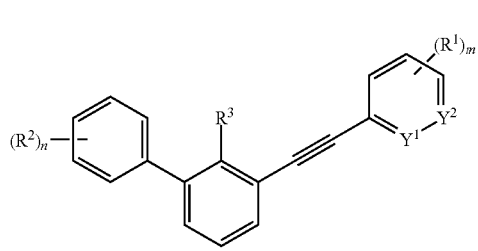

II-1-2A

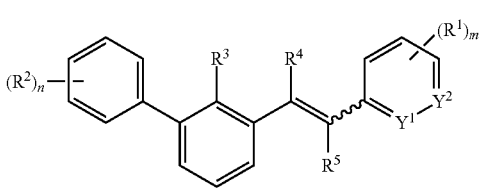

wherein, the wavy line, $R^1$, $R^2$, $R^3$, $R^4$, $R^5$, $Y^1$, $Y^2$, n and m are defined as above.

In a preferred embodiment of the present invention, formula II-1-1A or II-1-2A is preferably represented by II-1-1B or II-1-2B:

II-1-1B

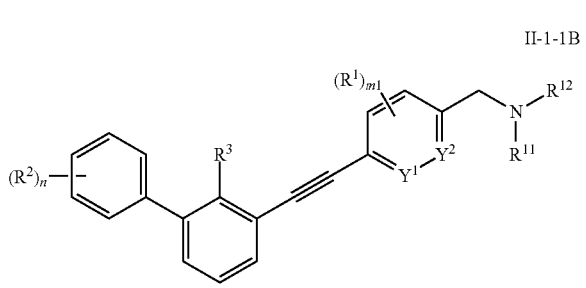

II-1-2B

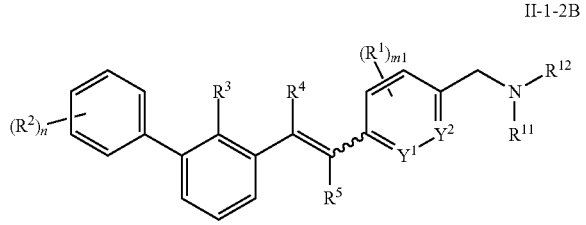

wherein, the wavy line, $R^1$, $R^2$, $R^3$, $R^4$, $R^5$, $Y^1$, $Y^2$ and n are defined as above, m1 is 0, 1 or 2.

In the present invention, the aromatic acetylene or aromatic ethylene compound represented by formula I is preferably selected from

1

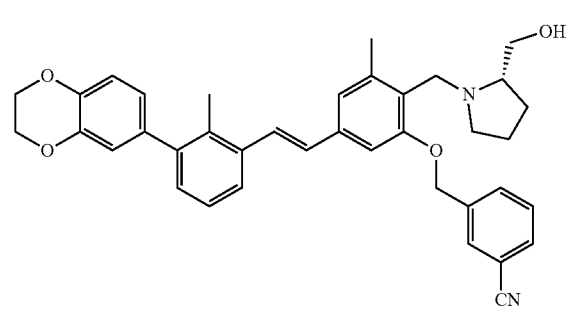

2

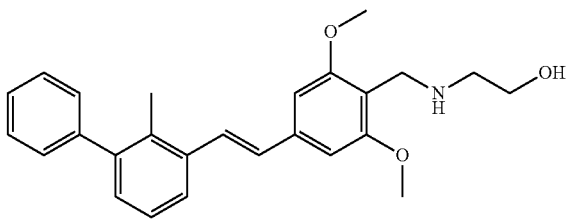

3

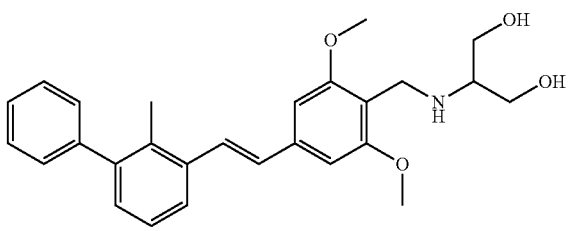

4

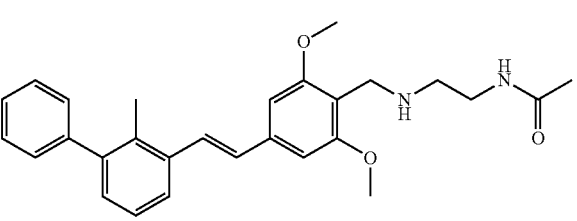

5

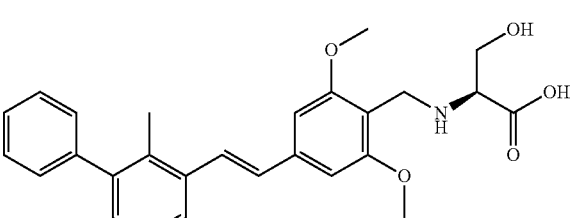

6

7

8
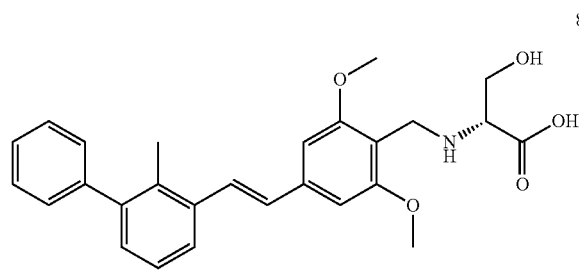
9
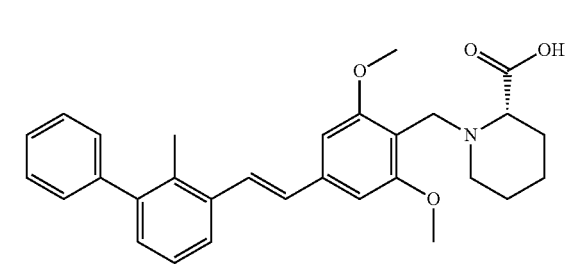
10
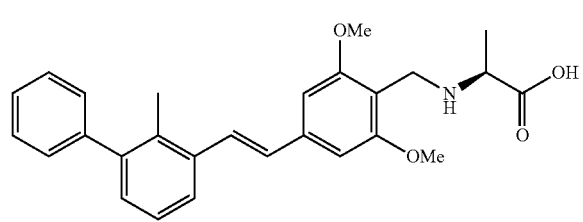
11
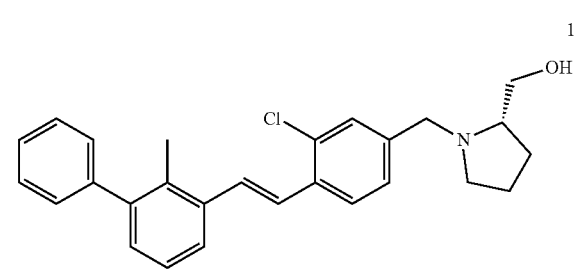
12
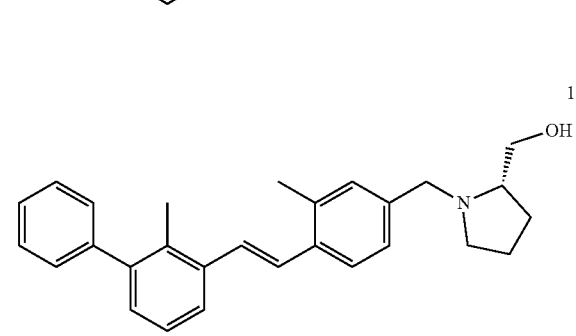
13
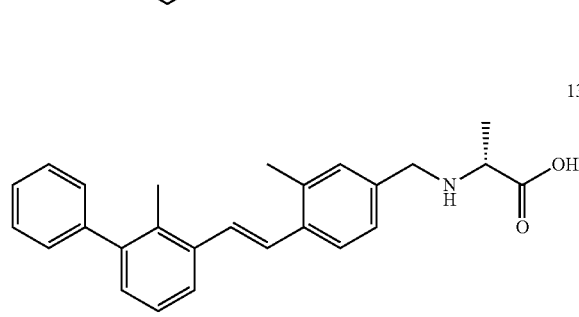
14
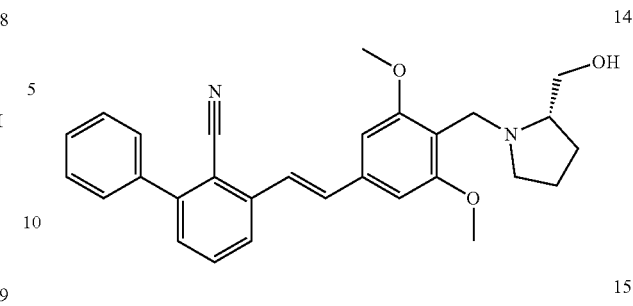
15
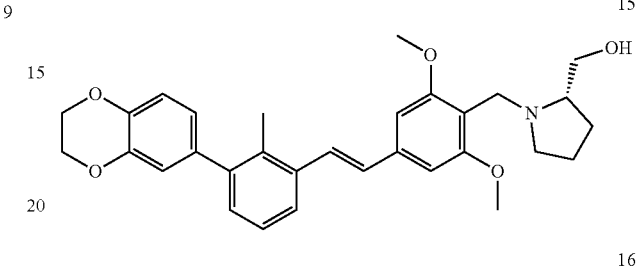
16
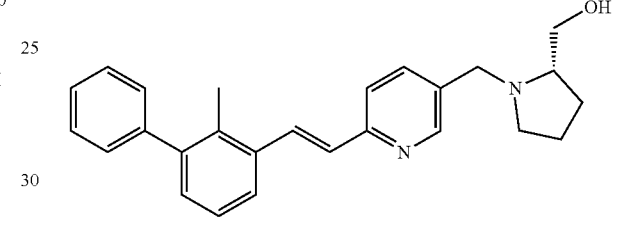
17
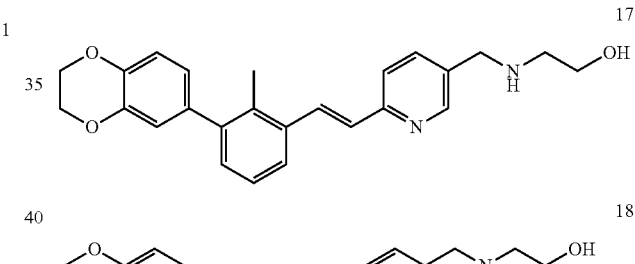
18
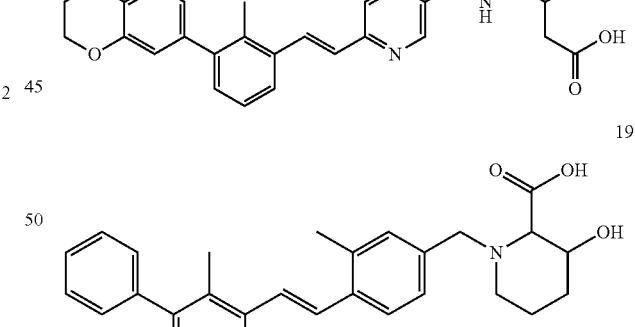
19
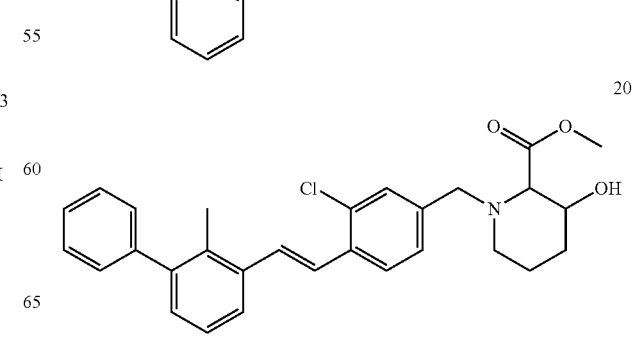

21
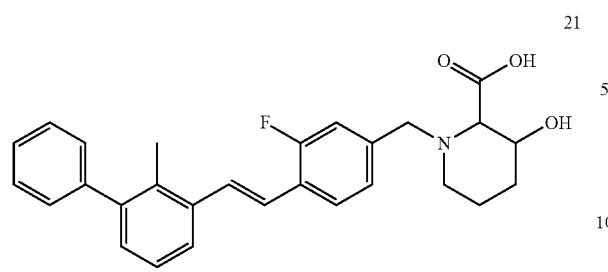
22
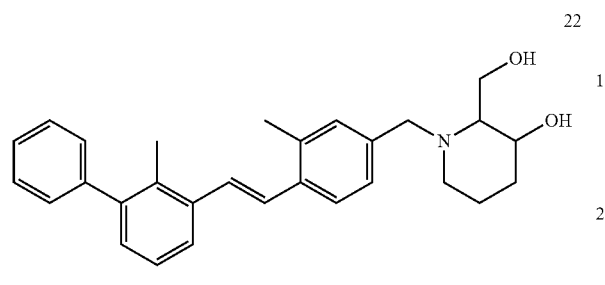
23
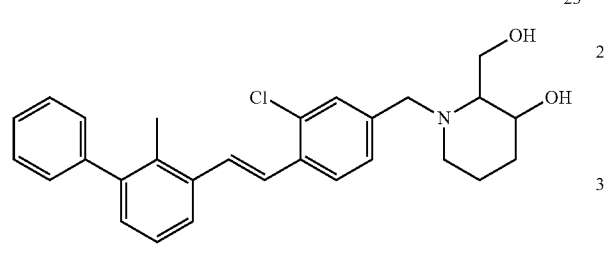
24
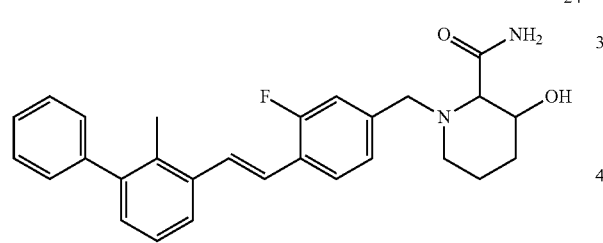
25
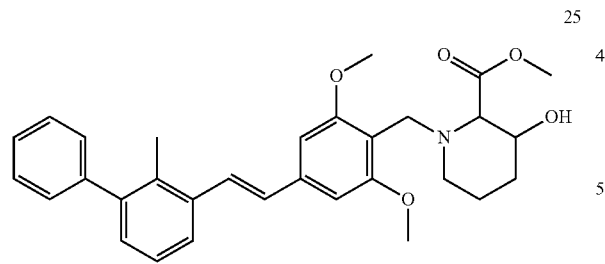
26
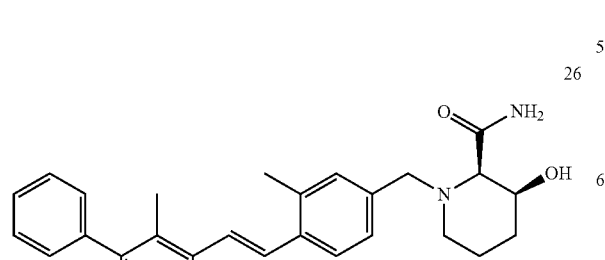
27
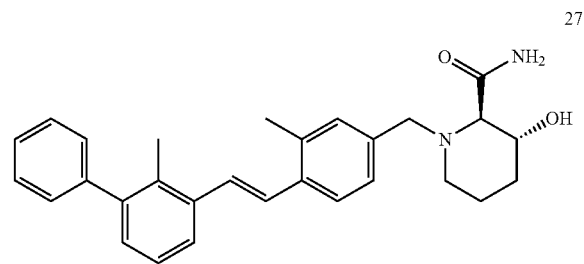
28
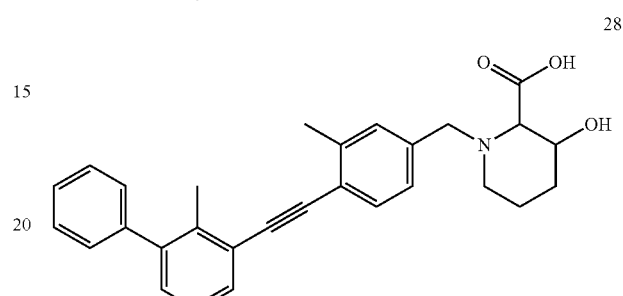
29
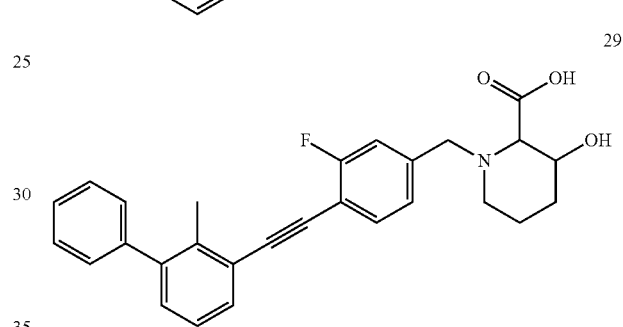
30
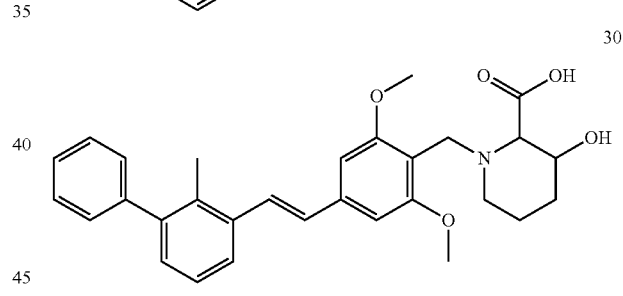
31
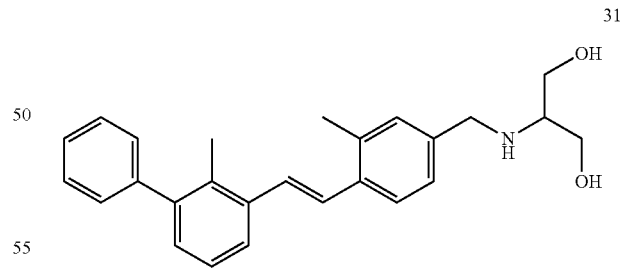
32
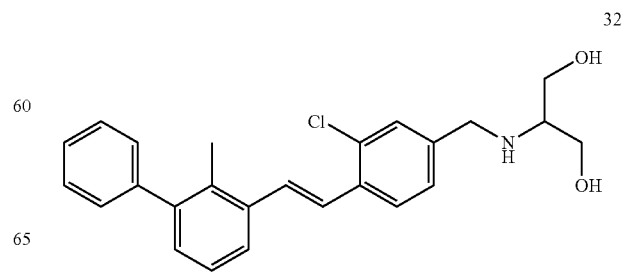

33
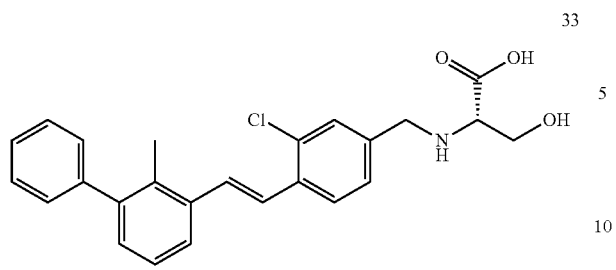
34
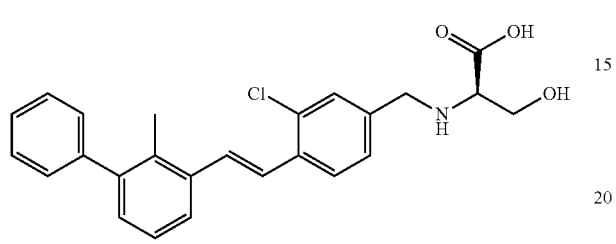
35
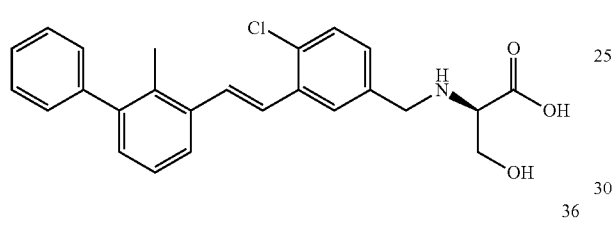
36
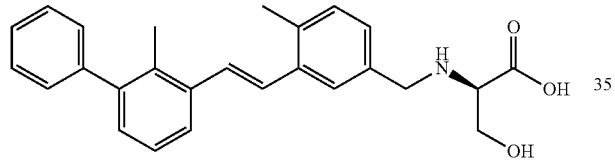
37
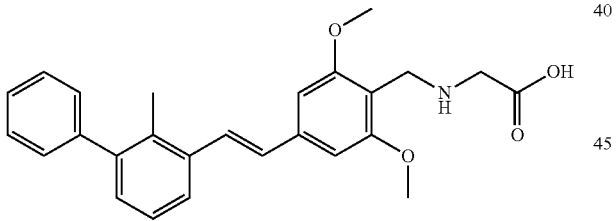
38
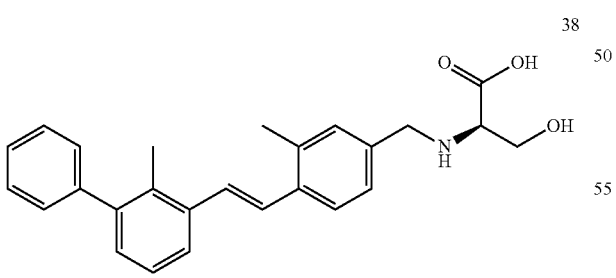
39
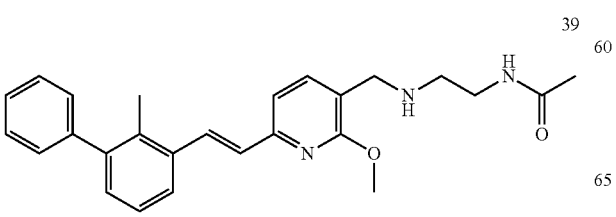
40
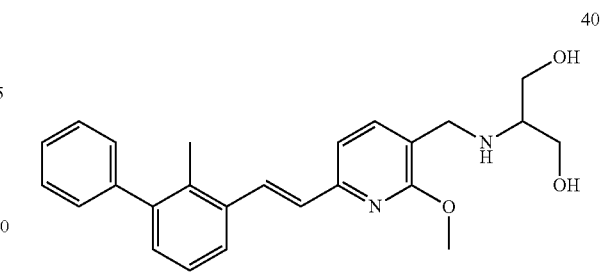
41
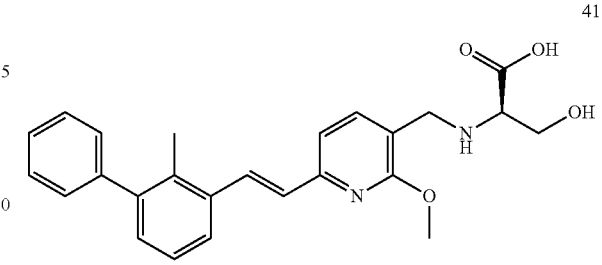
42
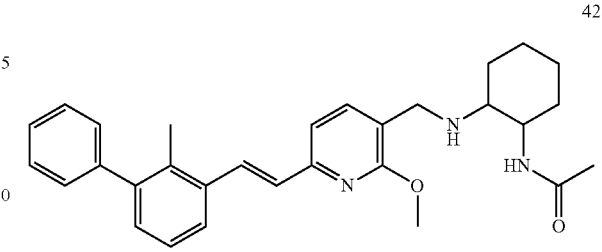
43
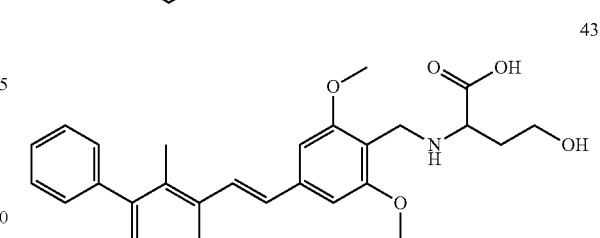
44
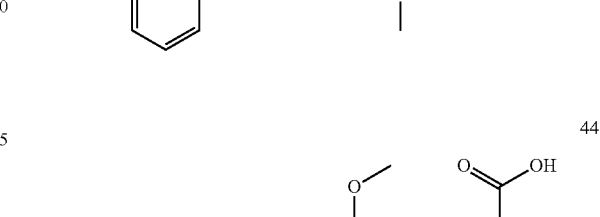
45
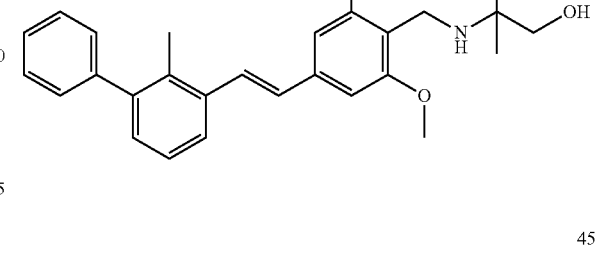
45
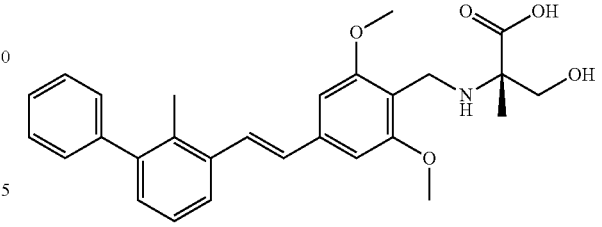

46
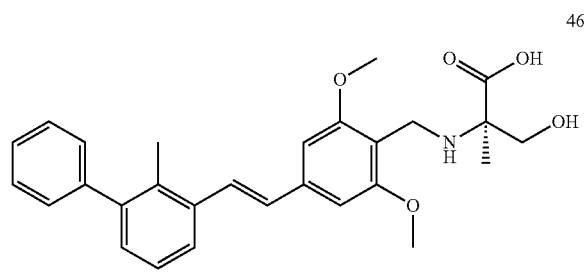
47
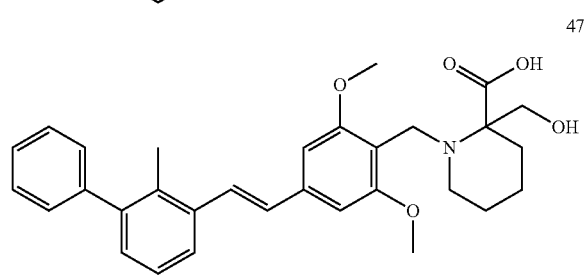
48
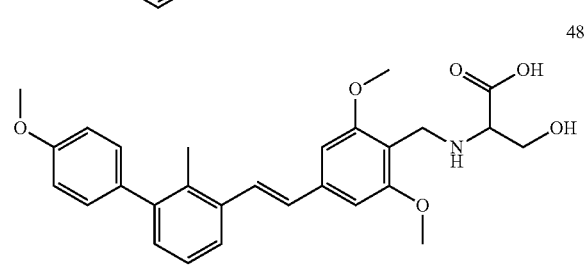
49
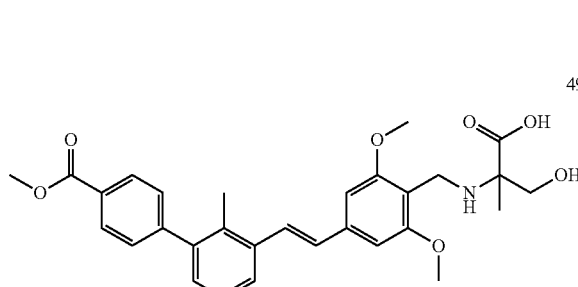
50
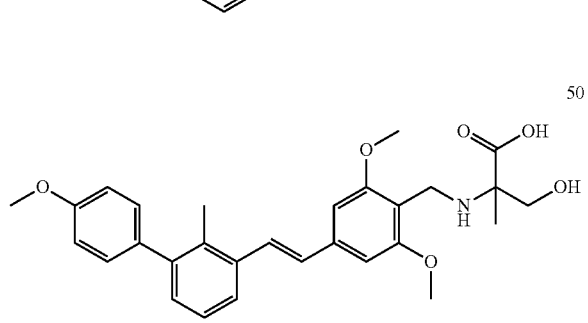
51
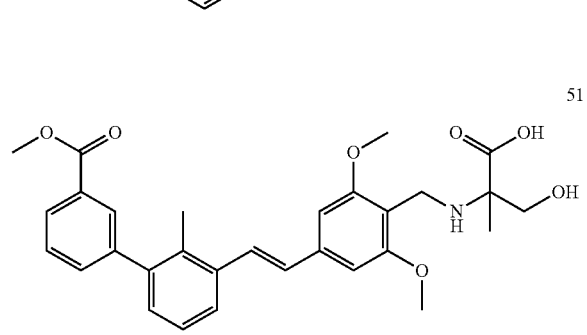
52
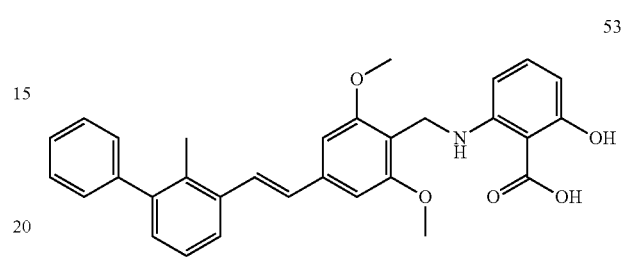
53
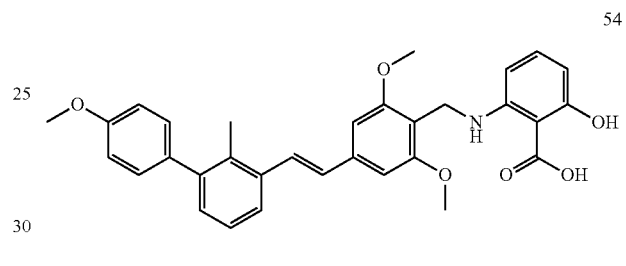
54
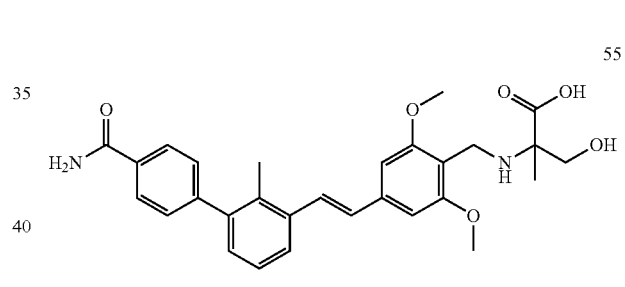
55
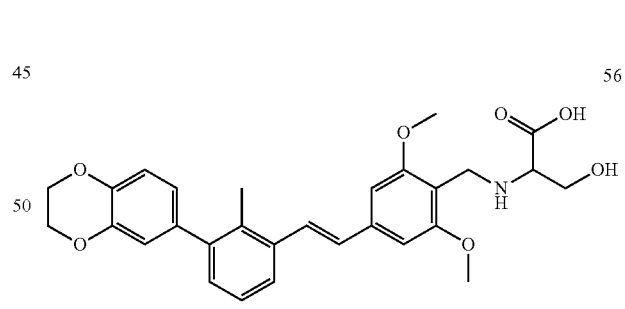
56
57
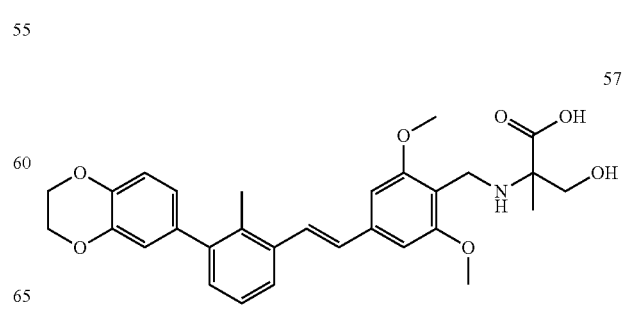

58
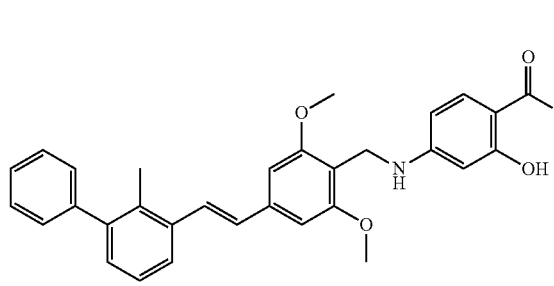
64
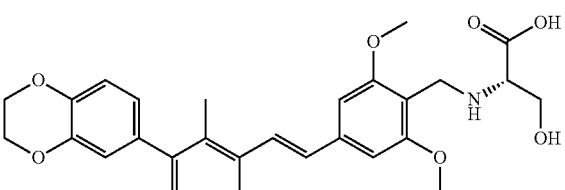
59
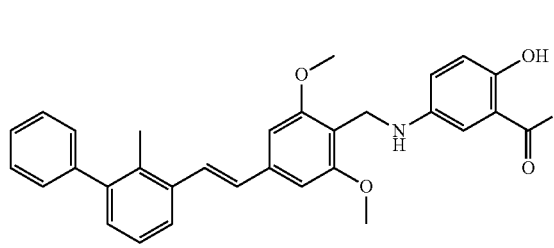
65
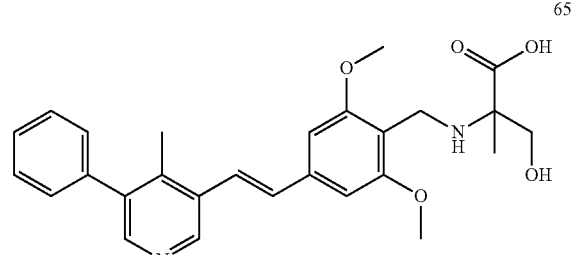
60
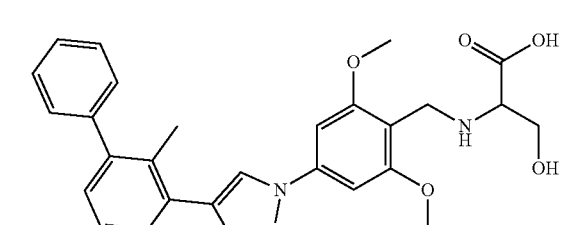
66
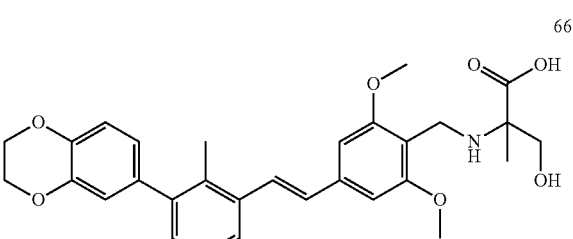
61
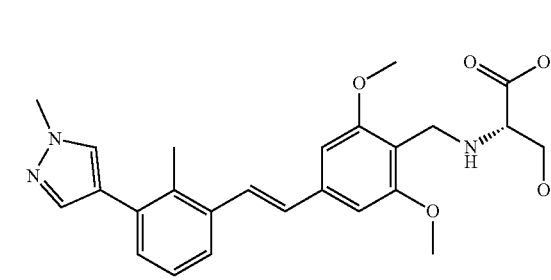
67
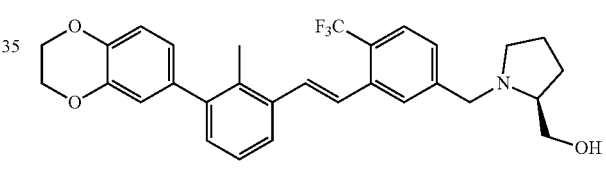
68
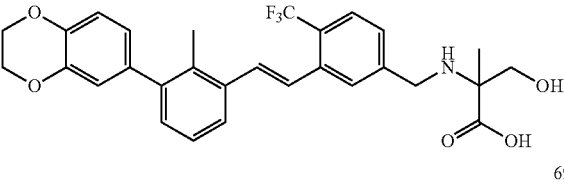
62
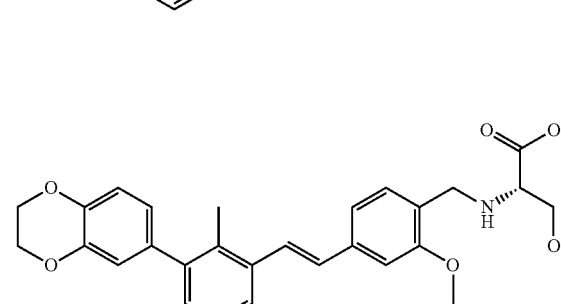
69
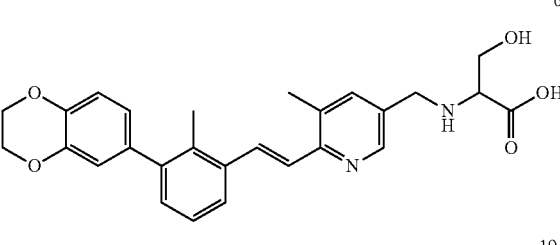
63
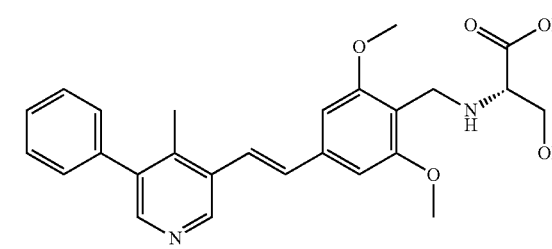
19-a
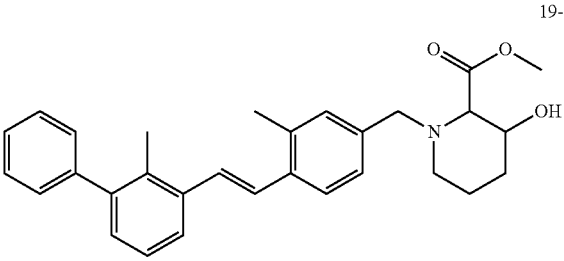

-continued 21-a
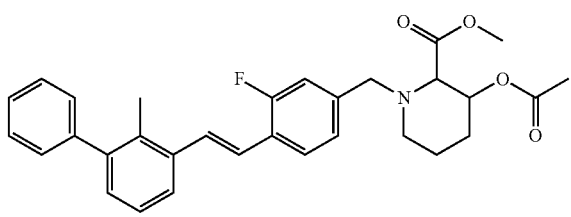

28-a
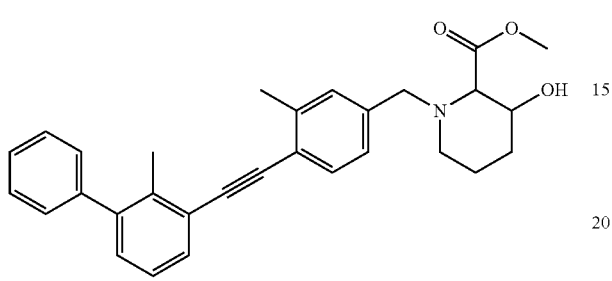

29-a
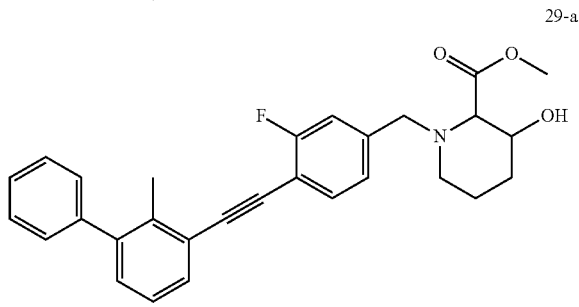

37-a
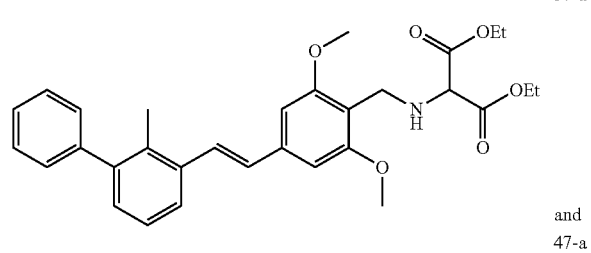
and 47-a
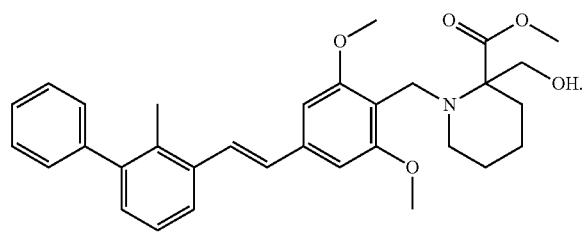

The present invention also provides a process for preparing the aromatic acetylene or aromatic ethylene compound represented by formula I, the pharmaceutically acceptable salt, the tautomer, the mesomer, the racemate, the stereoisomer, the metabolite, the metabolic precursor or the prodrug thereof, which can be synthesized by known methods using commercially available raw materials.

In the present invention, when formula I is represented by formula II-0, a process for preparing the compound represented by formula II-0 is preferably process 1 or process 2:

process 1 comprising conducting a reductive amination reaction of the compound represented by formula I-a with the compound represented by formula I-b as shown below in the presence of a reducing agent in a solvent to give the compound represented by formula II-0;

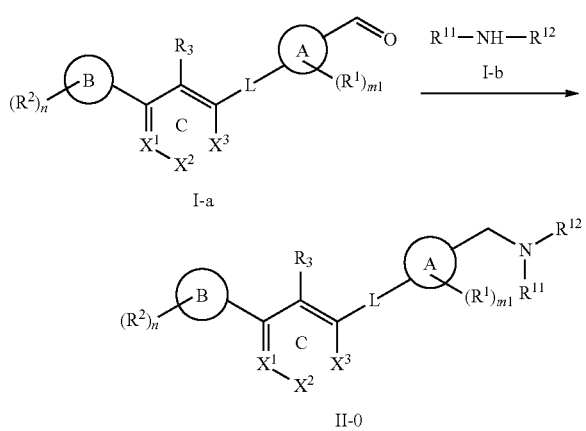

process 2 comprising conducting a substitution reaction of the compound represented by formula I-a1 and the compound represented by formula I-b as shown below in the presence of a base in a solvent to give the compound represented by formula II-0;

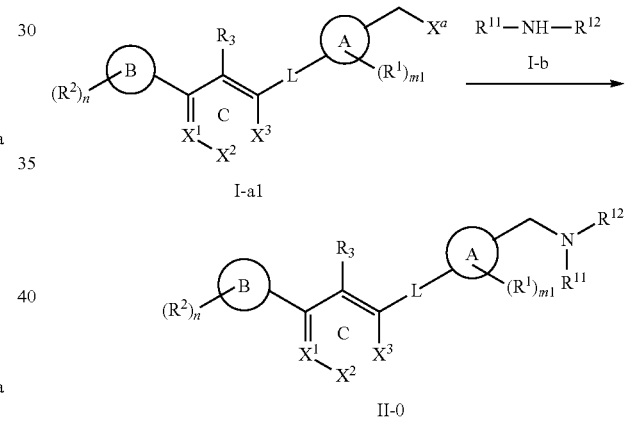

in formula I-a, formula I-a1, formula I-b and formula I, ring A, ring B, $R^1$, $R^2$, $R^3$, $R^{11}$, $R^{12}$, $X^1$, $X^2$, $X^3$, n and m1 are defined as above; in formula I-a1, $X^a$ is halogen (preferably F, Cl, Br or I).

In the process 1, the methods and conditions for the reductive amination reaction may be conventional methods and conditions for such reactions in the art.

In the process 1, an acid can also be present in the reductive amination reaction. The acid is preferably an inorganic acid and/or an organic acid. The inorganic acid is preferably hydrochloric acid and/or sulfuric acid. The organic acid is preferably glacial acetic acid. The molar ratio of the acid to the compound I-a is preferably 0.2:1 to 5:1 (e.g., 2:1).

In the process 1, the solvent is preferably an organic solvent and/or water. The organic solvent may be an organic solvent commonly used in such reactions in the art, preferably selected from the group consisting of alcohols solvent, chlorinated hydrocarbons solvent, ethers solvent and amides solvent. The alcohols solvent is preferably methanol and/or ethanol. The chlorinated hydrocarbons solvent is preferably dichloromethane. The ethers solvent is preferably 1,4-dioxane. The amides solvent is preferably N,N-dimethylformamide. The solvent is preferably a mixed solvent of an alcohols solvent and a chlorinated hydrocarbons solvent, e.g., a mixed solvent of methanol and dichloromethane. In the mixed solvent of a alcohols solvent and a chlorinated hydrocarbons solvent, the volume ratio of the alcohols solvent to the chlorinated hydrocarbons solvent is preferably 1:0.1 to 1:5 (e.g., 1:1). The amount of the solvent is not particularly limited as long as it does not affect the progress of the reaction, the volume/mass ratio of the solvent to the compound represented by formula I-a is preferably 10 mL/g to 110 mL/g.

In the process 1, the reducing agent may be a reducing agent commonly used in the art, preferably selected from the group consisting of sodium cyanoborohydride, sodium triacetoxyborohydride, sodium borohydride and lithium borohydride, preferably sodium cyanoborohydride. The molar ratio of the reducing agent to the compound represented by formula I-a is preferably 0.3:1 to 10:1 (e.g., 5:1).

In the process 1, in the reductive amination reaction, the molar ratio of the compound represented by formula I-a to the compound represented by formula I-b is preferably 1:1 to 1:3 (preferably 1:2).

In the process 1, the temperature of the reductive amination reaction is preferably 0° C. to 120° C., more preferably 0° C. to 50° C., more preferably room temperature (10° C. to 30° C.).

In the process 1, the progress of the reductive amination reaction can be monitored by TLC or HPLC, generally disappearance of the compound represented by formula I-a is seen as completion of the reaction.

In the process 1, after completion of the reductive amination reaction, the product can be further purified by a post-treatment. The post-treatment preferably comprises the methods selected from the group consisting of recrystallization, purification by preparative silica gel thin-layer chromatography (e.g., dichloromethane:methanol is 15:1), purification by silica gel column chromatography and purification by preparative high performance liquid chromatography (the mobile phase is water (10 mM ammonium bicarbonate) and acetonitrile; gradient is 25% to 55%).

In the process 2, the methods and conditions for the substitution reaction may be conventional methods and conditions for such reactions in the art.

In the process 2, the base is preferably an organic base, e.g., diisopropylethylamine. The molar ratio of the base to the compound I-a1 is preferably 1:1 to 1:50 (e.g., 1:5 to 1:15).

In the process 2, the solvent is preferably an organic solvent. The organic solvent may be an organic solvent commonly used in such reactions in the art, preferably a nitriles solvent. The nitriles solvent is preferably acetonitrile. The amount of the solvent is not particularly limited as long as it does not affect the progress of the reaction, the volume/mass ratio of the solvent to the compound represented by formula I-a is preferably 10 mL/g to 110 mL/g.

In the process 2, in the substitution reaction, the molar ratio of the compound represented by formula I-a1 to the compound represented by formula Ib is preferably 1:0.5 to 1:3 (preferably 1:1 to 1.2, more preferably 1:1.5 to 1:2).

In the process 2, the temperature of the substitution reaction is preferably 0° C. to 120° C., more preferably 0° C. to 100° C., more preferably 10° C. to 60° C.

In the process 2, the progress of the substitution reaction can be monitored by TLC or HPLC, generally disappearance of the compound represented by formula I-a1 is seen as completion of the reaction.

In the process 2, after completion of the substitution reaction, the product can be further purified by a post-treatment. The post-treatment preferably comprises the methods selected from the group consisting of recrystallization, purification by preparative silica gel thin layer chromatography, purification by silica gel column chromatography and purification by preparative high performance liquid chromatography.

In the reductive amination reaction, the compound represented by formula I-a can be prepared by the following processes:

process 1: when L is alkynyl in the compound represented by formula I-a, a process for preparing the compound represented by formula I-a preferably comprises conducting a coupling reaction of the compound represented by formula II-a' with the compound represented by formula II-b as shown below in the presence of a palladium catalyst in a solvent to give the compound represented by formula I-a';

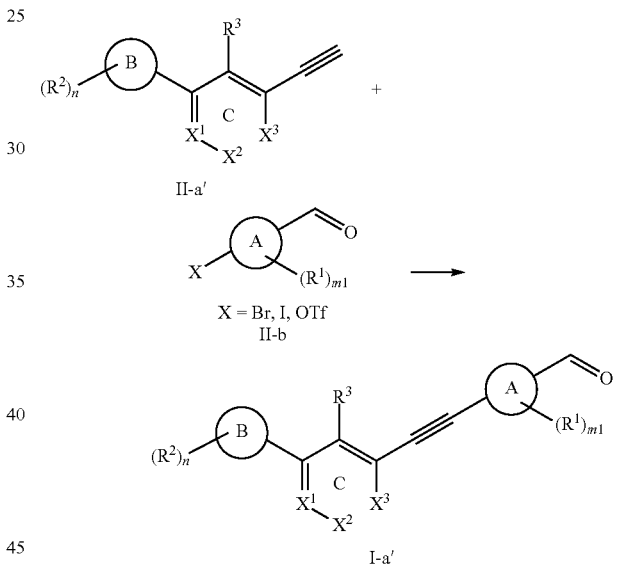

wherein, X is Br, I or OTf, in formula II-a', formula II-b and formula I-a', ring A, ring B, $R^1$, $R^2$, $R^3$, $X^1$, $X^2$, $X^3$, n and m1 are defined as above.

The methods and conditions for the coupling reaction may be conventional methods and conditions for such reactions in the art.

In the process for preparing the compound represented by formula I-a', preferably cuprous ion is present. The cuprous ion is preferably added to the reaction in the form of cuprous iodide. The molar ratio of the cuprous iodide to the compound II-b is preferably 0.01:1 to 2:1.

In the process for preparing the compound represented by formula I-a', a base can also be present. The base is preferably an organic base, more preferably triethylamine.

In the process for preparing the compound represented by formula I-a', the palladium catalyst can be a palladium catalyst commonly used in such reactions in the art, preferably selected from the group consisting of [1,1'-bis(diphenylphosphino)ferrocene]palladium dichloride, tris(dibenzylideneacetone)dipalladium, palladium acetate and tetrakis (triphenylphosphine)palladium. The molar ratio of the palladium catalyst to the compound represented by formula II-a' is preferably 0.005:1 to 0.5:1, more preferably 0.01:1 to 0.10:1.

In the process for preparing the compound represented by formula I-a', the molar ratio of the compound represented by formula II-a' to the compound represented by formula II-b is preferably 0.5:1 to 2:1, more preferably 0.9:1 to 1.5:1.

In the process for preparing the compound represented by formula I-a', the solvent is preferably an organic solvent and/or water. The organic solvent may be an organic solvent commonly used in such reactions in the art, preferably selected from the group consisting of an amides solvent, an ethers solvent and an aromatics solvent. The amides solvent is preferably N,N-dimethylformamide. The ethers solvent is preferably 1,4-dioxane and/or ethylene glycol dimethyl ether. The aromatics solvent is preferably toluene. The organic solvent is more preferably an amides solvent, e.g., N,N-dimethylformamide. The volume/mass ratio of the organic solvent to the compound represented by formula II-a' is preferably 5 mL/g to 100 mL/g.

In the process for preparing the compound represented by formula I-a', the temperature of the coupling reaction is preferably 50° C. to 150° C., e.g., 80° C.

In the process for preparing the compound represented by formula I-a', the progress of the coupling reaction can be monitored by TLC or HPLC, generally disappearance of the compound represented by formula I-b is seen as completion of the reaction.

In the process for preparing the compound represented by formula I-a', after completion of the coupling reaction, the product can be further purified by a post-treatment. The post-treatment preferably comprises the methods selected from the group consisting of recrystallization, purification by preparative silica gel thin layer chromatography (petroleum ether:ethyl acetate=3:1 (V/V)), purification by silica gel column chromatography and purification by preparative high performance liquid chromatography.

Process 2: when L is —C(R$^4$)=C(R$^5$)— in the compound represented by formula I-a, a process for preparing the compound represented by formula I-a preferably comprises conducting a hydrogenation addition reaction of the compound represented by formula I-a' as shown below in the presence of a palladium catalyst in a solvent to give the compound represented by formula I-a'';

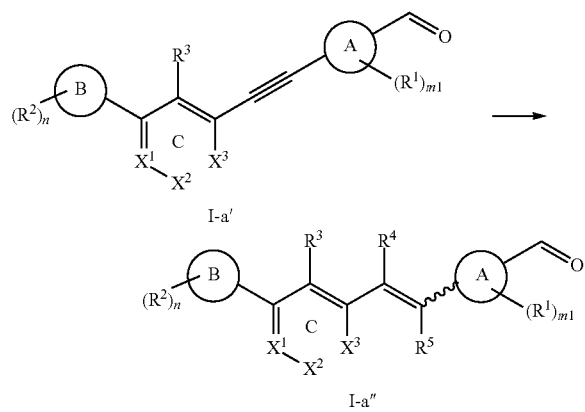

in formula I-a' and formula I-a'', wavy line, ring A, ring B, $R^1$, $R^2$, $R^3$, $X^1$, $X^2$, $X^3$, n and m1 are defined as above.

The methods and conditions for the hydrogenation addition reaction may be conventional methods and conditions for such reactions in the art.

In the process for preparing the compound represented by formula I-a'', the solvent is preferably an organic solvent and/or water. The organic solvent may be an organic solvent commonly used in such reactions in the art, preferably selected from the group consisting of an aromatics solvent, an ethers solvent and an amides solvent. The aromatics solvent is preferably toluene. The ethers solvent is preferably 1,4-dioxane and/or ethylene glycol dimethyl ether. The amides solvent is preferably N,N-dimethylformamide. The organic solvent is more preferably a mixed solvent of an organic solvent and water. In the mixed solvent, the volume ratio of the organic solvent to water is preferably 1:1 to 100:1 (e.g., 10:1). The volume/mass ratio of the solvent to the compound represented by formula I-a' is preferably 5 mL/g to 100 mL/g.

In the process for preparing the compound represented by formula I-a'', preferably copper ion is present. The copper ion is preferably added to the reaction system in the form of copper sulfate. The molar ratio of the copper sulfate to compound I-a' is preferably 0.01:1 to 2:1.

In the process for preparing the compound represented by formula I-a'', silane can be present. The silane is preferably trialkylsilane, more preferably triethylsilane.

In the process for preparing the compound represented by formula I-a'', an organophosphorus ligand can also be present. The organophosphorus ligand is preferably 1,1'-bis(diphenylphosphino)ferrocene, tetrakis(triphenylphosphine) and 4,5-bisdiphenylphosphino-9,9-dimethylxanthene, more preferably 1,1'-bis(diphenylphosphino)ferrocene.

In the process for preparing the compound represented by formula I-a'', the palladium catalyst can be a palladium catalyst commonly used in such reactions in the art, preferably selected from the group consisting of [1,1'-bis(diphenylphosphino)ferrocene]palladium dichloride, tris(dibenzylideneacetone)dipalladium, palladium acetate and tetrakis(triphenylphosphine)palladium. The molar ratio of the palladium catalyst to the compound represented by formula I-a' is preferably 0.005:1 to 0.5:1, more preferably 0.01:1 to 0.10:1.

In the process for preparing the compound represented by formula I-a'', the temperature of the coupling reaction is preferably 50° C. to 150° C., e.g., 100° C.

In the process for preparing the compound represented by formula I-a'', the progress of the coupling reaction can be monitored by TLC or HPLC, generally disappearance of the compound represented by formula I-a' is seen as completion of the reaction.

In the process for preparing the compound represented by formula I-a'', after completion of the coupling reaction, the product can be further purified by a post-treatment. The post-treatment preferably comprises the methods selected from the group consisting of recrystallization, purification by preparative silica gel thin layer chromatography (petroleum ether:ethyl acetate=3:1 (V/V)), purification by silica gel column chromatography and purification by preparative high performance liquid chromatography.

Process 3: when L is —C(R$^4$)=C(R$^5$)— in the compound represented by formula I-a, a process for preparing the compound represented by formula I-a preferably comprises conducting a coupling reaction of the compound represented by formula II-a'' with the compound represented by formula II-b as shown below in the presence of a palladium catalyst in a solvent to give the compound represented by formula I-a'';

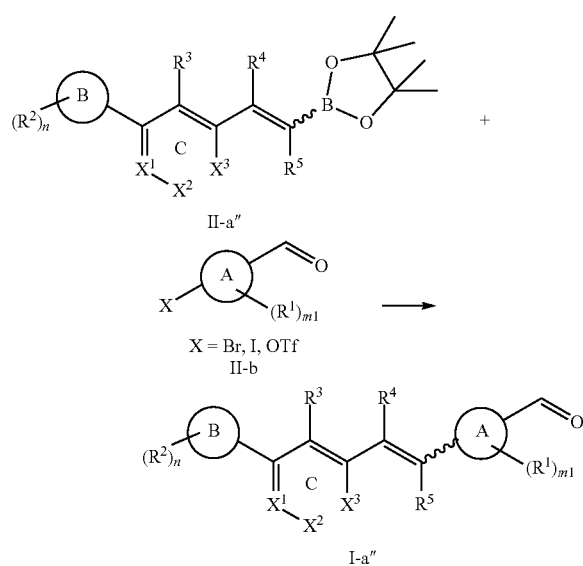

in formula II-a'', formula II-b and formula I-a'', wavy line, ring A, ring B, $R^1$, $R^2$, $R^3$, $R^4$, $R^5$, X, $X^1$, $X^2$, $X^3$, n and m1 are defined as above.

The methods and conditions for the coupling reaction may be conventional methods and conditions for such reactions in the art.

In the process for preparing the compound represented by formula I-a'', a base can also be present in the coupling reaction. The base is preferably an alkali metal carbonate, more preferably sodium carbonate, potassium carbonate or cesium carbonate. The molar ratio of the base to the compound II-a'' is preferably 1:1 to 5:1.

In the process for preparing the compound represented by formula I-a'', the solvent is preferably an organic solvent and/or water. The organic solvent may be an organic solvent commonly used in such reactions in the art, preferably selected from the group consisting of an ethers solvent, an aromatics solvent and an amides solvent. The ethers solvent is preferably 1,4-dioxane and/or ethylene glycol dimethyl ether. The aromatics solvent is preferably toluene. The amides solvent is preferably N,N-dimethylformamide. The organic solvent is more preferably a mixed solvent of an organic solvent and water. In the mixed solvent, the volume ratio of the organic solvent to water is preferably 100:1 to 1:1 (e.g., 20:1). The volume/mass ratio of the solvent to the compound represented by formula I-a is preferably 10 mL/g to 110 mL/g.

In the process for preparing the compound represented by formula I-a'', the palladium catalyst can be a palladium catalyst commonly used in such reactions in the art, preferably selected from the group consisting of [1,1'-bis(diphenylphosphino)ferrocene]palladium dichloride, tris(dibenzylideneacetone)dipalladium, palladium acetate and tetrakis(triphenylphosphine)palladium. The molar ratio of the palladium catalyst to the compound represented by formula II-a'' is preferably 0.005:1 to 0.5:1, more preferably 0.01:1 to 0.10:1.

In the process for preparing the compound represented by formula I-a'', the temperature of the coupling reaction is preferably 50° C. to 150° C., e.g., 80° C.

In the process for preparing the compound represented by formula I-a'', the progress of the coupling reaction can be monitored by TLC or HPLC, generally disappearance of the compound represented by formula II-b is seen as completion of the reaction.

In the process for preparing the compound represented by formula I-a'', after completion of the coupling reaction, the product can be further purified by a post-treatment. The post-treatment preferably comprises the methods selected from the group consisting of recrystallization, purification by preparative silica gel thin layer chromatography, purification by silica gel column chromatography and purification by preparative high performance liquid chromatography.

It will be understood by those skilled in the art that after the structure of the compound of the present invention is known, the compound of the present invention can be obtained by a variety of methods well known in the art and known raw materials, e.g., chemical synthesis or extraction from plants. These methods are all comprised in the present invention. The raw materials used to prepare the compound of the present invention or an intermediate thereof are known in the art or commercially available unless otherwise specified or a process is provided.

In the present invention, each of the preferred conditions in the process can be arbitrarily combined, then the preferred embodiments of the present invention are obtained.

The present invention also provides a compound represented by formula I-a or formula I-a1:

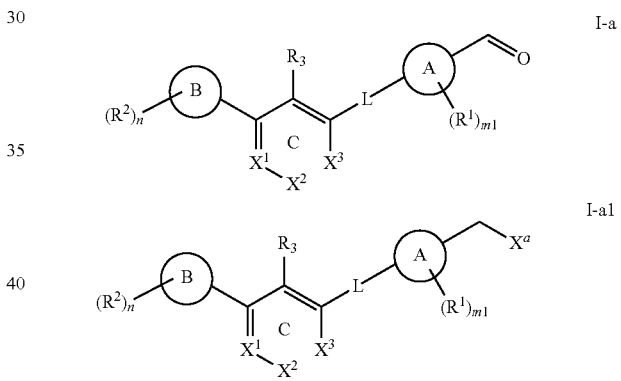

in the formula I-a, ring A, ring B, $R^1$, $R^2$, $R^3$, $X^1$, $X^2$, $X^3$, $X^a$, n and m1 are defined as above.

In a preferred embodiment of the present invention, formula I-a is preferably represented by formula I-a' or I-a'':

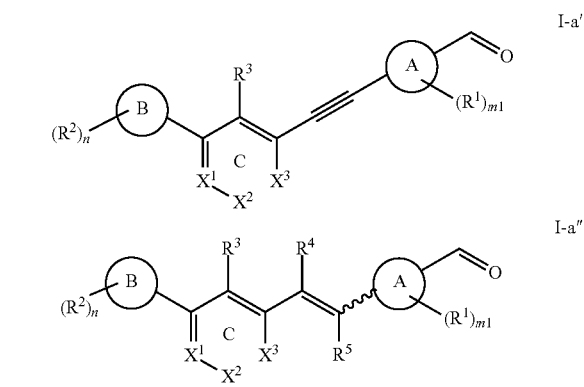

in formula I-a' and formula I-a", wavy line, ring A, ring B, $R^1$, $R^2$, $R^3$, $R^4$, $R^5$, $X^1$, $X^2$, $X^3$, n and m1 are defined as above.

In a preferred embodiment of the present invention, formula I-a1 is preferably represented by formula I-a1' or I-a1":

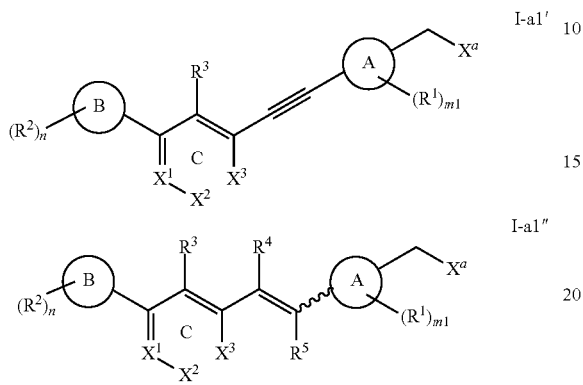

in formula I-a1' and formula I-a1", wavy line, ring A, ring B, $R^1$, $R^2$, $R^3$, $R^4$, $R^5$, $X^1$, $X^2$, $X^3$, n and m1 are defined as above.

The compound represented by formula I-a or formula I-a1 is preferably selected from

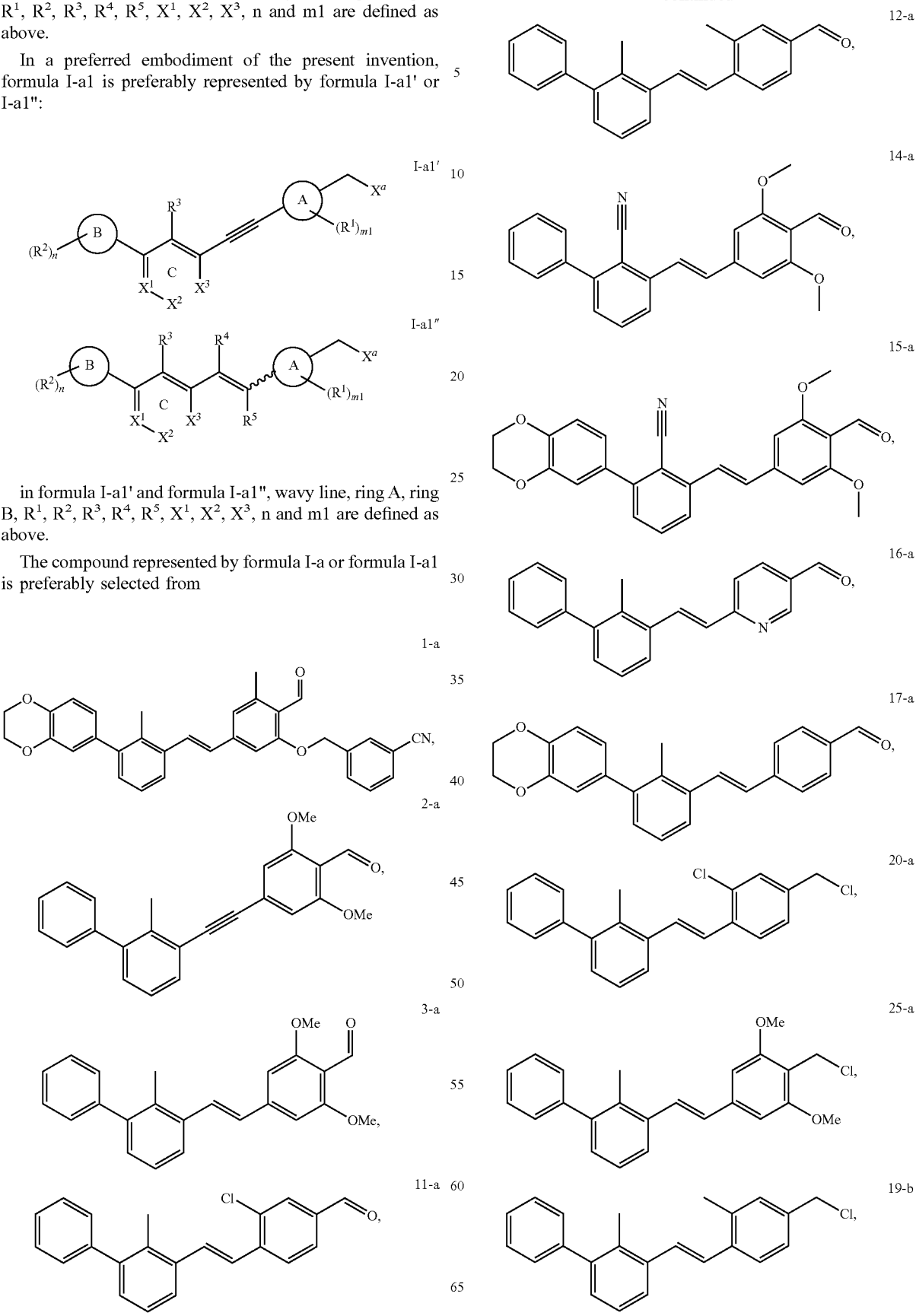

28-b
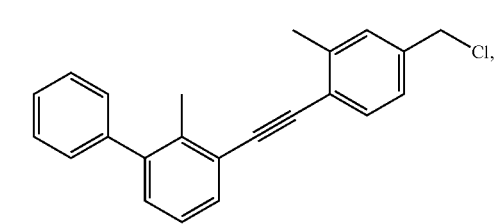
29-b
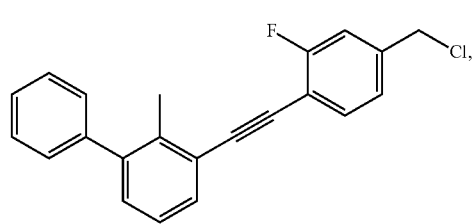
35-a
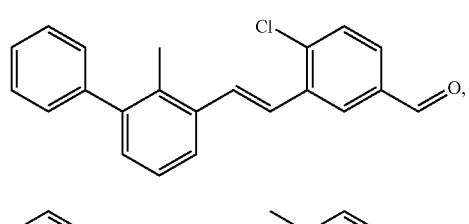
36-a
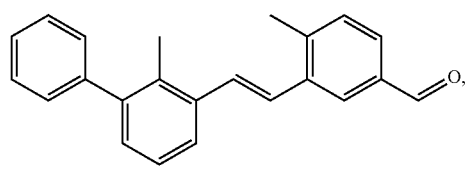
39-a
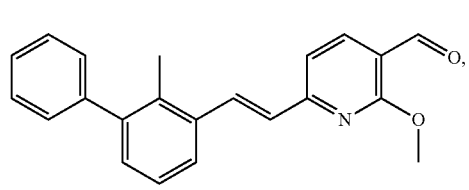
42-a
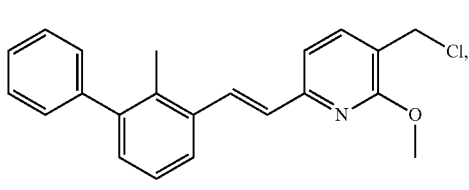
48-a
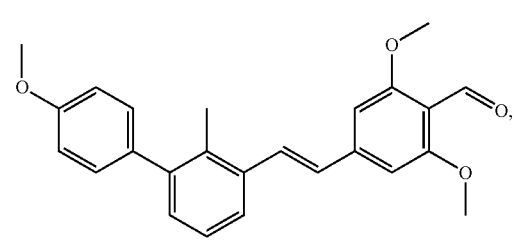
49-a
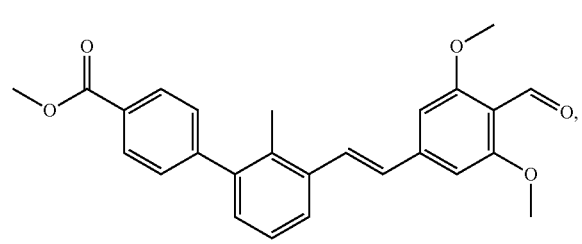
51-a
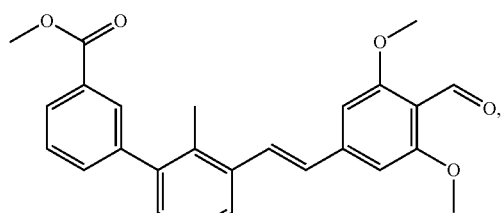
52-a
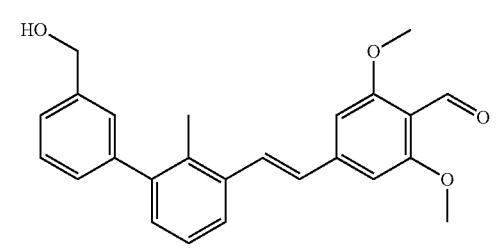
55-a
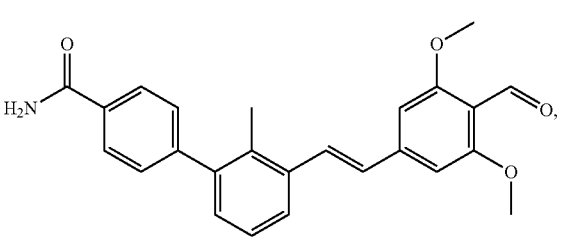
60-a
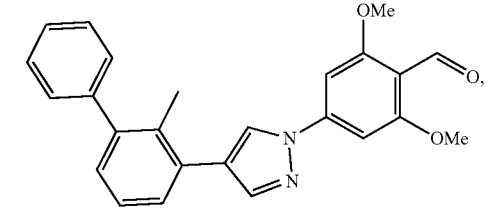
61-a
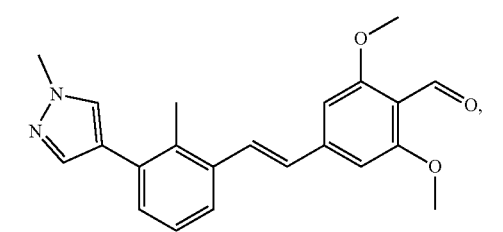
62-a
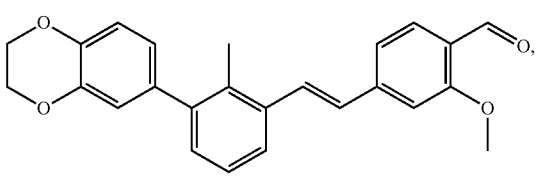
63-a
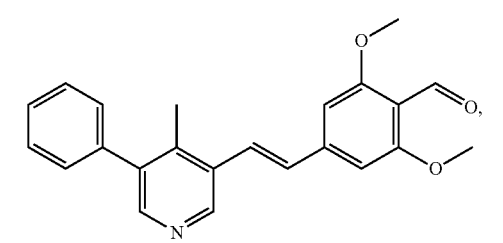

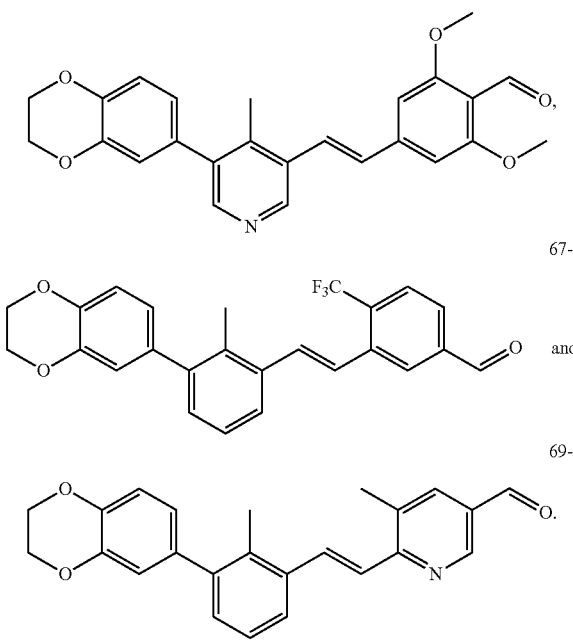

The present invention also provides a use of the aromatic acetylene or aromatic ethylene compound represented by formula I, the pharmaceutically acceptable salt, the tautomer, the mesomer, the racemate, the stereoisomer, the metabolite, the metabolic precursor or the prodrug thereof in manufacturing a PD-1 inhibitor and/or a PD-L1 inhibitor.

The present invention also provides a use of the compound selected from the group consisting of the aromatic acetylene or aromatic ethylene compound represented by formula I, the pharmaceutically acceptable salt, the tautomer, the mesomer, the racemate, the stereoisomer, the metabolite, the metabolic precursor and the prodrug thereof in manufacturing a medicament for preventing, alleviating or treating a cancer, an infection, an autoimmune disease or related diseases.

The cancer is preferably selected from the group consisting of lung cancer, esophageal cancer, gastric cancer, colon cancer, liver cancer, nasopharyngeal cancer, brain tumor, breast cancer, cervical cancer, blood cancer and bone cancer.

The present invention also provides a pharmaceutical composition comprising a therapeutically and/or prophylactically effective amount of the aromatic acetylene or aromatic ethylene compound represented by formula I, the pharmaceutically acceptable salt, the tautomer, the mesomer, the racemate, the stereoisomer, the metabolite, the metabolic precursor or the prodrug thereof, and a pharmaceutically acceptable carrier and/or diluent.

In the present invention, according to therapeutic purposes, the pharmaceutical composition can be formulated into various unit dosage forms such as tablets, pills, powders, liquids, suspensions, emulsion, granules, capsules, suppositories and injections (solutions and suspensions) and the like, preferably liquids, suspensions, emulsion, suppositories and injections (solutions and suspensions) and the like.

In order to form a pharmaceutical composition in the form of a tablet, any known and widely used excipients in the art can be used, e.g., carriers, such as lactose, white sugar, sodium chloride, glucose, urea, starch, calcium carbonate, kaolin, crystalline cellulose and silicic acid and the like; adhesives, such as water, ethanol, propanol, ordinary syrup, glucose solution, starch solution, gelatin solution, carboxymethyl cellulose, shellac, methylcellulose and potassium phosphate, polyvinylpyrrolidone and the like; disintegrants, such as dry starch, sodium alginate, agar powder and kelp powder, sodium bicarbonate, calcium carbonate, fatty acid ester of polythene dehydrated sorbitol, sodium lauryl sulfate, stearic acid monoglyceride, starch and lactose and the like; disintegration inhibitors, such as white sugar, glyceryl tristearate, coconut oil and hydrogenated oil; adsorption accelerators, such as quaternary ammonium bases and sodium lauryl sulfate and the like; wetting agents, such as glycerin, starch and the like; adsorbents, such as starch, lactose, kaolin, bentonite and colloidal silicic acid and the like; and lubricants, such as pure talc, stearates, boric acid powder and polyethylene glycol, and the like It can also be made into sugar-coated tablets, gelatin membrane-coated tablets, enteric-coated tablets, film-coated tablets, bilayer tablets and multilayered tablets by use of conventional coated materials when necessary.

In order to form the pharmaceutical composition in the form of a pill, any known and widely used excipients in the art can be used, e.g, carriers, such as lactose, starch, coconut oil, hardened vegetable oil, kaolin and talc and the like; adhesives, such as gum arabic powder, tragacanth powder, gelatin and ethanol and the like; disintegrants, such as agar and kelp powder and the like.

In order to form the pharmaceutical composition in the form of a suppository, any known and widely used excipients in the art can be used, e.g., polyethylene glycol, coconut oil, higher alcohols, higher alcohol esters, gelatin and semi-synthetic glycerides and the like.

In order to prepare a pharmaceutical composition in the form of an injection, the solution or suspension may be sterilized (preferably by adding an appropriate amount of sodium chloride, glucose or glycerol, etc.) to form a blood-isotonic injection with the isotonic pressure of the blood. Any suitable carriers in the art may also be used in the preparation of the injection. For example, water, ethanol, propanediol, ethoxylated isostearyl alcohol, polyoxylated isostearyl alcohol and polyethylene sorbitan fatty acid ester. In addition, conventional solubilizers, buffers and analgesics and the like may be added.

In the pharmaceutical composition, the diluent may be a conventional diluent in the art.

The pharmaceutical composition of the present invention may be in a form suitable for oral use or in the form of a sterile injectable aqueous solution. Oral or injectable compositions may be prepared according to any method known in the art for preparing pharmaceutical compositions.

Unless otherwise specified, the following terms when used in the description and the claims of the present invention have the following meanings:

"Alkyl" used herein (including used alone and contained in other groups) refers to a saturated linear and branched aliphatic hydrocarbyl having 1 to 20 carbon atoms, preferably having 1 to 10 carbon atoms, more preferably having 1 to 8 carbon atoms, e.g., methyl, ethyl, n-propyl, iso-propyl, n-butyl, tert-butyl, iso-butyl, pentyl, hexyl, heptyl, octyl, nonyl, decyl, 4,4-dimethylpentyl, 2,2,4-trimethylpentyl, undecyl, dodecyl, and isomers thereof.

The term "carbocycle" or "cycloalkyl" (including used alone and contained in other groups) refers to a saturated or partially unsaturated (having 1 or 2 double bonds) cyclic hydrocarbon group having 1 to 3 rings, including monocycloalkyl, bicycloalkyl and tricycloalkyl, having 3 to 20 carbons enabling to form a ring, preferably 3 to 10 carbons, e.g., cyclopropyl, cyclobutyl, cyclopentyl, cyclohexyl, cycloheptyl, cyclooctyl, cyclodecyl and cyclododecyl, cyclohexenyl.

The term "alkoxy" refers to a cyclic or non-cyclic alkyl having the indicated number of carbon atoms linked by an oxygen bridge. Therefore, "alkoxy" includes the definitions of the alkyl and the cycloalkyl.

The term "carbon heterocycle", "heterocycle" or "heterocyclyl" used herein refers to a 5-10 membered aromatic or non-aromatic heterocyclic ring having 1-4 heteroatoms selected from the group consisting of O, N and S, and a bicyclic group is included therein. Therefore, "heterocyclyl" includes the heteroaryl and the dihydro- or tetrahydro-analogues thereof. The examples of the "heterocycle" include but not limited to benzimidazolyl, benzofuranyl, benzofurazinyl, benzopyrazolyl, benzotriazolyl, benzothienyl, benzoxazolyl, carbazyl, carbazolyl, cinnolinyl, furanyl, imidazolyl, indolinyl, indolyl, indazolyl, isobenzofuranyl, pseudoindolyl, isoquinolyl, isothiazolyl, isoxazolyl, naphthalene pyrimidinyl, oxadiazolyl, oxazolyl, oxazoline, isoxazoline, oxycyclobutyl, pyranyl, pyrazinyl, pyrazolyl, pyridazinyl, pyridopyridyl, pyridazinyl, pyridyl, pyrimidyl, pyrryl, quinazolyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydropyridyl, dihydropyrimidinyl, dihydropyrryl, dihydroquinolyl, dihydrotetrazolyl, dihydrothiadiazolyl, dihydrothiazolyl, dihydrothienyl, dihydrotriazolyl, dihydro-azetidinyl, methylenedioxybenzoyl, tetrahydrofuranyl, tetrahydrothienyl and N-oxides thereof.

The term "alkenyl" refers to a straight, branched, or cyclic non-aromatic hydrocarbyl having the indicated number of carbon atoms and at least one carbon-carbon double bond. Alkenyl is preferably having one carbon-carbon double bond, and up to four non-aromatic carbon-carbon double bonds can be present. Therefore, "$C_{2-12}$ alkenyl" refers to an alkenyl having 2 to 12 carbon atoms. "$C_{2-6}$ alkenyl" refers to an alkenyl having 2 to 6 carbon atoms, including vinyl, propenyl, butenyl, 2-methylbutenyl and cyclohexenyl. The straight chain, branched chain or cyclic portion of alkenyl can contain double bond, and if it is indicated as substituted alkenyl, the alkenyl can be substituted.

The term "alkynyl" refers to a straight, branched, or cyclic hydrocarbyl having the indicated number of carbon atoms and at least one carbon-carbon triple bond. Up to three carbon-carbon triple bonds can be present. Therefore, "$C_{2-12}$ alkynyl" refers to an alkynyl having 2 to 12 carbon atoms. "$C_{2-6}$ alkynyl" refers to an alkynyl having 2 to 6 carbon atoms, including but not limited to ethynyl, propynyl, butynyl, and 3-methylbutynyl.

The term "halogen" used herein refers to fluorine, chlorine, bromine, iodine or astatine.

The term "hydroxy" used herein refers to

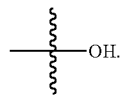

The term "amino" used herein refers to

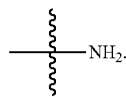

The term "cyano" used herein refers to —CN.
The term "carboxyl" used herein refers to —COOH.
The term "ester group" used herein refers to —COO—.

The term "aromatic ring" used herein refers to any stable monocyclic or bicyclic carbocycle with up to 7 atoms in each ring and at least one of the rings is an aromatic ring. The examples of the aromatic ring unit include phenyl, naphthyl, tetrahydronaphthyl, 2,3-dihydroindenyl, biphenyl, phenanthryl, anthryl or acenaphthyl. It can be understood that when the aryl substituent is a bicyclic substituent and one of the ring is a non-aromatic ring, the linkage is made through the aromatic ring.

The term "heteroaromatic ring" used herein refers to a stable monocyclic or bicyclic ring with up to 7 atoms in each ring and at least one of the ring is an aromatic ring having 1-4 heteroatoms selected from the group consisting of O, N and S. In this definition, the heteroaromatic ring includes but not limited to acridine, carbazole, cinnoline, carboline, quinoxaline, imidazole, pyrazole, pyrrole, indole, indoline, benzotriazole, benzimidazole, furan, thiophen, isothiazole, benzothiophene, dihydrobenzothiophene, benzofuran, isobenzofuran, benzoxazole, benzofuraxan, benzopyrazole, quinoline, isoindoline, isoquinoline, oxazole, oxadiazole, isoxazole, indole, pyrazine, pyridopyridine, tetrazolopyridine, pyridazine, pyridine, naphthalene pyrimidine, pyrimidine, pyrrole, tetrazole, thiadiazole, thiazole, thiophene, triazole, quinazoline, tetrahydroquinoline, dihydrobenzimidazole, dihydrobenzofuran, dihydrobenzoxazole, dihydroquinoline. As defined for the following heterocycle, "heteroaromatic ring" is also understood to include N-oxide derivatives of any nitrogenous heteroaromatic ring. Where the heteroaryl substituent is a bicyclic substituent and one of the rings is a non-aromatic ring or contains no heteroatom, it can be understood that the linkage is made through the aromatic ring or the heteroatom on the ring.

The term "therapeutically effective amount" refers to an amount of the compound administered to a subject sufficient to treat the diseases involved in the present invention. Though a therapeutically effective amount of a compound will vary depending on the compound, the condition and its severity, and the age of the subject to be treated, it can be determined by a person skilled in the art according to the conventional method.

As used in the present invention, when the specific salt, pharmaceutical composition, composition, excipient are mentioned to be "pharmaceutically acceptable", it means that the salt, pharmaceutical composition, composition, excipient are generally non-toxic, safe and suitable to be administered to the subject; the subject is preferably a mammal, more preferably human.

The term "pharmaceutically acceptable salt" used herein refers to a pharmaceutically acceptable organic or inorganic salt of the compound of the present invention. Typical examples include but not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisate, fumarate, gluconate, glucuronate, saccharate, formate, benzoate, glutamate, methylsulfonate, ethylsulfonate, benzene sulfonate, tosilate, embonate (i.e. 1-1-methylene-bis(2-hydroxyl-3-naphthoate)).

The term "prodrug" used herein refers to a derivative of a compound containing biological reactive functional groups, which can be cleaved from the compound or react in other ways to provide the compound under biological condition (in vivo or in vitro). Generally, the prodrug does not have activity, or have less activity than the compound itself, this makes the compound exhibit effects until the biological reactive functional group cleaved from the compound. The biological reactive functional group can hydrolyze or oxidize under biological condition to provide the compound. For example, the prodrug can include biologically hydrolysable groups. The biologically hydrolysable groups include but not limited to a biologically hydrolysable phosphate, a biologically hydrolysable ester, a biologically hydrolysable amide, a biologically hydrolysable carbonate, a biologically hydrolysable carbamate and a biologically hydrolysable ureide.

The compound of the present invention can contain one or more asymmetric centers ("stereoisomers"). As used herein, the term "stereoisomer" refers to cis- and trans-isomer, R- and S-enantiomer and diastereomer. These stereoisomers can be prepared by methods of asymmetric synthesis or chiral separation (e.g. separation, crystallization, thin layer chromatography, column chromatography, gas chromatography, high performance liquid chromatography). These stereoisomers may also be derived from a diastereomer obtained by reacting a mixture of the enantiomers or racemates with a proper chiral compound, followed by crystallizing or any other proper common method.

As used herein, the term "subject" refers to any animal to be administered or has been administered with the compound or the pharmaceutical composition according to the example of the present invention, preferably a mammal, most preferably human. As used herein, the term "mammal" includes any mammal. Typical mammal includes but not limited to cattle, horse, sheep, pig, cat, dog, mouse, rat, rabbit, Guinea pig, monkey, human and so on, the most preferable human.

In one embodiment, "treat" or "treating" refers to an improvement, prevention or reversion of a disease or a condition or at least one distinguished symptom thereof. In another embodiment, "treat" or "treating" refers to an improvement, prevention or reversion of at least one of measurable body parameters of a disease or a condition which is being treated, which may not been distinguished in a mammal. However, in another embodiment, "treat" or "treating" refers to slowing the development of a disease or a condition, or refers to stabilizing in body, such as a recognizable symptom, or refers to stabilizing in physiology, such as body parameters, or refers to both. In another embodiment, "treat" or "treating" refers to slowing the initiation of a disease or a condition.

In certain embodiments, the compound of the present invention is administered for prevention. As used herein, "prevent" or "preventing" refers to lowering a risk of having a disease or a condition. In a preferred example, administering an indicated compound to a subject for a preventive purpose, such as the subject having a tendency to catch or having a family history of cancer or autoimmune diseases.

Without violating the common sense in the art, the above preferred conditions can be arbitrarily combined, then preferred embodiments of the present invention are obtained.

The reagents and raw materials used in the present invention are commercially available.

The positive effect achieved by the present invention is that the aromatic acetylene or aromatic ethylene compound of the present invention has a significant inhibitory effect on PD-1 and/or PD-L1, and can effectively alleviate or treat cancer and other related diseases.

DETAILED DESCRIPTION OF THE PREFERRED EMBODIMENT

In the following embodiments, room temperature refers to 10° C. to 30° C.; reflux refers to the reflux temperature of a solvent; overnight refers to 8 to 24 hours, preferably 12 to 18 hours.

The structure of the compound was confirmed by nuclear magnetic resonance (NMR) or mass spectrometry (MS). The nuclear magnetic resonance spectrum was determined by a Bruker Avance-500 instrument using deuterated dimethyl sulfoxide, deuterated chloroform, deuterated methanol and the like as a solvent, and tetramethylsilane (TMS) as an internal standard. Mass spectrum was determined by liquid chromatography-mass spectrometry (LC-MS) Agilent Technologies 6110 using an ESI ion source.

The microwave reaction was carried out in an Explorer automatic microwave synthesizer manufactured by CEM Corporation of the United States. The frequency of magnetron was 2450 MHz and the continuous microwave output power was 300 W.

The instrument used for preparative high performance liquid chromatography was Gilson 281, and the preparation column used was Shimadazu Shim-Pack, PRC-ODS, 20×250 mm, 15 m.

Embodiment 1

(S,E)-3-((5-(3-(2,3-Dihydrobenzo[b][1,4]dioxin-6-yl)-2-methylstyryl)-2-((2-(hydroxymethyl)pyrrolidin-1-yl)methyl)-3-methylphenoxy)methyl)benzonitrile 1

Synthetic Route

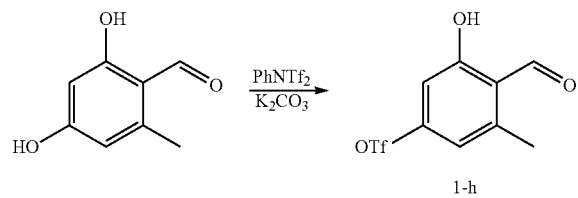

1-h

-continued
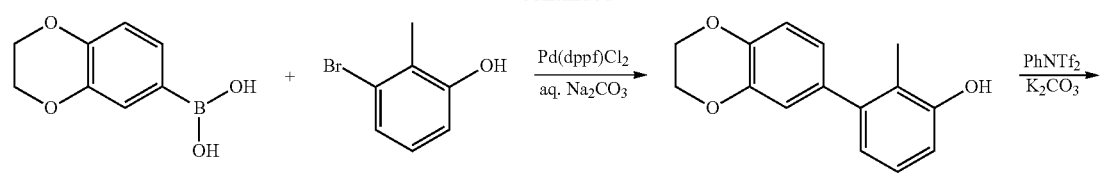
1-g
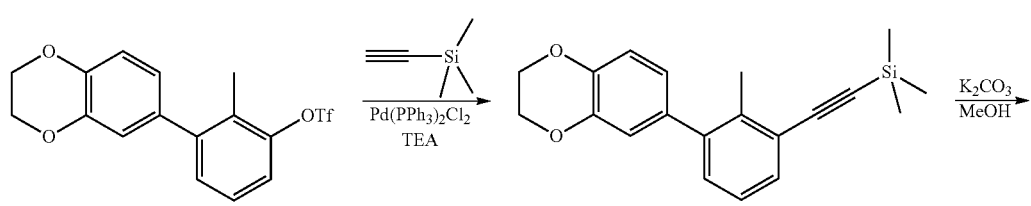
1-f → 1-e
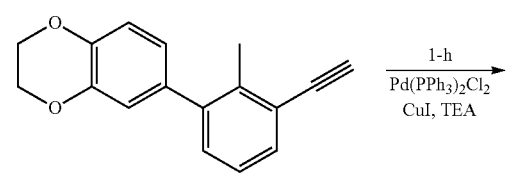
1-d
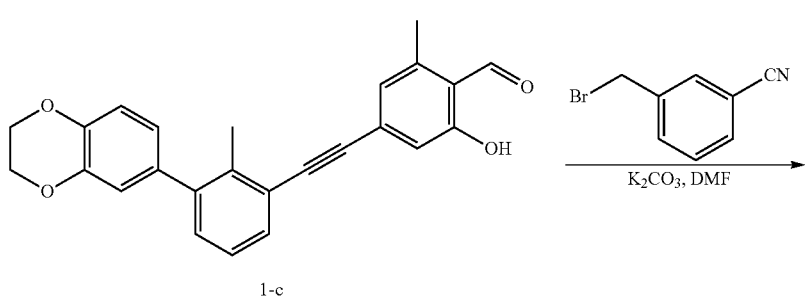
1-c
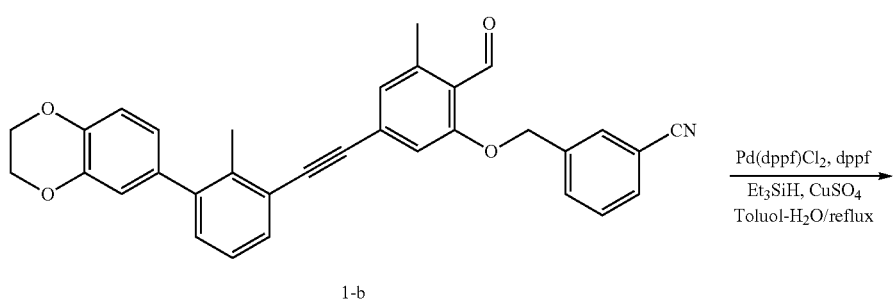
1-b
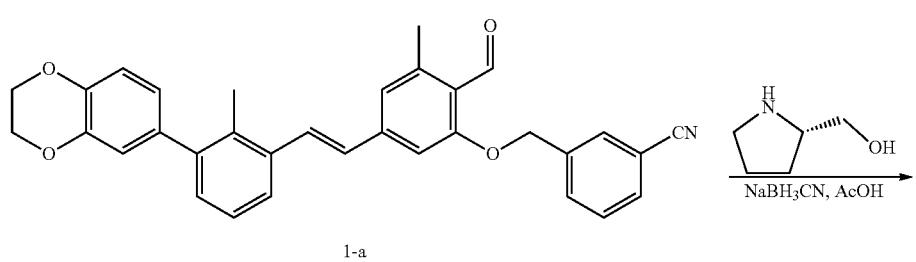
1-a -continued

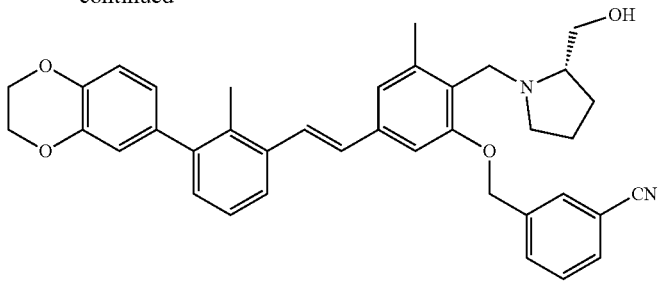

1

Synthesis of Compound 1-h

A solution of 2,4-dihydroxy-6-methylbenzaldehyde (500 mg, 3.29 mmol) in acetone (20 mL) was cooled to 0° C. under nitrogen atmosphere, followed by addition of N-phenylbis(trifluoromethanesulfonimide) (1.42 g, 3.95 mmol) and potassium carbonate (910 mg, 6.58 mmol). The mixture was stirred at room temperature for 24 hours, then evaporated under reduced pressure, followed by addition of water (50 mL) and the mixture was extracted with ethyl acetate (50 mL×3). The organic layers were combined, washed successively with water (50 mL×3) and saturated brine (50 mL), dried over anhydrous sodium sulfate, filtered and evaporated under reduced pressure. The residue was purified by silica gel preparative thin layer chromatography (petroleum ether:ethyl acetate=5:1) to give 1-h as a white solid (488 mg, yield 43.6%). LC-MS (ESI): m/z=340 [M+H]$^+$.

$^1$H NMR (400 MHz, CDCl$_3$) δ (ppm): 12.15 (s, 1H), 10.31 (s, 1H), 6.76 (s, 1H), 6.67 (s, 1H), 2.67 (s, 3H).

Synthesis of Compound 1-g

[1,1'-Bis(diphenylphosphino)ferrocene]palladium dichloride (44.2 mg, 0.051 mmol) and sodium carbonate (139 mg, 1.263 mmol) were added to a mixed solution of benzo 1,4-dioxane-6-boronic acid (100 g, 0.56 mmol) and 3-bromo-2-methylphenol (94.5 mg, 0.505 mmol) in 1,4-dioxane (10 mL) and water (0.5 mL). After the reaction system was purged three times with nitrogen, the reaction solution was heated to 80° C. and stirred overnight. Then the reaction solution was cooled to room temperature and filtered through celite. The filter cake was washed three times with ethyl acetate (30 mL). The organic layers were combined, washed three times with water (30 mL) and once with saturated brine (30 mL), dried over anhydrous sodium sulfate and evaporated under reduced pressure. The residue was purified by silica gel column chromatography (petroleum ether:ethyl acetate=10:1 to 5:1) to give compound 1-g (111 mg, yield 82.2%). LC-MS (ESI): m/z=242 [M+H]$^+$.

$^1$H NMR (400 MHz, CDCl$_3$) δ (ppm): 7.07-7.05 (m, 1H), 6.91-6.89 (m, 1H), 6.83-6.75 (m, 4H), 5.43 (s, 1H), 4.29 (s, 4H), 2.17 (s, 3H).

Synthesis of Compound 1-f

A solution of compound 1-g (110 mg, 0.454 mmol) in acetone (10 mL) was cooled to 0° C., followed by addition of N-phenylbis(trifluoromethanesulfonimide) (162.2 mg, 0.454 mmol) and potassium carbonate (94.2 mg, 0.681 mmol). The reaction solution was stirred at room temperature for 24 hours. After completion of the reaction, the reaction solution was evaporated under reduced pressure. The residue was partitioned with ethyl acetate (20 mL) and water (20 mL). The aqueous phase was extracted with ethyl acetate (30 mL×2). The obtained organic phase was washed once with saturated sodium chloride solution (30 mL), dried over anhydrous sodium sulfate and evaporated under reduced pressure. The residue was purified by silica gel preparative thin layer chromatography (petroleum ether: ethyl acetate=10:1) to give compound 1-f (115 mg, yield 67.6%).

$^1$H NMR (400 MHz, CDCl$_3$) δ: 7.27-7.81 (m, 3H), 6.93-6.91 (d, 1H), 6.81-6.80 (d, 1H), 6.77-6.75 (d, 1H), 4.31 (s, 4H), 2.27 (s, 3H) ppm.

Synthesis of Compound 1-e

[1,1'-Bis(diphenylphosphino)ferrocene]palladium dichloride (14 mg, 0.019 mmol) and triethylamine (313.3 mg, 3.096 mmol) were added to a solution of compound 1-f (145 mg, 0.387 mmol) and trimethylsilylacetylene (57 mg, 0.581 mmol) in N,N-dimethylformamide (10 mL). After the reaction system was purged three times with nitrogen, the reaction solution was heated to 70° C. under nitrogen atmosphere and stirred for 16 hours. Then the reaction solution was cooled to room temperature, diluted with ethyl acetate (20 mL), washed with water (20 mL×3) and saturated brine (20 mL). The obtained organic phase was dried over anhydrous sodium sulfate and evaporated under reduced pressure. The residue was purified by preparative silica gel thin layer chromatography (petroleum ether:ethyl acetate=100:1) to give compound 1-e (77 mg, yield 61.6%).

$^1$H NMR (400 MHz, CDCl$_3$) δ (ppm): 7.24-7.21 (m, 1H), 6.95-6.91 (m, 2H), 6.71-6.69 (d, J=8 Hz, 1H), 6.60-6.59 (m, 1H), 6.56-6.53 (m, 1H), 4.10 (s, 4H), 2.17 (s, 3H), 0.03 (s, 9H).

Synthesis of Compound 1-d

Potassium carbonate (99 mg, 0.716 mmol) was added to a solution of compound 1-e (77 mg, 0.239 mmol) in methanol (5 mL). The reaction solution was stirred at room temperature for 3 hours, then evaporated under reduced pressure. The obtained solid was diluted with ethyl acetate (20 mL), washed with water (20 mL) and saturated brine (20 mL). The obtained organic phase was dried over anhydrous sodium sulfate and evaporated under reduced pressure. The residue was purified by preparative silica gel thin layer chromatography (petroleum ether:ethyl acetate=100:1) to give compound 1-d (38 mg, yield 63.3%).

$^1$H NMR (400 MHz, CDCl$_3$) δ (ppm): 7.35-7.33 (m, 1H), 7.07-7.04 (m, 2H), 6.79-6.77 (d, J=8.4 Hz, 1H), 6.69-6.68 (m, 1H), 6.65-6.62 (m, 1H), 4.18 (s, 4H), 3.17 (s, 1H), 2.27 (s, 3H).

Synthesis of Compound 1-c

[1,1'-Bis(diphenylphosphino)ferrocene]palladium dichloride (6.0 mg, 0.0084 mmol) and cuprous iodide (3.2 mg, 0.0167 mmol) were added to a mixed solution of compound 1-d (50 mg, 0.2 mmol) and compound 1-h (47.4 mg, 0.1667 mmol) in N,N-dimethylformamide (4 mL) and triethylamine (1 mL). After the reaction system was purged three times with nitrogen, the reaction solution was heated to 80° C. under nitrogen atmosphere and stirred for 16 hours. After completion of the reaction, the reaction solution was cooled to room temperature, diluted with ethyl acetate (20 mL), washed with water (20 mL×3) and saturated brine (20 mL). The organic phase was dried over anhydrous sodium sulfate and evaporated under reduced pressure. The residue was purified by preparative silica gel thin layer chromatography (petroleum ether:ethyl acetate=3:1) to give compound 1-c (8 mg, yield 10.4%).

$^1$H NMR (400 MHz, CDCl$_3$) δ (ppm): 11.95 (s, 1H), 10.29 (s, 1H), 7.51-7.49 (m, 1H), 7.22-7.19 (m, 2H), 6.98 (s, 1H), 6.93-6.88 (m, 2H), 6.83-6.82 (m, 1H), 6.79-6.76 (m, 1H), 4.31 (s, 4H), 2.61 (s, 3H), 2.44 (s, 3H).

Synthesis of Compound 1-b

Potassium carbonate (36 mg, 0.26 mmol) was added to a solution of compound 1-c (40 mg, 0.104 mmol) and 3-(bromomethyl)benzonitrile (20.4 mg, 0.104 mmol) in N,N-dimethylformamide (2 mL). The reaction solution was stirred at room temperature for 16 hours, diluted with ethyl acetate (20 mL), washed with water (20 mL×3) and saturated brine (20 mL). The organic phase was dried over anhydrous sodium sulfate and evaporated under reduced pressure. The residue was purified by preparative silica gel thin layer chromatography (petroleum ether:ethyl acetate=3:1) to give compound 1-b (56 mg, yield 98%). LC-MS (ESI): m/z=500.0 [M+H]$^+$.

$^1$H NMR (400 MHz, CDCl$_3$) δ (ppm): 10.68 (s, 1H), 7.74-7.66 (m, 3H), 7.57-7.49 (m, 2H), 7.23-7.21 (m, 2H), 7.06 (s, 1H), 7.02 (s, 1H), 6.93-6.91 (d, J=8.4, 1H), 6.83-6.82 (m, 1H), 6.79-6.76 (m, 1H), 5.21 (s, 2H), 4.32 (s, 4H), 2.60 (s, 3H), 2.45 (s, 3H).

Synthesis of Compound 1-a

[1,1'-Bis(diphenylphosphino)ferrocene]palladium dichloride (1.46 mg, 0.0168 mmol), 1,1'-bis(diphenylphosphino)ferrocene (1.55 mg, 0.0028 mmol), triethylsilane (13 mg, 0.112 mmol) and copper sulfate (1.34 mg, 0.0084 mmol) were added to a mixed solution of compound 1-b (28 mg, 0.056 mmol) in toluene (3 mL) and water (0.3 mL). The reaction solution was stirred under reflux for 24 hours, then quenched with saturated brine (20 mL) and extracted with ethyl acetate (20 mL×2). The obtained organic layers were combined, dried over anhydrous sodium sulfate and evaporated under reduced pressure. The residue was purified by preparative silica gel thin layer chromatography (petroleum ether:ethyl acetate=3:1) to give compound 1-a (24 mg, yield 85.7%). LC-MS (ESI): m/z=502.0 [M+H]$^+$.

Synthesis of Compound 1

Glacial acetic acid (13.87 mg, 0.231 mmol) was added to a mixed solution of compound 1-a (58 mg, 0.116 mmol) and (S)-prolinol (23.4 mg, 0.231 mmol) in methanol (2 mL) and dichloromethane (2 mL). After the reaction solution was stirred at room temperature for 1 hour, sodium cyanoborohydride (36.5 mg, 0.58 mmol) was added and the resulting mixture was stirred for 16 hours. Then the mixture was diluted with ethyl acetate (20 mL), washed with water (20 mL×3) and saturated brine (20 mL). The organic phase was dried over anhydrous sodium sulfate and evaporated under reduced pressure. The residue was purified by high performance liquid chromatography (mobile phase: water (10 mM ammonium bicarbonate), acetonitrile; gradient: 25% to 55% (the initial mobile phase was 25% water and 75% acetonitrile, and the final mobile phase was 55% water and 45% acetonitrile, where % refers to percent of volume)) to give compound 1 (6 mg, yield 35.3%). LC-MS (ESI): m/z=587.0 [M+H]$^+$.

$^1$H NMR (400 MHz, CDCl$_3$) δ (ppm): 7.79 (s, 1H), 7.72-7.70 (m, 1H), 7.65-7.63 (m, 1H), 7.54-7.51 (m, 2H), 7.34-7.30 (m, 1H), 7.23-7.21 (m, 1H), 7.16-7.14 (m, 1H), 7.04 (s, 1H), 6.92-6.82 (m, 4H), 6.79-6.76 (m, 2H), 5.36-5.34 (m, 2H), 5.23 (s, 2H), 4.31 (s, 4H), 3.76-3.73 (m, 2H), 3.64-3.63 (br, 1H), 2.47 (s, 3H), 2.30 (s, 3H), 2.24-2.20 (m, 2H), 2.02-1.96 (m, 4H), 1.87-1.84 (m, 2H).

Embodiment 2

(S)-(1-(2,6-Dimethoxy-4-((2-methyl-biphenyl-3-yl) ethynyl)benzyl)pyrrolidin-2-yl)methanol 2

Synthetic Route

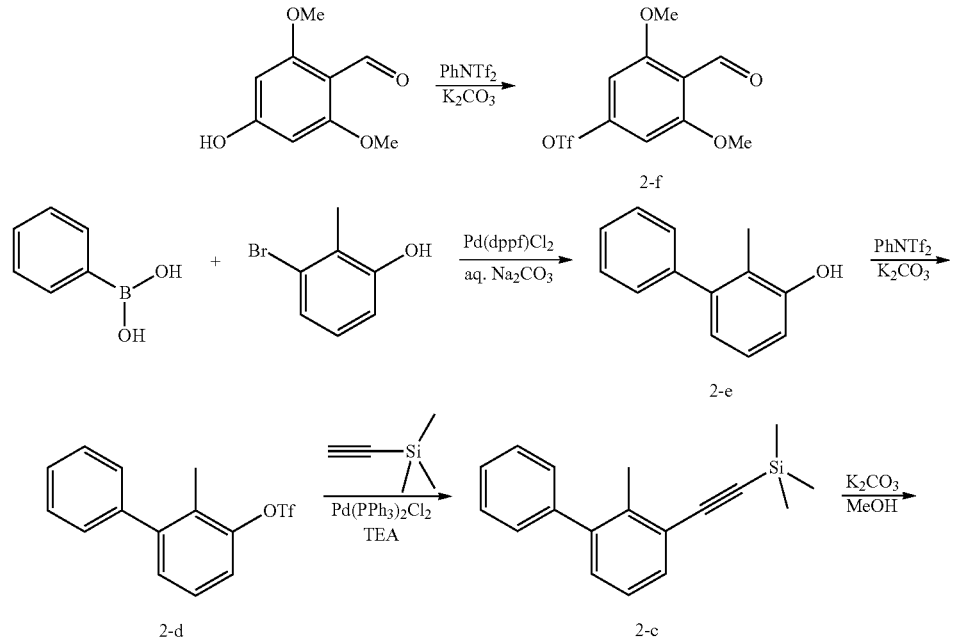

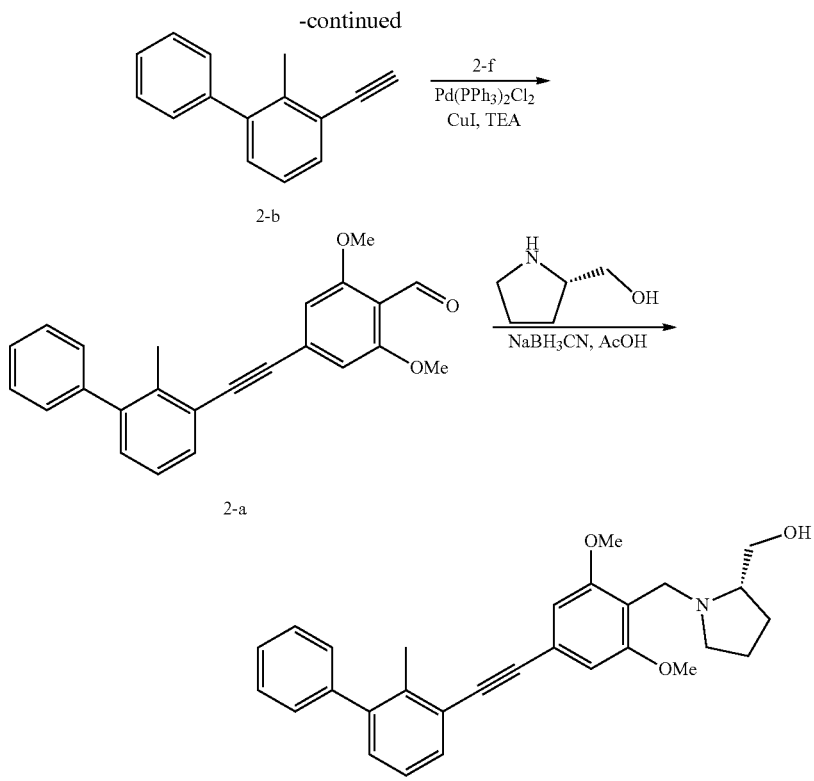

Synthesis of Compound 2-f

Potassium carbonate (304 mg, 2.20 mmol) was added to a solution of 2,6-dimethoxy-4-hydroxybenzaldehyde (200 mg, 1.10 mmol) and N-phenylbis(trifluoromethanesulfonimide) (393 mg, 1.10 mmol) in acetone (10 mL). The reaction solution was stirred at 35° C. for 48 hours, then evaporated under reduced pressure. The residue was diluted with ethyl acetate (20 mL), then washed successively with water (20 mL) and saturated brine (20 mL). The organic phase was dried over anhydrous sodium sulfate and evaporated under reduced pressure. The residue was purified by silica gel column chromatography (petroleum ether:ethyl acetate=10:1 to 3:1) to give compound 2-f (266 mg, yield 77.1%).

$^1$H NMR (400 MHz, CDCl$_3$) δ: 10.43 (s, 1H), 6.49 (s, 2H), 3.93 (s, 6H) ppm.

Synthesis of Compound 2-e

Phenylboronic acid (143.9 mg, 1.18 mmol) and 3-bromo-2-methylphenol (200 mg, 1.07 mmol) were dissolved in a mixed solvent of toluene (20 mL) and water (1 mL), followed by addition of [1,1'-bis(diphenylphosphino)ferrocene]palladium dichloride (92.6 mg, 0.107 mmol) and sodium carbonate (283.6 mg, 2.675 mmol). After the reaction system was purged three times with nitrogen, the reaction solution was heated to 80° C. and stirred overnight. Then the reaction solution was cooled to room temperature, diluted with ethyl acetate (20 mL), washed successively with water (20 mL×3) and saturated brine (20 mL). The obtained organic phase was dried over anhydrous sodium sulfate and evaporated under reduced pressure. The residue was purified by preparative silica gel thin layer chromatography (petroleum ether:ethyl acetate=3:1) to give compound 2-e (218 mg, yield 98%).

$^1$H NMR (400 MHz, CDCl$_3$) δ: 7.35-7.32 (m, 2H), 7.28-7.23 (m, 3H), 7.06-7.02 (m, 1H), 6.79-6.72 (m, 2H), 4.91 (br, 1H), 2.08 (s, 3H) ppm.

Synthesis of Compound 2-d

Compound 2-e (200 mg, 1.09 mmol) was dissolved in acetone (10 mL), followed by addition of N-phenylbis (trifluoromethanesulfonimide) (387.8 mg, 1.09 mmol) and potassium carbonate (301.3 mg, 2.18 mmol). The reaction solution was stirred at room temperature for 24 hours, then evaporated under reduced pressure. Ethyl acetate (20 mL) and water (20 mL) were added to the residue. The organic phase was dried over anhydrous sodium sulfate and evaporated under reduced pressure. The residue was purified by preparative silica gel thin layer chromatography (petroleum ether:ethyl acetate=10:1) to give compound 2-d (231 mg, yield 67.3%).

$^1$H NMR (400 MHz, CDCl$_3$) δ: 7.37-7.32 (m, 3H), 7.23-7.18 (m, 5H), 2.19 (s, 3H), 1.49 (s, 1H) ppm.

Synthesis of Compound 2-c

[1,1'-Bis(diphenylphosphino)ferrocene]palladium dichloride (25.5 mg, 0.0364 mmol) and triethylamine (588.9 mg, 5.82 mmol) were added to a solution of compound 2-d (230 mg, 0.727 mmol) and trimethylsilylacetylene (107.1 mg, 1.09 mmol) in N,N-dimethylformamide (10 mL). After the reaction system was purged three times with nitrogen, the reaction solution was heated to 70° C. and stirred overnight. Then the reaction solution was diluted with ethyl acetate (20 mL). The obtained organic phase was washed successively with water (20 mL×3) and saturated brine (20 mL), dried over anhydrous sodium sulfate and evaporated under reduced pressure. The residue was purified by preparative silica gel thin layer chromatography (petroleum ether:ethyl acetate=100:1) to give compound 2-c (142 mg, yield 73.9%).

$^1$H NMR (400 MHz, CDCl$_3$) δ: 7.39-7.37 (m, 1H), 7.34-7.32 (m, 2H), 7.29-7.27 (m, 1H), 7.21-7.18 (m, 2H), 7.10-7.09 (m, 2H), 2.28 (s, 3H), 0.19 (s, 9H) ppm.

Synthesis of Compound 2-b

Potassium carbonate (222.7 mg, 1.611 mmol) was added to a solution of compound 2-c (142 mg, 0.537 mmol) in methanol (10 mL). The reaction solution was stirred at room temperature for 2 hours, then evaporated under reduced pressure. The residue was dissolved in ethyl acetate (20 mL), washed successively with water (20 mL) and saturated brine (20 mL). The organic phase was dried over anhydrous sodium sulfate and evaporated under reduced pressure. The residue was purified by preparative silica gel thin layer chromatography (petroleum ether:ethyl acetate=100:1) to give compound 2-b (84 mg, yield 81.6%).

$^1$H NMR (400 MHz, CDCl$_3$) δ: 7.43-7.40 (m, 1H), 7.36-7.32 (m, 2H), 7.29-7.28 (m, 1H), 7.22-7.20 (m, 2H), 7.14-7.11 (m, 2H), 3.22 (s, 3H), 2.30 (s, 3H) ppm.

Synthesis of Compound 2-a

[1,1'-Bis(diphenylphosphino)ferrocene]palladium dichloride (12.6 mg, 0.018 mmol) and cuprous iodide (6.9 mg, 0.036 mmol) were added to a mixed solution of compound 2-b (84 mg, 0.437 mmol) and compound 2-h (114.4 mg, 0.364 mmol) in N,N-dimethylformamide (8 mL) and triethylamine (2 mL). After the reaction system was purged three times with nitrogen, the reaction solution was heated to 80° C. and stirred for 16 hours. The reaction solution was diluted with ethyl acetate (20 mL), washed successively with water (20 mL×3) and saturated brine (20 mL). The organic phase was dried over anhydrous sodium sulfate and evaporated under reduced pressure. The residue was purified by preparative silica gel thin layer chromatography (petroleum ether:ethyl acetate=3:1) to give compound 2-a (23 mg, yield 17.8%). LC-MS (ESI): m/z=357.0 [M+H]$^+$.

Synthesis of Compound 2

Glacial acetic acid (7.7 mg, 0.129 mmol) was added to a mixed solution of compound 2-a (23 mg, 0.065 mmol) and (S)-prolinol (13 mg, 0.129 mmol) in methanol (2 mL) and dichloromethane (2 mL). The reaction solution was stirred at room temperature for 1 hour, followed by addition of sodium cyanoborohydride (20.4 mg, 0.325 mmol), and the resulting mixture was stirred for another 16 hours. The reaction solution was evaporated under reduced pressure, and the residue was purified by preparative silica gel thin layer chromatography (dichloromethane:methanol=15:1) to give compound 2 (6 mg, yield 28.6%). LC-MS (ESI): m/z=442.0 [M+H]$^+$.

$^1$H NMR (400 MHz, CDCl$_3$): δ 7.54 (t, J=4.4 Hz, 1H), 7.45-7.42 (m, 2H), 7.39-7.37 (m, 1H), 7.32-7.30 (m, 2H), 7.25-7.24 (m, 2H), 6.78 (s, 2H), 4.44-4.41 (d, J=12.8 Hz, 1H), 4.30-4.27 (d, J=12.8 Hz, 1H), 3.95 (s, 6H), 3.82-3.80 (m, 2H), 3.62-3.56 (m, 2H), 3.13-3.07 (m, 1H), 2.44 (s, 3H), 2.22-2.01 (m, 4H) ppm.

Embodiment 3

(S,E)-(1-(2,6-Dimethoxy-4-((2-methylbiphenyl-3-yl)vinyl)benzyl)pyrrolidin-2-yl)methanol 3

Synthetic Route

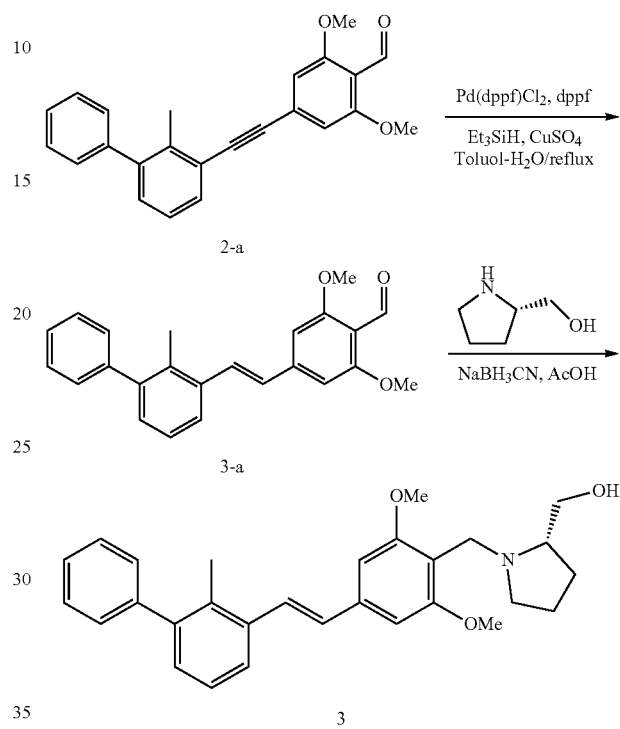

Synthesis of Compound 3-a

Compound 2-a (88 mg, 0.247 mmol), [1,1'-bis(diphenylphosphino)ferrocene]palladium dichloride (3.2 mg, 0.0037 mmol), 1,1'-bis (diphenylphosphino)ferrocene (6.9 mg, 0.0124 mmol), triethylsilane (57.5 mg, 0.494 mmol) and copper sulfate (5.9 mg, 0.037 mmol) were dissolved in a mixed solvent of toluene (2 mL) and water (0.2 mL), the mixture was sealed in a microwave tube. The reaction solution in the microwave tube was ultrasonicated for 1 minute in an ultrasonic wave, then heated to 100° C. and stirred at reflux overnight. The reaction solution was cooled to room temperature and filtered through celite. The filter cake was washed with ethyl acetate (10 mL×3). The obtained filtrate was evaporated under reduced pressure, and the residue was purified by preparative silica gel thin layer chromatography (petroleum ether:ethyl acetate=3:1) to give compound 3-a (40 mg, yield 45.5%).

$^1$H NMR (400 MHz, CDCl$_3$) δ: 10.40 (s, 1H), 7.43-7.40 (m, 2H), 7.36-7.35 (m, 1H), 7.26-7.24 (m, 2H), 7.18-7.14 (m, 3H), 6.95-6.92 (d, J=12 Hz, 1H), 6.61-6.58 (d, J=12 Hz, 1H), 6.34 (s, 2H), 3.63 (s, 6H), 2.18 (s, 3H) ppm.

Synthesis of Compound 3

Compound 3-a (27 mg, 0.075 mmol) and (S)-prolinol (15.3 mg, 0.151 mmol) were dissolved in a mixed solvent of methanol (2 mL) and dichloromethane (2 mL), followed by addition of glacial acetic acid (9.1 mg, 0.151 mmol). The reaction solution was stirred at room temperature for 1 hour, followed by addition of sodium cyanoborohydride (23.6 mg, 0.375 mmol), and the resulting mixture was stirred for another 16 hours. The reaction solution was evaporated under reduced pressure, and the residue was purified by high performance liquid chromatography (mobile phase: water (10 mM ammonium bicarbonate), acetonitrile; gradient: 25%-55%) to give compound 3 (28 mg, yield 84.8%). LC-MS (ESI): m/z=444.0 [M+H]$^+$.

$^1$H NMR (400 MHz, CDCl$_3$) δ: 7.35-7.31 (m, 2H), 7.29-7.25 (m, 1H), 7.19-7.17 (m, 2H), 7.12-7.11 (m, 2H), 7.09-7.06 (m, 1H), 6.71-6.68 (d, J=12 Hz, 1H), 6.52-6.49 (d, J=12 Hz, 1H), 6.26 (s, 2H), 3.82 (s, 1H), 3.76-3.68 (m, 2H), 3.49 (s, 6H), 3.32-3.28 (m, 1H), 2.83-2.81 (m, 1H), 2.68-2.67 (m, 1H), 2.09 (s, 3H), 1.95-1.93 (m, 1H), 1.80-1.75 (m, 1H), 1.66-1.56 (m, 4H) ppm.

Embodiment 4

(E)-2-((2,6-Dimethoxy-4-(2-(2-methylbiphenyl-3-yl)vinyl)benzyl)amino)ethan-1-ol 4

Synthetic Route

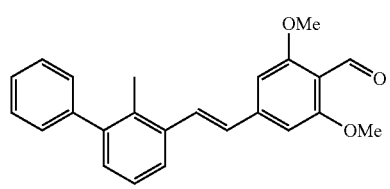
3-a

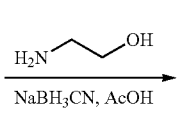

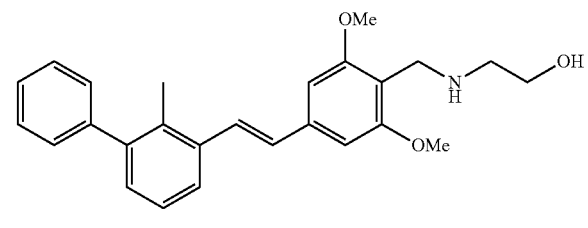
4

Synthesis of Compound 4

Compound 3 (60 mg, 0.167 mmol) and 2-aminoethanol (20.5 mg, 0.335 mmol) were dissolved in a mixed solvent of methanol (2 mL) and dichloromethane (2 mL), followed by addition of glacial acetic acid (20.1 mg, 0.335 mmol). The reaction solution was stirred at room temperature for 1 hour, followed by addition of sodium cyanoborohydride (52.5 mg, 0.835 mmol) and the resulting mixture was stirred for another 16 hours. The reaction solution was evaporated under reduced pressure, and the residue was purified by preparative silica gel thin layer chromatography (dichloromethane:methanol=15:1) to give compound 4 (42 mg, yield 62.2%). LC-MS (ESI): m/z=404.0 [M+H]$^+$.

$^1$H NMR (400 MHz, CDCl$_3$) δ: 7.56-7.54 (m, 1H), 7.44-7.40 (m, 3H), 7.37-7.35 (m, 1H), 7.31-7.29 (m, 2H), 7.26-7.24 (m, 1H), 7.20-7.19 (m, 1H), 6.96-6.92 (d, J=16 Hz, 1H), 6.73 (s, 2H), 4.34 (s, 3H), 3.96 (s, 6H), 3.89 (br, 2H), 3.08 (br, 2H), 2.30 (s, 3H) ppm.

Embodiment 5

(E)-2-((2,6-Dimethoxy-4-(2-(2-methylbiphenyl-3-yl)vinyl)benzyl)amino)propane-1,3-diol 5

Synthetic Route

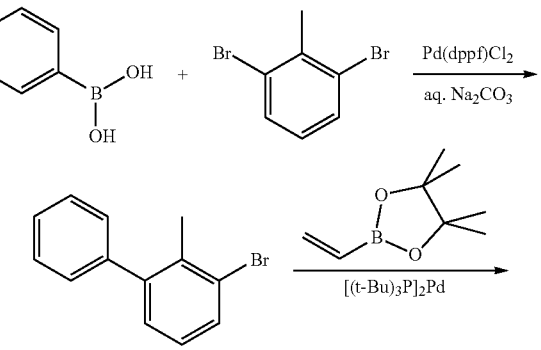

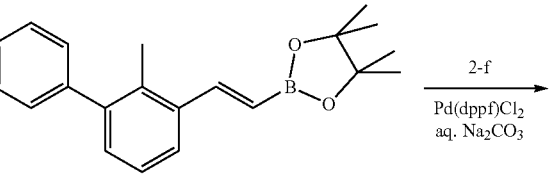
5-c

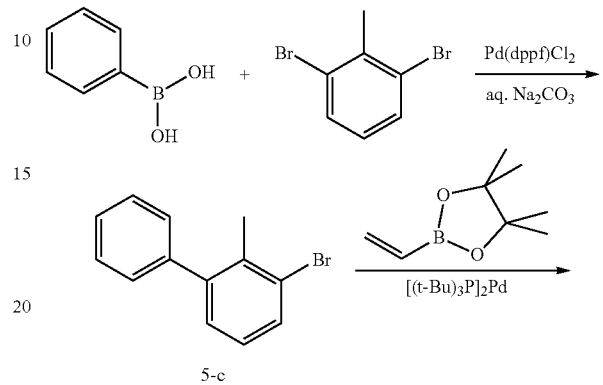
5-b

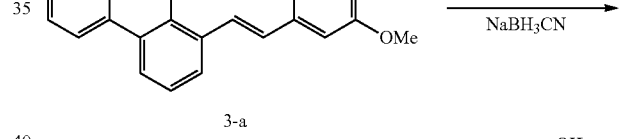
3-a

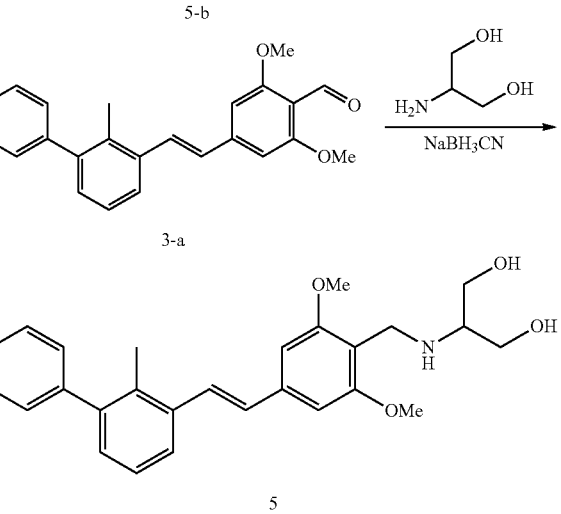
5

Synthesis of Compound 5-c

Phenylboronic acid (1.626 g, 13.34 mmol) and 2,6-dibromotoluene (5.0 g, 20.0 mmol) were dissolved in a mixed solvent of 1,4-dioxane (60 mL) and water (3 mL), followed by addition of [1,1'-bis(diphenylphosphino)ferrocene]palladium dichloride (1.154 g, 1.334 mmol) and sodium carbonate (3.535 g, 33.35 mmol). After the reaction system was purged with nitrogen three times, the reaction solution was heated to 80° C. and stirred for 16 hours. The reaction solution was cooled to room temperature, diluted with ethyl acetate (100 mL), washed successively with water (100 mL×3) and saturated brine (100 mL). The obtained organic phase was dried over anhydrous sodium sulfate and evaporated under reduced pressure. The residue was purified by silica gel column chromatography (petroleum ether) to give compound 5-c (1.9 g, yield 57.2%).

$^1$H NMR (400 MHz, CDCl$_3$) δ: 7.56-7.54 (m, 1H), 7.44-7.35 (m, 3H), 7.28-7.25 (m, 2H), 7.17-7.15 (m, 1H), 7.08 (t, J=8 Hz, 1H), 2.31 (s, 3H) ppm.

Synthesis of Compound 5-b

Compound 5-c (1.071 g, 4.33 mmol) and vinylboronic acid pinacol ester (800.9 mg, 5.20 mmol) were dissolved in toluene (50 mL), followed by addition of bis(tri-tert-butylphosphine)palladium (154.8 mg, 0.303 mmol) and triethylamine (3.51 g, 34.64 mmol). After the reaction system was purged three times with nitrogen, the reaction solution was heated to 80° C. and stirred for 16 hours. The reaction solution was cooled to room temperature, diluted with ethyl acetate (50 mL), washed successively with water (50 mL×3) and saturated brine (50 mL). The obtained organic phase was dried over anhydrous sodium sulfate and evaporated under reduced pressure. The residue was purified by silica gel column chromatography (petroleum ether) to give compound 5-b (0.89 g, yield 64.1%).

$^1$H NMR (400 MHz, CDCl$_3$) δ: 7.75-7.71 (d, J=18 Hz, 1H), 7.56-7.54 (m, 1H), 7.41-7.39 (m, 2H), 7.36-7.34 (m, 1H), 7.30-7.28 (m, 2H), 7.23-7.17 (m, 2H), 6.12-6.07 (d, J=18 Hz, 1H), 2.82 (s, 3H), 1.32 (s, 12H) ppm.

Synthesis of Compound 3-a

Compound 5-b (0.89 g, 2.78 mmol) and compound 2-f (0.795 g, 2.53 mmol) were dissolved in a mixed solvent of 1,4-dioxane (20 mL) and water (1 mL), followed by addition of [1,1'-bis(diphenylphosphino)ferrocene]palladium dichloride (0.241 g, 0.278 mmol) and sodium carbonate (0.67 g, 6.325 mmol). After the reaction system was purged three times with nitrogen, the reaction solution was heated to 80° C. and stirred for 16 hours. The reaction solution was cooled to room temperature, diluted with ethyl acetate (50 mL), washed successively with water (50 mL×3) and saturated brine (50 mL). The obtained organic phase was dried over anhydrous sodium sulfate and evaporated under reduced pressure. The residue was purified by silica gel column chromatography (petroleum ether:ethyl acetate=3:1) to give compound 3-a (0.572 g, yield 63.1%).

$^1$H NMR (400 MHz, CDCl$_3$) δ: 10.49 (s, 1H), 7.60-7.58 (d, J=7.6 Hz, 1H), 7.54-7.50 (d, J=16 Hz, 1H), 7.45-7.42 (m, 2H), 7.38-7.37 (m, 1H), 7.32-7.28 (m, 3H), 7.23-7.21 (m, 1H), 6.98-6.94 (d, J=16 Hz, 1H), 6.72 (s, 2H), 3.97 (s, 6H), 2.33 (s, 3H) ppm.

Synthesis of Compound 5

Compound 3-a (90 mg, 0.251 mmol) and 2-amino-1,3-propanediol (45.7 mg, 0.502 mmol) were dissolved in a mixed solvent of methanol (3 mL) and dichloromethane (3 mL), followed by addition of glacial acetic acid (30.2 mg, 0.502 mmol). The reaction solution was stirred at room temperature for 1 hour. Then sodium cyanoborohydride (78.9 mg, 1.255 mmol) was added and the resulting mixture was stirred for another 16 hours. The reaction solution was evaporated under reduced pressure, and the residue was purified by preparative silica gel thin layer chromatography (dichloromethane:methanol=15:1) to give compound 5 (85 mg, yield 77.9%). LC-MS (ESI): m/z=434.0 [M+H]$^+$.

$^1$H NMR (400 MHz, CDCl$_3$) δ: 7.55-7.53 (m, 1H), 7.43-7.39 (m, 3H), 7.36-7.34 (m, 1H), 7.30-7.28 (m, 2H), 7.24-7.22 (m, 1H), 7.19-7.17 (m, 1H), 6.95-6.91 (d, J=16 Hz, 1H), 6.72 (s, 2H), 4.42 (s, 2H), 3.95 (s, 6H), 3.91 (m, 2H), 3.84 (m, 2H), 3.10 (s, 1H), 2.29 (s, 3H) ppm.

Embodiment 6

(E)-N-(2-((2,6-Dimethoxy-4-(2-(2-methylbiphenyl-3-yl)vinyl)benzyl)amino) ethyl)acetamide 6

Synthetic Route

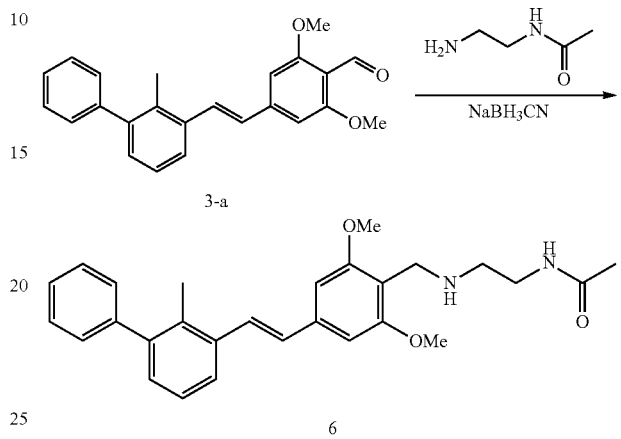

Synthesis of Compound 6

Compound 3-a (90 mg, 0.251 mmol) and N-acetylethylenediamine (51.3 mg, 0.502 mmol) were dissolved in a mixed solvent of methanol (3 mL) and dichloromethane (3 mL), followed by addition of glacial acetic acid (30.2 mg, 0.502 mmol). The reaction solution was stirred at room temperature for 1 hour. Then sodium cyanoborohydride (78.9 mg, 1.255 mmol) was added and the resulting mixture was stirred for another 16 hours. The reaction solution was evaporated under reduced pressure, and the residue was purified by preparative silica gel thin layer chromatography (dichloromethane:methanol=15:1) to give compound 6 (96 mg, yield 86.0%). LC-MS (ESI): m/z=445.0 [M+H]$^+$.

$^1$H NMR (400 MHz, CDCl$_3$) δ: 7.57-7.55 (m, 1H), 7.44-7.40 (m, 3H), 7.37-7.35 (m, 1H), 7.32-7.29 (m, 2H), 7.26-7.24 (m, 1H), 7.20-7.19 (m, 1H), 6.96-6.92 (d, J=16 Hz, 1H), 6.72 (s, 2H), 4.23 (s, 2H), 3.94 (s, 6H), 3.53 (m, 2H), 3.10 (m, 2H), 2.31 (s, 3H), 2.02 (s, 3H) ppm.

Embodiment 7

(S,E)-2-(2,6-Dimethoxy-4-(2-(2-methylbiphenyl-3-yl)vinyl)benzylamino)-3-hydroxypropionic Acid Synthetic Route

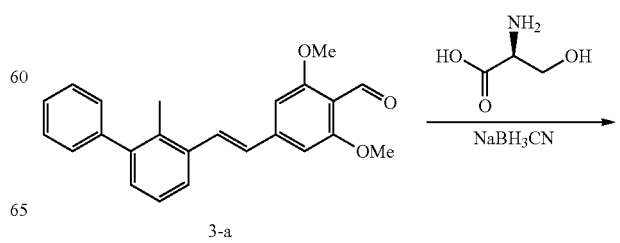

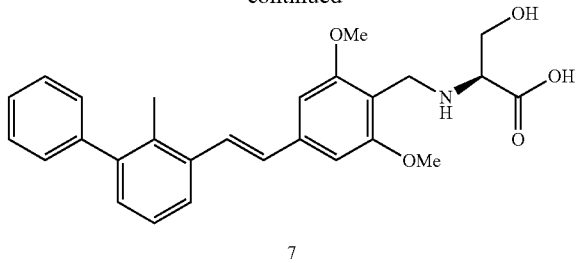

7

Synthesis of Compound 7

Compound 3-a (96 mg, 0.268 mmol) and L-serine (56.3 mg, 0.536 mmol) were dissolved in a mixed solvent of methanol (3 mL) and dichloromethane (3 mL), followed by addition of glacial acetic acid (32.2 mg, 0.536 mmol). The reaction solution was stirred at room temperature for 1 hour. Then sodium cyanoborohydride (84.2 mg, 1.34 mmol) was added and the resulting mixture was stirred for another 16 hours. The reaction solution was evaporated under reduced pressure, and the residue was purified by preparative silica gel thin layer chromatography (dichloromethane:methanol=15:1) to give compound 7 (51 mg, yield 42.5%). LC-MS (ESI): m/z=446.0 [M+H]$^+$.

$^1$H NMR (400 MHz, CDCl$_3$) δ: 7.46-7.45 (m, 1H), 7.36-7.25 (m, 4H), 7.23-7.21 (m, 2H), 7.17-7.15 (m, 1H), 7.12-7.10 (m, 1H), 6.86-6.82 (d, J=15.6 Hz, 1H), 6.61 (s, 2H), 4.33 (br, 3H), 4.03 (m, 2H), 3.81 (s, 6H), 3.59 (m, 1H), 2.21 (s, 3H) ppm.

Embodiment 8

(R,E)-2-(2,6-Dimethoxy-4-(2-(2-methylbiphenyl-3-yl)vinyl)benzylamino)-3-hydroxypropionic Acid 8

Synthetic Route

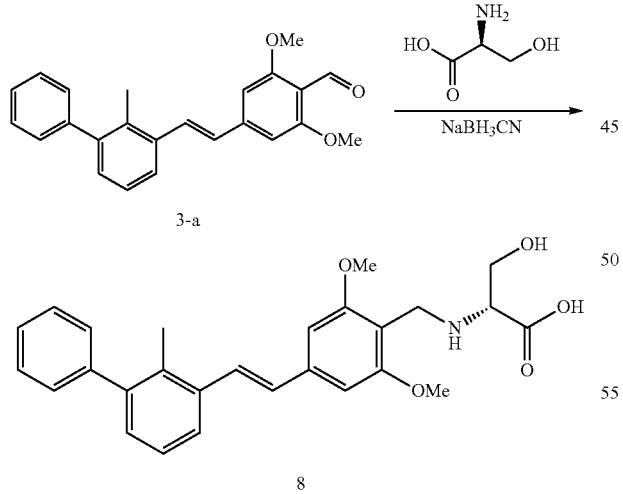

Synthesis of Compound 8

Compound 3-a (96 mg, 0.268 mmol) and D-serine (56.3 mg, 0.536 mmol) were dissolved in a mixed solvent of methanol (3 mL) and dichloromethane (3 mL), followed by addition of glacial acetic acid (32.2 mg, 0.536 mmol). The reaction solution was stirred at room temperature for 1 hour. Then sodium cyanoborohydride (84.2 mg, 1.34 mmol) was added and the resulting mixture was stirred for another 16 hours. The reaction solution was evaporated under reduced pressure, and the residue was purified by preparative silica gel thin layer chromatography (dichloromethane:methanol=15:1) to give compound 8 (17 mg, yield 14.2%). LC-MS (ESI): m/z=446.0 [M+H]$^+$.

$^1$H NMR (400 MHz, CDCl$_3$) δ: 7.46-7.45 (m, 1H), 7.36-7.25 (m, 4H), 7.23-7.21 (m, 2H), 7.17-7.15 (m, 1H), 7.12-7.10 (m, 1H), 6.86-6.82 (d, J=15.6 Hz, 1H), 6.61 (s, 2H), 4.33 (br, 3H), 4.03 (m, 2H), 3.81 (s, 6H), 3.59 (m, 1H), 2.21 (s, 3H) ppm.

Embodiment 9

(S,E)-1-(2,6-Dimethoxy-4-(2-(2-methylbiphenyl-3-yl)vinyl)benzyl)piperidin-2-carboxylic Acid 9

Synthetic Route

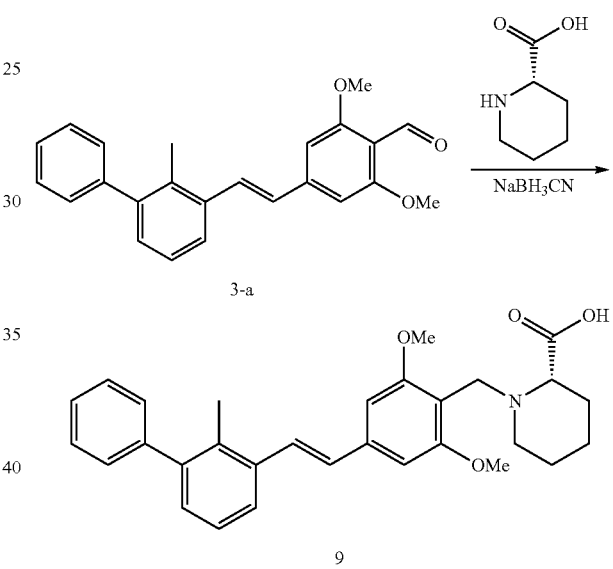

Synthesis of Compound 9

Compound 3-a (96 mg, 0.268 mmol) and L-2-piperidinecarboxylic acid (69.2 mg, 0.536 mmol) were dissolved in a mixed solvent of methanol (3 mL) and dichloromethane (3 mL), followed by addition of glacial acetic acid (32.2 mg, 0.536 mmol). The reaction solution was stirred at room temperature for 1 hour. Then sodium cyanoborohydride (84.2 mg, 1.34 mmol) was added and the resulting mixture was stirred for another 16 hours. The reaction solution was evaporated under reduced pressure, and the residue was purified by preparative silica gel thin layer chromatography (dichloromethane:methanol=15:1) to give compound 9 (19 mg, yield 15.1%). LC-MS (ESI): m/z=470.0 [M+H]$^+$.

$^1$H NMR (400 MHz, CDCl$_3$) δ: 7.58-7.56 (m, 1H), 7.46-7.41 (m, 3H), 7.38-7.36 (m, 1H), 7.32-7.29 (m, 2H), 7.28-7.26 (m, 1H), 7.22-7.20 (m, 1H), 6.98-6.94 (d, J=16 Hz, 1H), 6.73 (s, 2H), 4.68-4.65 (d, J=13.2 Hz, 1H), 4.47-4.44 (d, J=13.2 Hz, 1H), 3.95 (s, 6H), 3.56-3.50 (m, 2H), 2.78 (m, 1H), 2.32 (s, 3H), 2.22-2.14 (m, 2H), 1.88-1.87 (m, 1H), 1.79-1.71 (m, 2H), 1.53-1.51 (m, 1H) ppm.

Embodiment 10

(S,E)-2-(2,6-Dimethoxy-4-(2-(2-methylbiphenyl-3-yl)vinyl)benzylamino)propanoic Acid 10

Synthetic Route

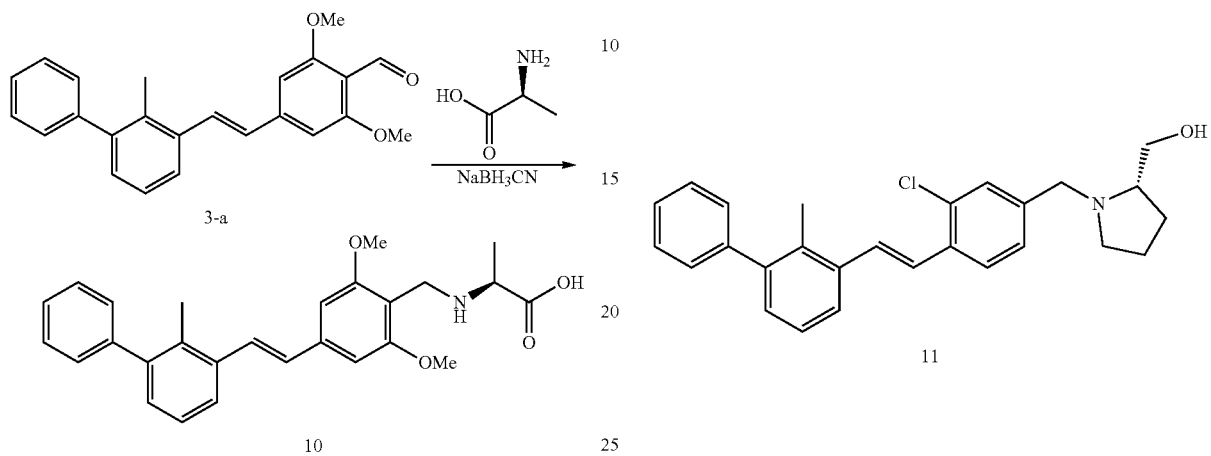

Synthesis of Compound 10

Compound 3-a (96 mg, 0.268 mmol) and (S)-2-aminopropionic acid (47.8 mg, 0.536 mmol) were dissolved in a mixed solvent of methanol (3 mL) and dichloromethane (3 mL), followed by addition of glacial acetic acid (32.2 mg, 0.536 mmol). The reaction solution was stirred at room temperature for 1 hour. Then sodium cyanoborohydride (84.2 mg, 1.34 mmol) was added and the resulting mixture was stirred for another 16 hours. The reaction solution was evaporated under reduced pressure, and the residue was purified by preparative silica gel thin layer chromatography (dichloromethane:methanol=15:1) to give compound 10 (25 mg, yield 21.6%). LC-MS (ESI): m/z=430.0 [M+H]$^+$.

$^1$H NMR (400 MHz, CDCl$_3$) δ: 7.55-7.53 (m, 1H), 7.43-7.34 (m, 4H), 7.30-7.29 (2H, m), 7.25-7.23 (m, 1H), 7.19-7.18 (m, 1H), 6.94-6.91 (d, J=12.4 Hz, 1H), 6.69 (s, 2H), 4.35-4.28 (m, 2H), 3.89 (s, 6H), 3.56 (s, 1H), 3.49-3.48 (m, 1H), 2.29 (s, 3H), 1.56-1.51 (m, 3H) ppm.

Embodiment 11

(S,E)-(1-(3-Chloro-4-(2-(2-methylbiphenyl-3-yl)vinyl)benzyl)pyrrolidin-2-yl)methanol 11

Synthetic Route

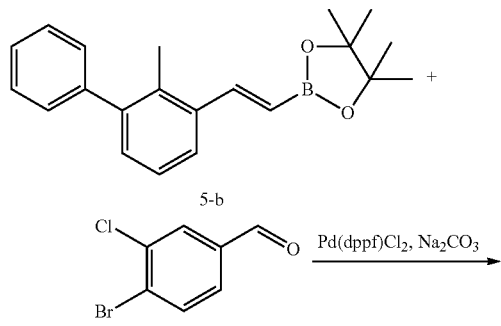

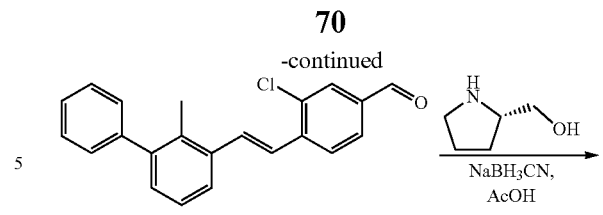

Synthesis of Compound 11-a

Compound 5-b (192 mg, 0.6 mmol) and 3-chloro-4-bromobenzaldehyde (154 mg, 0.7 mmol) were dissolved in 1,4-dioxane (20 mL), followed by addition of [1,1'-bis(diphenylphosphino)ferrocene]palladium dichloride dichloromethane complex (60 mg, 0.073 mmol) and sodium carbonate (250 mg, 2.35 mmol). After the reaction system was purged three times with nitrogen, the reaction solution was heated to 80° C. and stirred for 16 hours. The reaction solution was cooled to room temperature and evaporated under reduced pressure. The residue was purified by silica gel column chromatography (petroleum ether:ethyl acetate=15:1) to give compound 11-a (72 mg, yield 36%).

Synthesis of Compound 11

Compound 11-a (66 mg, 0.2 mmol) and L-prolinol (106 mg, 1.0 mmol) were dissolved in a mixed solvent of methanol (10 mL) and dichloromethane (10 mL), followed by addition of a drop of glacial acetic acid. The reaction solution was stirred at room temperature for 0.5 hour. Then sodium cyanoborohydride (63 mg, 1.0 mmol) was added and the resulting mixture was stirred for another 18 hours. The reaction solution was evaporated under reduced pressure, and the residue was washed with water (10 mL×3). The obtained solid crude product was dried in vacuum, and purified by recrystallization with petroleum ether to give compound 11 (35 mg, yield 41.8%). LC-MS (ESI): m/z=418 [M+H]$^+$.

$^1$H NMR (400 MHz, CD$_3$Cl) δ: 7.66 (d, J=8.4 Hz, 1H), 7.63 (d, J=7.6 Hz, 1H), 7.42-7.45 (m, 2H), 7.35-7.38 (m, 4H), 7.28-7.33 (m, 3H), 7.19-7.23 (m, 2H), 3.96 (d, J=13.2 Hz, 1H), 3.68 (dd, J=13.2, 3.2 Hz, 1H), 3.46 (dd, J=13.2, 2.0 Hz, 1H), 3.35 (d, J=13.2 Hz, 1H), 2.98-3.03 (m, 1H), 2.72-2.78 (m, 1H), 2.31 (s, 3H), 2.26-2.33 (m, 1H), 1.93-1.98 (m, 1H), 1.81-1.87 (m, H), 1.70-1.76 (m, 2H) ppm.

Embodiment 12

(S,E)-1-(3-Methyl-4-(2-(2-methylbiphenyl-3-yl)vinyl)benzyl)pyrrolidin-2-yl) Methanol 12

Synthetic Route

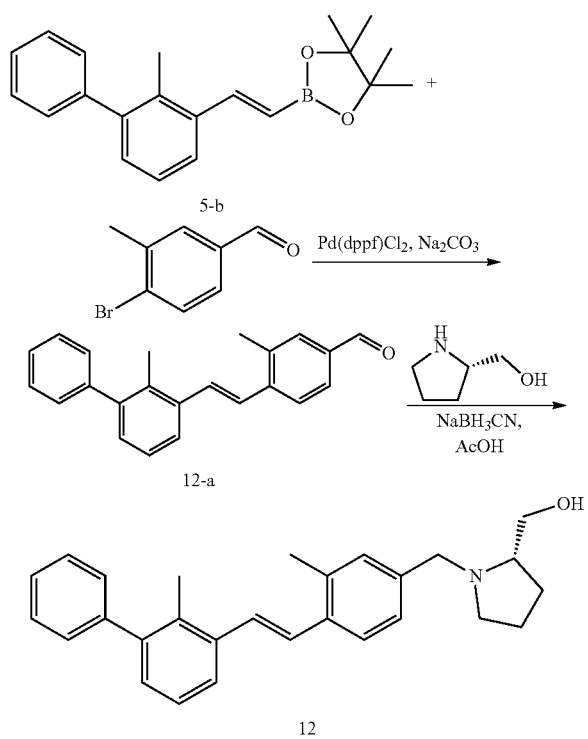

Synthesis of Compound 12-a

Compound 5-b (192 mg, 0.6 mmol) and 3-methyl-4-bromobenzaldehyde (140 mg, 0.7 mmol) were dissolved in 1,4-dioxane (20 mL), followed by addition of [1,1'-bis(diphenylphosphino)ferrocene]palladium dichloride dichloromethane complex (60 mg, 0.073 mmol) and sodium carbonate (250 mg, 2.35 mmol). After the reaction system was purged three times with nitrogen, the reaction solution was heated to 80° C. and stirred for 4 hours. Then the reaction solution was cooled to room temperature and evaporated under reduced pressure. The residue was purified by silica gel column chromatography (petroleum ether:ethyl acetate=15:1) to give compound 12-a (130 mg, yield 69%).

Synthesis of Compound 12

Compound 12-a (62 mg, 0.2 mmol) and L-prolinol (60 mg, 0.6 mmol) were dissolved in a mixed solvent of methanol (10 mL) and dichloromethane (10 mL), followed by addition of a drop of glacial acetic acid. The reaction solution was stirred at room temperature for 1 hour. Then sodium cyanoborohydride (63 mg, 1.0 mmol) was added and the resulting mixture was stirred for another 16 hours. The reaction solution was evaporated under reduced pressure, and the residue was washed with water (10 mL×3). The obtained solid crude product was dried in vacuum, and purified by recrystallization with petroleum ether to give compound 12 (40 mg, yield 50.2%). LC-MS (ESI): m/z=398 [M+H]$^+$.

$^1$H NMR (400 MHz, CD$_3$OD) δ: 7.62 (d, J=7 Hz, 2H), 7.42-7.45 (m, 2H), 7.36-7.39 (m, 2H), 7.30-7.32 (m, 2H), 7.25-7.28 (m, 2H), 7.22-7.23 (m, 2H), 7.13 (d, J=6.4 Hz, 1H), 4.06-4.09 (m, 1H), 3.61-3.64 (m, 1H), 3.50-3.53 (m, 1H), 3.43-3.46 (m, 1H), 2.95-2.98 (m, 1H), 2.69-2.76 (m, 1H), 2.46 (s, 3H), 2.35-2.39 (m, 1H), 2.30 (s, 3H), 1.97-2.02 (m, 1H), 1.70-1.77 (m, 3H) ppm.

Embodiment 13

(R,E)-2-(3-Methyl-4-(2-(2-methylbiphenyl-3-yl)vinyl)benzylamino)propanoic Acid 13

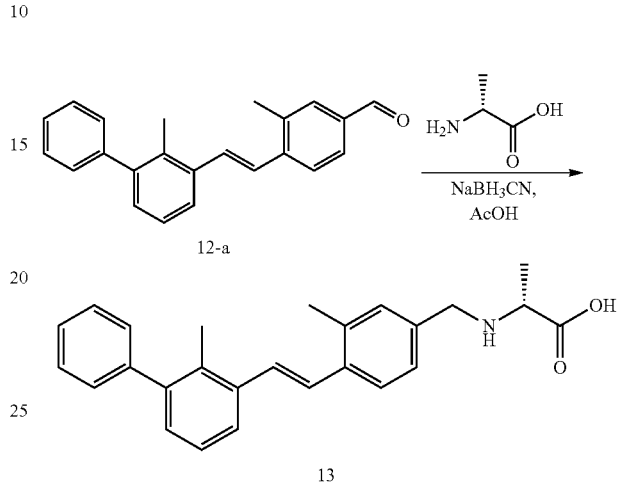

Synthesis of Compound 13

Compound 12-a (62 mg, 0.2 mmol) and L-alanine (36 mg, 0.4 mmol) were dissolved in a mixed solvent of methanol (10 mL) and dichloromethane (10 mL), followed by addition of a drop of glacial acetic acid. The reaction solution was stirred at room temperature for 1 hour. Then sodium cyanoborohydride (38 mg, 0.6 mmol) was added and the resulting mixture was stirred for another 16 hours. The reaction solution was evaporated under reduced pressure, and the residue was washed with water (10 mL×3). The obtained solid crude product was dried in vacuum, and purified by recrystallization with methanol to give compound 13 (20 mg, yield 25.9%). LC-MS (ESI): m/z=386 [M+H]$^+$.

$^1$H NMR (400 MHz, CD3OD) δ: 7.68 (d, J=8.5 Hz, 2H), 7.59 (d, J=7.5 Hz, 1H), 7.38-7.43 (m, 3H), 7.33-7.35 (m, 2H), 7.27-7.31 (m, 3H), 7.22 (d, J=18 Hz, 1H), 7.16 (d, J=7 Hz, 1H), 4.17 (d, J=14 Hz, 1H), 4.05 (d, J=14 Hz, 1H), 3.52-3.55 (m, 1H), 2.45 (s, 3H), 2.29 (s, 3H), 1.50 (d, J=7 Hz, 3H) ppm.

Embodiment 14

(S,E)-3-(4-((2-Hydroxymethylpyrrolidin-1-yl)methyl)-3,5-dimethoxystyryl)biphenyl-2-carbonitrile 14

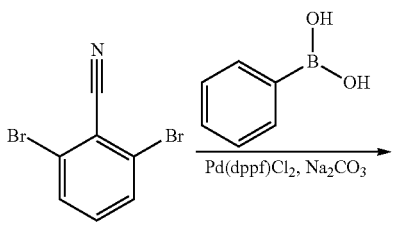

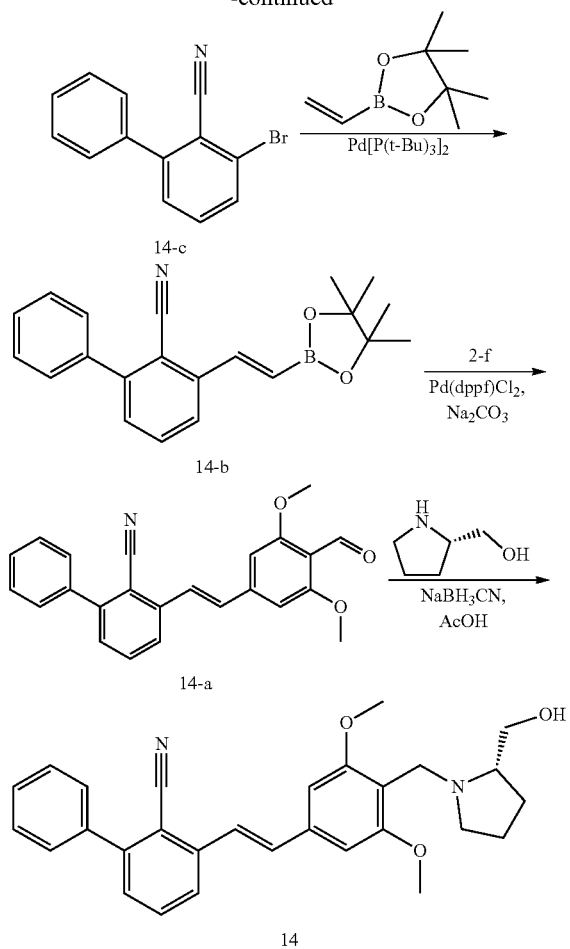

Synthesis of Compound 14-c

Phenylboronic acid (363 mg, 3 mmol) and 2,6-dibromobenzonitrile (783 mg, 3 mmol) were dissolved in a mixed solvent of 1,4-dioxane (20 mL) and water (4 mL), followed by addition of [1,1'-bis(diphenylphosphino)ferrocene]palladium dichloride dichloromethane complex (171 mg, 0.21 mmol) and sodium carbonate (1.06 g, 10 mmol). After the reaction system was purged three times with nitrogen, the reaction solution was heated to 80° C. and stirred for 16 hours. Then the reaction solution was cooled to room temperature and evaporated under reduced pressure. The residue was purified by silica gel column chromatography (petroleum ether) to give compound 14-c (280 mg, yield 36%).

Synthesis of Compound 14-b

Compound 14-c (258 mg, 1 mmol) and vinylboronic acid pinacol ester (231 mg, 1.5 mmol) were dissolved in toluene (10 mL), followed by addition of bis(tri-tert-butylphosphine)palladium (50 mg, 0.1 mmol) and triethylamine (404 mg, 4.0 mmol). After the reaction system was purged three times with nitrogen, the reaction solution was heated to 80° C. and stirred for 6 hours. Then the reaction solution was cooled to room temperature and evaporated under reduced pressure. The residue was purified by silica gel column chromatography (petroleum ether:ethyl acetate=100:1) to give compound 14-b (220 mg, yield 66%).

Synthesis of Compound 14-a

Compound 14-b (200 mg, 0.6 mmol) and compound 2-f (246 mg, 0.78 mmol) were dissolved in a mixed solvent of 1,4-dioxane (15 mL) and water (3 mL), followed by addition of [1,1'-bis(diphenylphosphino)ferrocene]palladium dichloride dichloromethane complex (50 mg, 0.06 mmol) and sodium carbonate (212 mg, 2 mmol). After the reaction system was purged three times with nitrogen, the reaction solution was heated to 80° C. and stirred for 16 hours. Then the reaction solution was cooled to room temperature and evaporated under reduced pressure. The residue was purified by silica gel column chromatography (petroleum ether:ethyl acetate=3:1) to give compound 14-a (80 mg, yield 36%). LC-MS (ESI): m/z=370 [M+H]$^+$.

Synthesis of Compound 14

Compound 14-a (74 mg, 0.2 mmol) and L-prolinol (60 mg, 0.6 mmol) were dissolved in a mixed solvent of methanol (5 mL) and dichloromethane (5 mL), followed by addition of a drop of glacial acetic acid. The reaction solution was stirred at room temperature for 1 hour. Then sodium cyanoborohydride (63 mg, 1.0 mmol) was added and the resulting mixture was stirred for another 16 hours. The reaction solution was evaporated under reduced pressure, and the residue was washed with water (10 mL×3). The obtained solid crude product was dried in vacuum, and purified by recrystallization with petroleum ether to give compound 14 (35 mg, yield 38.4%). LC-MS (ESI): m/z=455 [M+H]$^+$.

$^1$H NMR (400 MHz, CDCl$_3$) δ: 7.80-7.82 (m, 1H), 7.60-7.64 (m, 1H), 7.56-7.58 (m, 2H), 7.46-7.51 (m, 3H), 7.37-7.39 (m, 1H), 7.24-7.28 (m, 2H), 6.78 (s, 2H), 3.90 (s, 6H), 3.79-3.83 (m, 1H), 3.64-3.67 (m, 1H), 3.38-3.41 (m, 1H), 2.89-2.92 (m, 1H), 2.75-2.78 (m, 1H), 2.45-2.52 (m, 1H), 1.84-1.91 (m, 1H)), 1.63-1.75 (m, 4H) ppm.

Embodiment 15

(S,E)-1-(4-(3-(2,3-Dihydrobenzo[b][1,4]dioxin-6-yl)-2-methylstyryl)-2,6-dim ethoxybenzyl)pyrrolidin-2-yl)methanol 15

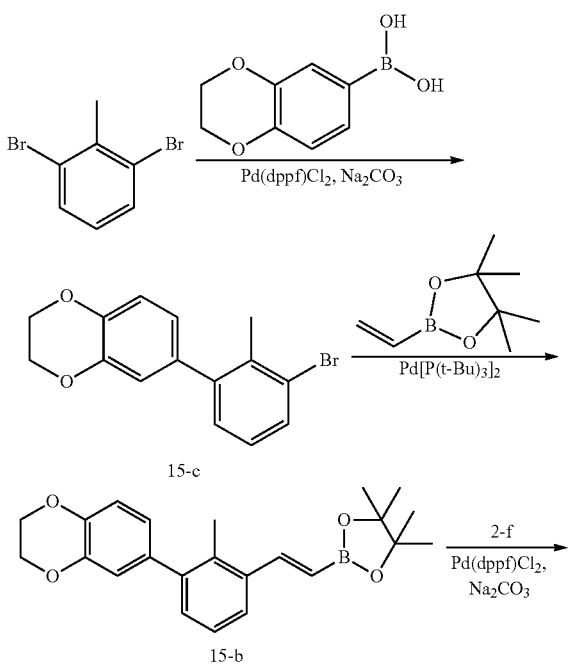

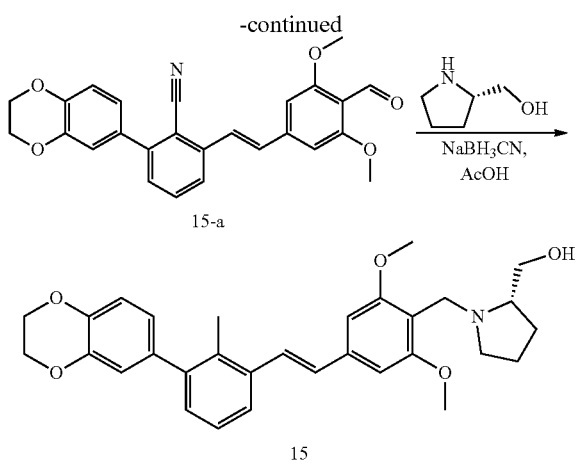

Synthesis of Compound 15-c 1,4-Dioxane-6-benzeneboronic acid (3.60 g, 20 mmol) and 2,6-dibromotoluene (7.50 g, 30 mmol) were dissolved in a mixed solvent of 1,4-dioxane (100 mL) and water (15 mL), followed by addition of [1,1'-bis(diphenylphosphino)ferrocene]palladium dichloride dichloromethane complex (817 mg, 1 mmol) and sodium carbonate (6.38 g, 60 mmol). After the reaction system was purged three times with nitrogen, the reaction solution was heated to 80° C. and stirred for 16 hours. Then the reaction solution was cooled to room temperature and evaporated under reduced pressure. The residue was purified by silica gel column chromatography (petroleum ether) to give compound 15-c (2.70 g, yield 44%).

Synthesis of Compound 15-b

Compound 15-c (915 mg, 3 mmol) and vinylboronic acid pinacol ester (924 mg, 6 mmol) were dissolved in toluene (10 mL), followed by addition of bis(tri-tert-butylphosphine)palladium (120 mg, 0.24 mmol) and triethylamine (2.0 g, 20 mmol). After the reaction system was purged three times with nitrogen, the reaction solution was heated to 80° C. and stirred for 6 hours. Then the reaction solution was cooled to room temperature and evaporated under reduced pressure. The residue was purified by silica gel column chromatography (petroleum ether:ethyl acetate=10:1) to give compound 15-b (540 mg, yield 48%).

Synthesis of Compound 15-a

Compound 15-b (264.8 mg, 0.7 mmol) and compound 2-f (200 mg, 0.636 mmol) were dissolved in a mixed solvent of 1,4-dioxane (20 mL) and water (1 mL), followed by addition of [1,1'-bis(diphenylphosphino)ferrocene]palladium dichloride (50 mg, 0.06 mmol) and sodium carbonate (212 mg, 2 mmol). After the reaction system was purged three times with nitrogen, the reaction solution was heated to 80° C. and stirred for 16 hours. Then the reaction solution was cooled to room temperature, washed successively with ethyl acetate (10 mL×3) and saturated brine (10 mL). The organic phase was dried over anhydrous sodium sulfate and evaporated under reduced pressure. The residue was purified by silica gel column chromatography (petroleum ether:ethyl acetate=5:1 to 3:1) to give compound 15-a (155 mg, yield 58.5%). LC-MS (ESI): m/z=417 [M+H]$^+$.

Synthesis of Compound 15

Compound 15-a (155 mg, 0.37 mmol) and L-prolinol (75.3 mg, 0.74 mmol) were dissolved in a mixed solvent of methanol (10 mL) and dichloromethane (10 mL), followed by addition of glacial acetic acid (44.7 mg, 0.74 mmol). The reaction solution was stirred at room temperature for 1 hour. Then sodium cyanoborohydride (116.9 mg, 1.86 mmol) was added and the resulting mixture was stirred for another 16 hours. The reaction solution was evaporated under reduced pressure, and the residue was purified by preparative silica gel thin layer chromatography (dichloromethane:methanol=15:1) to give compound 15 (136 mg, yield 72.7%). LC-MS (ESI): m/z=502 [M+H]$^+$.

$^1$H NMR (400 MHz, CDCl$_3$) δ:7.55-7.53 (d, J=7.6 Hz, 1H), 7.46-7.42 (d, J=16 Hz, 1H), 7.24-7.17 (m, 2H), 6.97-6.90 (m, 2H), 6.83 (s, 1H), 6.79-6.74 (m, 3H), 4.43-4.40 (d, J=12.4 Hz, 1H), 4.31 (s, 4H), 4.30-4.27 (d, J=12.4 Hz, 1H), 3.98 (s, 6H), 3.81-3.80 (m, 2H), 3.63-3.62 (m, 2H), 3.15-3.11 (m, 1H), 2.34 (s, 3H), 2.21-2.10 (m, 4H) ppm.

Embodiment 16

(S,E)-(1-((6-(2-(2-Methylbiphenyl-3-yl)vinyl)pyridin-3-yl)methyl)pyrrolidin-2-yl)methanol 16

Synthetic Route

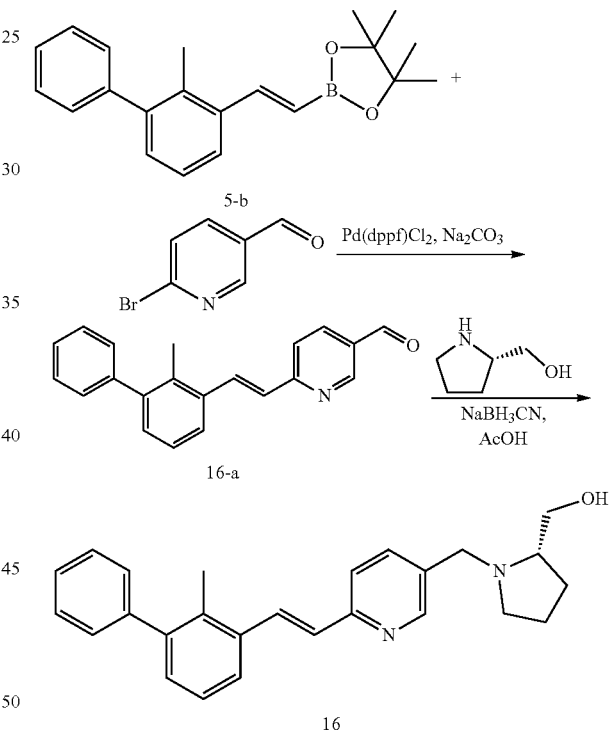

Synthesis of Compound 16-a

Compound 5-b (192 mg, 0.6 mmol) and 2-bromo-5-pyridinecarboxaldehyde (130 mg, 0.7 mmol) were dissolved in 1,4-dioxane (20 mL), followed by addition of [1,1'-bis(diphenylphosphino)ferrocene]palladium dichloride dichloromethane complex (60 mg, 0.073 mmol) and sodium carbonate (250 mg, 2.35 mmol). After the reaction system was purged three times with nitrogen, the reaction solution was heated to 80° C. and stirred for 4 hours. Then the reaction solution was cooled to room temperature and evaporated under reduced pressure. The residue was purified by silica gel column chromatography (petroleum ether:ethyl acetate=15:1) to give compound 16-a (86 mg, yield 48%). LC-MS (ESI): m/z=301 [M+H]$^+$.

Synthesis of Compound 16

Compound 16-a (60 mg, 0.2 mmol) and L-prolinol (60 mg, 0.6 mmol) were dissolved in a mixed solvent of methanol (10 mL) and dichloromethane (10 mL), followed by addition of a drop of glacial acetic acid. The reaction solution was stirred at room temperature for 1 hour. Then sodium cyanoborohydride (63 mg, 1.0 mmol) was added and the resulting mixture was stirred for another 16 hours. The reaction solution was evaporated under reduced pressure, and the residue was washed with water (10 mL×3). The obtained solid crude product was dried in vacuum, and purified by recrystallization with petroleum ether to give compound 16 (35 mg, yield 45.4%). LC-MS (ESI): m/z=385 [M+H]$^+$.

$^1$H NMR (400 MHz, CD$_3$OD) δ: 8.51 (s, 1H), 7.95 (d, J=18 Hz, 1H), 7.83 (d, J=8 Hz, 1H), 7.67 (d, J=8 Hz, 1H), 7.61 (d, J=8 Hz, 1H), 7.42-7.45 (m, 2H), 7.34-7.38 (m, 1H), 7.26-7.30 (m, 3H), 7.12-7.18 (m, 2H), 4.16 (d, J=13 Hz, 1H), 3.56-3.64 (m, 2H), 3.48 (d, J=13 Hz, 1H), 2.91-2.94 (m, 1H), 2.70-2.75 (m, 1H), 2.32 (s, 3H), 2.31-2.34 (m, 1H), 1.96-2.03 (m, 1H), 1.70-1.78 (m, 3H) ppm.

Embodiment 17

(E)-2-((6-(3-(2,3-Dihydrobenzo[b][1,4]dioxin-6-yl)-2-methylstyryl)pyridin-3-yl)methylamino)ethanol 17

Synthetic Route

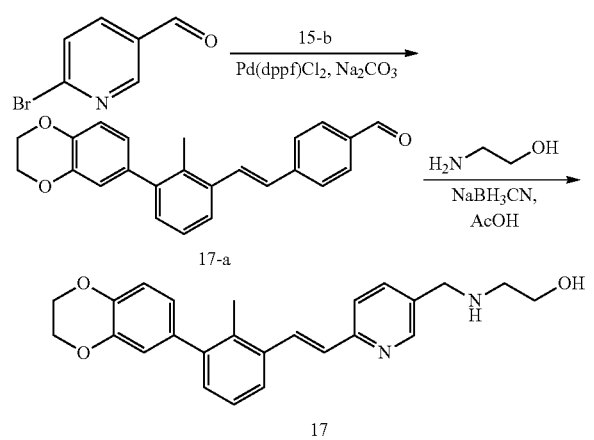

Synthesis of Compound 17-a

Compound 15-b (190 mg, 0.5 mmol) and 2-bromo-5-pyridinecarboxaldehyde (112 mg, 0.6 mmol) were dissolved in a mixed solvent of 1,4-dioxane (15 mL) and water (3 mL), followed by addition of [1,1'-bis(diphenylphosphino)ferrocene]palladium dichloride dichloromethane complex (41 mg, 0.05 mmol) and sodium carbonate (160 mg, 2 mmol). After the reaction system was purged three times with nitrogen, the reaction solution was heated to 80° C. and stirred for 16 hours. Then the reaction solution was cooled to room temperature and evaporated under reduced pressure. The residue was purified by silica gel column chromatography (petroleum ether:ethyl acetate=5:1) to give compound 17-a (75 mg, yield 42%). LC-MS (ESI): m/z=358 [M+H]$^+$.

Synthesis of Compound 17

Compound 17-a (25 mg, 0.07 mmol) and aminoethanol (25 mg, 0.4 mmol) were dissolved in a mixed solvent of methanol (10 mL) and dichloromethane (10 mL), followed by addition of a drop of glacial acetic acid. The reaction solution was stirred at room temperature for 1 hour. Then sodium cyanoborohydride (25 mg, 0.4 mmol) was added and the resulting mixture was stirred for another 16 hours. The reaction solution was evaporated under reduced pressure, and the residue was washed with water (10 mL×3). The obtained solid crude product was dried in vacuum, and purified by recrystallization with petroleum ether to give compound 17 (20 mg, yield 70.8%). LC-MS (ESI): m/z=403 [M+H]$^+$.

$^1$H NMR (400 MHz, CDCl$_3$) δ: 8.54 (s, 1H), 7.92 (d, J=16 Hz, 1H), 7.63 (m, 2H), 7.38 (d, J=8.0 Hz, 1H), 7.17-7.26 (m, 2H), 7.06 (d, J=16 Hz, 1H), 6.90 (d, J=8.4 Hz, 1H), 6.76-6.83 (m, 2H), 4.30 (s, 4H), 3.83 (s, 2H), 3.67-3.70 (m, 2H), 2.79-2.81 (m, 2H), 2.36 (s, 3H) ppm.

Embodiment 18

(E)-4-((6-(3-(2,3-Dihydrobenzo[b][1,4]dioxin-6-yl)-2-methylstyryl)pyridin-3-yl)methylamino)-3-hydroxybutanoic Acid 18

Synthetic Route

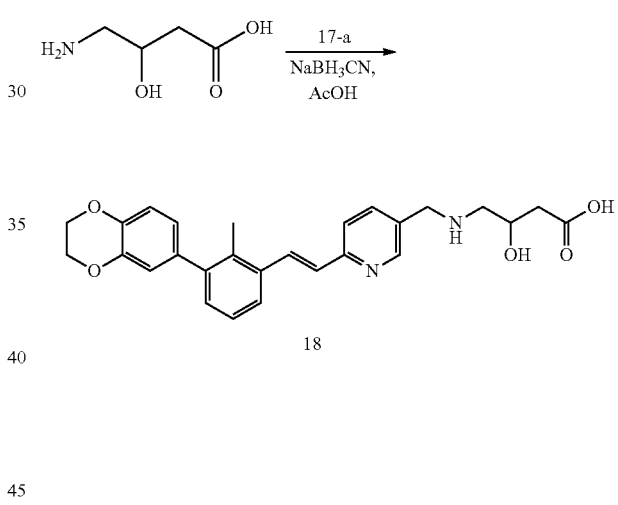

Synthesis of Compound 18

Compound 17-a (47 mg, 0.13 mmol) and 4-amino-3-hydroxybutyric acid (46 mg, 0.4 mmol) were dissolved in a mixed solvent of methanol (10 mL) and dichloromethane (10 mL), followed by addition of a drop of glacial acetic acid. The reaction solution was stirred at room temperature for 1 hour. Then sodium cyanoborohydride (25 mg, 0.4 mmol) was added and the resulting mixture was stirred for another 16 hours. The reaction solution was evaporated under reduced pressure, and the residue was washed with water (10 mL×3). The obtained solid crude product was dried in vacuum, and purified by recrystallization with methanol to give compound 18 (30 mg, yield 50%). LC-MS (ESI): m/z=461 [M+H]$^+$.

$^1$H NMR (400 MHz, CD$_3$OD) δ: 8.57 (s, 1H), 7.96 (d, J=16 Hz, 1H), 7.89 (d, J=8.0 Hz, 1H), 7.56-7.63 (m, 2H), 7.24-7.27 (m, 1H), 7.19-7.21 (m, 1H), 7.08 (d, J=16 Hz, 1H), 6.90-6.92 (m, 1H), 6.76-6.81 (m, 2H), 4.32 (s, 4H), 4.13-4.17 (m, 3H), 3.05-3.08 (m, 1H), 2.92-2.97 (m, 1H), 2.52-2.53 (m, 2H), 2.36 (s, 3H) ppm.

Embodiment 19

(E)-3-Hydroxy-1-(3-methyl-4-(2-(2-methylbiphenyl-3-yl)vinyl)benzyl)piperidin-2-carboxylic Acid 19

Synthetic Route

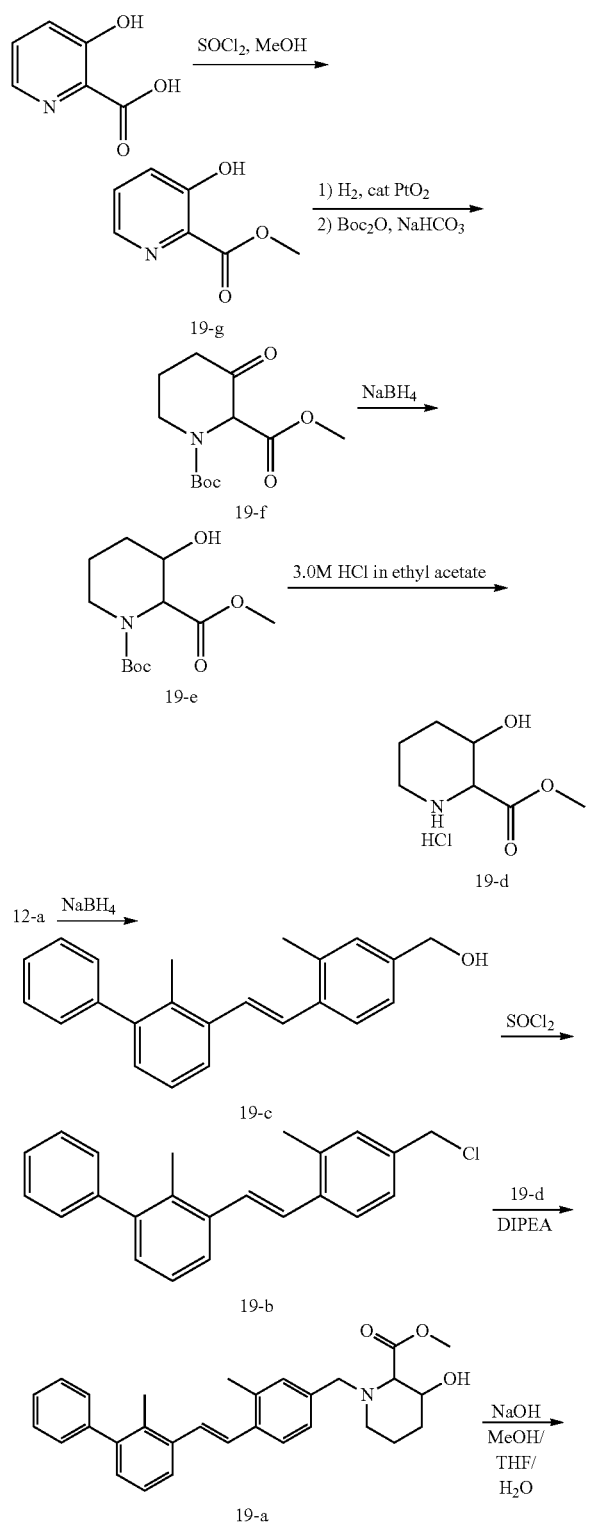

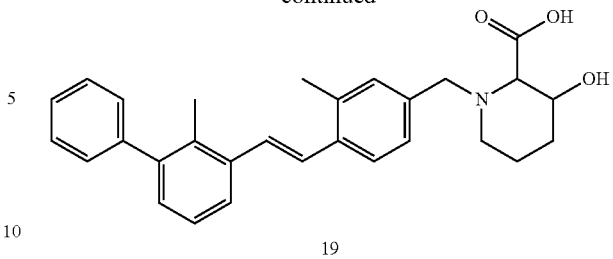

19

Synthesis of Compound 19-g

3-Hydroxypyridin-2-carboxylic acid (12 g, 86.33 mmol) was suspended in anhydrous methanol (150 mL), and thionyl chloride (20 mL) was slowly added. After the addition of thionyl chloride, the reaction solution was heated at reflux for 24 hours and turned clear. The reaction solution was cooled to room temperature and evaporated under reduced pressure. The residue was washed with ethyl acetate (50 mL), dried in vacuum to give 19-g as a pale yellow solid (15 g, yield 92%), which was directly used in the next step without further purification.

Synthesis of Compound 19-f

Compound 19-g (15 g, 79.3 mmol) was dissolved in methanol (250 mL), followed by addition of platinum oxide (0.3 g). After the reaction system was purged three times with nitrogen and three times with hydrogen, the reaction solution was stirred at room temperature under one atmospheric pressure for 20 hours. The reaction solution was filtered through celite and washed with methanol (50 mL). The filtrate was adjusted to pH 10 with a saturated sodium bicarbonate solution. Di-tert-butyl dicarbonate (24.2 g, 111.02 mmol) was added and the reaction solution was stirred at room temperature for 2 hours. Then the reaction solution was evaporated under reduced pressure and diluted with ethyl acetate (250 mL×2). The organic phase was washed with water (200 mL), dried over anhydrous sodium sulfate, filtered and evaporated under reduced pressure. The residue was purified by silica gel column chromatography (petroleum ether:ethyl acetate=10:1) to give compound 19-f as a yellow oil (11 g, yield 53%).

Synthesis of Compound 19-e

Compound 19-f (2.3 g, 8.94 mmol) was dissolved in anhydrous methanol (50 mL), then the solution was cooled to 0° C., followed by addition of sodium borohydride (340 mg, 8.94 mmol) in batches. The reaction solution was stirred at room temperature for 1 hour, then evaporated under reduced pressure. The residue was diluted with water (50 mL), extracted with ethyl acetate (50 mL×3). The organic layers were combined, dried over anhydrous sodium sulfate, filtered and evaporated under reduced pressure to give 19-e as a yellow oil (2.2 g, yield 98%), which was directly used in the next step without further purification.

Synthesis of Compound 19-d

Compound 19-f (1.0 g, 3.86 mmol) was added to a solution of hydrogen chloride in ethyl acetate (3.0M, 50 mL), and the reaction solution was sealed and stirred at room temperature for 3 hours. A large amount of white solid precipitated, then was filtered and dried in vacuum to give compound 19-d (589 mg, yield 78.2%), which was directly used in the next step without further purification.

Synthesis of Compound 19-c

Compound 12-a (180 mg, 0.576 mmol) was dissolved in tetrahydrofuran (5 mL), followed by addition of sodium borohydride (37.83 mg, 0.576 mmol). The mixture was stirred at room temperature for 3 hours, then the reaction was quenched with water (4 mL) and ethyl acetate (10 mL). The organic phase was separated, washed with saturated brine (20 mL×2), dried over anhydrous sodium sulfate, filtered and evaporated under reduced pressure. The residue was purified by silica gel column chromatography (petroleum ether:ethyl acetate=5:1) to give compound 19-c (120 mg, yield 66.24%).

Synthesis of Compound 19-b

Compound 19-c (100 mg, 0.315 mmol) was added to thionyl chloride (5 mL). The mixture was stirred at room temperature for 2 hours, then evaporated under reduced pressure to give compound 19-b (100 mg, yield 94.46%), which was directly used in the next step without further purification.

Synthesis of Compound 19-a

Compound 19-b (95 mg, 0.28 mmol), compound 19-d (83 mg, 0.43 mmol) and diisopropylethylamine (116 mg, 0.9 mmol) were dissolved in acetonitrile (5 mL). The reaction solution was heated to 60° C. and stirred for 16 hours, then cooled to room temperature and evaporated under reduced pressure. The residue was purified by silica gel column chromatography (petroleum ether:ethyl acetate=4:1) to give compound 19-a (55 mg, yield 39.3%). LC-MS (ESI): m/z=456 [M+H]$^+$.

Synthesis of Compound 19

Compound 19-a (55 mg, 0.12 mmol) and aqueous sodium hydroxide (4M, 0.065 mL) were added to a mixed solvent of methanol (1.6 mL), tetrahydrofuran (1.6 mL) and water (1.6 mL). The reaction solution was stirred at room temperature for 16 hours. Then hydrochloric acid (2M, 10 mL) and water (20 mL) were slowly added dropwise to the reaction solution, and a white solid precipitated. The mixture was filtered, and the filter cake was washed with water (5 mL×2), dried in vacuum to give 19 as a white solid (25 mg, yield 47.2%). LC-MS (ESI): m/z=442 [M+H]$^+$.

$^1$H NMR (400 MHz, DMSO-$d_6$) δ: 7.68 (d, J=8.4 Hz, 2H), 7.46 (t, J=7.2 Hz, 2H), 7.19-7.40 (m, 8H), 7.14 (d, J=7.2 Hz, 1H), 3.67-3.84 (m, 3H), 3.48 (s, 2H), 2.93-2.95 (m, 1H), 2.41-2.44 (m, 3H), 2.26 (s, 3H) ppm.

Embodiment 20

(E)-Methyl 1-(3-chloro-4-(2-(2-methylbiphenyl-3-yl)vinyl)benzyl)-3-hydroxypiperidin-2-carboxylate 20

Synthetic Route

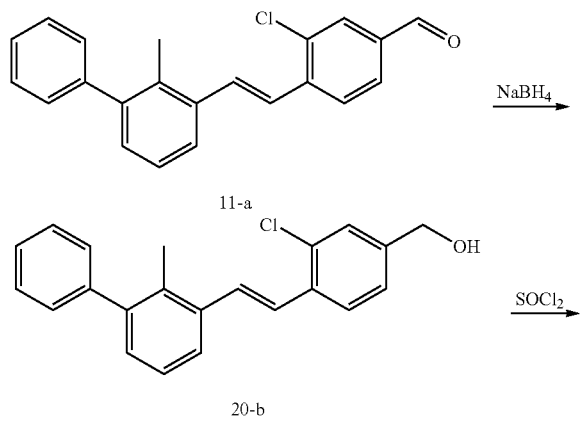

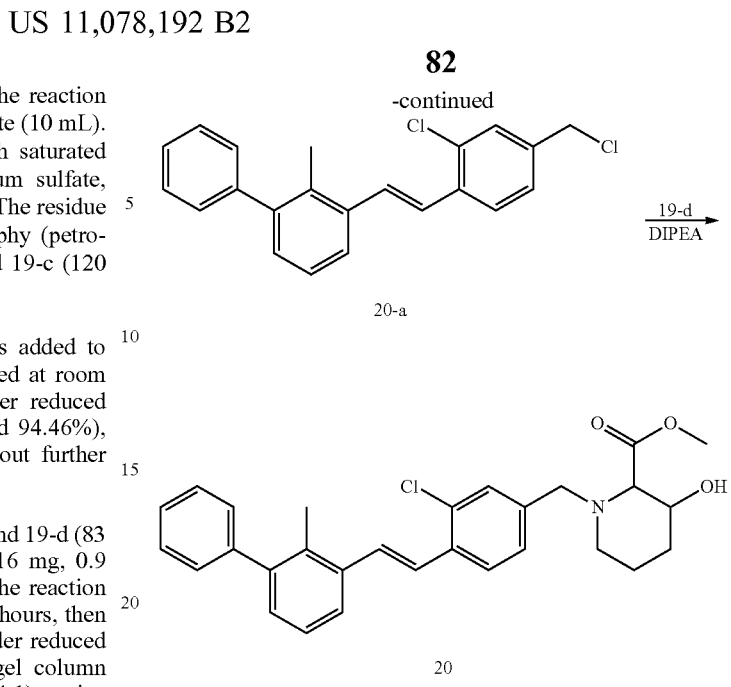

Synthesis of Compound 20-b

Compound 11-a (300 mg, 0.9 mmol) was dissolved in a mixed solvent of tetrahydrofuran (10 mL) and ethanol (10 mL), followed by addition of sodium borohydride (69 mg, 1.8 mmol). The mixture was stirred at room temperature for 16 hours, then the reaction was quenched with hydrochloric acid (1N, 20 mL). The mixture was extracted with ethyl acetate (30 mL×3). The organic phase was washed saturated brine (20 mL×2), dried over anhydrous sodium sulfate, filtered and evaporated under reduced pressure to give compound 20-b (300 mg, yield 99%), which was directly used in the next step without further purification.

Synthesis of Compound 20-a

Compound 20-b (90 mg, 0.27 mmol) was dissolved in dichloromethane (10 mL), followed by addition of thionyl chloride (0.5 mL). The mixture was stirred at room temperature for 2 hours, then evaporated under reduced pressure to give compound 20-a, which was directly used in the next step without further purification.

Synthesis of Compound 20

Compound 20-a (95 mg, 0.27 mmol), compound 19-d (79 mg, 0.40 mmol) and diisopropylethylamine (390 mg, 3 mmol) were dissolved in acetonitrile (5 mL). The reaction solution was heated to 60° C. and stirred for 16 hours. Then the reaction solution was cooled to room temperature and evaporated under reduced pressure. The residue was purified by silica gel column chromatography (petroleum ether:ethyl acetate=1:1) to give compound 20 (53 mg, yield 41.4%). LC-MS (ESI): m/z=475.9 [M+H]$^+$.

$^1$H NMR (400 MHz, CDCl$_3$) δ: 7.56 (t, J=8.4 Hz, 2H), 7.16-7.37 (m, 1H), 7.12 (d, J=7.2 Hz, 1H), 3.93 (s, 1H), 3.72-3.75 (m, 4H), 3.36-3.39 (m, 2H), 2.70-2.75 (m, 2H), 2.14-2.23 (m, 4H), 1.58-1.76 (m, 2H), 1.42-1.48 (m, 1H) ppm.

Embodiment 21

(E)-3-Hydroxy-1-(3-fluoro-4-(2-(2-methylbiphenyl-3-yl)vinyl)benzyl)piperidin-2-carboxylic Acid 21

Synthetic Route

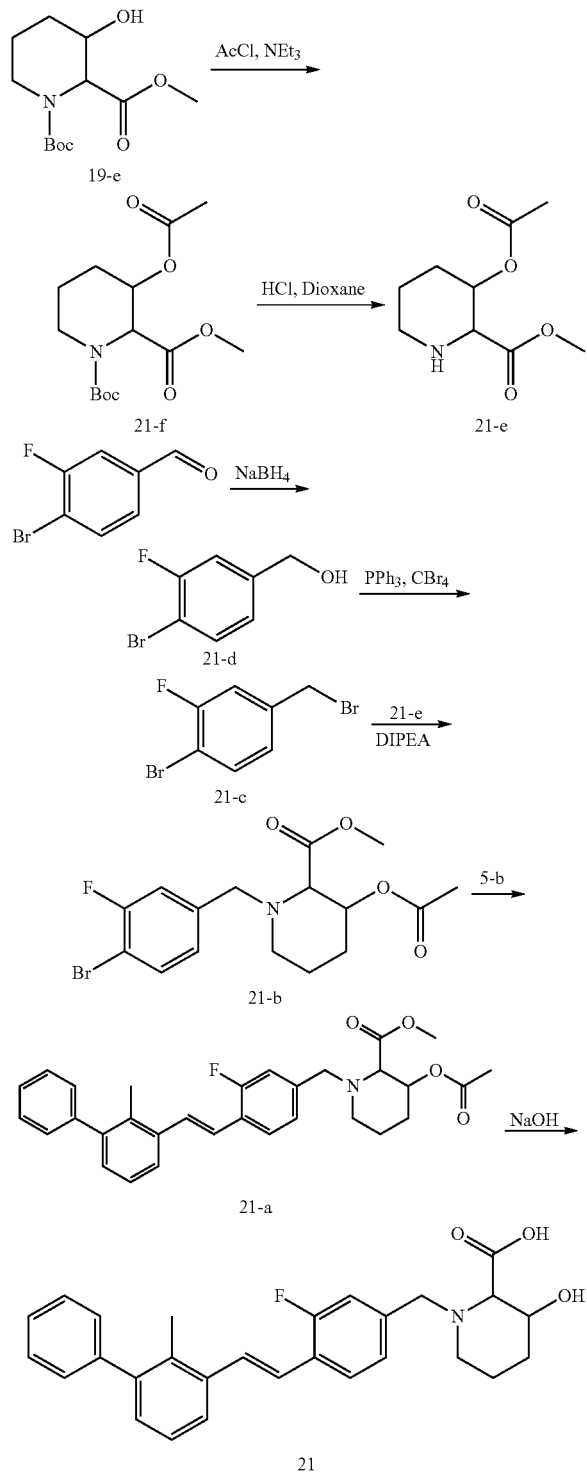

Synthesis of Compound 21-f

Compound 19-e (1.75 g, 6.7 mmol) and triethylamine (1.36 g, 13.5 mmol) were dissolved in dichloromethane (20 mL), the mixture was cooled to 0° C., followed by dropwise addition of acetyl chloride (690 mg, 8.8 mmol). The mixture was allowed to warm to room temperature and stirred for another 1 hour, then evaporated under reduced pressure. The residue was purified by silica gel column chromatography (petroleum ether:ethyl acetate=15:1) to give compound 21-f (1.32 g, yield 65%). LC-MS (ESI): m/z=324 [M+Na]$^+$.

Synthesis of Compound 21-e

Compound 21-f (1.32 g, 4.4 mmol) was dissolved in tetrahydrofuran (20 mL), followed by addition of a solution of hydrogen chloride in 1,4-dioxane (3.0M, 20 mL). The reaction solution was sealed and stirred for 16 hours, then evaporated under reduced pressure. The residue was diluted with saturated aqueous sodium bicarbonate (20 mL) and extracted with ethyl acetate (30 mL×3). The organic phase was dried over anhydrous sodium sulfate and evaporated under reduced pressure. The residue was purified by silica gel column chromatography (dichloromethane:methanol=5:1) to give compound 21-e (670 mg, yield 76%). LC-MS (ESI): m/z=202 [M+H]$^+$.

Synthesis of Compound 21-d

4-Bromo-3-fluorobenzaldehyde (500 mg, 2.46 mmol) was dissolved in methanol (10 mL), followed by addition of sodium borohydride (465.9 mg, 12.31 mmol). The mixture was stirred at room temperature for 2 hours, then evaporated under reduced pressure. The residue was diluted with ethyl acetate (50 mL), washed with saturated brine (20 mL) and water (20 mL). The organic phase was dried over anhydrous sodium sulfate, filtered and evaporated under reduced pressure to give compound 21-d (501 mg, yield 99%), which was directly used in the next step without further purification.

$^1$H NMR (400 MHz, CDCl$_3$) δ: 7.54-7.50 (m, 1H), 7.17-7.12 (m, 1H), 7.03-7.01 (m, 1H), 4.67 (s, 2H), 1.90 (br, 1H) ppm.

Synthesis of Compound 21-c

Compound 21-d (501 mg, 2.69 mmol) was dissolved in tetrahydrofuran (20 mL), followed by addition of triphenylphosphine (1.06 g, 4.03 mmol) and carbon tetrabromide (1.52 g, 4.57 mmol). The reaction solution was stirred at room temperature for 12 hours, then evaporated under reduced pressure. The residue was diluted with ethyl acetate (50 mL), washed with saturated brine (20 mL) and water (20 mL). The organic phase was dried over anhydrous sodium sulfate, filtered and evaporated under reduced pressure. The residue was purified by silica gel column chromatography (petroleum ether:ethyl acetate=10:1) to give compound 21-c (810 mg, yield 99%).

$^1$H NMR (400 MHz, CDCl$_3$) δ: 7.54-7.50 (m, 1H), 7.18-7.16 (m, 1H), 7.07-7.05 (m, 1H), 4.41 (s, 2H) ppm.

Synthesis of Compound 21-b

Compound 21-c (723.4 mg, 2.7 mmol), compound 21-e (542 mg, 2.7 mmol) and diisopropylethylamine (871 mg, 6.74 mmol) were dissolved in acetonitrile (20 mL). The reaction solution was heated to 60° C. and stirred for 3 hours. Then the reaction solution was cooled to room temperature, and evaporated under reduced pressure. The residue was diluted with ethyl acetate (50 mL), washed with saturated brine (20 mL) and water (20 mL). The organic phase was dried over anhydrous sodium sulfate, filtered and evaporated under reduced pressure. The residue was purified by silica gel column chromatography (petroleum ether:ethyl acetate=5:1) to give compound 21-b (597 mg, yield 57.2%). LC-MS (ESI): m/z=388 [M+H]$^+$.

Synthesis of Compound 21-a

Compound 5-b (198 mg, 0.618 mmol) and 21-b (112 mg, 0.6 mmol) were dissolved in a mixed solvent of 1,4-dioxane (20 mL) and water (1 mL), followed by addition of [1,1'-bis(diphenylphosphino)ferrocene]palladium dichloride (45 mg, 0.05 mmol) and sodium carbonate (136.8 mg, 1.29 mmol). After the reaction system was purged three times with nitrogen, the reaction solution was heated to 80° C. and stirred for 16 hours. The reaction solution was cooled to room temperature, diluted with ethyl acetate (50 mL), washed with water (20 mL×3) and saturated brine (20 mL). The organic phase was dried over anhydrous sodium sulfate, filtered and evaporated under reduced pressure. The residue was purified by silica gel column chromatography (petroleum ether:ethyl acetate=3:1) to give compound 21-a (180 mg, yield 69.8%). LC-MS (ESI): m/z=502 [M+H]$^+$.

Synthesis of Compound 21

Compound 21-a (180 mg, 0.359 mmol) was dissolved in a mixed solvent of methanol (5 mL) and tetrahydrofuran (5 mL), followed by addition of 10% aqueous sodium hydroxide solution (3 mL). The reaction solution was stirred at room temperature for 16 hours, then evaporated under reduced pressure. The residue was diluted with water (20 mL), adjusted to pH 5 with citric acid and a white solid precipitated. The mixture was filtered, and the filter cake was washed with water (5 mL×2), then dried in vacuum to give 21 as a white solid (71 mg, yield 44.3%). LC-MS (ESI): m/z=446 [M+H]$^+$.

$^1$H NMR (400 MHz, CDCl$_3$) δ: 7.68 (t, 1H), 7.60-7.56 (m, 1H), 7.52 (s, 1H), 7.44-7.40 (m, 2H), 7.37-7.35 (m, 1H), 7.31-7.30 (m, 2H), 7.27-7.25 (m, 3H), 7.21-7.19 (m, 1H), 7.13-7.09 (d, J=16.4 Hz, 1H), 4.57-4.53 (d, J=13.2 Hz, 1H), 4.70-4.36 (d, J=13.6 Hz, 1H), 4.43 (s, 1H), 3.49-3.41 (m, 2H), 2.76-2.70 (m, 1H), 2.29 (s, 3H), 2.24-2.18 (m, 1H), 2.02-1.96 (m, 1H), 1.69-1.54 (m, 2H) ppm.

Embodiment 22

(E)-2-Hydroxymethyl-1-(3-methyl-4-(2-(2-methylbiphenyl-3-yl)vinyl)benzyl)piperidin-3-ol 22

Synthetic Route

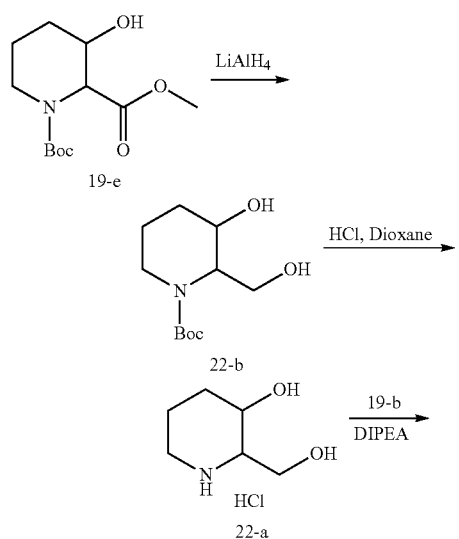

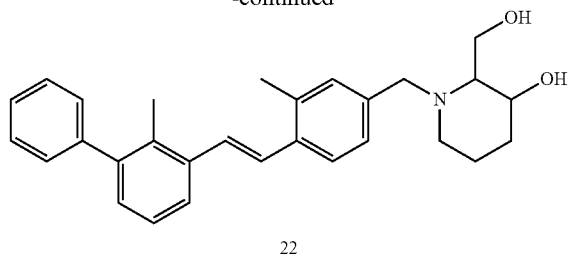

22

Synthesis of Compound 22-b

Compound 19-e (2.1 g, 8.11 mmol) was dissolved in anhydrous tetrahydrofuran (10 mL) and cooled to 0° C., followed by addition of a solution of lithium aluminium hydride in tetrahydrofuran (1.0 M, 16.5 mL, 16.5 mmol). The reaction solution was stirred at 0° C. for 2 hours. Then sodium sulfate decahydrate (10 g) was added to the reaction solution. After the mixture was stirred for 0.5 hour, anhydrous sodium sulfate (10 g) was added. The mixture was filtered, and the filter cake was washed with tetrahydrofuran (10 mL×3). The filtrate was evaporated under reduced pressure. The residue was purified by silica gel column chromatography (petroleum ether:ethyl acetate=1:1) to give compound 22-b (780 mg, yield 42%).

Synthesis of Compound 22-a

Compound 22-b (780 mg, 3.37 mmol) was dissolved in ethyl acetate (10 mL), followed by addition of a solution of hydrogen chloride in 1,4-dioxane (4.0M, 10 mL). The reaction solution was sealed and stirred at room temperature for 16 hours, then evaporated under reduced pressure to give compound 22-a (430 mg, yield 76%), which was directly used in the next step without further purification.

Synthesis of Compound 22

Compound 19-b (95 mg, 0.27 mmol), compound 22-a (72 mg, 0.43 mmol) and diisopropylethylamine (390 mg, 3 mmol) were dissolved in acetonitrile (5 mL). The reaction solution was heated to 60° C. and stirred for 5 hours. Then the reaction solution was cooled to room temperature, and evaporated under reduced pressure. The residue was purified by silica gel column chromatography (dichloromethane:methanol=10:1) to give compound 20 (70 mg, yield 57.4%). LC-MS (ESI): m/z=428 [M+H]$^+$.

$^1$H NMR (400 MHz, CD$_3$OD) δ: 7.76-7.78 (m, 1H), 7.64 (d, J=7.6 Hz, 1H), 7.27-7.48 (m, 10H), 7.17 (d, J=7.6 Hz, 1H), 4.08-4.62 (m, 5H), 3.32 (s, 2H), 2.88-2.96 (m, 1H), 2.52 (s, 3H), 2.30 (s, 3H), 1.68-1.89 (m, 4H) ppm.

Embodiment 23

(E)-2-Hydroxymethyl-1-(3-chloro-4-(2-(2-methylbiphenyl-3-yl)vinyl)benzyl) piperidin-3-ol 23

Synthetic Route

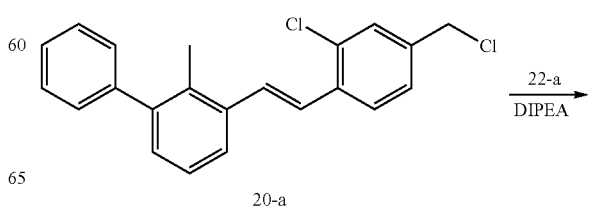

20-a

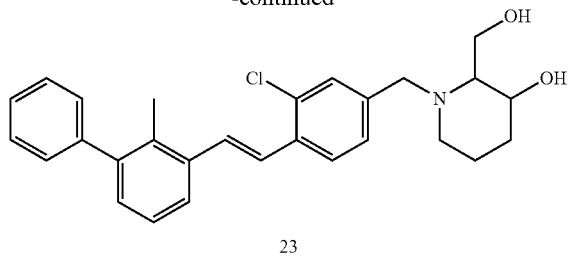

Synthesis of Compound 23

Compound 19-b (95 mg, 0.27 mmol), compound 22-a (67 mg, 0.40 mmol) and diisopropylethylamine (390 mg, 3 mmol) were dissolved in acetonitrile (5 mL). The reaction solution was heated to 60° C. and stirred for 16 hours. Then the reaction solution was cooled to room temperature, and evaporated under reduced pressure. The residue was purified by silica gel column chromatography (dichloromethane: methanol=10:1) to give compound 23 (25 mg, yield 20.8%). LC-MS (ESI): m/z=448 [M+H]$^+$.

$^1$H NMR (400 MHz, CD$_3$OD) δ: 7.92 (d, J=8.0 Hz, 1H), 7.59-7.67 (m, 3H), 7.28-7.52 (m, 8H), 7.19 (d, J=6.8 Hz, 1H), 4.89 (s, 1H), 4.07-4.60 (m, 4H), 3.10-3.33 (m, 2H), 2.53-2.98 (m, 1H), 2.31 (s, 1H), 1.63-1.94 (m, 4H) ppm.

Embodiment 24

(E)-1-(3-Fluoro-4-(2-(2-methylbiphenyl-3-yl)vinyl)benzyl)-3-hydroxypiperidin-2-carboxamide Synthetic Route

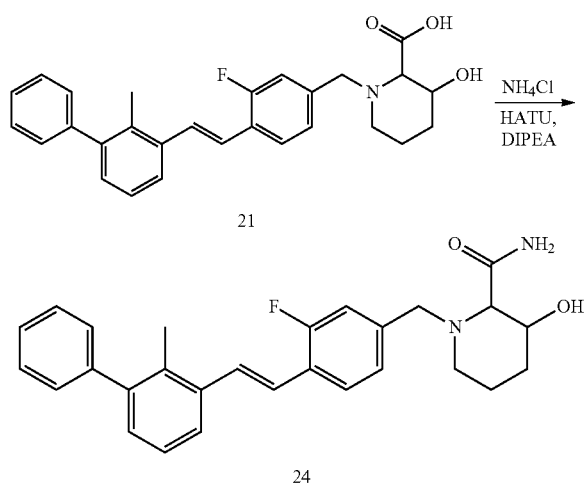

Synthesis of Compound 24

Compound 21 (45 mg, 0.101 mmol) was dissolved in N,N-dimethylformamide (2 mL), then ammonium chloride (27 mg, 0.505 mmol), 2-(7-azabenzotriazol)-N,N,N',N'-tetramethyluronium hexafluorophosphate (46 mg, 0.121 mmol) and diisopropylethylamine (39.2 mg, 0.303 mmol) were successively added. The reaction solution was stirred at room temperature for 16 hours, then evaporated under reduced pressure. The residue was purified by preparative silica gel thin layer chromatography (dichloromethane: methanol=10:1) to give compound 24 (8 mg, yield 17.8%). LC-MS (ESI): m/z=445 [M+H]$^+$.

$^1$H NMR (400 MHz, CDCl$_3$) δ: 7.62-7.56 (m, 2H), 7.51-7.47 (d, J=16.4 Hz, 1H), 7.44-7.41 (m, 2H), 7.37-7.35 (m, 1H), 7.32-7.29 (m, 2H), 7.20-7.18 (m, 1H), 7.15-7.11 (d, J=16.0 Hz, 1H), 7.10-7.06 (m, 3H), 5.62 (s, 1H), 4.09-4.04 (m, 2H), 3.97-3.94 (d, J=13.6 Hz, 1H), 3.65-3.62 (d, J=13.6 Hz, 1H), 3.30 (s, 1H), 2.88-2.83 (m, 1H), 2.47-2.41 (m, 1H), 2.30 (s, 3H), 1.86 (m, 1H), 1.73-1.67 (m, 4H) ppm.

Embodiment 25

(E)-Methyl 1-(2,6-dimethoxy-4-(2-(2-methylbiphenyl-3-yl)vinyl)benzyl)-3-hydroxypiperidin-2-carboxylate 25

Synthetic Route

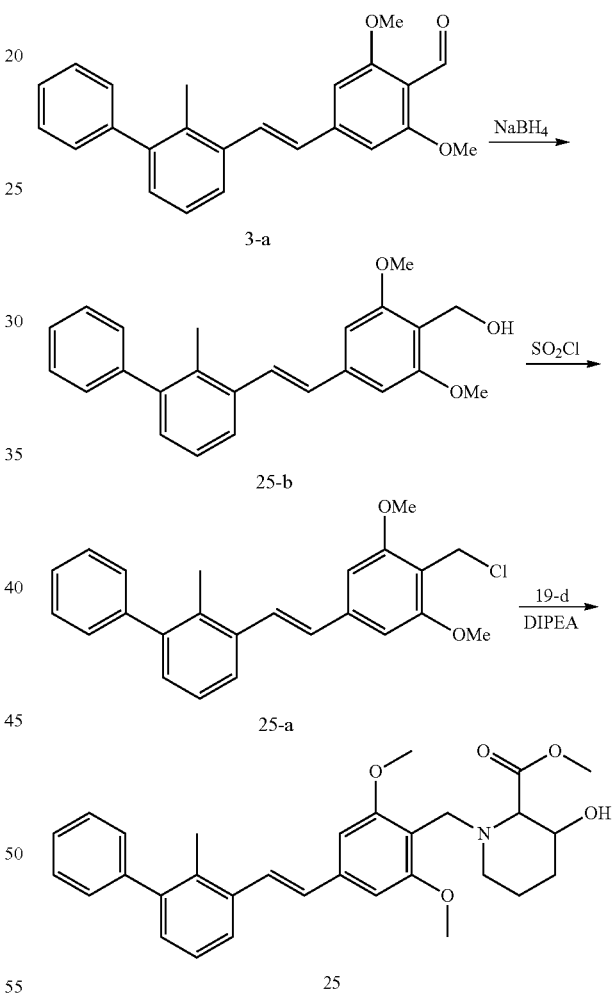

Synthesis of Compound 25-b

Compound 3-a (793 mg, 2.23 mmol) was dissolved in a mixed solvent of methanol (25 mL) and tetrahydrofuran (25 mL), followed by addition of sodium borohydride (423.7 mg, 11.2 mmol) in batches. The mixture was stirred at room temperature for 2 hours, then evaporated under reduced pressure. The residue was diluted with ethyl acetate (50 mL), washed with saturated brine (20 mL) and water (20 mL). The organic phase was dried over anhydrous sodium sulfate, filtered and evaporated under reduced pressure to give compound 25-b (754 mg, yield 94.8%), which was directly used in the next step without further purification. LC-MS (ESI): m/z=343 [M−H$_2$O]$^+$.

Synthesis of Compound 25-a

Compound 25-b (100 mg, 0.28 mmol) was dissolved in dichloromethane (25 mL), followed by addition of thionyl chloride (0.1 mL, 1.39 mmol). The reaction solution was stirred at room temperature for 2 hours, then evaporated under reduced pressure to give compound 25-a (105 mg, yield 98%), which was directly used in the next step without further purification.

Synthesis of Compound 25

Compound 25-a (105 mg, 0.28 mmol), compound 19-d (55 mg, 0.28 mmol) and diisopropylethylamine (181 mg, 1.4 mmol) were dissolved in acetonitrile (10 mL). The reaction solution was heated to 60° C. and stirred for 16 hours. Then the reaction solution was cooled to room temperature, and evaporated under reduced pressure. The residue was purified by silica gel column chromatography (dichloromethane: methanol=10:1) to give compound 25 (10 mg, yield 7.2%). LC-MS (ESI): m/z=502 [M+H]$^+$.

$^1$H NMR (400 MHz, CDCl$_3$) δ: 7.58-7.56 (m, 1H), 7.43-7.41 (m, 2H), 7.37-7.31 (m, 4H), 7.28-7.24 (m, 1H), 7.19-7.18 (m, 1H), 6.98-6.94 (d, J=16.0 Hz, 1H), 6.71 (s, 2H), 4.07-4.03 (d, J=13.2 Hz, 1H), 3.98-3.95 (d, J=13.2 Hz, 1H), 3.98 (m, 1H), 3.83 (s, 9H), 3.35 (m, 1H), 3.01 (m, 1H), 2.31 (s, 3H), 2.22-2.16 (m, 2H), 2.02-1.71 (m, 4H) ppm.

Embodiment 26 and 27

(2R,3S,E)-3-Hydroxy-1-(3-methyl-4-(2-(2-methylbiphenyl-3-yl)vinyl)benzyl)piperidin-2-carboxamide 26

(2R,3R,E)-3-Hydroxy-1-(3-methyl-4-(2-(2-methylbiphenyl-3-yl)vinyl)benzyl)piperidin-2-carboxamide 27

Synthetic Route

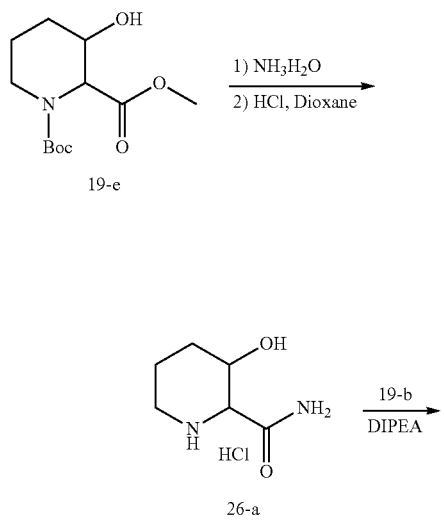

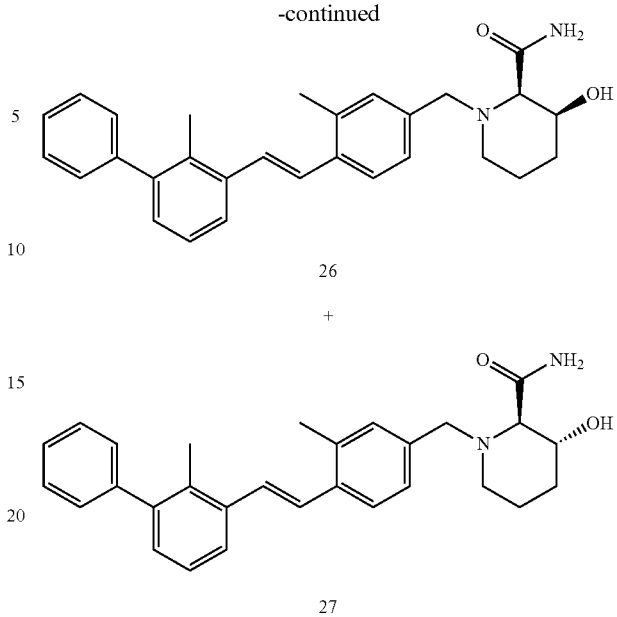

Synthesis of Compound 26-a

Compound 19-e (1.5 g, 5.79 mmol) and 30% aqueous ammonia (15 mL) were added to a sealed tube. The mixture was stirred at 70° C. for 24 hours, then cooled to room temperature and evaporated under reduced pressure. The residue was dissolved in ethyl acetate (10 mL), followed by addition of a solution of hydrogen chloride in dioxane (4M, 10 mL). The mixture was stirred at room temperature for 16 hours, then evaporated under reduced pressure. The residue was diluted with ethyl acetate (20 mL), stirred for 1 hour and filtered. The filter cake was washed with ethyl acetate (5 mL), dried in vacuum to give 26-a as a white solid (780 mg, yield 75%), which was directly used in the next step without further purification.

Synthesis of Compound 26 and 27

Compound 26-a (65 mg, 0.36 mmol), compound 19-b (80 mg, 0.26 mmol) and diisopropylethylamine (390 mg, 3 mmol) were dissolved in acetonitrile (5 mL). The reaction solution was heated to 90° C. and stirred for 16 hours. Then the reaction solution was cooled to room temperature, evaporated under reduced pressure. The residue was diluted with water (20 mL), extracted with ethyl acetate (25 mL×2). The organic phase was dried over anhydrous sodium sulfate, filtered and evaporated under reduced pressure. The residue was purified by preparative high performance liquid chromatography to give compound 26 (5 mg, yield 5%) and compound 27 (23 mg, yield 25%). LC-MS (ESI): m/z=441 [M+H]$^+$.

Compound 26: LC-MS (ESI): m/z=441 [M+H]$^+$.

$^1$H-NMR (400 MHz, CDCl$_3$) δ: 7.58 (d, J=8 Hz, 2H), 7.42 (m, 2H), 7.32 (m, 4H), 7.26 (m, 1H), 7.09-7.20 (m, 4H), 6.85 (br, 1H), 5.55 (br, 1H), 3.92 (d, J=14 Hz, 1H), 3.69 (m, 1H), 3.28 (d, J=14 Hz, 1H), 2.95 (m, 2H), 2.72 (d, J=8 Hz, 1H), 2.43 (s, 3H), 2.29 (s, 3H), 2.08 (m, 2H) ppm.

Compound 27: LC-MS (ESI): m/z=441 [M+H]$^+$.

$^1$H-NMR (400 MHz, CDCl$_3$) δ: 7.58 (d, J=8 Hz, 2H), 7.42 (m, 2H), 7.32 (m, 4H), 7.27 (m, 1H), 7.16-7.20 (m, 4H), 7.12 (br, 1H), 5.63 (br, 1H), 4.26 (m, 1H), 4.03 (m, 1H), 3.94 (d, J=14 Hz, 1H), 3.62 (d, J=14 Hz, 1H), 3.61 (d, J=4 Hz, 1H), 2.86 (m, 1H), 2.49 (m, 1H), 2.43 (s, 3H), 2.29 (s, 3H), 1.92 (m, 1H) ppm.

Embodiment 28

1-(3-Methyl-4-((2-methylbiphenyl-3-yl)ethynyl)benzyl)-3-hydroxypiperidine-2-carboxylic Acid 28

Synthetic Route

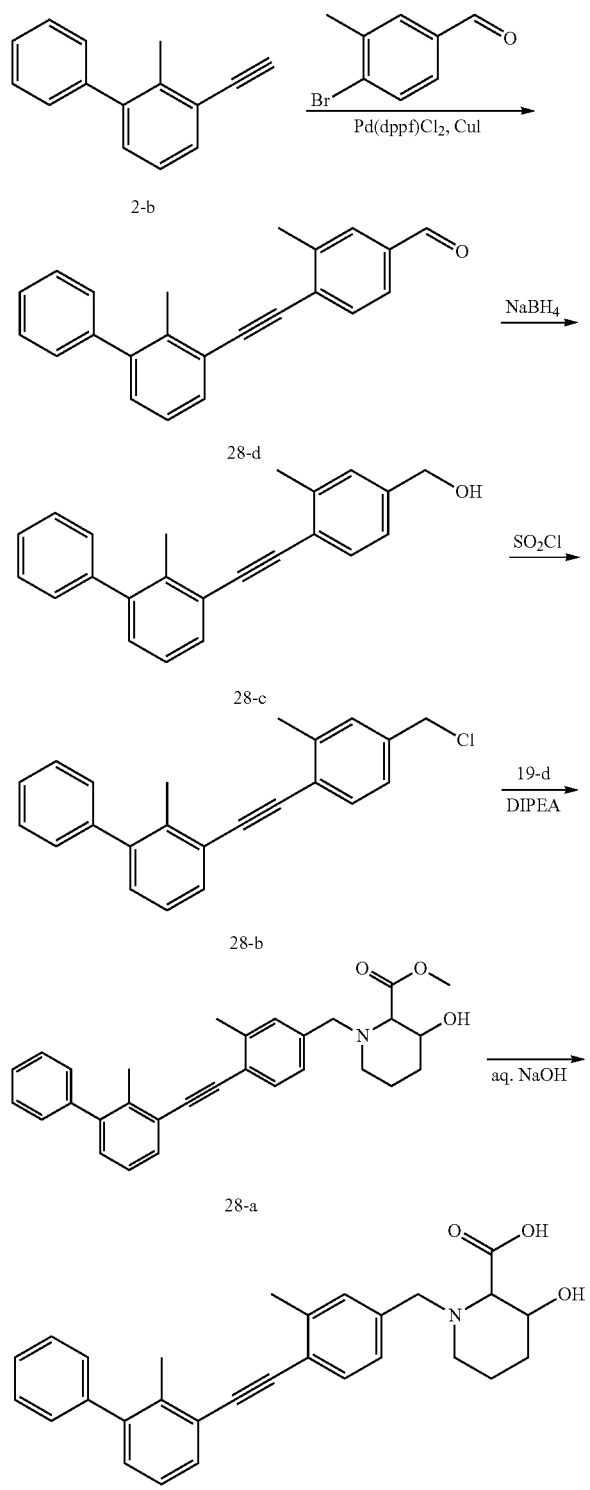

Synthesis of Compound 28-d

[1,1'-Bis(diphenylphosphino)ferrocene]palladium dichloride (91.3 mg, 0.13 mmol) and cuprous iodide (49.5 mg, 0.26 mmol) were added to a mixed solution of compound 2-b (500 mg, 2.6 mmol) and 3-methyl-4-bromobenzaldehyde (517.5 mg, 2.6 mmol) in N,N-dimethylformamide (8 mL) and triethylamine (2 mL). After the reaction system was purged three times with nitrogen, the reaction solution was heated to 80° C. and stirred for 16 hours. The reaction solution was diluted with ethyl acetate (200 mL), washed successively with water (20 mL×3) and saturated brine (20 mL). The organic phase was dried over anhydrous sodium sulfate and evaporated under reduced pressure. The residue was purified by silica gel column chromatography (petroleum ether:ethyl acetate=10:1) to give compound 28-d (410 mg, yield 50.8%).

$^1$H NMR (400 MHz, CDCl$_3$) δ: 9.99 (s, 1H), 7.76-7.66 (m, 4H), 7.56-7.53 (m, 2H), 7.48-7.42 (m, 2H), 7.39-7.37 (m, 1H), 7.33-7.31 (m, 2H), 2.61 (s, 3H), 2.46 (s, 3H) ppm.

Synthesis of Compound 28-c

Compound 28-d (410 mg, 1.32 mmol) was dissolved in a mixed solvent of methanol (10 mL) and tetrahydrofuran (10 mL), followed by addition of sodium borohydride (250 mg, 6.61 mmol) in batches. The mixture was stirred at room temperature for 2 hours, then evaporated under reduced pressure. The residue was diluted with ethyl acetate (50 mL), washed with saturated brine (20 mL) and water (20 mL). The organic phase was dried over anhydrous sodium sulfate, filtered and evaporated under reduced pressure to give compound 28-c (315 mg, yield 76.8%), which was directly used in the next step without further purification.

Synthesis of Compound 28-b

Compound 28-c (100 mg, 0.32 mmol) was dissolved in dichloromethane (10 mL), followed by addition of thionyl chloride (0.2 mL, 1.60 mmol). The reaction solution was stirred at room temperature for 2 hours, then evaporated under reduced pressure to give compound 28-b (106 mg, yield 98%), which was directly used in the next step without further purification.

Synthesis of Compound 28-a

Compound 28-b (106 mg, 0.32 mmol), compound 19-d (62.6 mg, 0.32 mmol) and diisopropylethylamine (206.8 mg, 1.60 mmol) were dissolved in acetonitrile (10 mL). The reaction solution was heated to 60° C. and stirred for 16 hours. Then the reaction solution was cooled to room temperature, and evaporated under reduced pressure. The residue was purified by preparative silica gel thin layer chromatography (dichloromethane:methanol=20:1) to give compound 28-a (137 mg, yield 93.8%). LC-MS (ESI): m/z=454 [M+H]$^+$.

Synthesis of Compound 28

Compound 28-a (137 mg, 0.302 mmol) was dissolved in a mixed solvent of methanol (6 mL) and tetrahydrofuran (6 mL), followed by addition of 10% aqueous sodium hydroxide solution (0.6 mL, 0.604 mmol). The reaction solution was stirred at room temperature for 3 hours, then evaporated under reduced pressure. The residue was diluted with water (20 mL) and adjusted to pH 4 with 1M hydrochloric acid, then extracted with ethyl acetate (15 mL×3). The organic phase was washed with saturated brine (15 mL), dried over anhydrous sodium sulfate, filtered and evaporated under reduced pressure. The residue was purified by preparative silica gel thin layer chromatography (dichloromethane:methanol=10:1) to give compound 28 (124 mg, yield 93.2%). LC-MS (ESI): m/z=440 [M+H]$^+$.

$^1$H NMR (400 MHz, CD$_3$OD) δ: 7.49-7.47 (m, 1H), 7.43-7.42 (m, 1H), 7.38 (s, 1H), 7.35-7.32 (m, 2H), 7.28-

7.26 (m, 2H), 7.22-7.18 (m, 2H), 7.16-7.11 (m, 2H), 4.46-4.43 (d, J=16 Hz, 1H), 4.28-4.25 (d, J=16 Hz, 1H), 4.28 (s, 1H), 3.36 (s, 1H), 2.83 (t, 1H), 2.73-2.67 (q, 1H), 2.46 (s, 3H), 2.32 (s, 3H), 2.07-2.04 (m, 1H), 1.80-1.77 (m, 1H), 1.55 (m, 2H) ppm.

Embodiment 29

1-(3-Fluoro-4-((2-methylbiphenyl-3-yl)ethynyl)benzyl)-3-hydroxypiperidin-2-carboxylic Acid 29

Synthetic Route

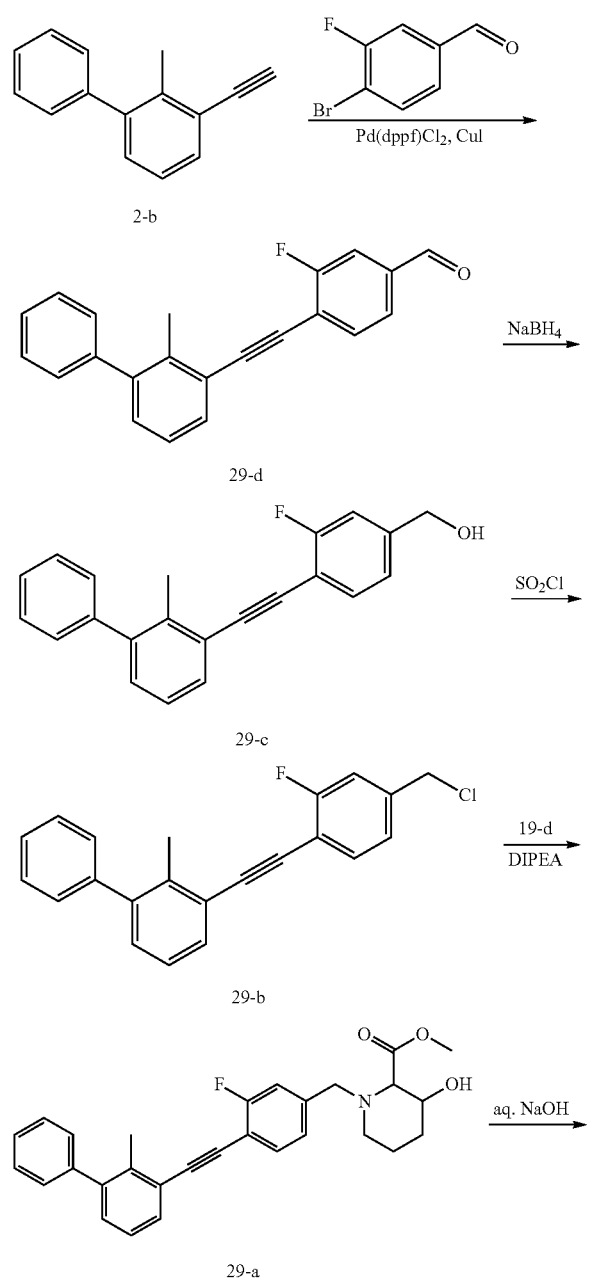

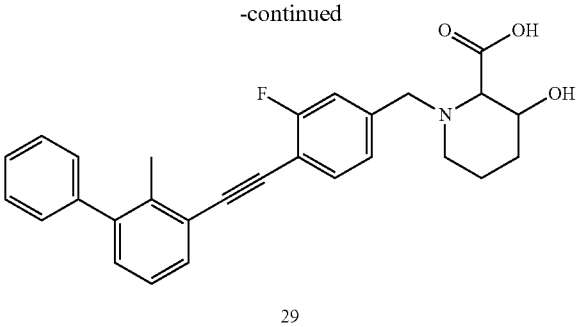

Synthesis of Compound 29-d

[1,1'-Bis(diphenylphosphino)ferrocene]palladium dichloride (91.3 mg, 0.13 mmol) and cuprous iodide (49.5 mg, 0.26 mmol) were added to a mixed solution of compound 2-b (500 mg, 2.6 mmol) and 3-fluoro-4-bromobenzaldehyde (527.8 mg, 2.6 mmol) in N,N-dimethylformamide (16 mL) and triethylamine (4 mL). After the reaction system was purged three times with nitrogen, the reaction solution was heated to 80° C. and stirred for 16 hours. The reaction solution was cooled to room temperature, diluted with ethyl acetate (200 mL), washed successively with water (20 mL×3) and saturated brine (20 mL). The organic phase was dried over anhydrous sodium sulfate and evaporated under reduced pressure. The residue was purified by silica gel column chromatography (petroleum ether:ethyl acetate=10:1) to give compound 29-d (286 mg, yield 35.1%).

$^1$H NMR (400 MHz, CDCl$_3$) δ: 9.98 (s, 1H), 7.71-7.65 (m, 2H), 7.63-7.60 (m, 1H), 7.58-7.56 (m, 1H), 7.45-7.42 (m, 2H), 7.39-7.37 (m, 1H), 7.32-7.30 (m, 2H), 7.27-7.25 (m, 2H), 2.46 (s, 3H) ppm.

Synthesis of Compound 29-c

Compound 29-d (346 mg, 1.1 mmol) was dissolved in a mixed solvent of methanol (10 mL) and tetrahydrofuran (10 mL), followed by addition of sodium borohydride (208 mg, 5.5 mmol) in batches. The mixture was stirred at room temperature for 2 hours, then evaporated under reduced pressure. The residue was diluted with ethyl acetate (50 mL), washed with saturated brine (20 mL) and water (20 mL). The organic phase was dried over anhydrous sodium sulfate, filtered and evaporated under reduced pressure to give 29-c (313 mg, yield 90.5%), which was directly used in the next step without further purification.

Synthesis of Compound 29-b

Compound 29-c (100 mg, 0.32 mmol) was dissolved in dichloromethane (10 mL), followed by addition of thionyl chloride (0.2 mL, 1.60 mmol). The reaction solution was stirred at room temperature for 2 hours, then evaporated under reduced pressure to give compound 29-b (106 mg, yield 98%), which was directly used in the next step without further purification.

Synthesis of Compound 29-a

Compound 29-b (106 mg, 0.32 mmol), compound 19-d (61.8 mg, 0.316 mmol and diisopropylethylamine (204.2 mg, 1.58 mmol) were dissolved in acetonitrile (10 mL). The reaction solution was heated to 60° C. and stirred for 16 hours. Then the reaction solution was cooled to room temperature, and evaporated under reduced pressure. The residue was purified by preparative silica gel thin layer chromatography (dichloromethane:methanol=20:1) to give compound 29-a (130 mg, yield 89.6%). LC-MS (ESI): m/z=454 [M+H]$^+$.

Synthesis of Compound 29

Compound 29-a (115 mg, 0.25 mmol) was dissolved in a mixed solvent of methanol (6 mL) and tetrahydrofuran (6 mL), followed by addition of 10% aqueous sodium hydroxide solution (50.4 mg, 0.5 mmol). The reaction solution was stirred at room temperature for 3 hours, then evaporated under reduced pressure. The residue was diluted with water (20 mL) and adjusted to pH 4 with 1M hydrochloric acid, then extracted with ethyl acetate (15 mL×3). The organic phase was washed with saturated brine (15 mL), dried over anhydrous sodium sulfate, filtered and evaporated under reduced pressure. The residue was purified by preparative silica gel thin layer chromatography (dichloromethane:methanol=10:1) to give compound 29 (109 mg, yield 97.8%). LC-MS (ESI): m/z=444 [M+H]$^+$.

$^1$H NMR (400 MHz, CDCl$_3$) δ: 7.56-7.53 (m, 1H), 7.44-7.41 (m, 1H), 7.36-7.32 (m, 3H), 7.29-7.27 (m, 2H), 7.22-7.20 (m, 2H), 7.18-7.13 (m, 2H), 4.51-4.48 (d, J=12.8 Hz, 1H), 4.28 (m, 1H), 4.24-4.21 (d, J=12.8 Hz, 1H), 3.39 (s, 1H), 2.83 (m, 1H), 2.73-2.67 (m, 1H), 2.31 (s, 3H), 2.06-2.03 (m, 1H), 1.81-1.78 (m, 1H), 1.60-1.54 (m, 2H) ppm.

Embodiment 30

(E)-1-(2,6-Dimethoxy-4-(2-(2-methylbiphenyl-3-yl)vinyl)benzyl)-3-hydroxy piperidin-2-carboxylic Acid 30

Synthetic Route

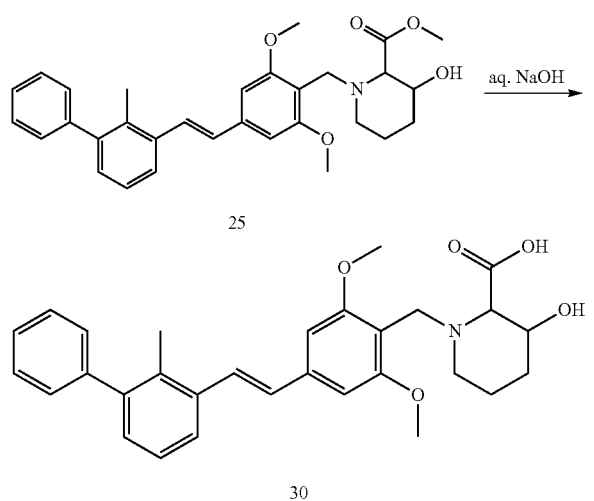

Synthesis of Compound 30

Compound 25 (154 mg, 0.307 mmol) was dissolved in a mixed solvent of methanol (6 mL) and tetrahydrofuran (6 mL), followed by addition of 10% aqueous sodium hydroxide solution (2.0 mL, 1.54 mmol). The reaction solution was stirred at room temperature for 16 hours, then evaporated under reduced pressure. The residue was diluted with water (20 mL) and adjusted to pH 5 with citric acid, then a white solid precipitated. The mixture was filtered and the filter cake was washed with water (5 mL×3), dried in vacuum to give compound 30 (27 mg, yield 17.5%). LC-MS (ESI): m/z=488 [M+H]$^+$.

$^1$H NMR (400 MHz, CDCl$_3$) δ: 7.58-7.56 (m, 1H), 7.46-7.41 (m, 3H), 7.38-7.36 (m, 1H), 7.32-7.30 (m, 2H), 7.26-7.25 (m, 1H), 7.21-7.20 (m, 1H), 6.98-6.94 (d, J=16 Hz, 1H), 6.73 (s, 2H), 4.63 (s, 2H), 4.32 (s, 1H), 3.94 (s, 6H), 3.61 (s, 1H), 3.52 (br, 1H), 2.80-2.79 (br, 1H), 2.31 (s, 3H), 2.02-2.00 (m, 1H), 1.88-1.59 (m, 4H) ppm.

Embodiment 31

(E)-2-(3-Methyl-4-(2-(2-methylbiphenyl-3-yl)vinyl)benzylamino)-1,3-propanediol 31

Synthetic Route

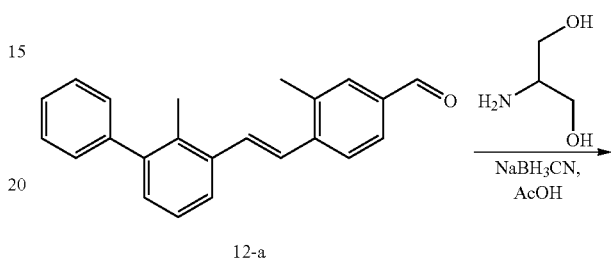

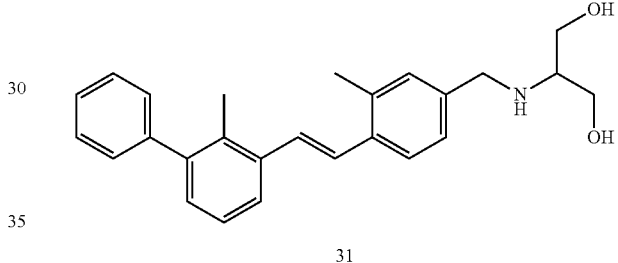

Synthesis of Compound 31

Compound 12-a (40 mg, 0.13 mmol) and 2-amino-1,3-propanediol (11.67 mg, 0.13 mmol) were dissolved in a mixed solvent of methanol (1 mL) and dichloromethane (1 mL), followed by addition of glacial acetic acid (15.38 mg, 0.27 mmol). The reaction solution was stirred at room temperature for 1 hour. Then sodium cyanoborohydride (40.23 mg, 0.64 mmol) was added and the resulting mixture was stirred for another 16 hours. The reaction solution was evaporated under reduced pressure, and the residue was diluted with ethyl acetate (10 mL), washed with saturated aqueous sodium bicarbonate solution (20 mL×2). The organic phase was evaporated under reduced pressure. Petroleum ether (7.5 mL) and ethyl acetate (2.5 mL) were added to the residue, then the mixture was stirred for 1 hour and filtered. The filter cake was dried in vacuum to give compound 31 (21 mg, yield 42.32%). LC-MS (ESI): m/z=388 [M+H]$^+$.

$^1$H NMR (400 MHz, CDCl$_3$) δ: 7.593-7.575 (d, J=7.2 Hz, 1H), 7.439-7.402 (m, 2H), 7.367-7.350 (m, 4H), 7.323-7.290 (m, 2H), 7.205-7.173 (m, 4H), 3.836 (s, 2H), 3.788-3.750 (m, 2H), 3.645-3.605 (m, 2H), 2.867-2.843 (m, 1H), 2.435 (s, 3H), 2.294 (s, 3H) ppm.

Embodiment 32

(E)-2-(3-Chloro-4-(2-(2-methylbiphenyl-3-yl)vinyl)benzylamino)-1,3-propanediol 32

Synthetic Route

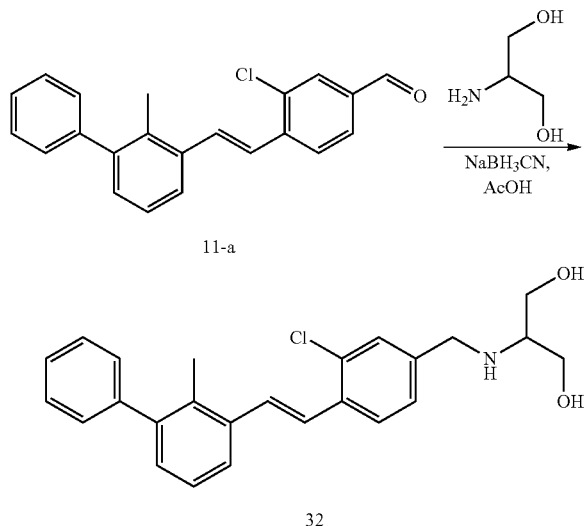

Synthesis of Compound 32

Compound 11-a (50 mg, 0.15 mmol) and 2-amino-1,3-propanediol (13.63 mg, 0.15 mmol) were dissolved in a mixed solvent of methanol (1 mL) and dichloromethane (1 mL), followed by addition of glacial acetic acid (18.04 mg, 0.30 mmol). The reaction solution was stirred at room temperature for 1 hour. Then sodium cyanoborohydride (47.20 mg, 0.75 mmol) was added and the resulting mixture was stirred for another 16 hours. The reaction solution was evaporated under reduced pressure, and the residue was diluted with ethyl acetate (10 mL), washed with saturated aqueous sodium bicarbonate solution (20 mL×2). The organic phase was evaporated under reduced pressure. Petroleum ether (7.5 mL) and ethyl acetate (2.5 mL) were added to the residue, then the mixture was stirred for 1 hour and filtered. The filter cake was dried in vacuum to give compound 32 (15 mg, yield 24.48%). LC-MS (ESI): m/z=408 [M+H]$^+$.

$^1$H NMR (400 MHz, CDCl$_3$) δ: 7.680-7.619 (m, 2H), 7.442-7.281 (m, 10H), 7.207-7.188 (m, 1H), 3.847 (s, 3H), 3.786-3.748 (m, 2H), 3.655-3.616 (m, 2H), 2.844-2.822 (m, 1H), 2.303 (s, 3H) ppm.

Embodiment 33

(S,E)-2-(3-Chloro-4-(2-(2-methylbiphenyl-3-yl)vinyl)benzylamino)-3-hydroxypropanamide 33

Synthetic Route

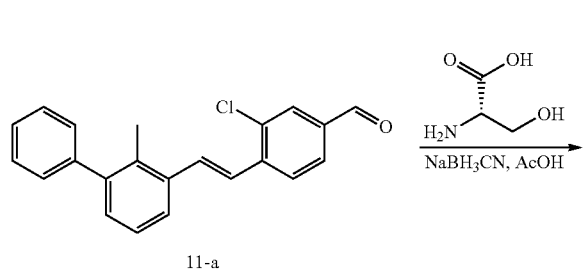

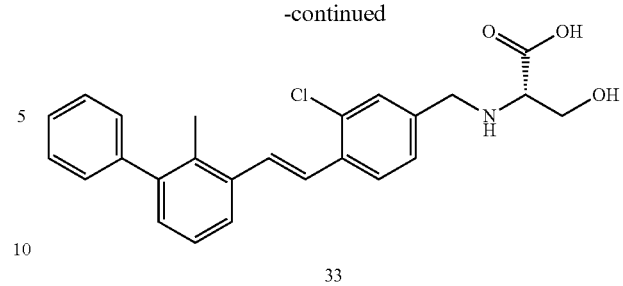

Synthesis of Compound 33

Compound 11-a (50 mg, 0.15 mmol) and L-serine (31.58 mg, 0.30 mmol) were dissolved in a mixed solvent of methanol (1 mL) and dichloromethane (1 mL), followed by addition of glacial acetic acid (18.04 mg, 0.30 mmol). The reaction solution was stirred at room temperature for 1 hour. Then sodium cyanoborohydride (47.20 mg, 0.75 mmol) was added and the resulting mixture was stirred for another 16 hours. The reaction solution was evaporated under reduced pressure, and the residue was diluted with ethyl acetate (10 mL), washed with saturated aqueous sodium bicarbonate solution (20 mL×2). The organic phase was evaporated under reduced pressure. The residue was purified by high performance liquid chromatography (mobile phase: water (10 mM ammonium bicarbonate), acetonitrile; gradient: 25%-55%) to give compound 33 (10 mg, yield 15.78%). LC-MS (ESI): m/z=421.9 [M+H]$^+$.

$^1$H NMR (400 MHz, CDCl$_3$) δ: 7.932-7.912 (d, J=8 Hz, 1H), 7.657-7.638 (m, 1H), 7.588-7.548 (m, 2H), 7.512-7.367 (m, 4H), 7.331-7.283 (m, 4H), 7.182-7.164 (m, 1H), 3.986-3.951 (m, 1H), 3.884-3.849 (m, 1H), 3.682-3.553 (m, 2H), 3.356-3.290 (m, 1H), 2.274 (s, 3H) ppm.

Embodiment 34

(R,E)-2-(3-Chloro-4-(2-(2-methylbiphenyl-3-yl)vinyl)benzylamino)-3-hydroxypropionamide 34

Synthetic Route

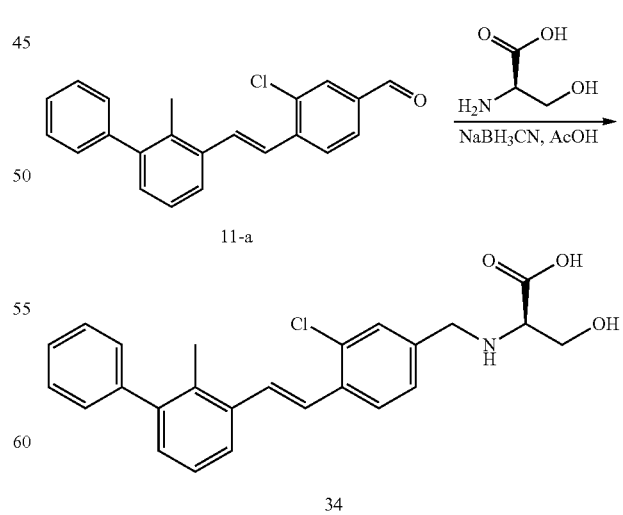

Synthesis of Compound 34

Compound 11-a (50 mg, 0.15 mmol) and D-serine (31.58 mg, 0.30 mmol) were dissolved in a mixed solvent of methanol (1 mL) and dichloromethane (1 mL), followed by addition of glacial acetic acid (18.04 mg, 0.30 mmol). The reaction solution was stirred at room temperature for 1 hour. Then sodium cyanoborohydride (47.20 mg, 0.75 mmol) was added and the resulting mixture was stirred for another 16 hours. The reaction solution was evaporated under reduced pressure, and the residue was diluted with ethyl acetate (10 mL), washed with saturated aqueous sodium bicarbonate solution (20 mL×2). The organic phase was evaporated under reduced pressure. The residue was purified by high performance liquid chromatography (mobile phase: water (10 mM ammonium bicarbonate), acetonitrile; gradient: 25%-55%) to give compound 34 (9 mg, yield 14.2%). LC-MS (ESI): m/z=422 [M+H]$^+$.

$^1$H NMR (400 MHz, CDCl$_3$) δ: 7.935-7.918 (d, J=6.8 Hz, 1H), 7.662-7.648 (m, 1H), 7.590-7.558 (m, 2H), 7.485-7.456 (m, 2H), 7.411-7.379 (m, 2H), 7.338-7.296 (m, 4H), 7.189-7.173 (m, 1H), 3.986-3.958 (m, 1H), 3.878-3.850 (m, 2H), 3.688-3.612 (m, 1H), 2.283 (s, 3H) ppm.

Embodiment 35

(R,E)-2-(4-Chloro-3-(2-(2-methylbiphenyl-3-yl) vinyl)benzylamino)-3-hydroxypropionic Acid 35

Synthetic Route

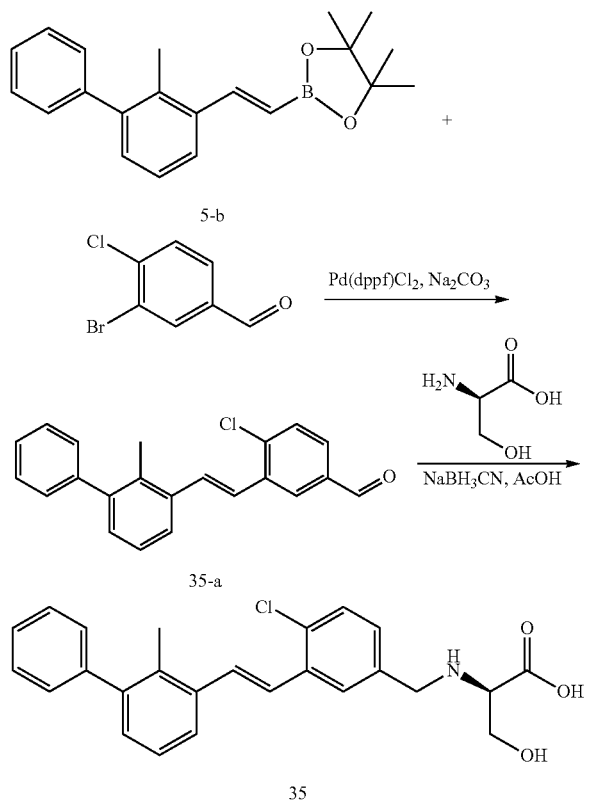

Synthesis of Compound 35-a

Compound 5-b (300 mg, 0.93 mmol) and 3-bromo-4-chlorobenzaldehyde (205 mg, 0.93 mmol) were dissolved in a mixed solvent of 1,4-dioxane (10 mL) and water (3 mL), followed by addition of [1,1'-bis(diphenylphosphino)ferrocene]palladium dichloride (68.04 mg, 0.093 mmol) and sodium carbonate (295.71 mg, 2.79 mmol). After the reaction system was purged three times with nitrogen, the reaction solution was heated to 90° C. and stirred for 16 hours. The reaction solution was cooled to room temperature, diluted with ethyl acetate (20 mL), washed successively with water (20 mL) and saturated brine (20 mL×2). The obtained organic phase was dried over anhydrous sodium sulfate and evaporated under reduced pressure. The residue was purified by silica gel column chromatography (petroleum ether:ethyl acetate=20:1) to give compound 35-a (90 mg, yield 28.87%).

Synthesis of Compound 35

Compound 35-a (90 mg, 0.27 mmol) and D-serine (56.84 mg, 0.54 mmol) were dissolved in a mixed solvent of methanol (1 mL) and dichloromethane (1 mL), followed by addition of glacial acetic acid (32.48 mg, 0.54 mmol). The reaction solution was stirred at room temperature for 1 hour. Then sodium cyanoborohydride (84.97 mg, 1.35 mmol) was added and the resulting mixture was stirred for another 16 hours. The reaction solution was evaporated under reduced pressure, and the residue was diluted with ethyl acetate (10 mL), washed with saturated aqueous sodium bicarbonate solution (20 mL×2). The organic phase was evaporated under reduced pressure. Petroleum ether (7.5 mL) and ethyl acetate (2.5 mL) were added to the residue, then the mixture was stirred for 1 hour and filtered. The filter cake was dried in vacuum to give compound 35 (9 mg, yield 8.76%). LC-MS (ESI): m/z=421.9 [M+H]$^+$.

$^1$H NMR (400 MHz, CDCl$_3$) δ: 7.964 (s, 1H), 7.658-7.642 (d, J=6.4 Hz, 1H), 7.574-7.541 (m, 1H), 7.490-7.448 (m, 3H), 7.385-7.298 (m, 6H), 7.186-7.171 (d, J=6 Hz, 1H), 4.029-3.902 (d, J=10.8 Hz, 2H), 3.684-3.613 (m, 2H), 3.179-3.159 (m, 1H), 2.286 (s, 3H) ppm.

Embodiment 36

(R,E)-2-(4-Methyl-3-(2-(2-methylbiphenyl-3-yl) vinyl)benzylamino)-3-hydroxypropionic Acid 36

Synthetic Route

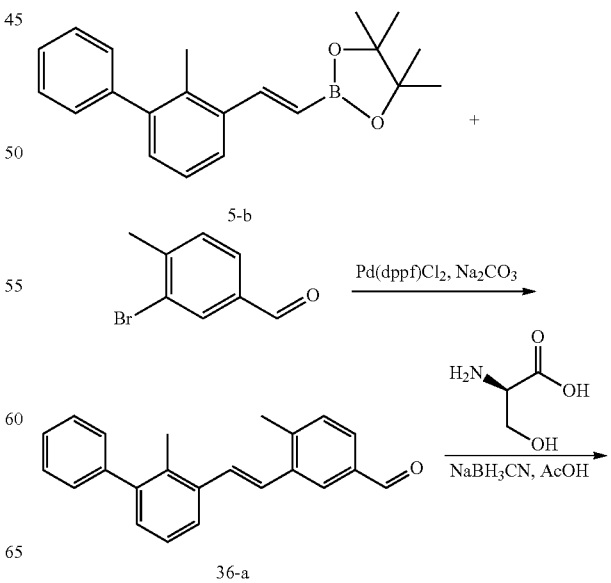

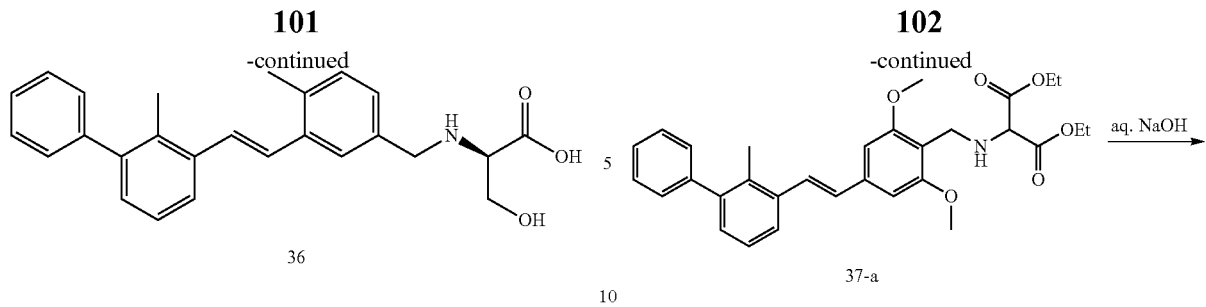

Synthesis of Compound 36-a

Compound 5-b (300 mg, 0.94 mmol) and 3-bromo-4-methylbenzaldehyde (155.3 mg, 0.78 mmol) were dissolved in a mixed solvent of 1,4-dioxane (20 mL) and water (1 mL), followed by addition of [1,1'-bis(diphenylphosphino)ferrocene]palladium dichloride (67.5 mg, 0.078 mmol) and sodium carbonate (206.7 mg, 1.95 mmol). After the reaction system was purged three times with nitrogen, the reaction solution was heated to 80° C. and stirred for 16 hours. The reaction solution was cooled to room temperature, diluted with ethyl acetate (100 mL), washed successively with water (50 mL×3) and saturated brine (50 mL). The organic phase was dried over anhydrous sodium sulfate and evaporated under reduced pressure. The residue was purified by silica gel column chromatography (petroleum ether:ethyl acetate=15:1) to give compound 36-a (374 mg, yield 97%).

Synthesis of Compound 36

Compound 36-a (100 mg, 0.32 mmol) and D-serine (67.3 mg, 0.64 mmol) were dissolved in a mixed solvent of methanol (3 mL) and dichloromethane (3 mL), followed by addition of glacial acetic acid (38.4 mg, 0.64 mmol). The reaction solution was stirred at room temperature for 1 hour. Then sodium cyanoborohydride (100.5 mg, 1.6 mmol) was added and the resulting mixture was stirred for another 16 hours. The reaction solution was evaporated under reduced pressure, and the residue was diluted with ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (petroleum ether:ethyl acetate=15:1) to give compound 35 (17 mg, yield 13.2%). LC-MS (ESI): m/z=402 [M+H]$^+$.

$^1$H NMR (400 MHz, DMSO-d$_6$) δ: 7.81 (s, 1H), 7.70-7.68 (m, 1H), 7.48-7.45 (m, 2H), 7.41-7.37 (m, 2H), 7.33-7.26 (m, 5H), 7.22-7.21 (m, 1H), 7.16-7.14 (m, 1H), 4.09-4.01 (m, 2H), 3.75-3.73 (m, 1H), 3.70-3.66 (m, 1H), 3.21-3.20 (m, 1H), 2.40 (s, 3H), 2.27 (s, 3H) ppm.

Embodiment 37

(E)-2-(2,6-Dimethoxy-4-(2-(2-methylbiphenyl-3-yl)vinyl)benzylamino)acetic Acid 37

Synthetic Route

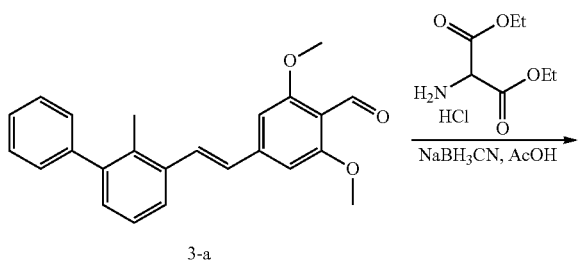

Synthesis of Compound 37-a

Compound 3-a (100 mg, 0.28 mmol) and diethyl aminomalonate hydrochloride (118.5 mg, 0.56 mmol) were dissolved in a mixed solvent of methanol (5 mL) and dichloromethane (5 mL), followed by addition of glacial acetic acid (33.6 mg, 0.56 mmol). The reaction solution was stirred at room temperature for 1 hour. Then sodium cyanoborohydride (88 mg, 1.4 mmol) was added and the resulting mixture was stirred for another 16 hours. The reaction solution was evaporated under reduced pressure, and the residue was diluted with ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (petroleum ether:ethyl acetate=15:1) to give compound 37-a (92 mg, yield 63.7%). LC-MS (ESI): m/z=518 [M+H]$^+$.

Synthesis of Compound 37

Compound 37-a (154 mg, 0.307 mmol) was dissolved in a mixed solvent of methanol (3 mL) and tetrahydrofuran (3 mL), followed by addition of 10% aqueous sodium hydroxide solution (72 mg, 1.8 mmol). The reaction solution was stirred at room temperature for 3 hours, then evaporated under reduced pressure. The residue was diluted with water (20 mL) and adjusted to pH 5 with citric acid, then a white solid precipitated. The mixture was filtered and the filter cake was washed with water (5 mL×3), dried in vacuum to give compound 37 (40 mg, yield 54.1%). LC-MS (ESI): m/z=416 [M−H]$^+$.

$^1$H NMR (400 MHz, CDCl$_3$) δ: 7.57-7.55 (m, 1H), 7.44-7.35 (m, 4H), 7.32-7.30 (m, 2H), 7.26-7.24 (m, 1H), 7.20-7.18 (m, 1H), 6.95-6.92 (d, J=12.8 Hz, 1H), 6.69 (s, 2H), 4.28 (s, 2H), 3.91 (s, 6H), 3.40 (s, 2H), 2.30 (s, 3H) ppm.

Embodiment 38

(R,E)-2-(3-Methyl-4-(2-(2-methylbiphenyl-3-yl)vinyl)benzylamino)-3-hydroxypropionic Acid 38

Synthetic Route

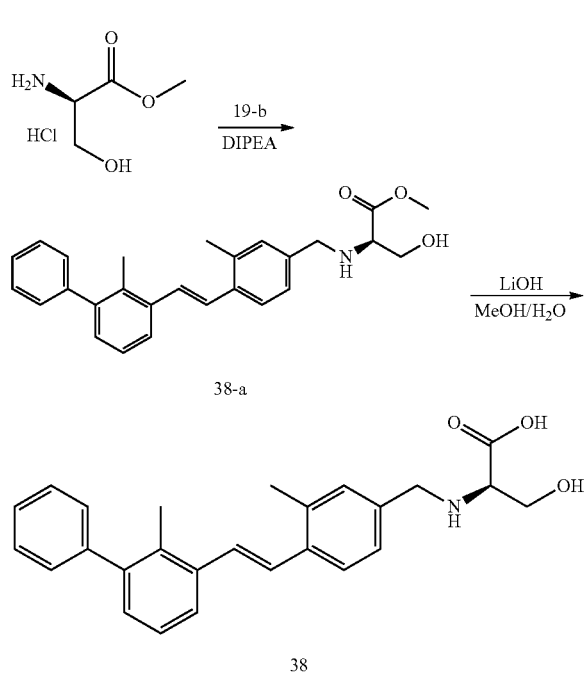

Synthesis of Compound 38-a

Compound 19-b (100 mg, 0.30 mmol), (R)-methyl 2-amino-3-hydroxypropanoate (53.7 mg, 0.45 mmol) and diisopropylethylamine (116 mg, 0.9 mmol) were dissolved in acetonitrile (5 mL). The reaction solution was heated to 90° C. and stirred for 16 h. Then the reaction solution was cooled to room temperature and evaporated under reduced pressure. The residue was purified by silica gel column chromatography (petroleum ether:ethyl acetate=10:1 to 2:1) to give compound 38-a (65 mg, yield 52.07%).

Synthesis of Compound 38

Compound 38-a (65 mg, 0.156 mmol) and lithium hydroxide (18.73 mg, 0.782 mmol) were dissolved in a mixed solvent of methanol (2 mL) and water (2 mL). The reaction solution was stirred at room temperature for 4 hours, then evaporated under reduced pressure to remove methanol. The residue was adjusted to pH 5.0 with aqueous hydrochloric acid solution (1.0M), then a white solid precipitated. The mixture was filtered and the filter cake was washed with water (5 mL×2), dried in vacuum to give compound 38 (20 mg, yield 31.84%). LC-MS (ESI): m/z=402 [M+H]$^+$.

$^1$H NMR (400 MHz, CDCl$_3$) δ: 7.72-7.64 (m, 4H), 7.46-7.19 (m, 10H), 7.14-7.11 (m, 1H), 4.01-3.91 (m, 2H), 3.68-3.57 (m, 2H), 3.19-3.11 (m, 1H), 2.41 (s, 3H), 2.18 (s, 3H) ppm.

Embodiment 39

(E)-N-(2-(((2-methoxy-6-(2-(2-methylbiphenyl)vinyl)pyridin-3-yl)methyl)amino)ethyl)acetamide 39

Synthetic Route

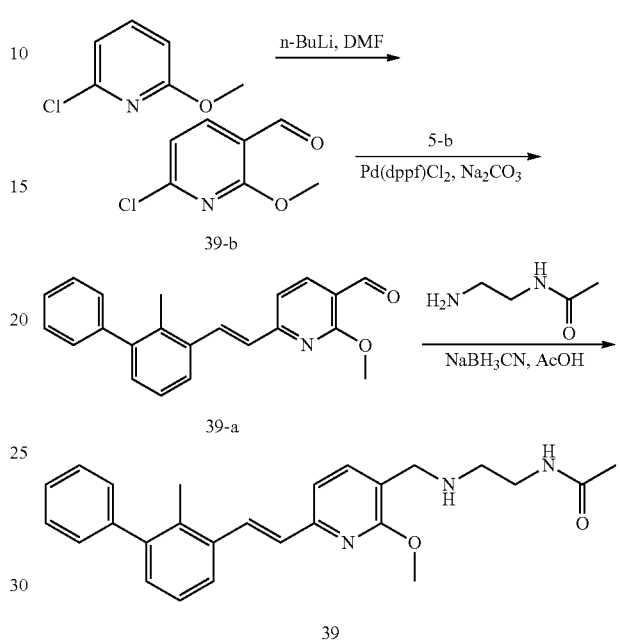

Synthesis of Compound 39-b

2-Chloro-6-methoxypyridine (1.5 mL, 12.5 mmol) and a solution of n-butyllithium (1.3M) in pentane (10.6 mL, 13.83 mmol) were added to anhydrous tetrahydrofuran (25 mL) at −78° C. The reaction solution was stirred at −78° C. for 1 hour, followed by addition of anhydrous N,N-dimethylformamide (1.5 mL, 12.5 mmol) and the resulting mixture was stirred at −78° C. for another 1.5 hours. The reaction was quenched with glacial acetic acid (1.43 mL, 12.5 mmol). The mixture was allowed to warm to room temperature, diluted with ethyl acetate (25 mL), washed successively with saturated aqueous sodium bicarbonate (20 mL) and brine (20 mL). The organic phase was dried over anhydrous sodium sulfate and evaporated under reduced pressure. The residue was purified by silica gel column chromatography (petroleum ether:ethyl acetate=10:1 to 2:1) to give compound 39-b (2.0 g, yield 93.3%).

$^1$H NMR (500 MHz, CDCl$_3$) δ: 10.31 (s, 1H), 8.07-8.06 (d, J=8.0 Hz, 1H), 7.04-7.02 (d, J=8 Hz, 1H), 4.09 (s, 3H) ppm.

Synthesis of Compound 39-a

Compound 5-b (1.12 g, 3.5 mmol) and compound 39-b (500 mg, 2.91 mmol) were dissolved in a mixed solvent of 1,4-dioxane (30 mL) and water (1.5 mL), followed by addition of [1,1'-bis(diphenylphosphino)ferrocene]palladium dichloride (251.7 mg, 0.291 mmol) and sodium carbonate (771.7 mg, 7.28 mmol). After the reaction system was purged three times with nitrogen, the reaction solution was heated to 80° C. and stirred for 16 hours. The reaction solution was cooled to room temperature, diluted with ethyl acetate (100 mL), washed successively with water (50 mL×3) and saturated brine (50 mL). The organic phase was dried over anhydrous sodium sulfate and evaporated under reduced pressure. The residue was purified by silica gel column chromatography (petroleum ether:ethyl acetate=15:1) to give compound 39-a (877 mg, yield 91.2%). LC-MS (ESI): m/z=330 [M+H]+.

Synthesis of Compound 39

Compound 39-a (100 mg, 0.303 mmol) and N-(2-aminoethyl)acetamide (61.9 mg, 0.606 mmol) were dissolved in a mixed solvent of methanol (5 mL) and dichloromethane (5 mL), followed by addition of glacial acetic acid (36.4 mg, 0.606 mmol). The reaction solution was stirred at room temperature for 1 hour. Then sodium cyanoborohydride (95.4 mg, 1.518 mmol) was added and the resulting mixture was stirred for another 16 hours. The reaction solution was evaporated under reduced pressure, and the residue was diluted with ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (dichloromethane:methanol=15:1) to give compound 39 (43 mg, yield 34.1%). LC-MS (ESI): m/z=416 [M+H]+.

$^1$H NMR (500 MHz, CDCl$_3$) δ: 8.03-8.00 (d, J=16 Hz, 1H), 7.63-7.62 (d, J=7.5 Hz, 1H), 7.46-7.41 (m, 3H), 7.37-7.31 (m, 3H), 7.28-7.25 (m, 1H), 7.20-7.18 (m, 1H), 6.98-6.95 (d, J=15.5 Hz, 1H), 6.90-6.89 (d, J=7.5 Hz, 1H), 6.10 (s, 1H), 4.05 (s, 3H), 3.74 (s, 2H), 3.37-3.34 (m, 2H), 2.74-2.72 (m, 2H), 2.33 (s, 3H), 1.99 (s, 3H) ppm.

Embodiment 40

(E)-2-((2-methoxy-6-(2-(2-methylbiphenyl-3-yl)vinyl)pyridin-3-yl)methylamino)ethyl)-1,3-propanediol 40

Synthetic Route

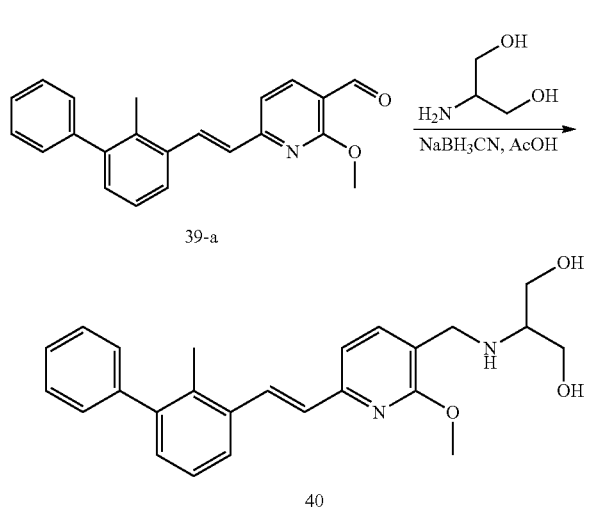

Synthesis of Compound 40

Compound 39-a (100 mg, 0.303 mmol) and 2-amino-1,3-propanediol (55.4 mg, 0.606 mmol) were dissolved in a mixed solvent of methanol (5 mL) and dichloromethane (5 mL), followed by addition of glacial acetic acid (36.4 mg, 0.606 mmol). The reaction solution was stirred at room temperature for 1 hour. Then sodium cyanoborohydride (95.4 mg, 1.518 mmol) was added and the resulting mixture was stirred for another 16 hours. The reaction solution was evaporated under reduced pressure, and the residue was diluted with ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (dichloromethane:methanol=15:1) to give compound 40 (37 mg, yield 30.3%). LC-MS (ESI): m/z=405 [M+H]+.

$^1$H NMR (400 MHz, CDCl$_3$) δ: 8.03-8.00 (d, J=15.5 Hz, 1H), 7.63-7.62 (d, J=7.5 Hz, 1H), 7.51-7.50 (d, J=7.5 Hz, 1H), 7.44-7.41 (m, 2H), 7.37-7.31 (m, 3H), 7.28-7.24 (m, 1H), 7.19-7.18 (d, J=7.0 Hz, 1H), 6.98-6.95 (d, J=15.5 Hz, 1H), 6.90-6.89 (d, J=7.5 Hz, 1H), 4.06 (3H, s), 3.81 (s, 2H), 3.77-3.74 (m, 2H), 3.62-3.58 (m, 2H), 2.81-2.79 (m, 1H), 2.33 (s, 3H) ppm.

Embodiment 41

(R,E)-3-Hydroxy-2-((2-methoxy-6-(2-(2-methylbiphenyl-3-yl)vinyl)pyridin-3-yl)methylamino)propanoic Acid 41

Synthetic Route

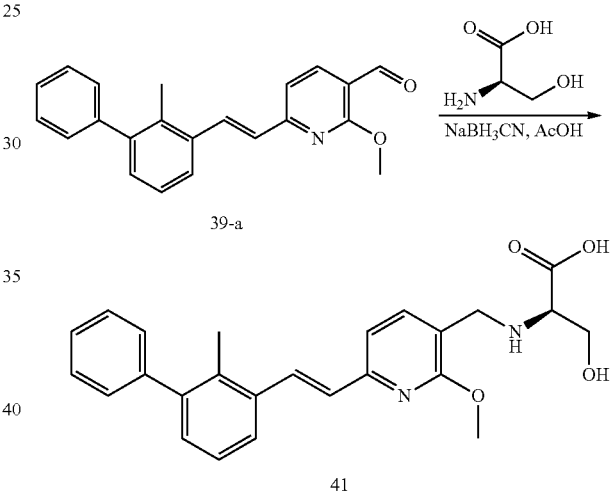

Synthesis of Compound 41

Compound 39-a (100 mg, 0.303 mmol) and 2-amino-1,3-propanediol (63.9 mg, 0.608 mmol) were dissolved in a mixed solvent of methanol (5 mL) and dichloromethane (5 mL), followed by addition of glacial acetic acid (36.4 mg, 0.608 mmol). The reaction solution was stirred at room temperature for 1 hour. Then sodium cyanoborohydride (95.4 mg, 1.518 mmol) was added and the resulting mixture was stirred for another 16 hours. The reaction solution was evaporated under reduced pressure, and the residue was diluted with ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (dichloromethane:methanol=10:1) to give compound 40 (4 mg, yield 3.15%). LC-MS (ESI): m/z=419 [M+H]+.

$^1$H NMR (400 MHz, CDCl$_3$) δ: 7.51 (br, s, 1H), 7.39-7.36 (m, 2H), 7.33-7.30 (m, 1H), 7.26-7.24 (m, 2H), 7.09-7.06 (m, 3H), 6.88-6.85 (d, J=12.5 Hz, 1H), 6.66-6.65 (d, J=7.5 Hz, 1H), 6.55-6.52 (d, J=12.5 Hz, 1H), 4.08 (s, 2H), 3.90 (s, 2H), 3.48 (s, 3H), 2.14 (s, 3H) ppm.

Embodiment 42

(E)-N-(2-((2-Methoxy-6-(2-(2-methylbiphenyl-3-yl)vinyl)pyridin-3-yl)methylamino)cyclohexyl acetamide 42

Synthetic Route

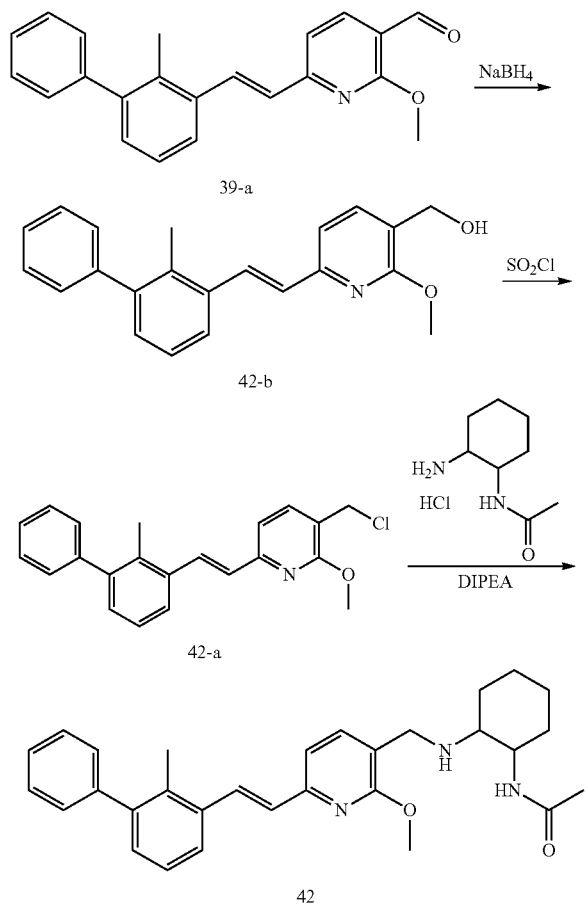

Synthesis of Compound 42-b

Compound 39-a (245 mg, 0.744 mmol) was dissolved in a mixed solvent of methanol (5 mL) and tetrahydrofuran (5 mL), followed by addition of sodium borohydride (140.7 mg, 3.72 mmol) in batches. The mixture was stirred at room temperature for 2 hours, then evaporated under reduced pressure. The residue was diluted with ethyl acetate (50 mL), washed with saturated brine (20 mL) and water (20 mL). The organic phase was dried over anhydrous sodium sulfate, filtered and evaporated under reduced pressure to give compound 42-b (212 mg, yield 86.6%), which was used directly in the next step without further purification. LC-MS (ESI): m/z=331 [M+H]+.

Synthesis of Compound 42-a

Compound 42-b (212 mg, 0.64 mmol) was dissolved in dichloromethane (10 mL), followed by addition of thionyl chloride (380.7 mg, 3.20 mmol). The mixture was stirred at room temperature for 0.5 hour, then evaporated under reduced pressure to give compound 42-a (210 mg, yield 99%), which was used directly in the next step without further purification.

Synthesis of Compound 42

Compound 42-a (105 mg, 0.30 mmol), N-(2-aminocyclohexyl)acetamide (57.8 mg, 0.30 mmol) and diisopropylethylamine (193.3 mg, 1.50 mmol) were dissolved in acetonitrile (10 mL). The reaction solution was heated to 60° C. and stirred for 16 hours. Then the reaction solution was cooled to room temperature and evaporated under reduced pressure. The residue was diluted with ethyl acetate (50 mL), washed with saturated brine (20 mL) and water (20 mL). The organic phase was dried over anhydrous sodium sulfate, filtered and evaporated under reduced pressure. The residue was purified by preparative silica gel thin layer chromatography (dichloromethane:methanol=15:1) to give compound 42 (13 mg, yield 9.2%). LC-MS (ESI): m/z=470 [M+H]+.

$^1$H NMR (500 MHz, CDCl$_3$) δ: 8.03-8.00 (d, J=15.5 Hz, 1H), 7.64-7.62 (d, J=7.0 Hz, 1H), 7.50-7.49 (d, J=7.0 Hz, 1H), 7.44-7.41 (m, 2H), 7.37-7.35 (m, 1H), 7.34-7.31 (m, 2H), 7.26-7.25 (m, 1H), 7.19-7.18 (m, 1H), 6.99-6.96 (d, J=16.0 Hz, 1H), 6.91-6.89 (d, J=7.5 Hz, 1H), 5.40-5.38 (m, 1H), 4.05 (s, 3H), 3.89-3.86 (d, J=14.5 Hz, 1H), 3.65-3.62 (m, 2H), 2.33 (s, 3H), 2.26-2.25 (m, 1H), 2.14-2.08 (m, 2H), 1.97 (s, 3H), 1.33-1.19 (m, 6H) ppm.

Embodiment 43

(E)-2-(2,6-Dimethoxy-4-(2-(2-methylbiphenyl-3-yl)vinyl)benzylamino)-4-hydroxybutanoic Acid 43

Synthetic Route

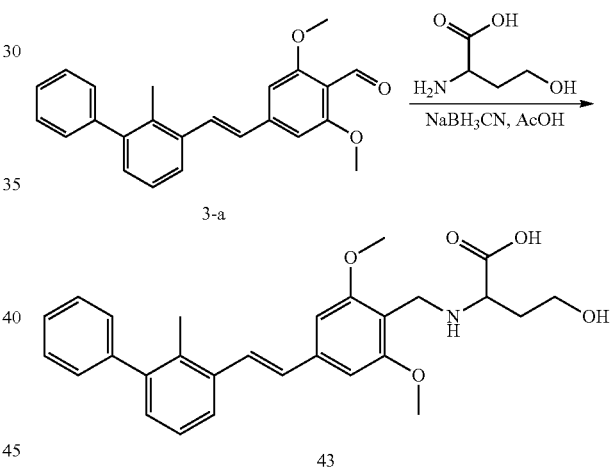

Synthesis of Compound 43

Compound 3-a (100 mg, 0.28 mmol) and 2-amino-4-hydroxybutanoic acid (58.6 mg, 0.56 mmol) were dissolved in a mixed solvent of methanol (5 mL) and dichloromethane (5 mL), followed by addition of glacial acetic acid (33.5 mg, 0.56 mmol). The reaction solution was stirred at room temperature for 1 hour. Then sodium cyanoborohydride (87.7 mg, 1.4 mmol) was added and the resulting mixture was stirred for another 16 hours. The reaction solution was evaporated under reduced pressure, and the residue was diluted with ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (dichloromethane:methanol=15:1) to give compound 43 (12 mg, yield 21.9%). LC-MS (ESI): m/z=460 [M−H]+.

$^1$H NMR (500 MHz, CDCl$_3$) δ: 7.56-7.55 (d, J=7.5 Hz, 1H), 7.43-7.40 (m, 3H), 7.37-7.34 (m, 1H), 7.31-7.25 (m, 3H), 7.20-7.19 (d, J=7.5 Hz, 1H), 6.96-6.93 (d, J=16.0 Hz,

1H), 6.72 (s, 2H), 4.38-4.31 (m, 2H), 3.92 (s, 6H), 3.89-3.88 (m, 1H), 3.66-3.61 (m, 1H), 3.50-3.48 (m, 1H), 2.31 (s, 3H), 2.07 (s, 2H) ppm.

Embodiment 44

(E)-2-(2,6-Dimethoxy-4-(2-(2-methylbiphenyl-3-yl)vinyl)benzylamino)-3-hydroxy-2-methylpropanoic Acid 44

Synthetic Route

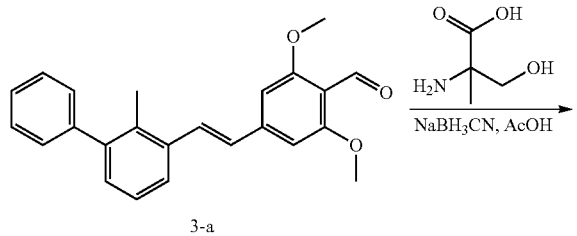

3-a

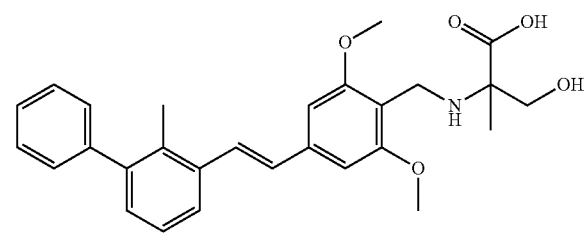

44

Synthesis of Compound 44

Compound 3-a (100 mg, 0.28 mmol) and 2-amino-3-hydroxy-2-methylpropanoic acid (58.6 mg, 0.56 mmol) were dissolved in a mixed solvent of methanol (5 mL) and dichloromethane (5 mL), followed by addition of glacial acetic acid (33.5 mg, 0.56 mmol). The reaction solution was stirred at room temperature for 1 hour. Then sodium cyanoborohydride (87.7 mg, 1.4 mmol) was added and the resulting mixture was stirred for another 16 hours. The reaction solution was evaporated under reduced pressure, and the residue was diluted with ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (dichloromethane:methanol=15:1) to give compound 44 (10 mg, yield 7.8%). LC-MS (ESI): m/z=460 [M−H]$^+$.

$^1$H NMR (500 MHz, CDCl$_3$) δ: 7.56-7.55 (d, J=7.5 Hz, 1H), 7.43-7.36 (m, 4H), 7.31-7.29 (m, 2H), 7.26-7.25 (m, 1H), 7.20-7.19 (d, J=7.5 Hz, 1H), 6.95-6.92 (d, J=16.0 Hz, 1H), 6.72 (s, 2H), 4.20-4.19 (m, 2H), 4.06-4.04 (m, 1H), 3.94 (s, 6H), 3.56-3.53 (m, 1H), 2.30 (s, 3H), 1.42 (s, 3H) ppm.

Embodiment 45

(S,E)-2-(2,6-Dimethoxy-4-(2-(2-methylbiphenyl-3-yl)vinyl)benzylamino)-3-hydroxy-2-methylpropanoic Acid 45

Synthetic Route

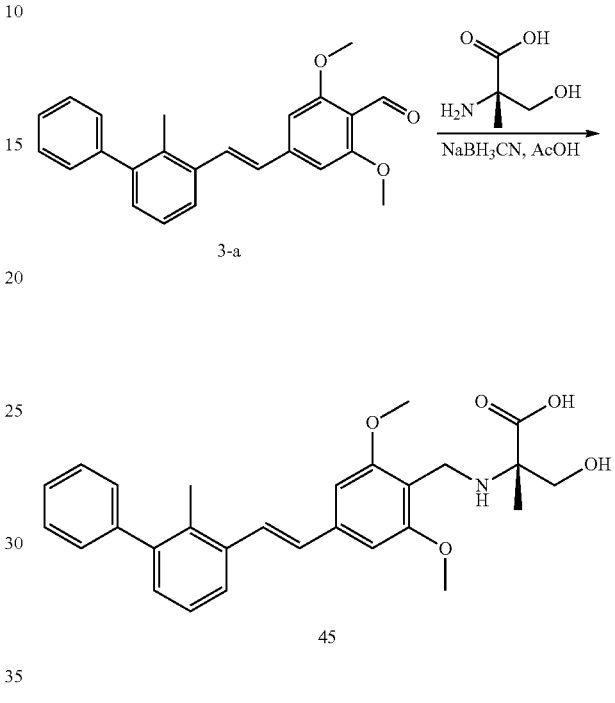

Synthesis of Compound 45

Compound 3-a (100 mg, 0.28 mmol) and (S)-2-amino-3-hydroxy-2-methylpropanoic acid (58.6 mg, 0.56 mmol) were dissolved in a mixed solvent of methanol (5 mL) and dichloromethane (5 mL), followed by addition of glacial acetic acid (33.5 mg, 0.56 mmol). The reaction solution was stirred at room temperature for 1 hour. Then sodium cyanoborohydride (87.7 mg, 1.4 mmol) was added and the resulting mixture was stirred for another 16 hours. The reaction solution was evaporated under reduced pressure, and the residue was diluted with ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (dichloromethane:methanol=15:1) to give compound 45 (49 mg, yield 38.3%). LC-MS (ESI): m/z=460 [M−H]$^+$.

$^1$H NMR (500 MHz, CDCl$_3$) δ: 7.56-7.55 (d, J=7.5 Hz, 1H), 7.43-7.36 (m, 4H), 7.31-7.29 (m, 2H), 7.26-7.25 (m, 1H), 7.20-7.19 (d, J=7.5 Hz, 1H), 6.95-6.92 (d, J=16.0 Hz, 1H), 6.72 (s, 2H), 4.20-4.19 (m, 2H), 4.06-4.04 (m, 1H), 3.94 (s, 6H), 3.56-3.53 (m, 1H), 2.30 (s, 3H), 1.42 (s, 3H) ppm.

Embodiment 46

(R,E)-2-(2,6-Dimethoxy-4-(2-(2-methylbiphenyl-3-yl)vinyl)benzylamino)-3-hydroxy-2-methylpropanoic Acid 46

Synthetic Route

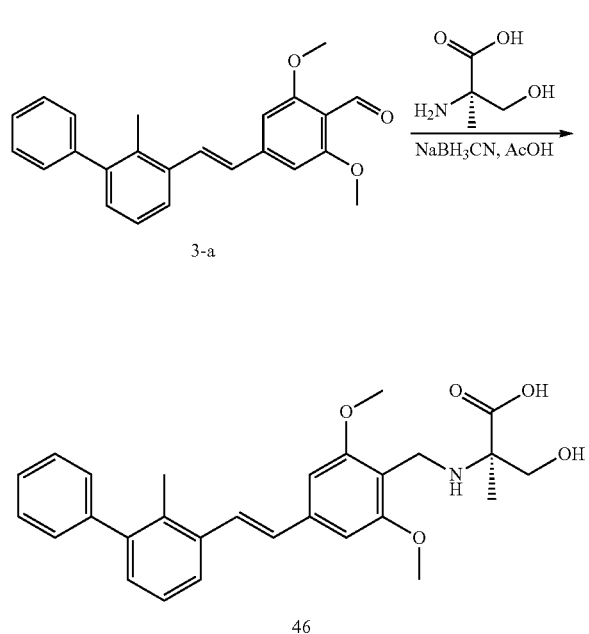

Embodiment 47

(E)-1-(2,6-Dimethoxy-4-(2-(2-methylbiphenyl-3-yl)vinyl)benzyl)-2-(hydroxymethylpiperidine-2-carboxylic Acid 47

Synthetic Route

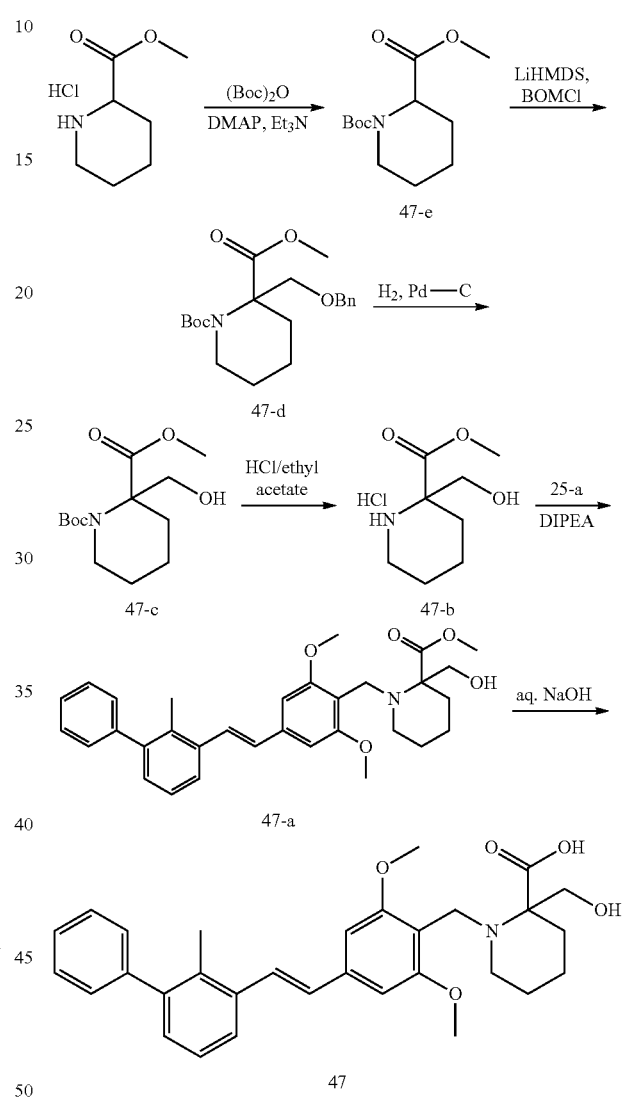

Synthesis of Compound 46

Compound 3-a (100 mg, 0.28 mmol) and (R)-2-amino-3-hydroxy-2-methylpropanoic acid (58.6 mg, 0.56 mmol) were dissolved in a mixed solvent of methanol (5 mL) and dichloromethane (5 mL), followed by addition of glacial acetic acid (33.5 mg, 0.56 mmol). The reaction solution was stirred at room temperature for 1 hour. Then sodium cyanoborohydride (87.7 mg, 1.4 mmol) was added and the resulting mixture was stirred for another 16 hours. The reaction solution was evaporated under reduced pressure, and the residue was diluted with ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (dichloromethane:methanol=15:1) to give compound 46 (28 mg, yield 21.9%). LC-MS (ESI): m/z=460 [M−H]+.

$^1$H NMR (500 MHz, CDCl$_3$) δ: 7.56-7.55 (d, J=7.5 Hz, 1H), 7.43-7.36 (m, 4H), 7.31-7.29 (m, 2H), 7.26-7.25 (m, 1H), 7.20-7.19 (d, J=7.5 Hz, 1H), 6.95-6.92 (d, J=16.0 Hz, 1H), 6.72 (s, 2H), 4.20-4.19 (m, 2H), 4.06-4.04 (m, 1H), 3.94 (s, 6H), 3.56-3.53 (m, 1H), 2.30 (s, 3H), 1.42 (s, 3H) ppm.

Synthesis of Compound 47-e

Methyl 2-piperidinecarboxylate (1.0 g, 5.57 mmol) was dissolved in dichloromethane (30 mL), then di-tert-butyl dicarbonate (3.04 g, 13.92 mmol), 4-dimethylaminopyridine (0.68 g, 5.57 mmol) and triethylamine (1.70 g, 16.71 mmol) were successively added. The reaction solution was stirred at room temperature for 16 hours, then evaporated under reduced pressure. The residue was purified by silica gel column chromatography (petroleum ether:ethyl acetate=10:1 to 3:1) to give compound 47-e (1.364 g, yield 98%).

$^1$H NMR (500 MHz, CDCl$_3$) δ: 4.90-4.73 (m, 1H), 4.03-3.91 (m, 1H), 3.73 (s, 3H), 2.97-2.86 (m, 1H), 2.24-2.17 (m, 1H), 1.69-1.62 (m, 3H), 1.47-1.44 (s, 9H), 1.31-1.21 (m, 2H) ppm.

Synthesis of Compound 47-d

A solution of lithium hexamethyldisilazide (1.0M) in tetrahydrofuran (7.5 mL, 7.49 mmol) was added to a solution of compound 47-e (1.36 g, 5.59 mmol) in anhydrous tetrahydrofuran (20 mL) at −78° C. The mixture was stirred at −78° C. for 2 hours, then warmed to −30° C., followed by addition of benzyl chloromethyl ether (1.173 g, 7.49 mmol), and the mixture was stirred for another 2 hours. The reaction solution was allowed to warm to room temperature, diluted with saturated aqueous ammonium chloride solution, extracted with ethyl acetate (50 mL×3), washed with saturated brine (50 mL) and water (50 mL), dried over anhydrous sodium sulfate and evaporated under reduced pressure. The residue was purified by silica gel column chromatography (petroleum ether:ethyl acetate=50:1 to 10:1) to give compound 47-d (938 mg, yield 46.2%).

$^1$H NMR (500 MHz, CDCl$_3$) δ: 7.35-7.31 (m, 4H), 7.28-7.26 (m, 1H), 4.58-4.52 (m, 2H), 3.83-3.81 (d, J=9.5 Hz, 1H), 3.73-3.71 (d, J=9.5 Hz, 1H), 3.70 (s, 3H), 3.22-3.16 (m, 1H), 2.22-2.18 (m, 1H), 1.74-1.61 (m, 6H), 1.40 (s, 9H) ppm.

Synthesis of Compound 47-c

10% Pd—C (200 mg) was added to a solution of compound 47-d (938 mg, 2.58 mmol) in methanol (20 mL) at room temperature. The reaction solution was stirred at one atmospheric pressure of hydrogen atmosphere for 16 hours. Then the reaction solution was filtered through celite, and the filter cake was washed with methanol (20 mL×3). The filtrate was evaporated under reduced pressure to give compound 47-c (684 mg, yield 97%), which was used directly in the next step without further purification.

Synthesis of Compound 47-b

Compound 47-c (684 mg, 2.50 mmol) was added to a solution of hydrogen chloride in ethyl acetate (3M, 20 mL). The reaction solution was stirred at room temperature for 2 hours, then evaporated under reduced pressure to give 47-b (611 mg, yield 98%), which was used directly in the next step without further purification.

$^1$H NMR (500 MHz, CDCl$_3$) δ: 4.32-4.29 (d, J=12.5 Hz, 1H), 3.92-3.89 (d, J=12.5 Hz, 1H), 3.89 (s, 3H), 3.84 (s, 1H), 3.61-3.59 (m, 1H), 3.30-3.26 (m, 1H), 1.99-1.93 (m, 1H), 1.85-1.76 (m, 3H), 1.34-1.25 (m, 2H) ppm.

Synthesis of Compound 47-a

Compound 47-b (293 mg, 1.40 mmol) and compound 25-a (530.5 mg, 1.40 mmol) were dissolved in acetonitrile (20 mL), followed by addition of diisopropylethylamine (904.7 mg, 7.0 mmol). The reaction solution was heated to 60° C. and stirred for 16 hours. Then the reaction solution was cooled to room temperature and evaporated under reduced pressure. The residue was purified by silica gel column chromatography (petroleum ether:ethyl acetate=10:1 to 1:1) to give compound 47-a (23 mg, yield 3.2%). LC-MS (ESI): m/z=516 [M+H]$^+$.

Synthesis of Compound 47

Compound 47-a (23 mg, 0.045 mmol) was dissolved in a mixed solvent of methanol (5 mL) and tetrahydrofuran (5 mL), followed by addition of 10% aqueous sodium hydroxide solution (1.0 mL, 0.223 mmol). The reaction solution was heated to 60° C. and stirred for 16 hours. Then the reaction solution was cooled to room temperature and evaporated under reduced pressure. The residue was diluted with dichloromethane (20 mL) and adjusted to pH 5 with citric acid. The organic phase was washed with saturated brine (5 mL) and water (5 mL), dried over anhydrous sodium sulfate and evaporated under reduced pressure. The residue was purified by preparative silica gel thin layer chromatography (dichloromethane:methanol=15:1) to give compound 47 (11 mg, yield 49.1%). LC-MS (ESI): m/z=502 [M+H]$^+$.

$^1$H NMR (500 MHz, CDCl$_3$) δ: 7.58-7.56 (d, J=8.0 Hz, 1H), 7.46-7.42 (m, 3H), 7.38-7.35 (m, 1H), 7.32-7.30 (m, 2H), 7.2-7.26 (m, 1H), 7.22-7.21 (m, 1H), 6.98-6.95 (d, J=16 Hz, 1H), 6.75 (s, 2H), 4.56-4.49 (m, 2H), 3.99 (s, 6H), 3.81-3.78 (m, 1H), 3.27-3.22 (m, 1H), 2.93-2.90 (m, 1H), 2.44-2.41 (m, 1H), 2.32 (s, 3H), 2.04-2.00 (m, 1H), 1.80-1.73 (m, 3H), 1.56 (br, s, 2H) ppm.

Embodiment 48

(S,E)-2-(2,6-Dimethoxy-4-(2-(4'-methoxy-2-methyl-biphenyl-3-yl)vinyl)benzylamino)-3-hydroxypropionic Acid 48

Synthetic Route

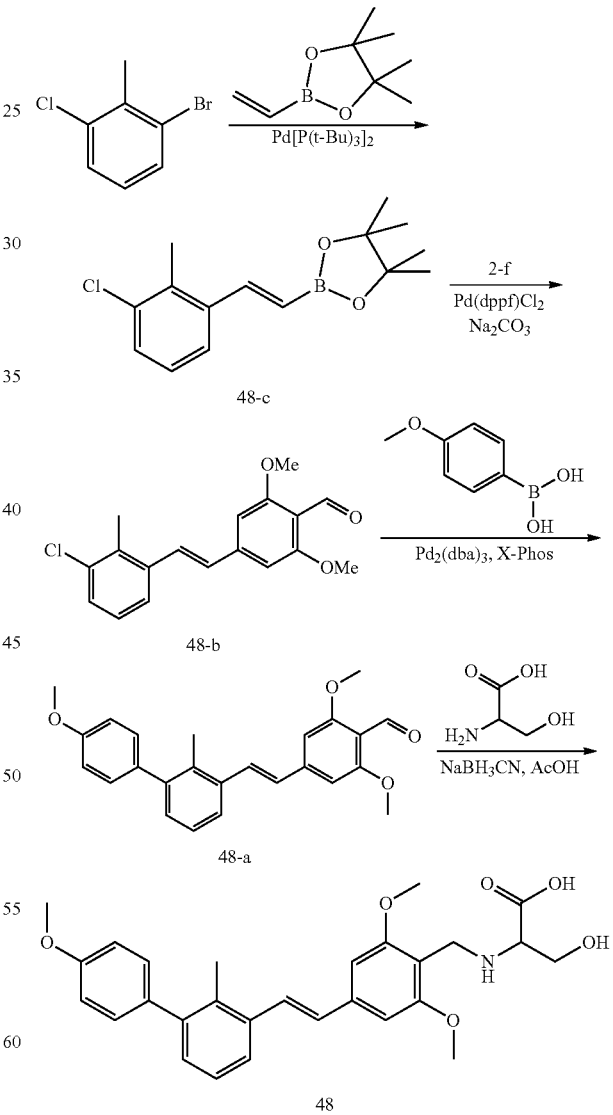

Synthesis of Compound 48-c

2-Bromo-6-chlorotoluene (8.0 g, 38.93 mmol) and vinylboronic acid pinacol ester (7.3 g, 46.72 mmol) were dissolved in toluene (100 mL), followed by addition of bis(tri-tert-butylphosphine)palladium (1.4 g, 2.73 mmol) and triethylamine (35.52 g, 311.44 mmol). After the reaction system was purged three times with nitrogen, the reaction solution was heated to 80° C. and stirred for 16 hours. Then the reaction solution was cooled to room temperature, diluted with ethyl acetate (100 mL), washed successively with water (100 mL×3) and saturated brine (100 mL). The organic phase was dried over anhydrous sodium sulfate. The residue was purified by silica gel column chromatography (petroleum ether) to give compound 48-c (7.19 g, yield 65.8%).

$^1$H NMR (400 MHz, CDCl$_3$) δ: 7.66-7.61 (d, J=23.0 Hz, 1H), 7.42-7.41 (d, J=9.5 Hz, 1H), 7.32-7.30 (d, J=9.5 Hz, 1H), 7.13-7.09 (t, 1H), 6.06-6.02 (d, J=22.5 Hz, 1H), 2.45 (s, 3H), 1.32 (s, 12H) ppm.

Synthesis of Compound 48-b

Compound 48-c (7.19 g, 25.81 mmol) and compound 2-f (6.76 mg, 25.51 mmol) were dissolved in a mixed solvent of 1,4-dioxane (120 mL) and water (6 mL), followed by addition of [1,1'-bis(diphenylphosphino)ferrocene]palladium dichloride (1.86 g, 2.15 mmol) and sodium carbonate (5.7 g, 53.77 mmol). After the reaction system was purged three times with nitrogen, the reaction solution was heated to 80° C. and stirred for 16 hours. Then the reaction solution was cooled to room temperature, diluted with ethyl acetate (100 mL), washed successively with water (100 mL×3) and saturated brine (100 mL). The organic phase was dried over anhydrous sodium sulfate and evaporated under reduced pressure. The residue was purified by silica gel column chromatography (petroleum ether:ethyl acetate=10:1 to 3:1) to give compound 48-b (9.17 g, yield 98%).

$^1$H NMR (400 MHz, CDCl$_3$) δ: 10.49 (s, 1H), 7.47-7.41 (m, 2H), 7.36-7.34 (d, J=8.0 Hz, 1H), (m, 2H), 7.18-7.14 (t, 1H), 6.92-6.89 (d, J=16.0 Hz, 1H), 6.69 (s, 2H), 3.97 (s, 6H), 2.49 (s, 3H) ppm.

Synthesis of Compound 48-a

4-Methoxyphenylboronic acid (127 mg, 0.83 mmol), potassium phosphate (443 mg, 2.1 mmol), 2-dicyclohexylphosphino-2',4',6'-triisopropylbiphenyl (44 mg, 0.088 mmol) and tris(dibenzylideneacetone)dipalladium (22 mg, 0.02 mmol) were added to a solution of compound 48-b (220 mg, 0.7 mmol) in toluene (15 mL). After the reaction system was purged three times with nitrogen, the reaction solution was heated to 80° C. and stirred for 12 hours. Then the reaction solution was cooled to room temperature and evaporated under reduced pressure. The residue was purified by silica gel column chromatography (petroleum ether:ethyl acetate=5:1) to give compound 48-a (170 mg, yield 63%) as a yellow solid. LC-MS (ESI): m/z=389 [M+H]$^+$.

Synthesis of Compound 48

Compound 48-a (170 mg, 0.44 mmol) and 2-amino-3-hydroxypropionic acid (104 mg, 0.88 mmol) were dissolved in a mixed solvent of methanol (15 mL) and dichloromethane (15 mL), followed by addition of glacial acetic acid (0.05 mL, 0.88 mmol). The reaction solution was stirred at room temperature for 2 hours, followed by addition of sodium cyanoborohydride (110 mg, 1.75 mmol), and the resulting mixture was stirred for another 12 hours. The reaction solution was evaporated under reduced pressure, and the residue was purified by high performance liquid chromatography (mobile phase: water (10 mM ammonium bicarbonate), acetonitrile; gradient: 25%-55% (the initial mobile phase was 25% water and 75% acetonitrile, and the final mobile phase was 55% water and 45% acetonitrile, where % refers to percent of volume)) to give compound 48 as a white solid (20 mg, yield 9.2%). LC-MS (ESI): m/z=476 [M−H]$^+$.

$^1$H NMR (400 MHz, DMSO-d$_6$) δ: 7.66-7.62 (m, 2H), 7.31-7.27 (m, 3H), 7.14-7.13 (m, 2H), 7.05-7.03 (m, 4H), 4.06 (s, 2H), 3.87 (s, 6H), 3.79 (s, 3H), 3.65-3.63 (d, J=8.8 Hz, 1H), 3.54-3.52 (d, J=8.8 Hz, 1H), 2.29 (s, 3H), 1.26 (s, 3H) ppm.

Embodiment 49

(E)-2-(2,6-Dimethoxy-4-(2-(4'-(methoxycarbonyl)-2-methylbiphenyl-3-yl)vinyl)benzylamino)-3-hydroxy-2-methylpropanoic Acid 49

Synthetic Route

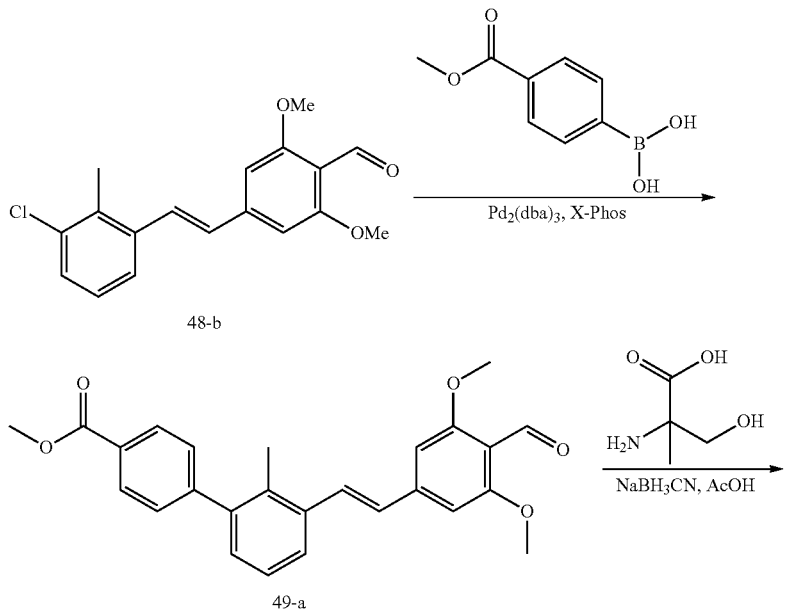

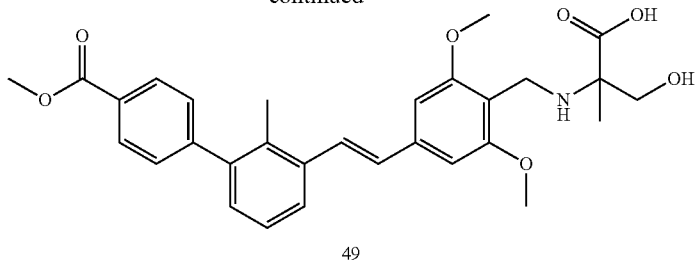

49

Synthesis of Compound 49-a

4-Methoxycarbonylphenylboronic acid (205 mg, 1.1 mmol), potassium phosphate (604 mg, 2.8 mmol), 2-dicyclohexylphosphino-2',4',6'-triisopropylbiphenyl (60 mg, 0.12 mmol) and tris(dibenzylideneacetone)dipalladium (30 mg, 0.03 mmol) were added to a solution of compound 48-b (300 mg, 0.95 mmol) in toluene (15 mL). After the reaction system was purged three times with nitrogen, the reaction solution was heated to 80° C. and stirred for 12 hours. Then the reaction solution was cooled to room temperature and evaporated under reduced pressure. The residue was purified by silica gel column chromatography (petroleum ether:ethyl acetate=5:1) to give compound 49-a (140 mg, yield 35%) as a yellow solid. LC-MS (ESI): m/z=417 [M+H]+.

Synthesis of Compound 49

Compound 49-a (100 mg, 0.24 mmol) and 2-amino-3-hydroxy-2-methylpropionic acid (57 mg, 0.48 mmol) were dissolved in a mixed solvent of methanol (15 mL) and dichloromethane (15 mL), followed by addition of glacial acetic acid (0.03 mL, 0.48 mmol). The reaction solution was stirred at room temperature for 2 hours, followed by addition of sodium cyanoborohydride (60 mg, 0.96 mmol), and the resulting mixture was stirred for another 12 hours. The reaction solution was evaporated under reduced pressure, and the residue was purified by high performance liquid chromatography (mobile phase: water (10 mM ammonium bicarbonate), acetonitrile; gradient: 35%-60% (the initial mobile phase was 35% water and 65% acetonitrile, and the final mobile phase was 60% water and 40% acetonitrile, where % refers to percent of volume)) to give compound 49 as a white solid (5 mg, yield 4%). LC-MS (ESI): m/z=518 [M−H]+.

$^1$H NMR (400 MHz, DMSO-d$_6$) δ: 8.05-8.01 (d, J=16 Hz, 2H), 7.70-7.68 (d, J=6 Hz, 1H), 7.61-7.56 (d, J=12 Hz, 1H), 7.49-7.47 (d, J=8 Hz, 2H), 7.33-7.30 (t, J=6 Hz, 1H), 7.17-7.12 (t, J=13.2 Hz, 2H), 6.99 (s, 2H), 4.06 (s, 2H), 3.88 (s, 9H), 3.65-3.62 (d, J=8.8 Hz, 1H), 3.53-3.51 (d, J=8 Hz, 1H), 2.49 (s, 3H), 1.26 (s, 3H) ppm.

Embodiment 50

(E)-2-(2,6-Dimethoxy-4-(2-(4'-methoxy-2-methylbiphenyl-3-yl)vinyl)benzyl amino)-3-hydroxy-2-methylpropionic Acid 50

Synthetic Route

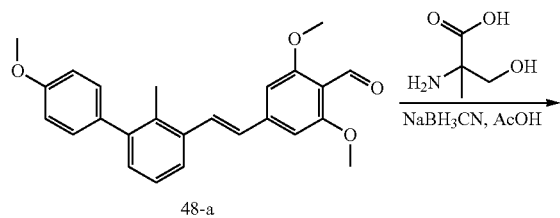

48-a

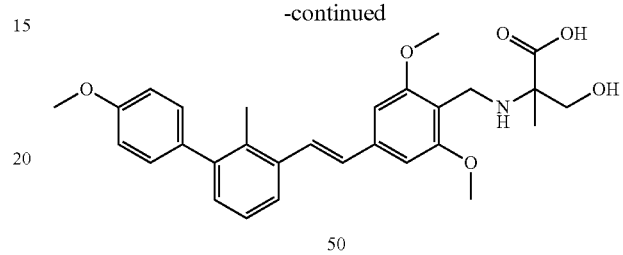

50

Synthesis of Compound 50

Compound 48-a (170 mg, 0.44 mmol) and 2-amino-3-hydroxy-2-methylpropionic acid (104 mg, 0.88 mmol) were dissolved in a mixed solvent of methanol (15 mL) and dichloromethane (15 mL), followed by addition of glacial acetic acid (0.05 mL, 0.88 mmol). The reaction solution was stirred at room temperature for 2 hours, followed by addition of sodium cyanoborohydride (110 mg, 1.75 mmol), and the resulting mixture was stirred for another 12 hours. The reaction solution was evaporated under reduced pressure, and the residue was purified by high performance liquid chromatography (mobile phase: water (10 mM ammonium bicarbonate), acetonitrile; gradient: 25%-55% (the initial mobile phase was 25% water and 75% acetonitrile, and the final mobile phase was 55% water and 45% acetonitrile, where % refers to percent of volume)) to give compound 50 as a white solid (20 mg, yield 9.2%). LC-MS (ESI): m/z=490 [M−H]+.

$^1$H NMR (400 MHz, DMSO-d$_6$) δ: 7.66-7.62 (m, 2H), 7.31-7.27 (m, 3H), 7.14-7.13 (m, 2H), 7.05-7.03 (m, 4H), 4.06 (s, 2H), 3.87 (s, 6H), 3.79 (s, 3H), 3.65-3.63 (d, J=8.8 Hz, 1H), 3.54-3.52 (d, J=8.8 Hz, 1H), 2.29 (s, 3H), 1.26 (s, 3H) ppm.

Embodiment 51

(E)-2-(2,6-Dimethoxy-4-(2-(3'-methoxycarbonyl-2-methylbiphenyl-3-yl)vinyl)benzylamino)-3-hydroxy-2-methylpropionic Acid 51

Synthetic Route

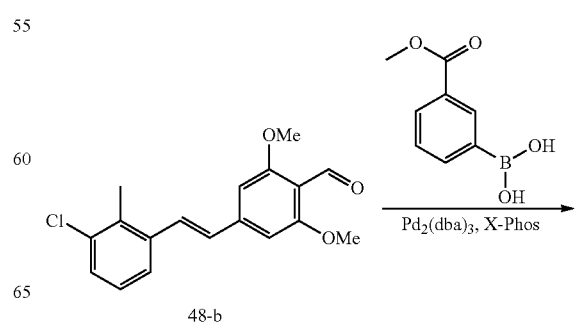

48-b

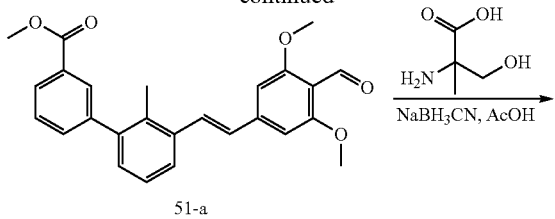

51-a

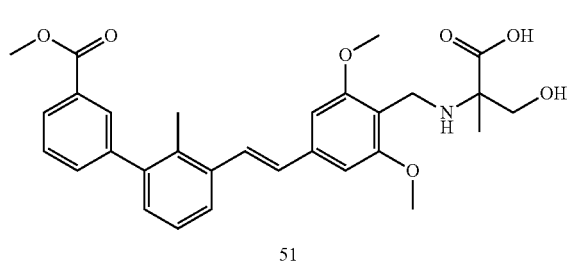

51

Synthesis of Compound 51-a

3-Methoxycarbonylphenylboronic acid (205 mg, 1.1 mmol), potassium phosphate (604 mg, 2.8 mmol), 2-dicyclohexylphosphino-2',4',6'-triisopropylbiphenyl (60 mg, 0.12 mmol) and tris(dibenzylideneacetone)dipalladium (30 mg, 0.03 mmol) were added to a solution of compound 48-b (300 mg, 0.95 mmol) in toluene (15 mL). After the reaction system was purged three times with nitrogen, the reaction solution was heated to 80° C. and stirred for 12 hours. Then the reaction solution was cooled to room temperature and evaporated under reduced pressure. The residue was purified by silica gel column chromatography (petroleum ether:ethyl acetate=4:1) to give compound 51-a as a yellow solid (300 mg, yield 76%). LC-MS (ESI): m/z=417 [M+H]+.

Synthesis of Compound 51

Compound 51-a (300 mg, 0.72 mmol) and 2-amino-3-hydroxy-2-methylpropionic acid (172 mg, 1.4 mmol) were dissolved in a mixed solvent of methanol (15 mL) and dichloromethane (15 mL), followed by addition of glacial acetic acid (0.08 mL, 1.4 mmol). The reaction solution was stirred at room temperature for 2 hours, followed by addition of sodium cyanoborohydride (181 mg, 2.9 mmol), and the resulting mixture was stirred for another 12 hours. The reaction solution was evaporated under reduced pressure, and the residue was purified by high performance liquid chromatography (mobile phase: water (10 mM ammonium bicarbonate), acetonitrile; gradient: 34%-64% (the initial mobile phase was 34% water and 66% acetonitrile, and the final mobile phase was 64% water and 36% acetonitrile, where % refers to percent of volume)) to give compound 51 as a white solid (120 mg, yield 32%). LC-MS (ESI): m/z=518 [M−H]+.

$^1$H NMR (400 MHz, DMSO-$d_6$) δ: 8.01-7.98 (m, 1H), 7.86 (s, 1H), 7.71-7.69 (d, J=8 Hz, 1H), 7.64-7.60 (m, 3H), 7.34-7.31 (t, J=8 Hz, 1H), 7.18-7.13 (m, 2H), 7.01 (s, 2H), 4.08 (s, 2H), 3.89 (s, 9H), 3.67-3.65 (d, J=8 Hz, 1H), 3.55-3.53 (d, J=8 Hz, 1H), 2.51 (s, 3H), 1.28 (s, 3H) ppm.

Embodiment 52

(E)-2-(2,6-Dimethoxy-4-(2-(3'-hydroxymethyl-2-methylbiphenyl-3-yl)vinyl) benzylamino)-3-hydroxy-2-methylpropionic Acid 52

Synthetic Route

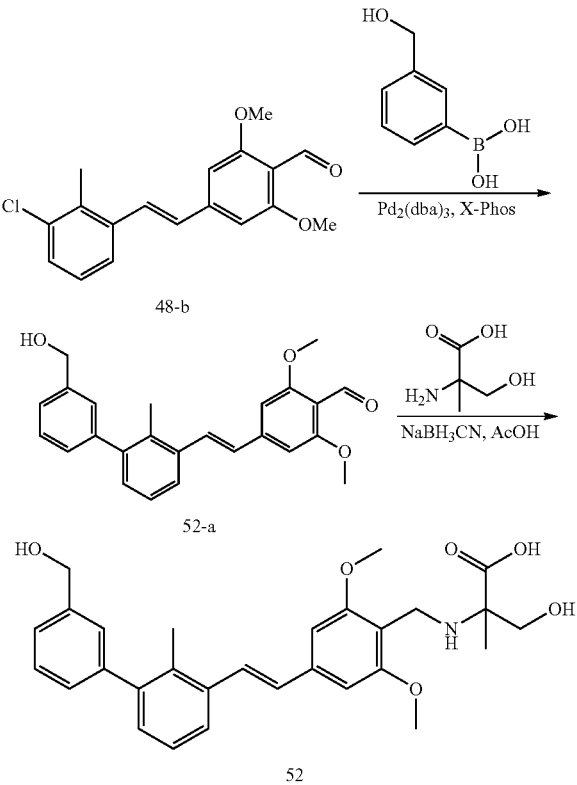

Synthesis of Compound 52-a

3-Hydroxymethylphenylboronic acid (173 mg, 1.1 mmol), potassium phosphate (604 mg, 2.8 mmol), 2-dicyclohexylphosphino-2',4',6'-triisopropylbiphenyl (60 mg, 0.12 mmol) and tris(dibenzylideneacetone)dipalladium (30 mg, 0.03 mmol) were added to a solution of compound 48-b (300 mg, 0.95 mmol) in toluene (15 mL). After the reaction system was purged three times with nitrogen, the reaction solution was heated to 80° C. and stirred for 12 hours. Then the reaction solution was cooled to room temperature and evaporated under reduced pressure. The residue was purified by silica gel column chromatography (petroleum ether:ethyl acetate=3:1) to give compound 52-a as a yellow solid (90 mg, yield 24%). LC-MS (ESI): m/z=389 [M+H]+.

Synthesis of Compound 52

Compound 52-a (90 mg, 0.23 mmol) and 2-amino-3-hydroxy-2-methylpropionic acid (55 mg, 0.46 mmol) were dissolved in a mixed solvent of methanol (15 mL) and dichloromethane (15 mL), followed by addition of glacial acetic acid (0.03 mL, 0.46 mmol). The reaction solution was stirred at room temperature for 2 hours, followed by addition of sodium cyanoborohydride (59 mg, 0.46 mmol), and the resulting mixture was stirred for another 12 hours. The reaction solution was evaporated under reduced pressure, and the residue was purified by high performance liquid chromatography (mobile phase: water (10 mM ammonium bicarbonate), acetonitrile; gradient: 25%-55% (the initial mobile phase was 25% water and 75% acetonitrile, and the final mobile phase was 55% water and 45% acetonitrile, where % refers to percent of volume)) to give compound 52 as a white solid (27 mg, yield 23.9%). LC-MS (ESI): m/z=490 [M−H]⁺.

¹H NMR (400 MHz, DMSO-d₆) δ: 7.66-7.59 (m, 2H), 7.41-7.39 (t, J=6 Hz, 1H), 7.33-7.31 (m, 3H), 7.19-7.17 (d, J=5.6 Hz, 1H), 7.15-7.12 (m, 2H), 7.01 (s, 2H), 4.56 (s, 2H), 4.08 (s, 2H), 3.89 (s, 6H), 3.66-3.64 (d, J=8.8 Hz, 1H), 3.56-3.54 (d, J=8.8 Hz, 1H), 2.51 (s, 3H), 1.28 (s, 3H) ppm.

Embodiment 53

(E)-2-(2,6-Dimethoxy-4-(2-(2-methylbiphenyl-3-yl)vinyl)benzylamino)-6-hydroxybenzoic Acid 53

Synthetic Route

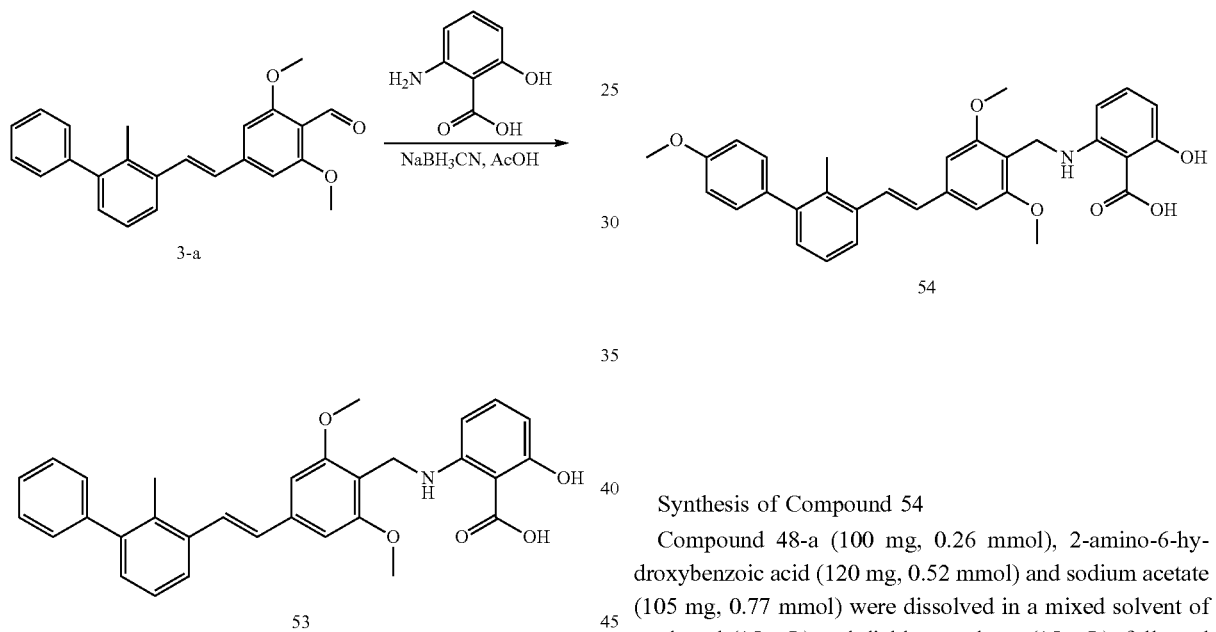

Synthesis of Compound 53

Compound 3-a (51 mg, 0.15 mmol) and 2-amino-6-hydroxybenzoic acid (45 mg, 0.3 mmol) were dissolved in a mixed solvent of methanol (5 mL) and dichloromethane (5 mL), followed by addition of a drop of glacial acetic acid. The reaction solution was stirred at room temperature for 1 hour. Then sodium cyanoborohydride (32 mg, 0.5 mmol) was added and the resulting mixture was stirred for another 3 hours. The reaction solution was evaporated under reduced pressure, and the residue was washed with water (10 mL×3). The obtained solid crude product was dried in vacuum, and purified by recrystallization with a mixed solvent of petroleum ether-ethyl acetate (3:1) to give compound 53 (10 mg, yield 13.4%). LC-MS (ESI): m/z=496 [M+H]⁺.

¹H NMR (500 MHz, CD₃OD) δ: 7.85 (s, 1H), 7.59 (d, J=8.0 Hz, 1H), 7.52 (d, J=16.0 Hz, 1H), 7.40-7.43 (m, 2H), 7.32-7.35 (m, 1H), 7.22-7.29 (m, 4H), 7.12 (d, J=7.0 Hz, 1H), 7.03 (d, J=16.0 Hz, 1H), 6.85 (s, 2H), 6.66-6.68 (m, 1H), 4.45 (s, 2H), 3.91 (s, 6H), 2.29 (s, 3H) ppm.

Embodiment 54

(E)-2-(2,6-Dimethoxy-4-(2-(4'-methoxy-2-methylbiphenyl-3-yl)vinyl)benzyl amino)-6-hydroxybenzoic Acid 54

Synthetic Route

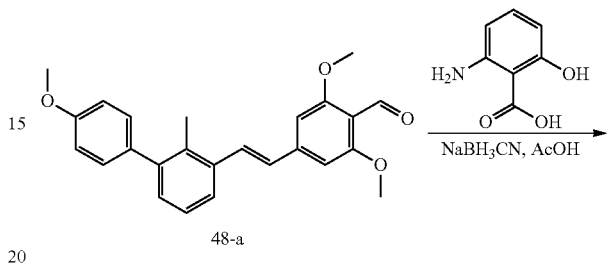

Synthesis of Compound 54

Compound 48-a (100 mg, 0.26 mmol), 2-amino-6-hydroxybenzoic acid (120 mg, 0.52 mmol) and sodium acetate (105 mg, 0.77 mmol) were dissolved in a mixed solvent of methanol (15 mL) and dichloromethane (15 mL), followed by addition of glacial acetic acid (0.03 mL, 0.46 mmol). The reaction solution was stirred at room temperature for 2 hours. Then sodium cyanoborohydride (65 mg, 1.03 mmol) was added and the resulting mixture was stirred for another 12 hours. The reaction solution was evaporated under reduced pressure, and the residue was purified by high performance liquid chromatography (mobile phase: water (10 mM ammonium bicarbonate), acetonitrile; gradient: 34%-64% (the initial mobile phase was 34% water and 66% acetonitrile, and the final mobile phase was 64% water and 36% acetonitrile, where % refers to percent of volume)) to give compound 54 as a white solid (69 mg, yield 50.5%). LC-MS (ESI): m/z=524 [M−H]⁺.

¹H NMR (400 MHz, DMSO-d₆) δ: 7.63-7.61 (d, J=5.6 Hz, 1H), 7.56-7.53 (d, J=12.8 Hz, 1H), 7.28-7.22 (m, 4H), 7.12-7.08 (m, 2H), 7.03-7.01 (d, J=5.2 Hz, 2H), 6.95 (s, 2H), 6.12-6.11 (d, J=6.4 Hz, 1H), 5.86-5.85 (d, J=6.4 Hz, 1H), 4.17 (s, 2H), 3.87 (s, 6H), 3.86 (s, 3H), 2.51 (s, 3H) ppm.

Embodiment 55

(E)-2-(2,6-Dimethoxy-4-(2-(4'-carbamoyl-2-methyl-biphenyl-3-yl)vinyl)benzylamino)-6-hydroxy-benzoic Acid 55

Synthetic Route

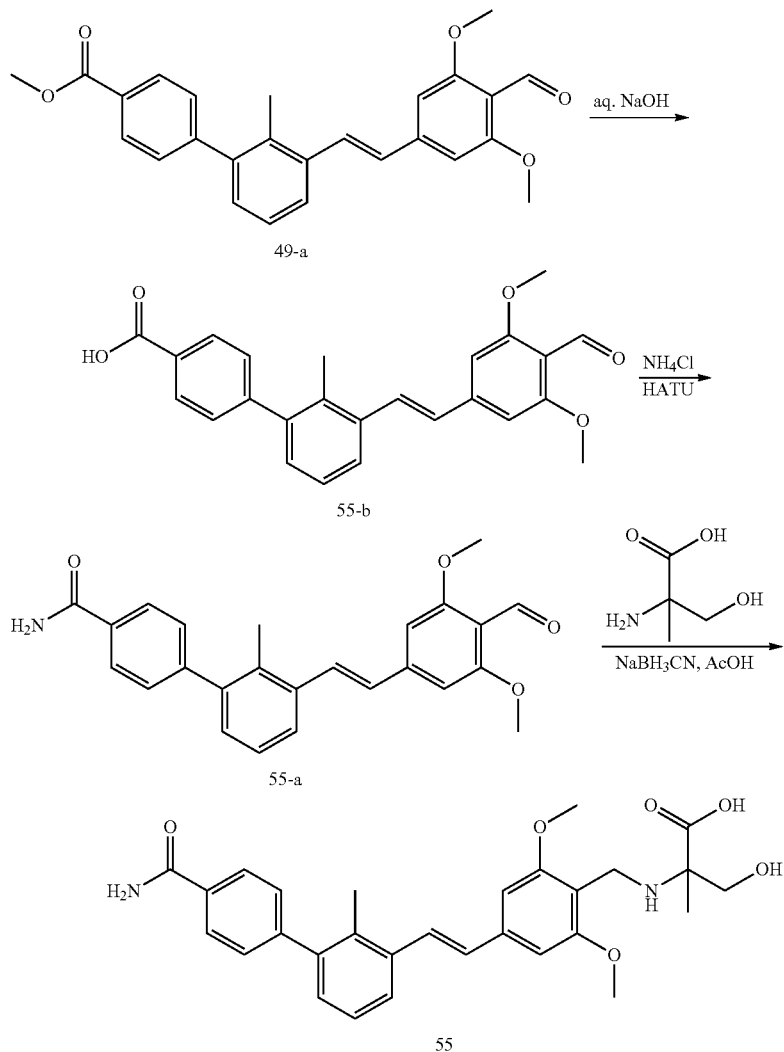

Synthesis of Compound 55-b

Compound 49-a (500 mg, 1.2 mmol) was dissolved in a mixed solvent of water (15 mL), methanol (15 mL) and tetrahydrofuran (15 mL), followed by addition of 10% aqueous sodium hydroxide solution (15 mL). The reaction solution was stirred at room temperature for 12 hours, then evaporated under reduced pressure. The residue was diluted with water (20 mL) and adjusted to pH 5 with 1M hydrochloric acid, then extracted with ethyl acetate (15 mL×3). The organic phase was washed with saturated brine (15 mL), dried over anhydrous sodium sulfate, filtered and evaporated under reduced pressure to give compound 55-b (300 mg, yield 62%), which was used directly in the next step without further purification. LC-MS (ESI): m/z=403 [M−H]$^+$.

Synthesis of Compound 55-a

Compound 55-b (300 mg, 0.75 mmol) was dissolved in N,N-dimethylformamide (20 mL), then ammonium chloride (160 mg, 3.0 mmol), 2-(7-azabenzotriazol)-N,N,N',N'-tetramethyluronium hexafluorophosphate (426 mg, 1.1 mmol) and triethylamine (0.3 mL, 2.2 mmol) were successively added. The reaction solution was stirred at room temperature for 12 hours, then diluted with water (20 mL), extracted with ethyl acetate (15 mL×3). The organic phase was washed with saturated brine (15 mL), dried over anhydrous sodium sulfate, filtered and evaporated under reduced pressure to give compound 55-a (110 mg, yield 37%), which was used directly in the next step without further purification. LC-MS (ESI): m/z=402 [M+H]$^+$.

Synthesis of Compound 55

Compound 55-a (60 mg, 0.15 mmol) and 2-amino-3-hydroxy-2-methylpropionic acid (36 mg, 0.3 mmol) were dissolved in a mixed solvent of methanol (15 mL) and dichloromethane (15 mL), followed by addition of glacial acetic acid (0.02 mL, 0.30 mmol). The reaction solution was stirred at room temperature for 2 hours. Then sodium cyanoborohydride (38 mg, 0.6 mmol) was added and the resulting mixture was stirred for another 12 hours. The reaction solution was evaporated under reduced pressure, and the residue was purified by high performance liquid chromatography (mobile phase: water (10 mM ammonium bicarbonate), acetonitrile; gradient: 30%-65%) to give compound 55 as a white solid (5 mg, yield 6.6%). LC-MS (ESI): m/z=503 [M–H]$^+$.

$^1$H NMR (400 MHz, DMSO-d$_6$) δ: 8.04 (s, 1H), 7.97-7.95 (d, J=6.8 Hz, 2H), 7.70-7.69 (d, J=6.4 Hz, 1H), 7.64-7.61 (d, J=12.8 Hz, 1H), 7.42-7.41 (d, J=6.8 Hz, 3H), 7.34-7.31 (t, J=6 Hz, 1H), 7.18-7.14 (m, 2H), 7.02 (s, 2H), 4.06 (s, 2H), 3.89 (s, 6H), 3.67-3.65 (d, J=8.8 Hz, 1H), 3.56-3.54 (d, J=8.8 Hz, 1H), 2.31 (s, 3H), 1.28 (s, 3H) ppm.

Embodiment 56

(E)-2-(4-(3-(2,3-Dihydrobenzo[b][1,4]dioxin-6-yl)-2-methylstyryl)-2,6-dimethoxybenzylamino)-3-hydroxypropanoic Acid 56

Synthetic Route

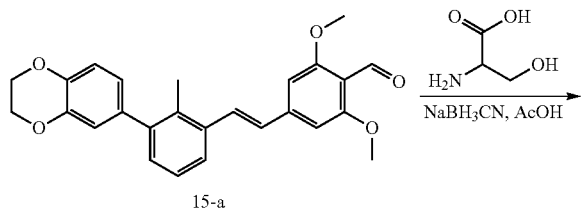

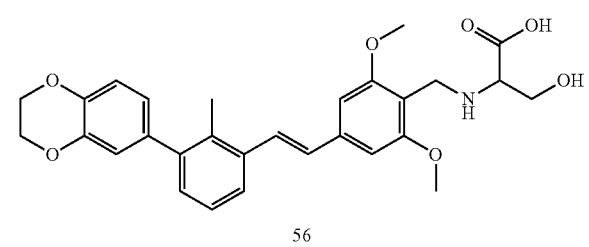

Synthesis of Compound 56

Compound 15-a (150 mg, 0.47 mmol) and 2-amino-3-hydroxypropionic acid (76 mg, 0.72 mmol) were dissolved in a mixed solvent of methanol (15 mL) and dichloromethane (15 mL), followed by addition of glacial acetic acid (0.04 mL, 0.72 mmol). The reaction solution was stirred at room temperature for 2 hours. Then sodium cyanoborohydride (38 mg, 0.6 mmol) was added and the resulting mixture was stirred for another 12 hours. The reaction solution was evaporated under reduced pressure, and the residue was purified by high performance liquid chromatography (mobile phase: water (10 mM ammonium bicarbonate), acetonitrile; gradient: 22%-55%) to give compound 56 as a white solid (79 mg, yield 33.2%). LC-MS (ESI): m/z=504 [M–H]$^+$.

$^1$H NMR (400 MHz, DMSO-d$_6$) δ: 7.62-7.57 (m, 2H), 7.27-7.24 (t, J=6 Hz, 1H), 7.11-7.08 (m, 2H), 6.99 (s, 2H), 6.93-6.91 (d, J=6.8 Hz, 1H), 6.79-6.75 (m, 2H), 4.29 (s, 4H), 4.17-4.08 (m, 2H), 3.87 (s, 6H), 3.78-3.75 (m, 1H), 3.61-3.57 (m, 1H), 3.13-3.10 (m, 1H), 2.30 (s, 3H) ppm.

Embodiment 57

(E)-2-(4-(3-(2,3-Dihydrobenzo[b][1,4]dioxin-6-yl)-2-methylstyryl)-2,6-dimethoxybenzylamino)-3-hydroxy-2-methylpropanoic Acid 57

Synthetic Route

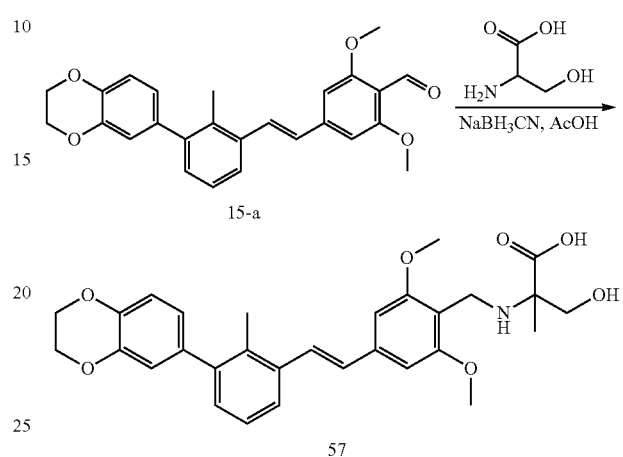

Synthesis of Compound 57

Compound 15-a (150 mg, 0.47 mmol) and 2-amino-3-hydroxy-2-methylpropionic acid (85 mg, 0.72 mmol) were dissolved in a mixed solvent of methanol (15 mL) and dichloromethane (15 mL), followed by addition of glacial acetic acid (0.04 mL, 0.72 mmol). The reaction solution was stirred at room temperature for 2 hours. Then sodium cyanoborohydride (91 mg, 1.4 mmol) was added and the resulting mixture was stirred for another 12 hours. The reaction solution was evaporated under reduced pressure, and the residue was purified by high performance liquid chromatography (mobile phase: water (10 mM ammonium bicarbonate), acetonitrile; gradient: 25%-55%) to give compound 55 as a white solid (130 mg, yield 53.2%). LC-MS (ESI): m/z=518 [M–H]$^+$.

$^1$H NMR (400 MHz, DMSO-d$_6$) δ: 7.62-7.57 (m, 2H), 7.27-7.24 (t, J=6.4 Hz, 1H), 7.13-7.09 (m, 2H), 6.99 (s, 2H), 6.93-6.91 (d, J=6.4 Hz, 1H), 6.79-6.75 (m, 2H), 4.29 (s, 4H), 4.07 (s, 2H), 3.89 (s, 6H), 3.67-3.64 (d, J=8.8 Hz, 1H), 3.55-3.53 (d, J=8.8 Hz, 1H), 2.3 (s, 3H), 1.28 (s, 3H) ppm.

Embodiment 58

(E)-4-(2,6-Dimethoxy-4-(2-(2-methylbiphenyl-3-yl)vinyl)benzylamino)-2-hydroxybenzoic Acid 58

Synthetic Route

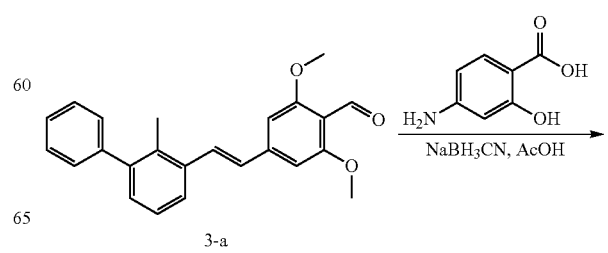

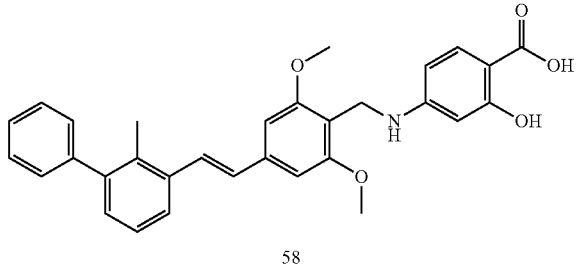

58

Synthesis of Compound 58

Compound 3-a (100 mg, 0.279 mmol) and 4-amino-2-hydroxybenzoic acid (85.5 mg, 0.558 mmol) were dissolved in a mixed solvent of methanol (5 mL) and dichloromethane (5 mL), followed by addition of glacial acetic acid (33.5 mg, 0.558 mmol). The reaction solution was stirred at room temperature for 1 hour. Then sodium cyanoborohydride (87.7 mg, 1.395 mmol) was added and the resulting mixture was stirred for another 16 hours. The reaction solution was evaporated under reduced pressure, and the residue was diluted with ethyl acetate (50 mL), washed with water (10 mL×3) and saturated brine (10 mL). The organic phase was dried over anhydrous sodium sulfate, filtered and evaporated under reduced pressure. The residue was purified by preparative silica gel thin layer chromatography (dichloromethane:methanol=10:1) to give compound 58 (16 mg, yield 11.6%). LC-MS (ESI): m/z=494 [M−H]+.

$^1$H NMR (500 MHz, CDCl$_3$) δ: 7.61-7.56 (m, 2H), 7.44-7.41 (m, 2H), 7.38-7.34 (m, 2H), 7.32-7.30 (m, 2H), 7.25-7.24 (m, 1H), 7.18-7.17 (m, 1H), 6.97-6.93 (d, J=16.0 Hz, 1H), 6.27 (s, 1H), 6.19-6.17 (d, J=7.5 Hz, 1H), 4.39 (s, 2H), 3.92 (s, 6H), 2.30 (s, 3H) ppm.

Embodiment 59

(E)-5-(2,6-Dimethoxy-4-(2-(2-methylbiphenyl-3-yl)vinyl)benzylamino)-2-hydroxybenzoic Acid 59

Synthetic Route

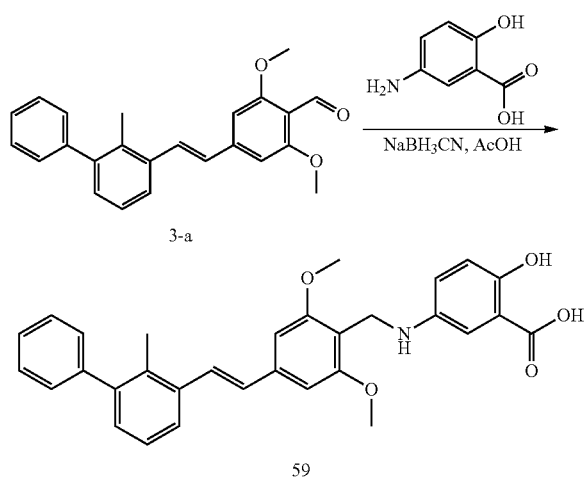

Synthesis of Compound 59

Compound 3-a (100 mg, 0.279 mmol) and 4-amino-2-hydroxybenzoic acid (85.5 mg, 0.558 mmol) were dissolved in a mixed solvent of methanol (5 mL) and dichloromethane (5 mL), followed by addition of glacial acetic acid (33.5 mg, 0.558 mmol). The reaction solution was stirred at room temperature for 1 hour. Then sodium cyanoborohydride (87.7 mg, 1.395 mmol) was added and the resulting mixture was stirred for another 16 hours. The reaction solution was evaporated under reduced pressure, and the residue was diluted with ethyl acetate (50 mL), washed with water (10 mL×3) and saturated brine (10 mL). The organic phase was dried over anhydrous sodium sulfate, filtered and evaporated under reduced pressure. The residue was purified by preparative silica gel thin layer chromatography (dichloromethane:methanol=10:1) to give compound 59 (54 mg, yield 39.1%). LC-MS (ESI): m/z=494 [M−H]+.

$^1$H NMR (500 MHz, CDCl$_3$) δ: 7.64 (s, 1H), 7.55-7.54 (d, J=7.0 Hz, 1H), 7.43-7.40 (m, 2H), 7.38-7.36 (m, 1H), 7.35-7.34 (m, 1H), 7.31-7.29 (m, 2H), 7.26-7.23 (t, 1H), 7.18-7.17 (m, 1H), 7.00-6.98 (m, 1H), 6.94-6.90 (d, J=16.0 Hz, 1H), 6.80-6.78 (d, J=9.0 Hz, 1H), 6.67 (s, 2H), 4.40 (s, 2H), 3.86 (s, 6H), 2.29 (s, 3H) ppm.

Embodiment 60

2-(2,6-Dimethoxy-4-(2-(2-methylbiphenyl-3-yl)-1H-pyrazol-1-yl)benzylamino)-3-hydroxypropanoic Acid 60

Synthetic Route

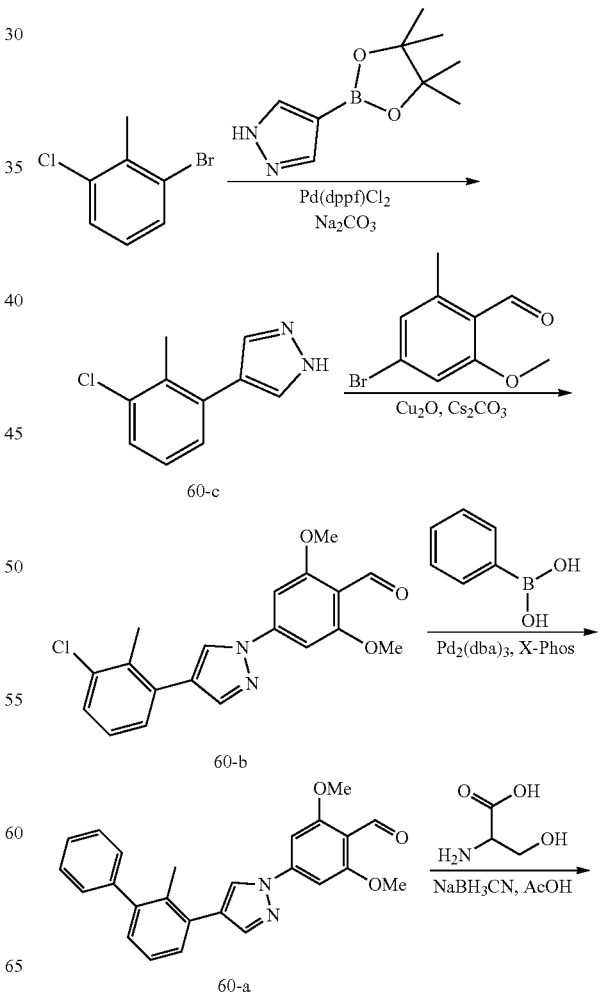

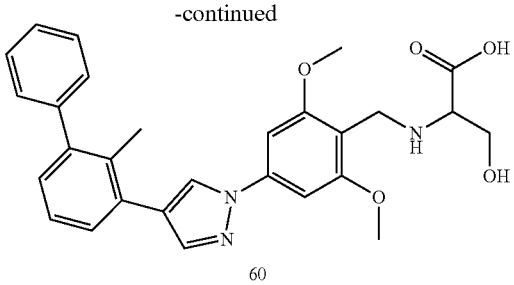

60

Synthesis of Compound 60-c

2-Bromo-6-chlorotoluene (2.05 g, 10.0 mmol) and pyrazole boronic acid ester (2.1 g, 11.0 mmol) were dissolved in a mixed solvent of 1,4-dioxane (50 mL) and water (5 mL), followed by addition of [1,1'-bis(diphenylphosphino)ferrocene]palladium dichloride (0.731 g, 1.0 mmol) and sodium carbonate (3.18 g, 30.0 mmol). After the reaction system was purged three times with nitrogen, the reaction solution was heated to 85° C. and stirred for 16 hours. Then the reaction solution was cooled to room temperature, diluted with ethyl acetate (100 mL), washed successively with water (50 mL×3) and saturated brine (50 mL). The organic phase was dried over anhydrous sodium sulfate and evaporated under reduced pressure. The residue was purified by silica gel column chromatography (petroleum ether:ethyl acetate=4:1 to 2:1) to give compound 60-c (1.4 g, yield 73%). LC-MS (ESI): m/z=193 [M+H]$^+$.

Synthesis of Compound 60-b

Compound 60-c (192 mg, 1.0 mmol) and 4-bromo-2,6-dimethoxybenzaldehyde (171.5 mg, 0.7 mmol) were dissolved in N,N-dimethylformamide (6 mL), then cuprous oxide (14.4 mg, 0.1 mmol) and cesium carbonate (455 mg, 1.4 mmol) were successively added. The reaction solution was heated to 85° C. and stirred for 16 hours, then diluted with water (40 mL), extracted with ethyl acetate (50 mL×3). The organic phase was dried over anhydrous sodium sulfate, filtered and evaporated under reduced pressure. The residue was purified by silica gel column chromatography (petroleum ether:ethyl acetate=5:1) to give compound 60-b as a yellow solid (106 mg, yield 29%). LC-MS (ESI): m/z=357 [M+H]$^+$.

Synthesis of Compound 60-a

Phenylboronic acid (73.3 mg, 0.6 mmol), potassium phosphate (318 mg, 1.5 mmol), 2-dicyclohexylphosphino-2',4',6'-triisopropylbiphenyl (50 mg, 0.1 mmol) and tris(dibenzylideneacetone)dipalladium (27.5 mg, 0.03 mmol) were added to a solution of compound 60-b (106 mg, 0.3 mmol) in toluene (30 mL). After the reaction system was purged three times with nitrogen, the reaction solution was heated to 100° C. and stirred for 16 hours. Then the reaction solution was cooled to room temperature and evaporated under reduced pressure. The residue was purified by silica gel column chromatography (petroleum ether:ethyl acetate=5:1) to give compound 60-a as a yellow solid (90 mg, yield 75%). LC-MS (ESI): m/z=399 [M+H]$^+$.

Synthesis of Compound 60

Compound 60-a (90 mg, 0.22 mmol) and 2-amino-3-hydroxypropionic acid (42 mg, 0.68 mmol) were dissolved in a mixed solvent of methanol (7 mL) and dichloromethane (7 mL), followed by addition of two drops of glacial acetic acid. The reaction solution was stirred at room temperature for 6 hours, followed by addition of sodium cyanoborohydride (43 mg, 0.68 mmol), and the resulting mixture was stirred for another 12 hours. The reaction solution was evaporated under reduced pressure, and the residue was purified by high performance liquid chromatography (mobile phase: water (10 mM ammonium bicarbonate), acetonitrile; gradient: 25%-55%) to give compound 60 as a white solid (18 mg, yield 16%). LC-MS (ESI): m/z=486 [M−H]$^+$.

$^1$H NMR: (400 MHz, CD$_3$OD) δ: 8.58 (s, 1H), 7.93 (s, 1H), 7.47-7.42 (m, 3H), 7.39-7.34 (m, 3H), 7.30 (t, J=6.4, 1H), 7.26 (s, 2H), 7.20 (d, J=6.4, 1H), 4.46-4.39 (q, 2H), 4.03 (s, 6H), 4.02-4.00 (m, 1H), 3.87-3.83 (dd, J$_1$=6.0, J$_2$=9.6, 1H), 3.56-3.54 (m, 1H), 2.31 (s, 3H) ppm.

Embodiment 61

(S,E)-2-(2,6-Dimethoxy-4-(2-methylbiphenyl-3-(1-methyl-1H-pyrazol-4-yl)styryl)benzylamino)-3-hydroxypropionic Acid 61

Synthetic Route

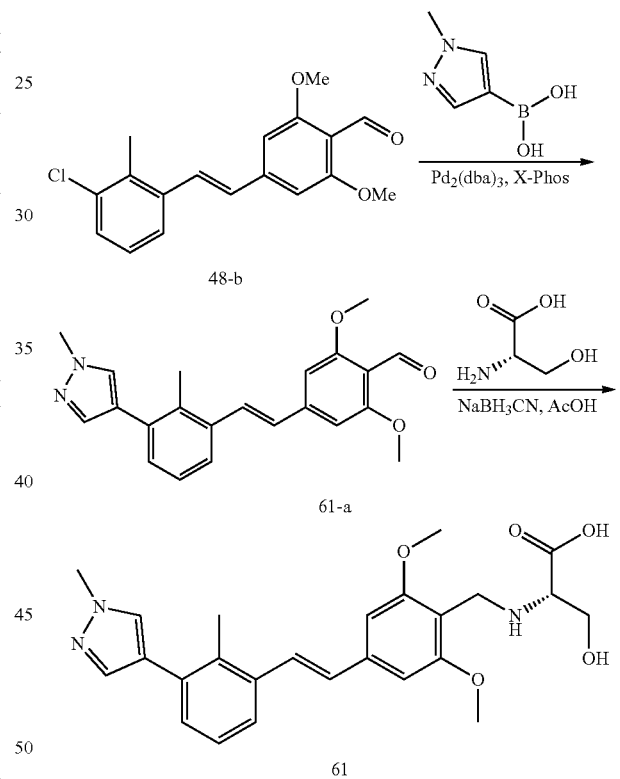

Synthesis of Compound 60-a

1-Methylpyrazole-4-boronic acid (300 mg, 2.4 mmol), potassium phosphate (1.02 g, 4.8 mmol), 2-dicyclohexylphosphino-2',4',6'-triisopropylbiphenyl (100 mg, 0.16 mmol) and tris(dibenzylideneacetone)dipalladium (120 mg, 0.16 mmol) were added to a solution of compound 48-b (500 mg, 1.6 mmol) in toluene (10 mL). After the reaction system was purged three times with nitrogen, the reaction solution was heated to 105° C. and stirred for 24 hours. Then the reaction solution was cooled to room temperature and evaporated under reduced pressure. The residue was purified by silica gel column chromatography (petroleum ether:ethyl acetate=3:1) to give compound 61-a as a yellow solid (370 mg, yield 65%). LC-MS (ESI): m/z=363 [M+H]$^+$.

Synthesis of Compound 61

Compound 61-a (100 mg, 0.27 mmol) and L-serine (57 mg, 0.54 mmol) were dissolved in a mixed solvent of methanol (5 mL) and dichloromethane (5 mL), followed by addition of glacial acetic acid (33 mg, 0.54 mmol). The reaction solution was stirred at room temperature for 3 hours, followed by addition of sodium cyanoborohydride (85 mg, 1.35 mmol), and the resulting mixture was stirred for another 16 hours. The reaction solution was evaporated under reduced pressure, and the residue was diluted with ethyl acetate (50 mL) and water (50 mL). The organic phase was dried over anhydrous sodium sulfate and evaporated under reduced pressure. The residue was purified by high performance liquid chromatography (mobile phase: water (10 mM ammonium bicarbonate), acetonitrile; gradient: 25%-55% (the initial mobile phase was 25% water and 75% acetonitrile, and the final mobile phase was 55% water and 45% acetonitrile, where % refers to percent of volume)) to give compound 61 as a white solid (43 mg, yield 35%). LC-MS (ESI): m/z=452 [M+H]$^+$.

$^1$H-NMR (500 MHz, CD$_3$OD) δ: 7.71 (s, 1H), 7.54-7.60 (m, 3H), 7.22-7.24 (m, 2H), 7.04 (d, J=15 Hz, 1H), 6.94 (s, 2H), 4.38 (m, 2H), 3.99 (m, 1H), 3.97 (s, 6H), 3.96 (s, 3H), 3.84 (m, 1H), 3.33 (m, 1H), 2.44 (s, 3H) ppm.

Embodiment 62

(S,E)-2-(4-(3-(2,3-Dihydrobenzo[b][1,4]dioxin-6-yl)-2-methylstyryl)-2-methoxybenzylamino)-3-hydroxypropanoic Acid 62

Synthetic Route

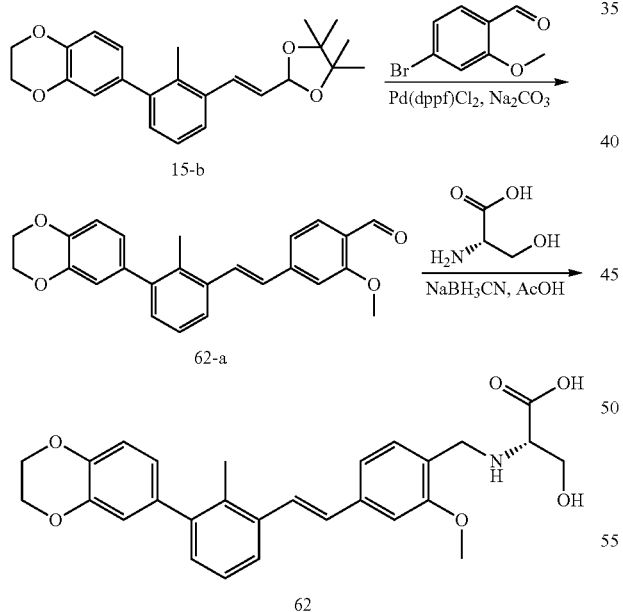

Synthesis of Compound 62-a

Compound 15-b (200 mg, 0.53 mmol) and 2-methoxy-4-bromobenzaldehyde (75 mg, 0.35 mmol) were dissolved in a mixed solvent of 1,4-dioxane (5 mL) and water (0.5 mL), followed by addition of [1,1'-bis(diphenylphosphino)ferrocene]palladium dichloride (33 mg, 0.04 mmol) and sodium carbonate (114 mg, 1.05 mmol). After the reaction system was purged three times with nitrogen, the reaction solution was heated to 80° C. and stirred for 16 hours. The reaction solution was cooled to room temperature and evaporated under reduced pressure. The residue was diluted with dichloromethane (50 mL) and water (50 mL). The organic phase was dried over anhydrous sodium sulfate and evaporated under reduced pressure. The residue was purified by silica gel column chromatography (petroleum ether:ethyl acetate=3:1) to give compound 62-a (78 mg, yield 38%). LC-MS (ESI): m/z=387 [M+H]$^+$.

Synthesis of Compound 62

Compound 62-a (78 mg, 0.21 mmol) and L-serine (44 mg, 0.42 mmol) were dissolved in a mixed solvent of methanol (5 mL) and dichloromethane (5 mL), followed by addition of glacial acetic acid (26 mg, 0.42 mmol). The reaction solution was stirred at room temperature for 3 hours, followed by addition of sodium cyanoborohydride (27 mg, 0.42 mmol), and the resulting mixture was stirred for another 16 hours. The reaction solution was evaporated under reduced pressure, and the residue was diluted with ethyl acetate (50 mL) and water (50 mL). The organic phase was dried over anhydrous sodium sulfate and evaporated under reduced pressure. The residue was purified by high performance liquid chromatography (mobile phase: water (10 mM ammonium bicarbonate), acetonitrile; gradient: 25%-55% (the initial mobile phase was 25% water and 75% acetonitrile, and the final mobile phase was 55% water and 45% acetonitrile, where % refers to percent of volume)) to give compound 62 as a white solid (32 mg, yield 33%). LC-MS (ESI): m/z=476 [M+H]$^+$.

$^1$H-NMR (500 MHz, DMSO-d$_6$) δ: 7.61 (d, J=9 Hz, 1H), 7.54 (d, J=15 Hz, 1H), 7.36 (d, J=9 Hz, 2H), 7.29 (s, 1H), 7.24 (m, 2H), 7.10 (m, 2H), 6.91 (d, J=8 Hz, 2H), 6.75 (m, 2H), 4.28 (s, 4H), 4.02 (s, 2H), 3.75 (s, 3H), 3.72 (m, 1H), 3.62 (m, 1H), 3.17 (m, 1H), 2.28 (s, 3H) ppm.

Embodiment 63

(S,E)-2-(2,6-dimethoxy-4-(2-(4-methyl-5-phenylpyridin-3-yl)vinyl)benzylamino)-3-hydroxypropanoic Acid 63

Synthetic Route

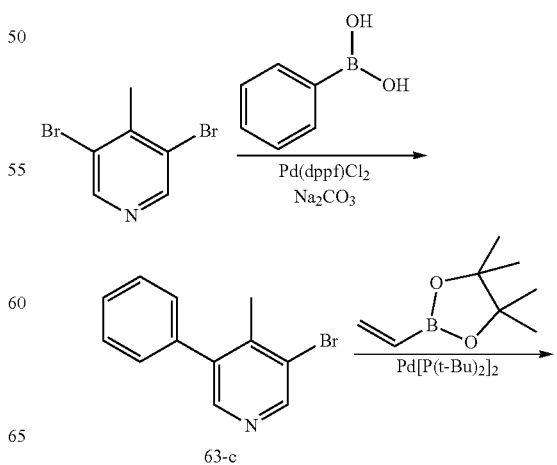

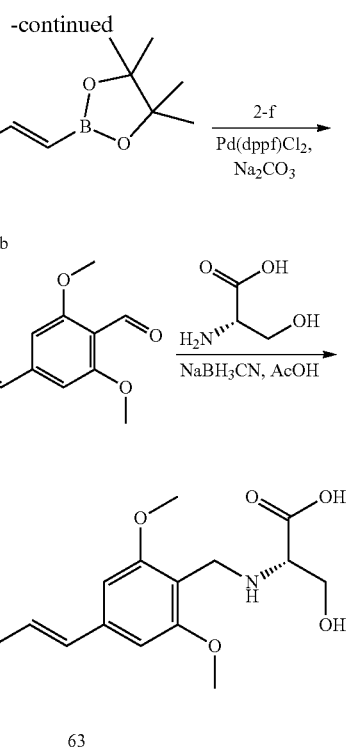

Synthesis of Compound 63-c

Phenylboronic acid (385 mg, 5.62 mmol) and 3,5-dibromo-4-methylpyridine (2.1 g, 8.43 mmol) were dissolved in a mixed solvent of 1,4-dioxane (5 mL) and water (0.5 mL), followed by addition of [1,1'-bis(diphenylphosphino)ferrocene]palladium dichloride (450 mg, 0.56 mmol) and sodium carbonate (1.8 g, 16.86 mmol). After the reaction system was purged three times with nitrogen, the reaction solution was heated to 80° C. and stirred for 16 hours. The reaction solution was cooled to room temperature and evaporated under reduced pressure. The residue was purified by silica gel column chromatography (petroleum ether:ethyl acetate=10:1) to give compound 63-c (980 mg, yield 71%). LC-MS (ESI): m/z=248 [M+H]+.

Synthesis of Compound 63-b

Compound 63-c (980 mg, 3.97 mmol) and vinylboronic acid pinacol ester (855 mg, 5.55 mmol) were dissolved in toluene (10 mL), followed by addition of bis(tri-tert-butylphosphine)palladium (200 mg, 0.4 mmol) and triethylamine (1.6 g, 15.88 mmol). After the reaction system was purged three times with nitrogen, the reaction solution was heated to 80° C. and stirred for 6 hours. Then the reaction solution was cooled to room temperature and evaporated under reduced pressure. The residue was purified by silica gel column chromatography (petroleum ether:ethyl acetate=3:1) to give compound 63-b (435 mg, yield 34%).

Synthesis of Compound 63-a

Compound 63-b (435 mg, 1.36 mmol) and compound 2-f (330 mg, 1.35 mmol) were dissolved in a mixed solvent of 1,4-dioxane (5 mL) and water (0.5 mL), followed by addition of [1,1'-bis(diphenylphosphino)ferrocene]palladium dichloride (100 mg, 0.13 mmol) and sodium carbonate (431 mg, 4.07 mmol). After the reaction system was purged three times with nitrogen, the reaction solution was heated to 80° C. and stirred for 16 hours. The reaction solution was cooled to room temperature and evaporated under reduced pressure. The residue was purified by silica gel column chromatography (petroleum ether:ethyl acetate=3:1) to give compound 63-a as a yellow solid (150 mg, yield 31%). LC-MS (ESI): m/z=360 [M+H]+.

Synthesis of Compound 63

Compound 63-a (150 mg, 0.42 mmol) and L-serine (88 mg, 0.84 mmol) were dissolved in a mixed solvent of methanol (5 mL) and dichloromethane (5 mL), followed by addition of glacial acetic acid (50 mg, 0.84 mmol). The reaction solution was stirred at room temperature for 3 hours, followed by addition of sodium cyanoborohydride (153 mg, 2.43 mmol), and the resulting mixture was stirred for another 16 hours. The reaction solution was evaporated under reduced pressure, and the residue was diluted with dichloromethane (50 mL), isopropanol (10 mL) and water (50 mL). The organic phase was dried over anhydrous sodium sulfate, filtered and evaporated under reduced pressure. The residue was purified by silica gel column chromatography (dichloromethane:methanol=10:1) to give compound 63 as a white solid (36 mg, yield 20%). LC-MS (ESI): m/z=449 [M+H]+.

$^1$H-NMR (500 MHz, CD$_3$OD) δ: 8.69 (s, 1H), 8.26 (s, 1H), 7.44-7.55 (m, 4H), 7.36-7.38 (m, 2H), 7.19 (d, J=15 Hz, 1H), 7.02 (s, 2H), 4.41 (m, 2H), 4.03 (m, 1H), 3.99 (s, 6H), 3.85 (m, 1H), 3.52 (m, 1H), 2.39 (s, 3H) ppm.

Embodiment 64

(S,E)-2-(4-(2-(5-(2,3-Dihydrobenzo[b][1,4]dioxin-6-yl)-4-methylpyridin-3-yl)vinyl)-2,6-dimethoxybenzylamino)-3-hydroxypropanoic Acid 64

Synthetic Route

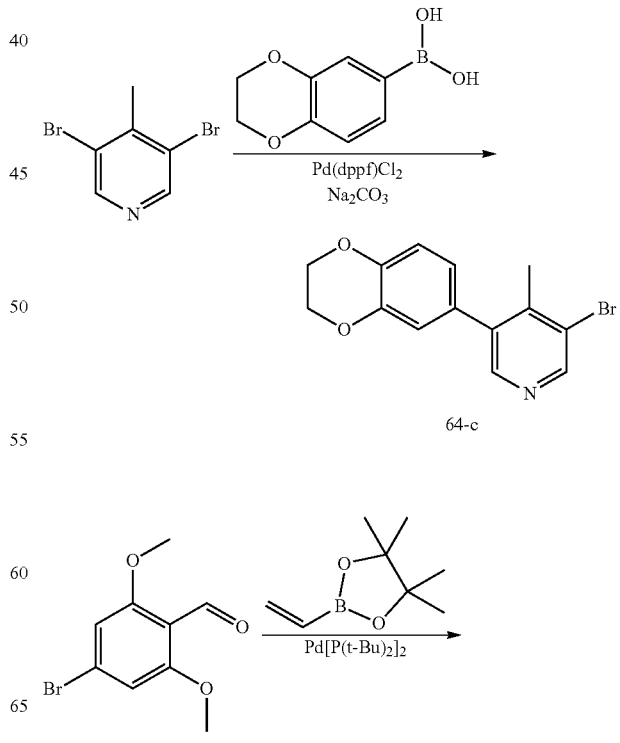

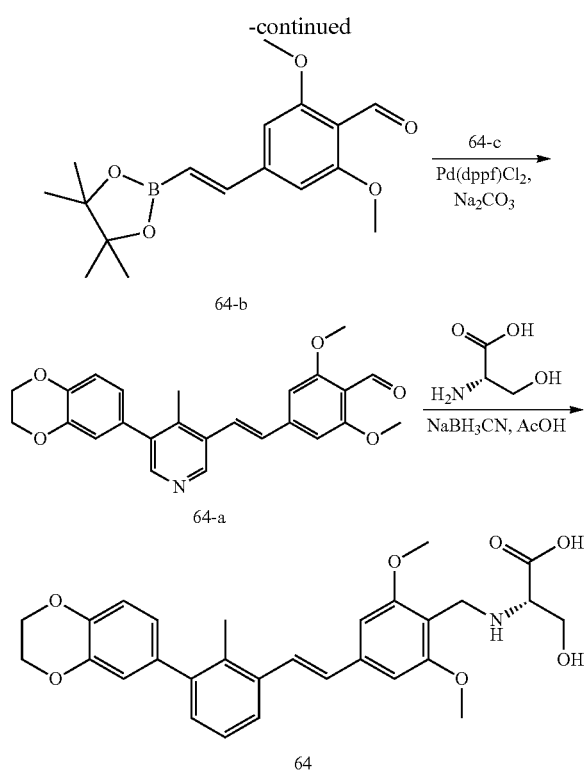

Synthesis of Compound 64-c 2,3-Dihydrobenzo[b][1,4]dioxin-6-phenylboronic acid (202 mg, 1.12 mmol) and 3,5-dibromo-4-methylpyridine (420 mg, 1.69 mmol) were dissolved in a mixed solvent of 1,4-dioxane (5 mL) and water (0.5 mL), followed by addition of [1,1'-bis(diphenylphosphino)ferrocene]palladium dichloride (50 mg, 0.06 mmol) and sodium carbonate (360 mg, 3.39 mmol). After the reaction system was purged three times with nitrogen, the reaction solution was heated to 85° C. and stirred for 16 hours. The reaction solution was cooled to room temperature and evaporated under reduced pressure. The residue was purified by silica gel column chromatography (petroleum ether:ethyl acetate=5:1) to give compound 64-c as a colorless oil (274 mg, yield 80%). LC-MS (ESI): m/z=306 [M+H]+.

Synthesis of Compound 64-b 2,6-Dimethoxy-4-bromobenzaldehyde (570 mg, 2.34 mmol) and vinylboronic acid pinacol ester (504 mg, 3.27 mmol) were dissolved in toluene (10 mL), followed by addition of bis(tri-tert-butylphosphine)palladium (200 mg, 0.4 mmol) and triethylamine (1.9 g, 18.72 mmol). After the reaction system was purged three times with nitrogen, the reaction solution was heated to 80° C. and stirred for 16 hours. Then the reaction solution was cooled to room temperature and evaporated under reduced pressure. The residue was purified by silica gel column chromatography (petroleum ether:ethyl acetate=3:1) to give compound 64-b as a pale brown solid (540 mg, yield 73%).

$^1$H-NMR (500 MHz, DMSO-$d_6$) δ: 10.32 (s, 1H), 7.31 (d, J=18 Hz, 1H), 6.96 (s, 2H), 6.42 (d, J=18 Hz, 1H), 3.86 (s, 6H), 1.26 (s, 12H) ppm.

Synthesis of Compound 64-a

Compound 64-c (201 mg, 0.66 mmol) and compound 64-b (292 mg, 0.92 mmol) were dissolved in a mixed solvent of 1,4-dioxane (5 mL) and water (0.5 mL), followed by addition of [1,1'-bis(diphenylphosphino)ferrocene]palladium dichloride (50 mg, 0.06 mmol) and sodium carbonate (208 mg, 1.96 mmol). After the reaction system was purged three times with nitrogen, the reaction solution was heated to 85° C. and stirred for 16 hours. The reaction solution was cooled to room temperature and evaporated under reduced pressure. The residue was purified by silica gel column chromatography (petroleum ether:ethyl acetate=1:1) to give compound 64-a as a yellow solid (211 mg, yield 77%). LC-MS (ESI): m/z=418 [M+H]+.

Synthesis of Compound 64

Compound 64-a (211 mg, 0.51 mmol) and L-serine (107 mg, 1.0 mmol) were dissolved in a mixed solvent of methanol (5 mL) and dichloromethane (5 mL), followed by addition of glacial acetic acid (61 mg, 1.01 mmol). The reaction solution was stirred at room temperature for 3 hours, followed by addition of sodium cyanoborohydride (161 mg, 2.55 mmol), and the resulting mixture was stirred for another 16 hours. The reaction solution was evaporated under reduced pressure, and the residue was diluted with dichloromethane (50 mL), isopropanol (5 mL) and water (50 mL). The organic phase was dried over anhydrous sodium sulfate, filtered and evaporated under reduced pressure. The residue was purified by silica gel column chromatography (dichloromethane:methanol=10:1) to give compound 64 as a white solid (35 mg, yield 14%). LC-MS (ESI): m/z=507 [M+H]+.

$^1$H-NMR (500 MHz, DMSO-$d_6$) δ: 8.73 (s, 1H), 8.25 (s, 1H), 7.53 (d, J=16 Hz, 1H), 7.22 (d, J=16 Hz, 1H), 7.03 (s, 2H), 6.97 (d, J=8 Hz, 1H), 6.88 (d, J=2 Hz, 1H), 6.83 (dd, J=8 Hz, J=2 Hz, 1H), 4.29 (s, 4H), 4.14 (m, 2H), 3.89 (s, 6H), 3.77 (m, 1H), 3.59 (m, 1H), 3.12 (m, 1H), 2.34 (s, 3H) ppm.

Embodiment 65

(E)-2-(2,6-Dimethoxy-4-(2-(4-methyl-5-phenylpyridin-3-yl)vinyl)benzylamino)-3-hydroxy-2-methyl-propionic Acid 64

Synthetic Route

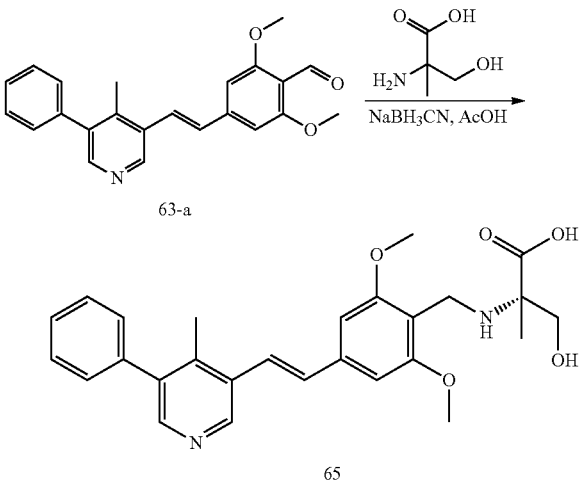

Synthesis of Compound 65

Compound 63-a (200 mg, 0.56 mmol) and 2-methylserine (133 mg, 1.12 mmol) were dissolved in a mixed solvent of methanol (5 mL) and dichloromethane (5 mL), followed by addition of glacial acetic acid (67 mg, 1.12 mmol). The reaction solution was stirred at room temperature for 3 hours, followed by addition of sodium cyanoborohydride (176 mg, 2.8 mmol), and the resulting mixture was stirred for another 16 hours. The reaction solution was evaporated under reduced pressure, and the residue was diluted with dichloromethane (50 mL), isopropanol (10 mL) and water (50 mL). The organic phase was dried over anhydrous sodium sulfate, filtered and evaporated under reduced pressure. The residue was purified by silica gel column chromatography (dichloromethane:methanol=10:1) to give compound 65 as a white solid (30 mg, yield 12%). LC-MS (ESI): m/z=463 [M+H]+.

1H-NMR (500 MHz, DMSO-d6) δ: 8.78 (s, 1H), 8.28 (s, 1H), 7.56 (d, J=16 Hz, 1H), 7.51 (m, 2H), 7.45 (m, 2H), 7.39 (m, 1H), 7.24 (d, J=16 Hz, 1H), 7.03 (s, 1H), 4.08 (s, 2H), 3.89 (s, 6H), 3.65 (d, J=11 Hz, 1H), 3.54 (d, J=11 Hz, 1H), 2.34 (s, 3H), 1.29 (m, 3H) ppm.

Embodiment 66

(E)-2-(4-(2-(5-(2,3-Dihydrobenzo[b][1,4]dioxin-6-yl)-4-methylpyridin-3-yl)vinyl)-2,6-dimethoxybenzylamino)-3-hydroxy-2-methylpropanoic Acid 66

Synthetic Route

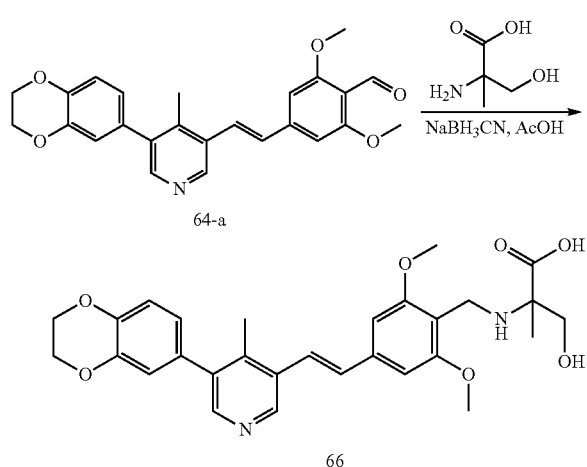

Synthesis of Compound 66

Compound 64-a (199 mg, 0.48 mmol) and 2-methylserine (114 mg, 0.96 mmol) were dissolved in a mixed solvent of methanol (5 mL) and dichloromethane (5 mL), followed by addition of glacial acetic acid (58 mg, 0.96 mmol). The reaction solution was stirred at room temperature for 3 hours, followed by addition of sodium cyanoborohydride (152 mg, 2.4 mmol), and the resulting mixture was stirred for another 16 hours. The reaction solution was evaporated under reduced pressure, and the residue was diluted with dichloromethane (50 mL), isopropanol (5 mL) and water (50 mL). The organic phase was dried over anhydrous sodium sulfate, filtered and evaporated under reduced pressure. The residue was purified by silica gel column chromatography (dichloromethane:methanol=10:1) to give compound 66 as a white solid (35 mg, yield 14%). LC-MS (ESI): m/z=521 [M+H]+.

1H-NMR (500 MHz, DMSO-d6) δ: 8.73 (s, 1H), 8.24 (s, 1H), 7.53 (d, J=16 Hz, 1H), 7.22 (d, J=16 Hz, 1H), 7.03 (s, 2H), 6.97 (d, J=8 Hz, 1H), 6.88 (d, J=2 Hz, 1H), 6.83 (dd, J=8 Hz, J=2 Hz, 1H), 4.29 (s, 4H), 4.07 (s, 2H), 3.89 (s, 6H), 3.65 (d, J=11 Hz, 1H), 3.55 (d, J=11 Hz, 1H), 2.34 (s, 3H), 1.28 (s, 3H) ppm.

Embodiment 67

(S,E)-(1-(3-(3-(2,3-Dihydrobenzo[b][1,4]dioxin-6-yl)-2-methylstyryl)-4-(trifluoromethyl)benzyl)pyrrolidin-2-yl)methanol 67

Synthetic Route

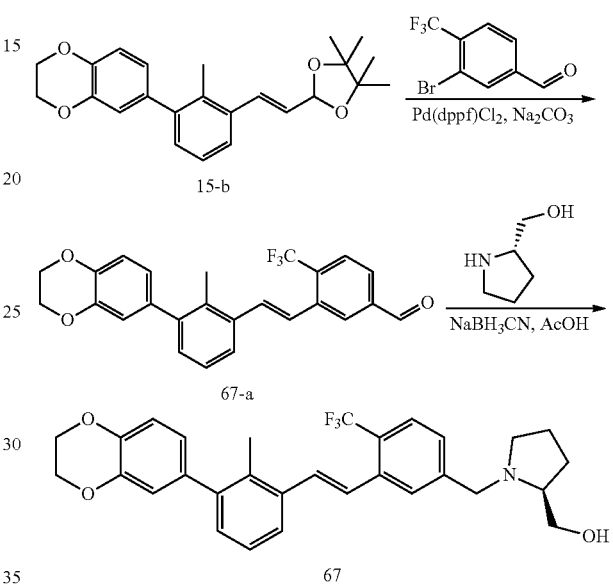

Synthesis of Compound 67-a

Compound 15-b (475 mg, 1.26 mmol) and 3-bromo-4-trifluoromethylbenzaldehyde (265.7 mg, 1.05 mmol) were dissolved in a mixed solvent of 1,4-dioxane (20 mL) and water (1 mL), followed by addition of [1,1'-bis(diphenylphosphino)ferrocene]palladium dichloride (90.8 mg, 0.105 mmol) and sodium carbonate (277.8 mg, 2.62 mmol). After the reaction system was purged three times with nitrogen, the reaction solution was heated to 80° C. and stirred for 16 hours. The reaction solution was cooled to room temperature and evaporated under reduced pressure. The residue was dissolved in ethyl acetate (50 mL), washed successively with water (20 mL×3) and saturated brine (20 mL). The organic phase was dried over anhydrous sodium sulfate and evaporated under reduced pressure. The residue was purified by silica gel column chromatography (petroleum ether ethyl acetate=10:1) to give compound 67-a (366 mg, yield 80.4%).

1H NMR (500 MHz, CDCl3) δ: 10.15 (s, 1H), 8.27 (s, 1H), 7.86 (s, 2H), 7.57-7.55 (d, J=7.5 Hz, 1H), 7.52-7.49 (d, J=16.0 Hz, 1H), 7.37-7.34 (m, 1H), 7.29-7.27 (m, 1H), 7.22-7.21 (m, 1H), 6.93-6.91 (d, J=8.5 Hz, 1H), 6.84-6.83 (m, 1H), 6.79-6.77 (m, 1H), 4.31 (s, 4H), 2.35 (s, 3H) ppm.

Synthesis of Compound 67

Compound 67-a (100 mg, 0.236 mmol) and S-prolinol (47.7 mg, 0.472 mmol) were dissolved in a mixed solvent of methanol (5 mL) and dichloromethane (5 mL), followed by addition of glacial acetic acid (28.3 mg, 0.472 mmol). The reaction solution was stirred at room temperature for 1 hour, followed by addition of sodium cyanoborohydride (74.2 mg, 1.18 mmol), and the resulting mixture was stirred for another 16 hours. The reaction solution was evaporated under reduced pressure, and the residue was dissolved in ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (dichloromethane:methanol=10:1) to give compound 67 (107 mg, yield 89.2%). LC-MS (ESI): m/z=510 [M+H]+.

$^1$H NMR (500 MHz, CDCl$_3$) δ: 7.64 (s, 1H), 7.57-7.55 (d, J=8.0 Hz, 1H), 7.48-7.47 (d, J=6.5 Hz, 1H), 7.29-7.27 (m, 3H), 7.19-7.16 (m, 1H), 7.12-7.10 (m, 1H), 6.84-6.83 (d, J=8.0 Hz, 1H), 6.76 (m, 1H), 6.72-6.70 (m, 1H), 4.23 (s, 4H), 4.05-4.02 (d, J=13.5 Hz, 1H), 3.65-3.62 (m, 1H), 3.46-3.41 (m, 2H), 3.00-2.98 (m, 1H), 2.78-2.77 (m, 1H), 2.33-2.27 (m, 1H), 2.26 (m, 3H), 1.93-1.89 (m, 1H), 1.82-1.78 (m, 1H), 1.72-1.68 (m, 2H) ppm.

Embodiment 68

(E)-2-(3-(3-(2,3-Dihydrobenzo[b][1,4]dioxin-6-yl)-2-methylstyryl)-4-(trifluoromethyl)benzyl)-3-hydroxy-2-methylpropanoic Acid 68

Synthetic Route

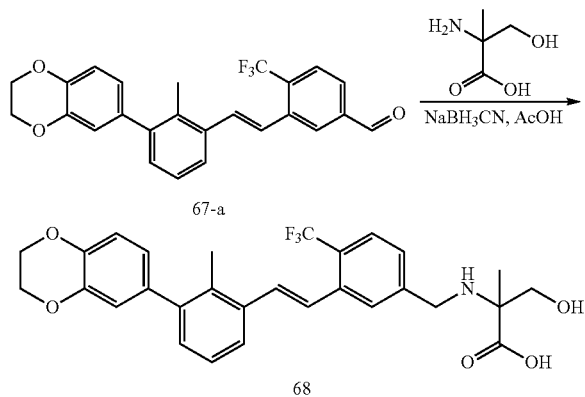

Synthesis of Compound 68

Compound 67-a (150 mg, 0.353 mmol) and 2-methylserine (84.2 mg, 0.707 mmol) were dissolved in a mixed solvent of methanol (5 mL) and dichloromethane (5 mL), followed by addition of glacial acetic acid (42.5 mg, 0.707 mmol). The reaction solution was stirred at room temperature for 1 hour, followed by addition of sodium cyanoborohydride (110.9 mg, 1.765 mmol), and the resulting mixture was stirred for another 16 hours. The reaction solution was evaporated under reduced pressure, and the residue was dissolved in ethyl acetate (50 mL), washed successively with water (20 mL) and saturated brine (20 mL). The organic phase was dried over anhydrous sodium sulfate and evaporated under reduced pressure. The residue was purified by preparative silica gel thin layer chromatography (dichloromethane:methanol=10:1) to give compound 68 (18 mg, yield 9.7%). LC-MS (ESI): m/z=526 [M+H]+.

$^1$H NMR (500 MHz, CDCl$_3$) δ: 7.88 (s, 1H), 7.54-7.53 (m, 1H), 7.44-7.37 (m, 3H), 7.22-7.12 (m, 3H), 6.87-6.84 (m, 1H), 6.74 (s, 1H), 6.69-6.67 (m, 1H), 4.26 (s, 4H), 4.02-3.91 (m, 2H), 3.55 (s, 2H), 2.25 (s, 3H), 1.25 (s, 3H) ppm.

Embodiment 69

(E)-2-((6-(3-(2,3-Dihydrobenzo[b][1,4]dioxin-6-yl)-2-methylstyryl)-5-methylpyridin-3-yl)methylamino)-3-hydroxypropanoic Acid 69

Synthetic Route

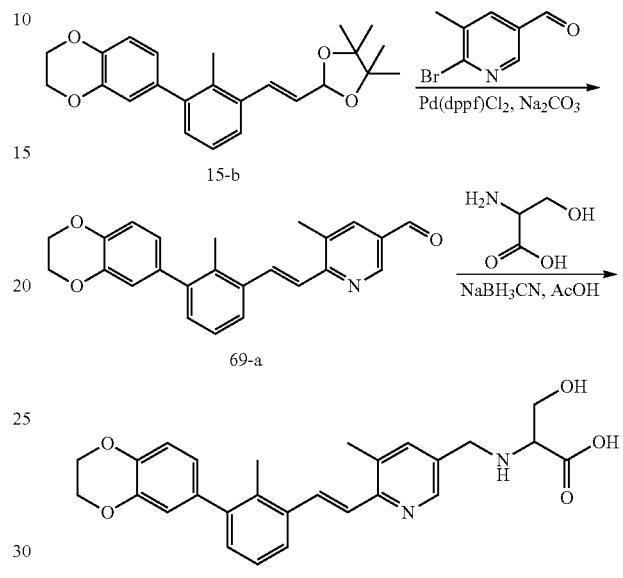

Synthesis of Compound 69-a

Compound 15-b (850 mg, 2.2 mmol) and 6-bromo-5-methyl nicotine aldehyde (300 mg, 1.5 mmol) were dissolved in a mixed solvent of 1,4-dioxane (20 mL) and water (2 mL), followed by addition of [1,1'-bis(diphenylphosphino)ferrocene]palladium dichloride (30 mg, 0.03 mmol) and sodium carbonate (397 mg, 3.7 mmol). After the reaction system was purged three times with nitrogen, the reaction solution was heated to 80° C. and stirred for 12 hours. The reaction solution was cooled to room temperature and evaporated under reduced pressure. The residue was purified by silica gel column chromatography (petroleum ether:ethyl acetate=5:1) to give compound 69-a as a yellow solid (220 mg, yield 40%). LC-MS (ESI): m/z=372 [M+H]+.

Synthesis of Compound 69

Compound 69-a (220 mg, 0.59 mmol) and serine (125 mg, 1.18 mmol) were dissolved in a mixed solvent of methanol (15 mL) and dichloromethane (15 mL), followed by addition of glacial acetic acid (0.07 mL, 1.18 mmol). The reaction solution was stirred at room temperature for 2 hours, followed by addition of sodium cyanoborohydride (91 mg, 1.4 mmol), and the resulting mixture was stirred for another 12 hours. The reaction solution was evaporated under reduced pressure, and the residue was diluted with ethyl acetate (50 mL) and water (50 mL). The organic phase was dried over anhydrous sodium sulfate and evaporated under reduced pressure. The residue was purified by high performance liquid chromatography (mobile phase: water (10 mM ammonium bicarbonate), acetonitrile; gradient: 15%-65% (the initial mobile phase was 15% water and 85% acetonitrile, and the final mobile phase was 65% water and 35% acetonitrile, where % refers to percent of volume)) to give compound 69 as a white solid (31 mg, yield 11.3%). LC-MS (ESI): m/z=461 [M+H]+.

¹H NMR (400 MHz, DMSO-d₆) δ: 8.43 (s, 1H), 8.07-8.04 (d, J=12 Hz, 1H), 7.75-7.74 (d, J=6 Hz, 1H), 7.64 (s, 1H), 7.33-7.25 (m, 2H), 7.14-7.13 (m, 1H), 6.92-6.91 (m, 1H), 6.77-6.75 (m, 2H), 4.28 (s, 4H), 3.99-3.96 (d, J=10.8 Hz, 1H), 3.89-3.86 (d, J=10.8 Hz, 1H), 3.70-3.67 (m, 1H), 3.64-3.61 (m, 1H), 3.18-3.16 (t, J=4.4 Hz, 1H), 2.44 (s, 3H), 2.28 (s, 3H) ppm.

Effect Embodiment

Homogeneous Time-Resolved Fluorescence (HTRF) binding assay was used to determine the binding activity of the compound of the present invention to PD-1/PD-L1.

The purchased kit (CisBio, #64CUS000C-1) contained reagents required for assays such as PD-1, PD-L1, anti-tag1-Eu, Anti-tag2-XL665, Dilute Buffer, and Detection Buffer.

Experimental Procedure

1. The compound was formulated to 10 concentrations with a 3-fold gradient with 100% DMSO.
2. The solution of the compound in DMSO was added to Dilute Buffer, mixed thoroughly, then transferred to a 96-well plate.
3. PD-L1 was diluted with Dilute Buffer, then added to the above 96-well plate.
4. PD-1 was diluted with Dilute Buffer and added to the above 96-well plate, which was then incubated at room temperature for 30 minutes.
5. A portion of anti-tag1-Eu and a portion of anti-tag2-XL665 were added to Detection Buffer, mixed thoroughly and transferred to the above 96-well plate.
6. The mixture in the above 96-well plate was incubated at room temperature for 1 to 24 hours.
7. HTRF values were read with Envision.

Experimental Result

The biological activity of the compound of the present invention was determined by the above assay, and the results were shown as follows (Table 1):

TABLE 1

IC₅₀ of partial compounds of the present invention binding to PD-1/PD-L1

| Compound | IC₅₀ (μM) | Compound | IC₅₀ (μM) |
|---|---|---|---|
| 1 | 1.53 | 2 | 1.34 |
| 3 | 2.70 | 4 | 0.28 |
| 5 | 0.06 | 6 | 0.15 |
| 7 | 0.05 | 8 | 0.08 |
| 9 | 0.06 | 10 | 0.17 |
| 11 | 0.46 | 12 | 0.41 |
| 13 | 0.24 | 14 | 0.39 |
| 15 | 0.24 | 16 | 0.59 |
| 17 | 0.31 | 18 | 0.19 |
| 19 | 0.33 | 20 | >10 |
| 21 | 0.78 | 22 | 0.55 |
| 23 | 0.69 | 24 | >10 |
| 25 | 5.95 | 26 | 1.30 |
| 27 | 0.92 | 28 | 2.16 |
| 29 | 2.82 | 30 | 0.46 |
| 31 | 0.24 | 32 | 0.25 |
| 33 | 0.48 | 34 | 0.34 |
| 35 | 0.25 | 36 | 0.10 |
| 37 | 0.10 | 38 | 0.23 |
| 39 | 0.17 | 40 | 0.09 |
| 41 | 5.09 | 42 | 1.10 |
| 43 | 0.13 | 44 | 0.059 |
| 45 | 0.049 | 46 | 0.048 |

TABLE 1-continued

IC₅₀ of partial compounds of the present invention binding to PD-1/PD-L1

| Compound | IC₅₀ (μM) | Compound | IC₅₀ (μM) |
|---|---|---|---|
| 47 | 0.92 | 48 | >10 |
| 49 | >10 | 50 | 7.978 |
| 51 | 0.815 | 52 | >10 |
| 53 | >10 | 54 | >10 |
| 55 | 4.50 | 56 | 0.10 |
| 57 | 0.07 | 58 | >10 |
| 59 | >10 | 60 | >10 |
| 61 | >10 | 62 | 0.120 |
| 63 | 3.9 | 64 | 4.2 |
| 65 | 2.0 | 66 | 2.9 |
| 67 | 2.4 | 68 | 0.018 |
| 69 | 0.036 | / | / |

It is to be understood that the foregoing description of the preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. An aromatic acetylene or aromatic ethylene compound represented by formula II-0, a pharmaceutically acceptable salt, a tautomer, a mesomer, a racemate or a stereoisomer thereof:

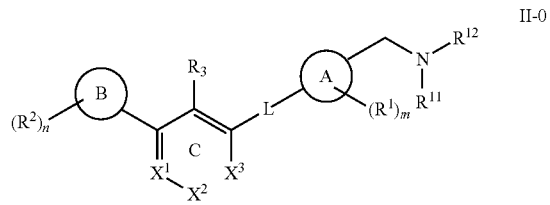

II-0 wherein, ring A and ring B are independently an aromatic ring or a heteroaromatic ring;
L is alkynyl, —C(R⁴)=C(R⁵)— or C₂-C₁₀ heteroaryl having at least one N; when L is C₂-C₁₀ heteroaryl, the N atom thereof links to the ring A, and the C atom thereof links to the ring C;
X¹ is N or —CR⁶;
X² is N or —CR⁷;
X³ is N or —CR⁸;
X¹, X² and X³ are not N simultaneously;
each of R¹ is independently hydrogen, deuterium, substituted or unsubstituted hydroxy, substituted or unsubstituted amino, halogen, substituted or unsubstituted alkyl or substituted or unsubstituted alkoxy;
each of R² is independently hydrogen, deuterium, substituted or unsubstituted hydroxy, substituted or unsubstituted amino, halogen, substituted or unsubstituted alkyl, substituted or unsubstituted alkoxy,

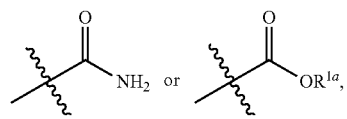

wherein $R^{1a}$ is $C_1$-$C_4$ alkyl; or two adjacent $R^2$ together with the two atoms on the ring B to which they are attached form a 5-7 membered substituted or unsubstituted carbocycle, or substituted or unsubstituted heterocycle; in the heterocycle, the heteroatom is oxygen and/or nitrogen, the number of the heteroatom(s) is 1-4;

$R^3$ is deuterium, halogen, cyano, or substituted or unsubstituted alkyl;

$R^4$ and $R^5$ are each independently hydrogen, deuterium, substituted or unsubstituted alkyl, or, substituted or unsubstituted cycloalkyl, or $R^4$ and $R^5$ together with the carbon-carbon double bond to which they are attached form a 5-7 membered substituted or unsubstituted carbocycle, or substituted or unsubstituted heterocycle; in the heterocycle, the heteroatom is selected from the group consisting of nitrogen, oxygen and sulfur, the number of the heteroatom(s) is 1-4;

$R^6$, $R^7$ and $R^8$ are each independently hydrogen, deuterium, substituted or unsubstituted hydroxy, halogen, substituted or unsubstituted amino, substituted or unsubstituted alkyl, or, substituted or unsubstituted alkoxy, or $R^6$ and $R^7$ together with the two atoms on the ring C to which they are attached form a 5-7 membered substituted or unsubstituted heterocycle; or $R^7$ and $R^8$ together with the two atoms on the ring C to which they are attached form a 5-7 membered substituted or unsubstituted heterocycle; in the heterocycle, the heteroatom is nitrogen and/or oxygen, the number of the heteroatom(s) is 1-4;

m1 is 0, 1 or 2;

n is 1 or 2;

in the definition of each $R^1$, the substituent in the substituted alkyl or the substituted alkoxy is selected from the group consisting of halogen, $C_1$-$C_4$ alkyl, hydroxy,

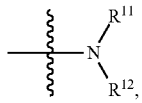

benzyl, benzyl substituted by cyano, $C_1$-$C_4$ alkoxy, $C_1$-$C_4$ carboxyl, $C_1$-$C_4$ ester group or $C_1$-$C_4$ acylamino; the substituent in the substituted hydroxy or the substituted amino is selected from the group consisting of $C_1$-$C_4$ alkyl, benzyl, benzyl substituted by cyano, $C_1$-$C_4$ alkoxy, $C_1$-$C_4$ carboxyl, $C_1$-$C_4$ ester group or $C_1$-$C_4$ acylamino;

in the definition of each $R^2$, the substituent in the substituted alkyl or the substituted alkoxy is selected from the group consisting of halogen, $C_1$-$C_4$ alkyl, hydroxy,

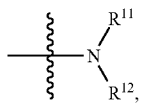

$C_1$-$C_4$ alkoxy, $C_1$-$C_4$ carboxyl, $C_1$-$C_4$ ester group or $C_1$-$C_4$ acylamino; the substituent in the substituted hydroxy or the substituted amino is selected from the group consisting of $C_1$-$C_4$ alkyl, benzyl, benzyl substituted by cyano, $C_1$-$C_4$ alkoxy, $C_1$-$C_4$ carboxyl, $C_1$-$C_4$ ester group or $C_1$-$C_4$ acylamino; when two adjacent $R^2$ together with the two atoms on the ring B to which they are attached form a 5-7 membered substituted carbocycle or substituted heterocycle, the substituent in the substituted carbocycle or in the substituted heterocycle is selected from the group consisting of halogen, $C_1$-$C_4$ alkyl, hydroxy,

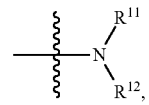

$C_1$-$C_4$ alkoxy, $C_1$-$C_4$ carboxyl, $C_1$-$C_4$ ester group or $C_1$-$C_4$ acylamino; when there are more substituents than one, the substituents are the same or different;

in the definition of $R^4$ or $R^5$, the substituent in the substituted alkyl or the substituted cycloalkyl is selected from the group consisting of halogen, $C_1$-$C_4$ alkyl, hydroxy, amino, $C_1$-$C_4$ alkoxy, $C_1$-$C_4$ carboxyl, $C_1$-$C_4$ ester group or $C_1$-$C_4$ acylamino; when $R^4$ and $R^5$ together with the carbon-carbon double bond to which they are attached form a 5-7 membered substituted carbocycle, or, substituted heterocycle, the substituent in the substituted carbocycle or the substituted heterocycle is selected from the group consisting of halogen, $C_1$-$C_4$ alkyl, hydroxy,

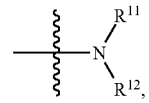

$C_1$-$C_4$ carboxyl, $C_1$-$C_4$ ester group or $C_1$-$C_4$ acylamino; when there are more substituents than one, the substituents are the same or different;

in the definition of $R^6$, $R^7$ or $R^8$, the substituent in the substituted alkyl or the substituted alkoxy is selected from the group consisting of halogen, $C_1$-$C_4$ alkyl, hydroxy,

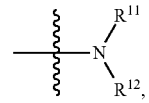

$C_1$-$C_4$ alkoxy, $C_1$-$C_4$ carboxyl, $C_1$-$C_4$ ester group or $C_1$-$C_4$ acylamino; the substituent in the substituted hydroxy or the substituted amino is selected from the group consisting of $C_1$-$C_4$ alkyl, benzyl, benzyl substituted by cyano, $C_1$-$C_4$ alkoxy, $C_1$-$C_4$ carboxyl, $C_1$-$C_4$ ester group or $C_1$-$C_4$ acylamino; when $R^6$ and $R^7$ together with the two atoms on the ring C to which they are attached form a 5-7 membered substituted heterocycle, or when $R^7$ and $R^8$ together with the two atoms on the ring C to which they are attached form a 5-7 membered substituted heterocycle, the substituent in the substituted heterocycle is selected from the group consisting of halogen, $C_{1\text{-}4}$ alkyl, hydroxy,

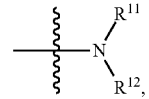

$C_1$-$C_4$ alkoxy, $C_1$-$C_4$ carboxyl, $C_1$-$C_4$ ester group or $C_1$-$C_4$ acylamino; when there are more substituents than one, the substituents are the same or different;

in

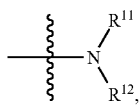

$R^{11}$ and $R^{12}$ are independently hydrogen, substituted or unsubstituted alkyl, alkoxy, hydroxyalkyl, aminoalkyl, substituted or unsubstituted $C_6$-$C_{14}$ aryl or substituted or unsubstituted $C_3$-$C_6$ cycloalkyl; or $R^{11}$ and $R^{12}$ together with the nitrogen atom to which they are attached form a 5-7 membered substituted or unsubstituted heterocycle; in the heterocycle, the heteroatom is nitrogen, or nitrogen and oxygen, the number of the heteroatom(s) is 1-4;

in the definition of $R^{11}$ or $R^{12}$, the substituent in the substituted alkyl, the substituted $C_6$-$C_{14}$ aryl or the substituted $C_3$-$C_6$ cycloalkyl is selected from the group consisting of halogen, $C_1$-$C_4$ alkyl, hydroxy,

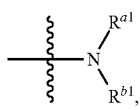

$C_1$-$C_4$ alkoxy, $C_1$-$C_4$ carboxyl, $C_1$-$C_4$ ester group or $C_1$-$C_4$ acylamino; when $R^{11}$ and $R^{12}$ together with the nitrogen atom to which they are attached form a 5-7 membered substituted or unsubstituted heterocycle, the substituent in the substituted heterocycle is selected from the group consisting of halogen, $C_1$-$C_4$ alkyl, substituted $C_1$-$C_4$ alkyl, hydroxy,

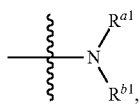

$C_1$-$C_4$ alkoxy, $C_1$-$C_4$ carboxyl, $C_1$-$C_4$ ester group or $C_1$-$C_4$ acylamino; the substituent in the substituted $C_1$-$C_4$ alkyl is selected from the group consisting of halogen, $C_1$-$C_4$ alkyl, hydroxy,

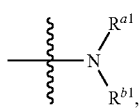

$C_1$-$C_4$ alkoxy, $C_1$-$C_4$ carboxyl, $C_1$-$C_4$ ester group or $C_1$-$C_4$ acylamino; when there are more substituents than one, the substituents are the same or different; in

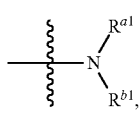

$R^{a1}$ and $R^{b1}$ are independently hydrogen, $C_1$-$C_4$ alkyl or

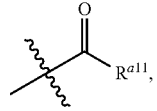

$R^{a11}$ is $C_1$-$C_4$ alkyl.

2. The aromatic acetylene or aromatic ethylene compound represented by formula II-0, the pharmaceutically acceptable salt, the tautomer, the mesomer, the racemate or the stereoisomerer thereof as defined in claim 1, wherein, L is alkynyl or —C($R^4$)=C($R^5$)—;

each of $R^2$ is independently hydrogen, deuterium, substituted or unsubstituted hydroxy, substituted or unsubstituted amino, halogen, substituted or unsubstituted alkyl, or, substituted or unsubstituted alkoxy;

in

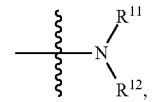

$R^{11}$ and $R^{12}$ are independently hydrogen, substituted or unsubstituted alkyl, alkoxy, hydroxyalkyl or aminoalkyl;

when $R^{11}$ and $R^{12}$ together with the nitrogen atom to which they are attached form a 5-7 membered substituted or unsubstituted heterocycle, the substituent in the substituted heterocycle is selected from the group consisting of halogen, $C_1$-$C_4$ alkyl, hydroxy,

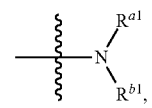

$C_1$-$C_4$ alkoxy, $C_1$-$C_4$ carboxyl, $C_1$-$C_4$ ester group or $C_1$-$C_4$ acylamino; in

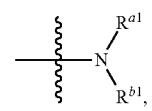

$R^{a1}$ and $R^{b1}$ are independently hydrogen or $C_1$-$C_4$ alkyl.

3. The aromatic acetylene or aromatic ethylene compound represented by formula II-0, the pharmaceutically acceptable salt, the tautomer, the mesomer, the racemate or the stereoisomer thereof as defined in claim 1, wherein, when the substituent in the substituted alkyl, the substituted alkoxy, the substituted cycloalkyl, the substituted carbocycle or the substituted heterocycle is halogen, the halogen is fluorine, chlorine, bromine or iodine;

or, when the substituent in the substituted hydroxy, the substituted amino, the substituted alkyl, the substituted alkoxy, the substituted cycloalkyl, the substituted carbocycle or the substituted heterocycle is $C_1$-$C_4$ alkyl, the $C_1$-$C_4$ alkyl is methyl, ethyl, n-propyl, isopropyl, n-butyl, isobutyl or tert-butyl;

or, when the substituent in the substituted alkyl, the substituted alkoxy, the substituted cycloalkyl, the substituted carbocycle or the substituted heterocycle is

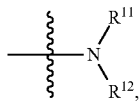

and $R^{11}$ and $R^{12}$ are independently substituted or unsubstituted alkyl, the substituted or unsubstituted alkyl is substituted or unsubstituted $C_1$-$C_4$ alkyl;

or, when the substituent in the substituted hydroxy, the substituted amino, the substituted alkyl, the substituted alkoxy, the substituted cycloalkyl, the substituted carbocycle or the substituted heterocycle is $C_1$-$C_4$ alkoxy, the $C_1$-$C_4$ alkoxy is methoxy, ethoxy, n-propoxy, isopropoxy, n-butoxy, isobutoxy or tert-butoxy;

or, when the substituent in the substituted hydroxy, the substituted amino, the substituted alkyl, the substituted alkoxy, the substituted cycloalkyl, the substituted carbocycle or the substituted heterocycle is $C_1$-$C_4$ carboxyl, the carboxyl is

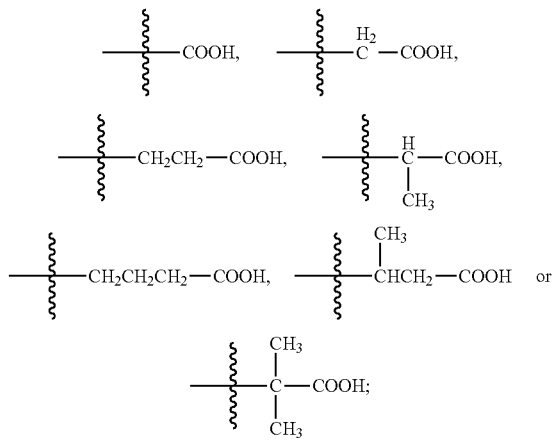

or, when the substituent in the substituted hydroxy, the substituted amino, the substituted alkyl, the substituted alkoxy, the substituted cycloalkyl, the substituted carbocycle or the substituted heterocycle is $C_1$-$C_4$ ester group, the $C_1$-$C_4$ ester group is

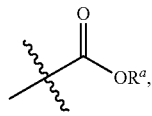

wherein $R^a$ is $C_1$-$C_4$ alkyl;

or, when the substituent in the substituted hydroxy, the substituted amino, the substituted alkyl, the substituted alkoxy, the substituted cycloalkyl, the substituted carbocycle or the substituted heterocycle is $C_1$-$C_4$ acylamino, the $C_1$-$C_4$ acylamino is

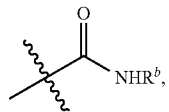

wherein $R^b$ is hydrogen or $C_1$-$C_4$ alkyl; in the definition of $R^b$, the $C_1$-$C_4$ alkyl is methyl, ethyl, n-propyl, isopropyl, n-butyl, isobutyl or tert-butyl.

4. The aromatic acetylene or aromatic ethylene compound represented by formula II-0, the pharmaceutically acceptable salt, the tautomer, the mesomer, the racemate or the stereoisomer thereof as defined in claim 1, wherein,
when the substituent in the substituted alkyl, the substituted alkoxy, the substituted cycloalkyl, the substituted carbocycle or the substituted heterocycle is

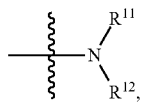

and $R^{11}$ and $R^{12}$ are independently substituted or unsubstituted alkyl, the substituted or unsubstituted alkyl is substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl or substituted or unsubstituted tert-butyl;

or, when the substituent in the substituted hydroxy, the substituted amino, the substituted alkyl, the substituted alkoxy, the substituted cycloalkyl, the substituted carbocycle or the substituted heterocycle is $C_1$-$C_4$ ester group, the $C_1$-$C_4$ ester group is

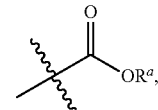

wherein $R^a$ is methyl, ethyl, n-propyl, isopropyl, n-butyl, isobutyl or tert-butyl.

5. The aromatic acetylene or aromatic ethylene compound represented by formula II-0, the pharmaceutically acceptable salt, the tautomer, the mesomer, the racemate or the stereoisomer thereof as defined in claim 1, wherein,
in the definition of ring A or ring B, the aromatic ring is $C_6$-$C_{14}$ aromatic ring;
or, in the definition of ring A or ring B, the heteroaromatic ring is $C_2$-$C_{10}$ heteroaromatic ring having 1-4 heteroatoms selected from nitrogen, oxygen and sulfur;
or, the halogen is fluorine, chlorine, bromine or iodine;
or, the alkyl is $C_1$-$C_4$ alkyl; and/or, the alkoxy is $C_1$-$C_4$ alkoxy; and/or, the cycloalkyl is $C_3$-$C_6$ cycloalkyl; and/or, the hydroxyalkyl is $C_1$-$C_4$ hydroxyalkyl; and/or, the aminoalkyl is $C_1$-$C_4$ aminoalkyl; and/or, the carbocycle is cyclopentane, cyclohexane or cycloheptane;
or, the heterocycle is preferably pyrrole ring or piperidine ring.

6. The aromatic acetylene or aromatic ethylene compound represented by formula II-0, the pharmaceutically acceptable salt, the tautomer, the mesomer, the racemate or the stereoisomer thereof as defined in claim 1, wherein, in the definition of ring A or ring B, the aromatic ring is $C_6$-$C_{10}$ aromatic ring;

or, in the definition of ring A or ring B, the heteroaromatic ring is $C_2$-$C_8$ heteroaromatic ring having 1-3 heteroatoms selected from nitrogen and oxygen;

or, the alkyl is methyl, ethyl, n-propyl, isopropyl, n-butyl, isobutyl or tert-butyl or, the alkoxy is methoxy, ethoxy, n-propoxy, isopropoxy or tert-butoxy;

or, the cycloalkyl is cyclopropyl, cyclobutyl, cyclopentyl or cyclohexyl;

or, the hydroxyalkyl is

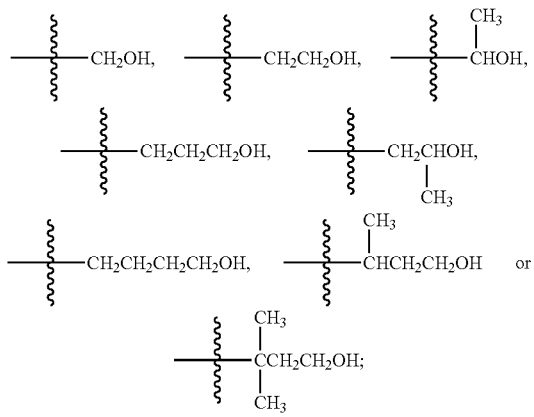

or, the aminoalkyl is

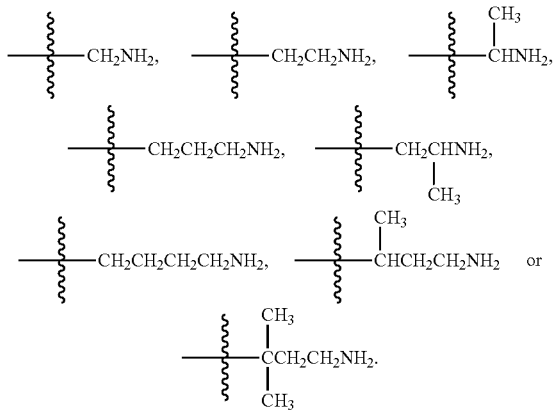

7. The aromatic acetylene or aromatic ethylene compound represented by formula II-0, the pharmaceutically acceptable salt, the tautomer, the mesomer, the racemate or the stereoisomer thereof as defined in claim 1, wherein, in the definition of ring A or ring B, the aromatic ring is benzene ring;

or, in the definition of ring A or ring B, the heteroaromatic ring is

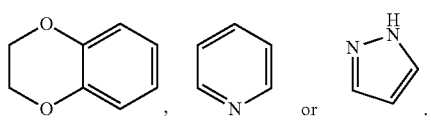

8. The aromatic acetylene or aromatic ethylene compound represented by formula II-0, the pharmaceutically acceptable salt, the tautomer, the mesomer, the racemate or the stereoisomer thereof as defined in claim 1, wherein, in formula II-0, each of $R^1$ is independently hydrogen, deuterium, halogen, substituted or unsubstituted hydroxy, substituted or unsubstituted alkyl, or, substituted or unsubstituted alkoxy, the substituent in the substituted alkyl is substituted by one or more than one

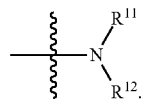

9. The aromatic acetylene or aromatic ethylene compound represented by formula II-0, the pharmaceutically acceptable salt, the tautomer, the mesomer, the racemate or the stereoisomer thereof as defined in claim 1, wherein, in formula II-0, each of $R^1$ is independently

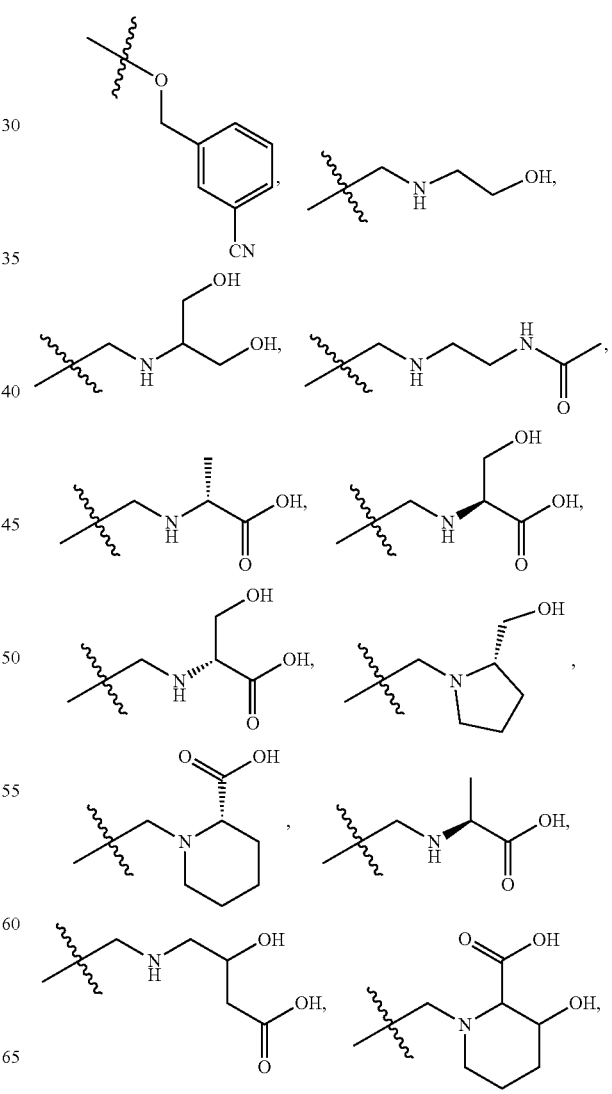

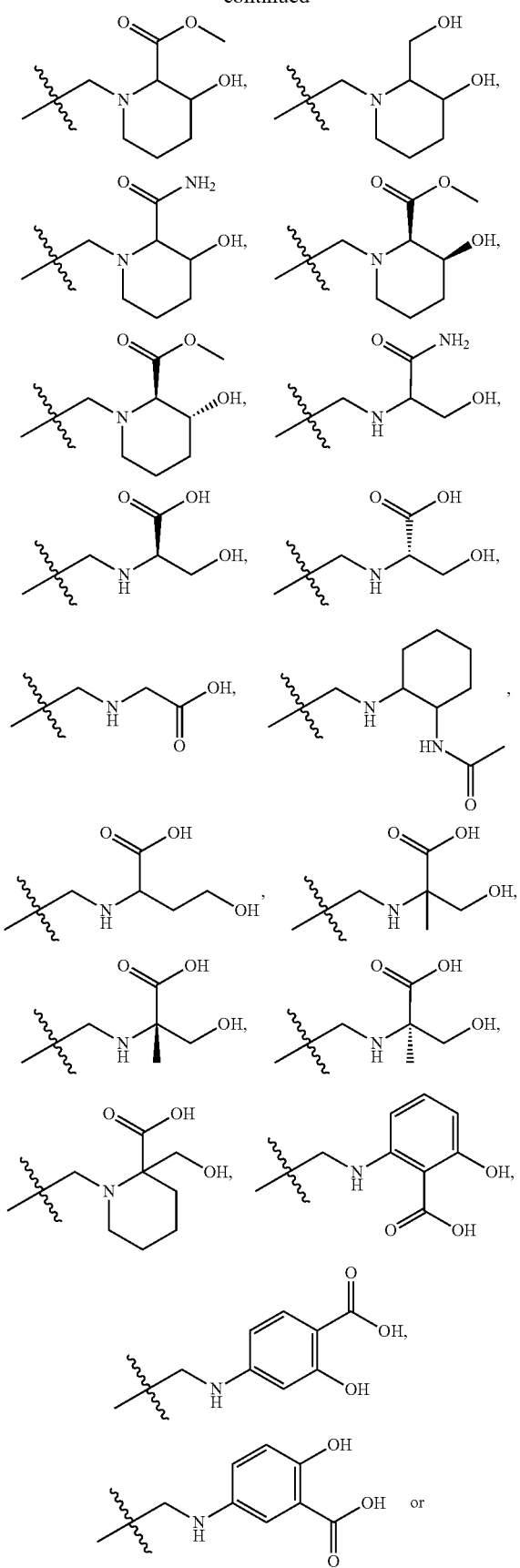
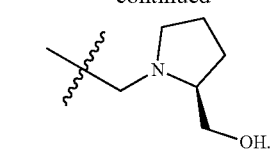
10. The aromatic acetylene or aromatic ethylene compound represented by formula II-0, the pharmaceutically acceptable salt, the tautomer, the mesomer, the racemate or the stereoisomer thereof as defined in claim 1, wherein,
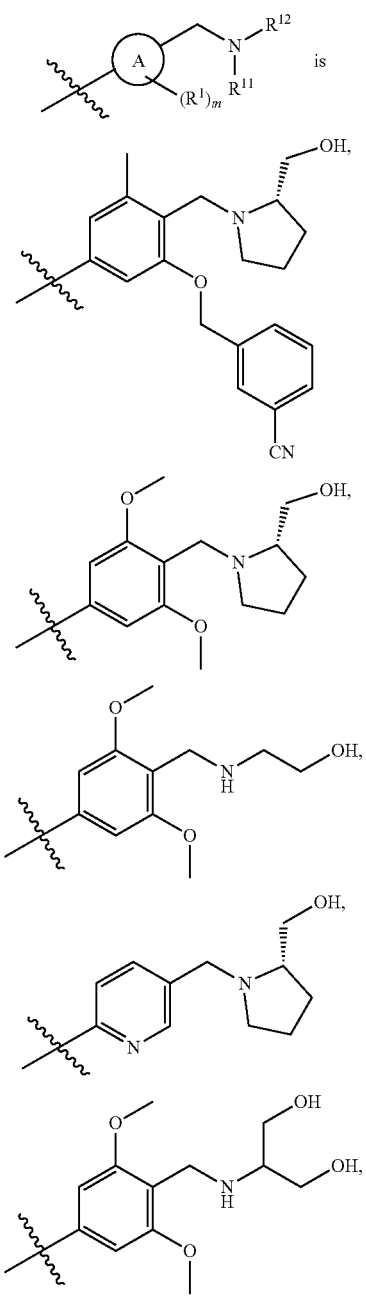

153
-continued
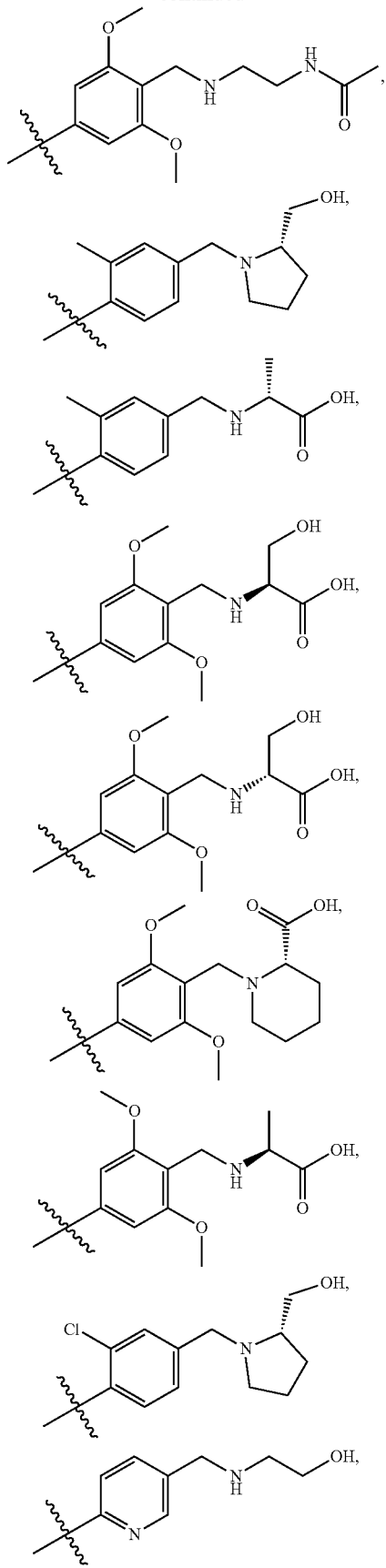
154
-continued
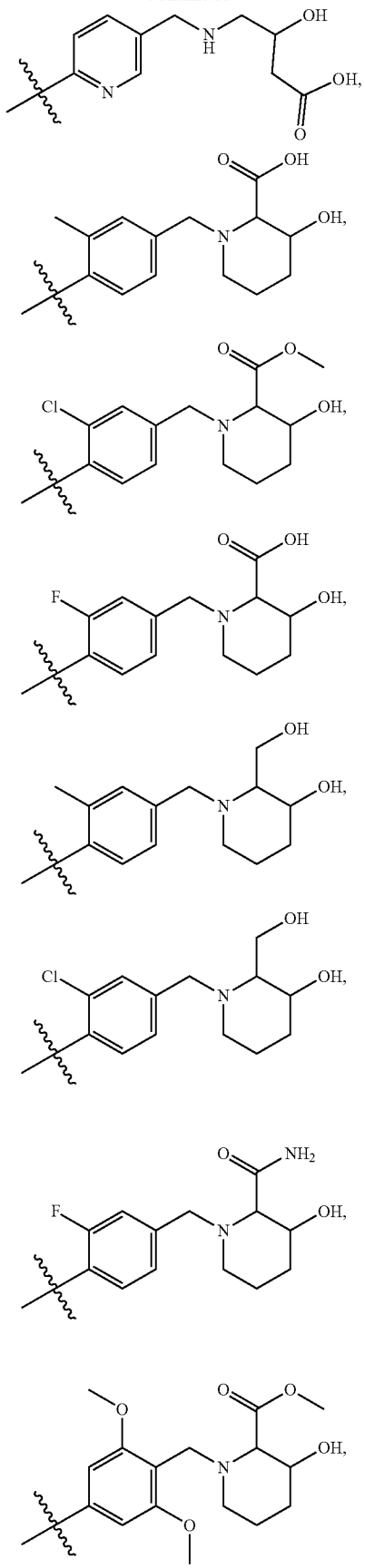

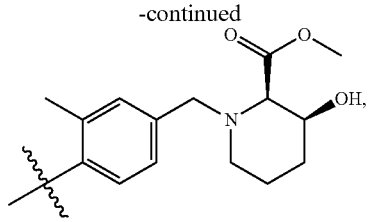
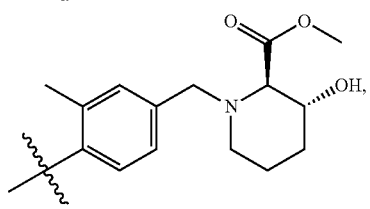
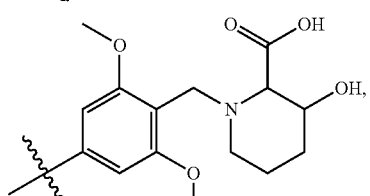
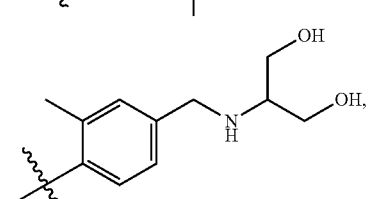
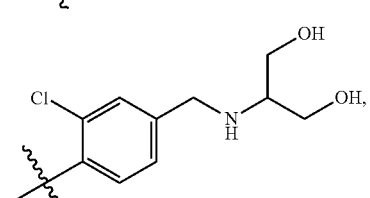
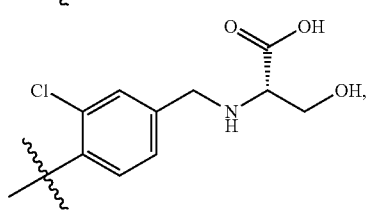
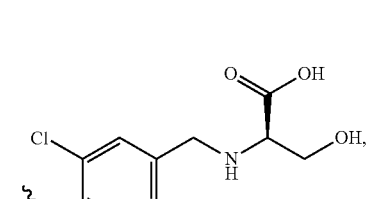
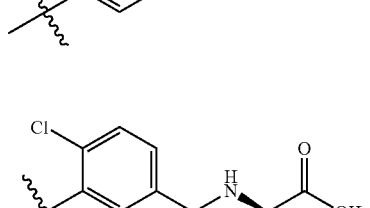
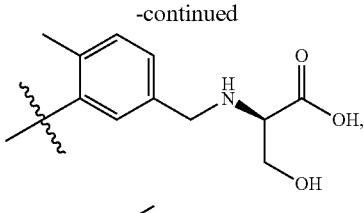
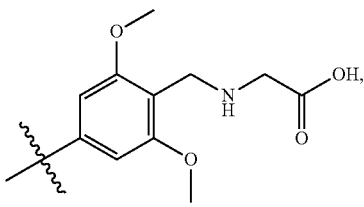
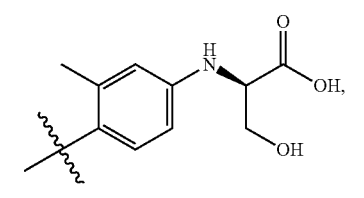
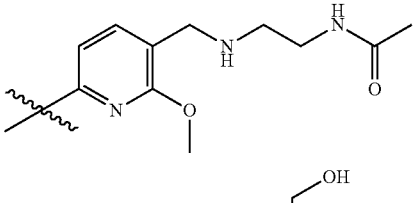
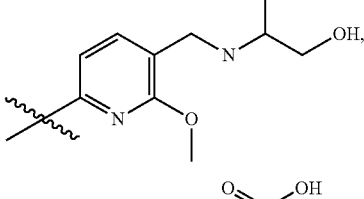
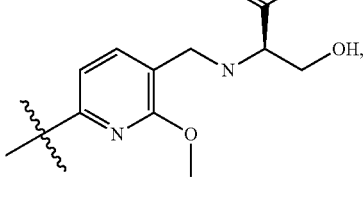
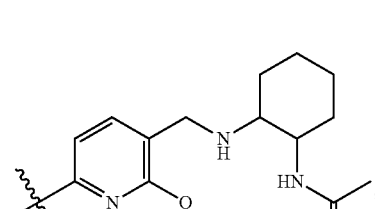
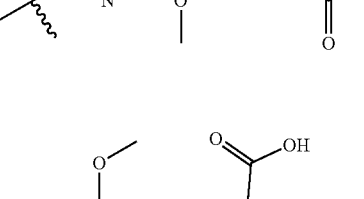
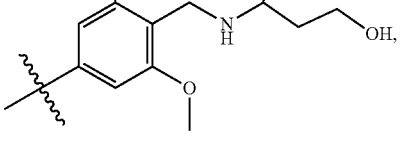

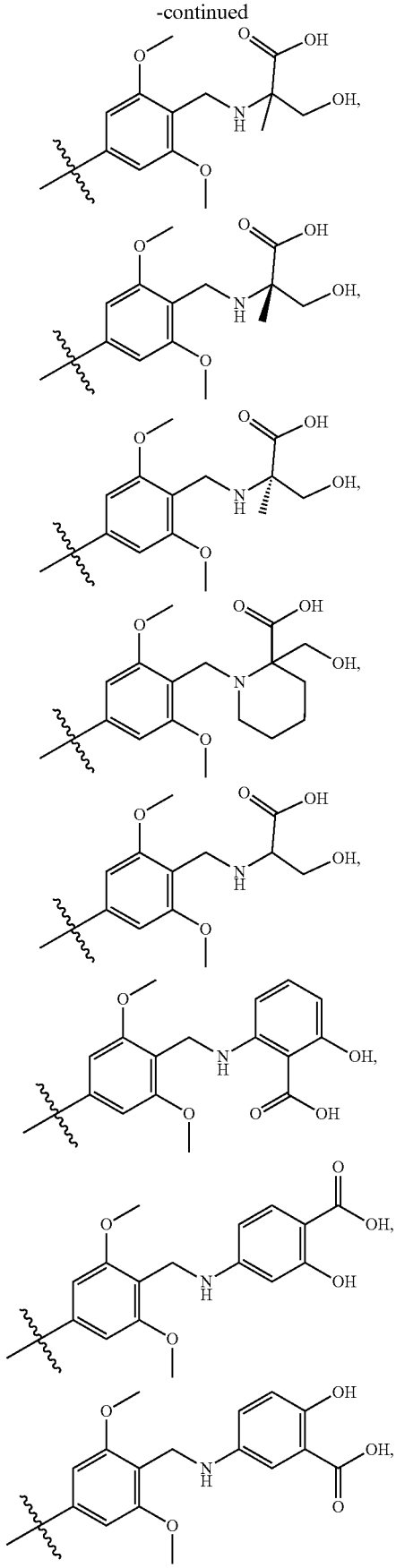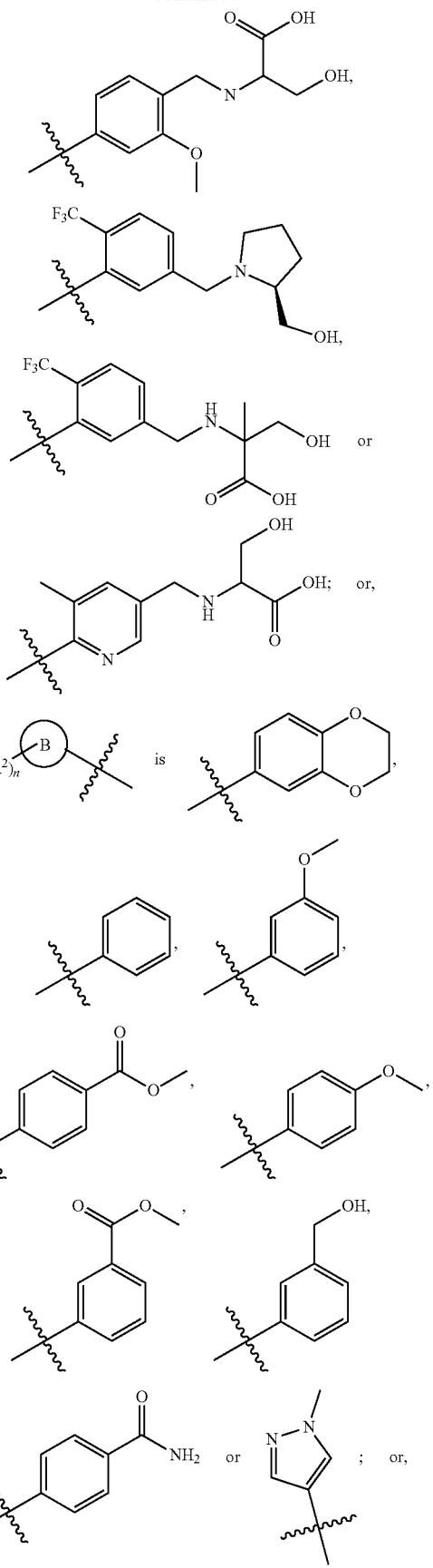

-continued

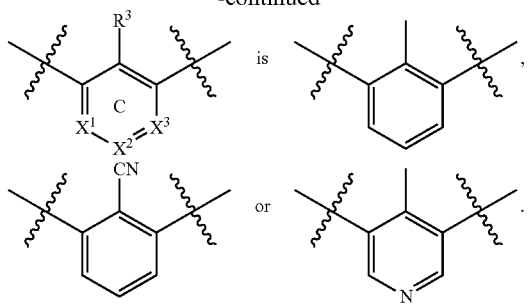 is 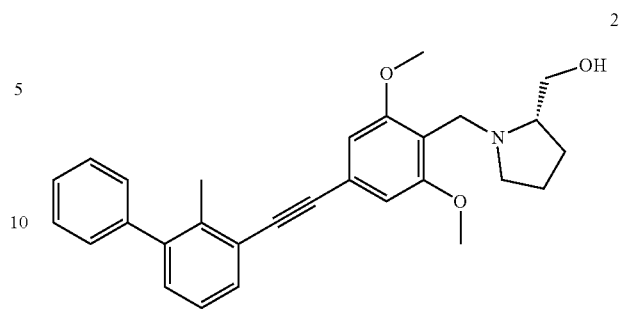,

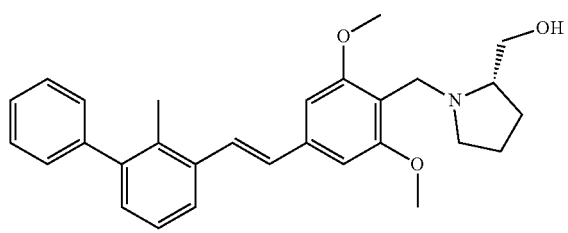

11. The aromatic acetylene or aromatic ethylene compound represented by formula II-0, the pharmaceutically acceptable salt, the tautomer, the mesomer, the racemate or the stereoisomer thereof as defined in claim 1, wherein, formula II-0 is the compound represented by formula II-1-1B or II-1-2B;

II-1-1B

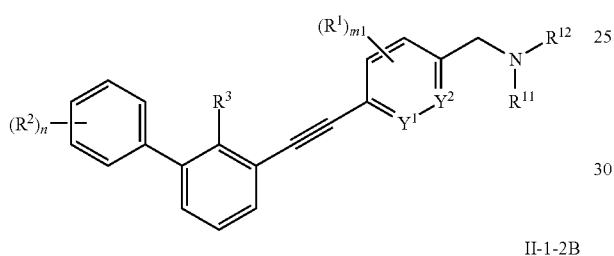

II-1-2B

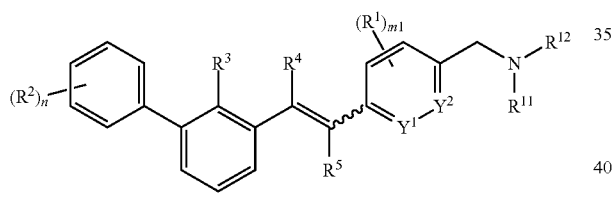

in any one of the above formulas, $Y^1$ is CH or N, $Y^2$ is CH or N, $R^1$, $R^2$, $R^3$, $R^4$, $R^5$, $R^{11}$, $R^{12}$, n and m1 are defined as claim 1.

12. The aromatic acetylene or aromatic ethylene compound represented by formula II-0, the pharmaceutically acceptable salt, the tautomer, the mesomer, the racemate or the stereoisomer thereof as defined in claim 1, wherein, the aromatic acetylene or aromatic ethylene compound represented by formula II-0 is selected from

1

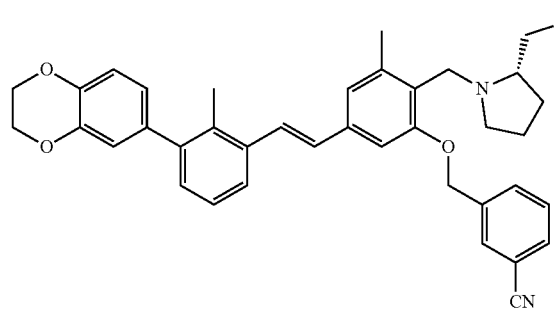

2

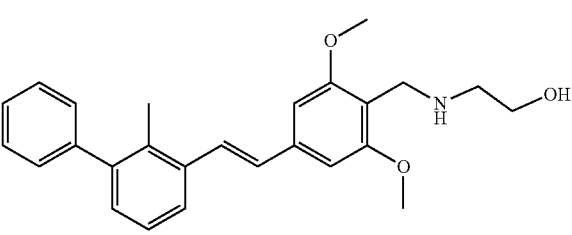

3

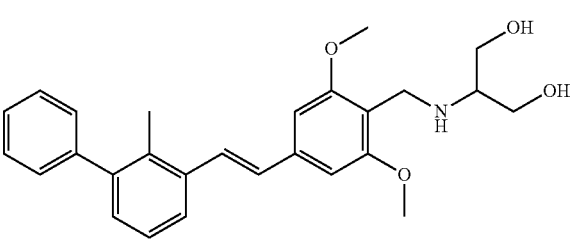

4

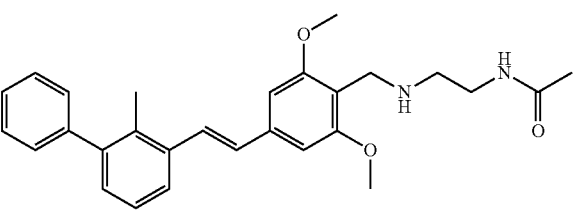

5

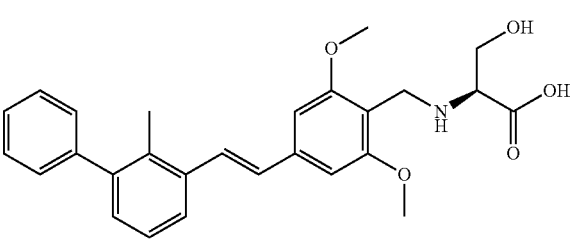

6

7

-continued
8
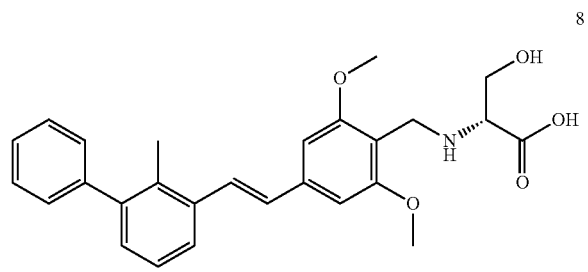
9
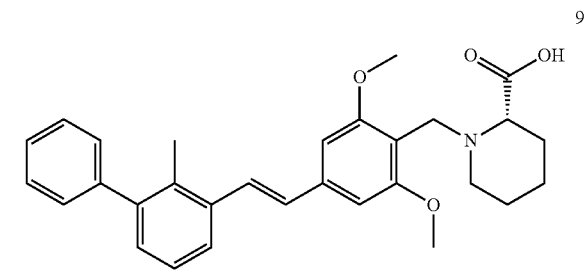
10
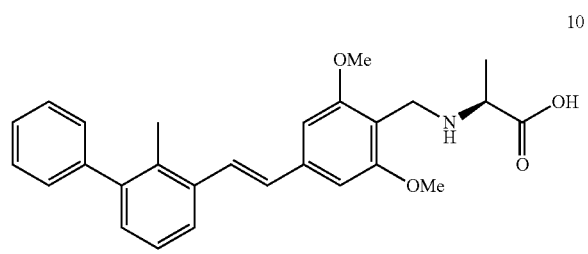
11
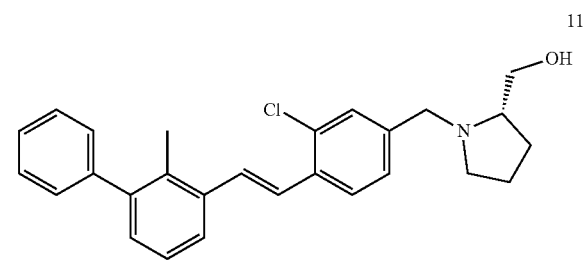
12
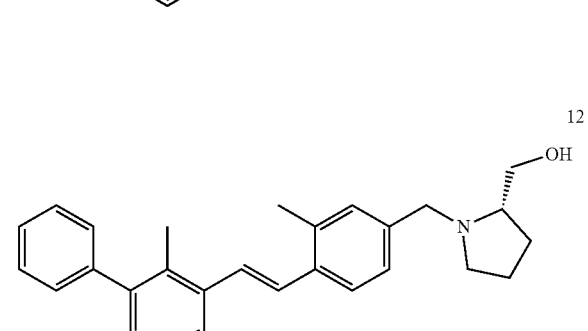
13
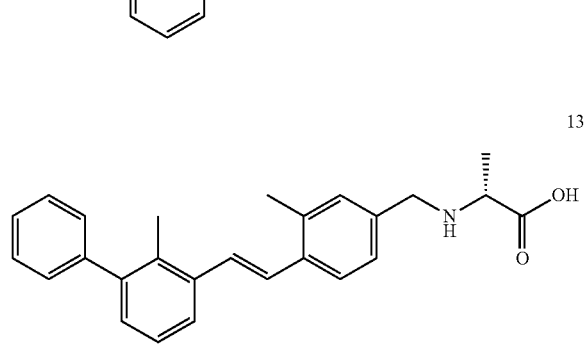
-continued
14
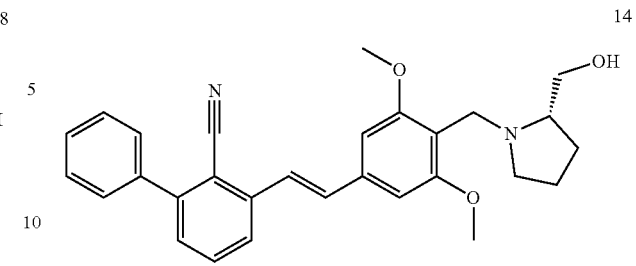
15
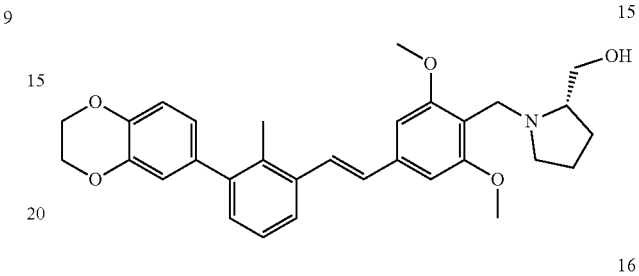
16
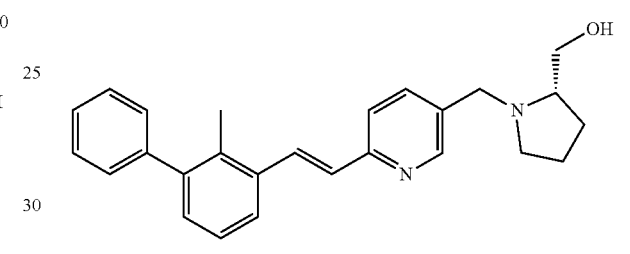
17
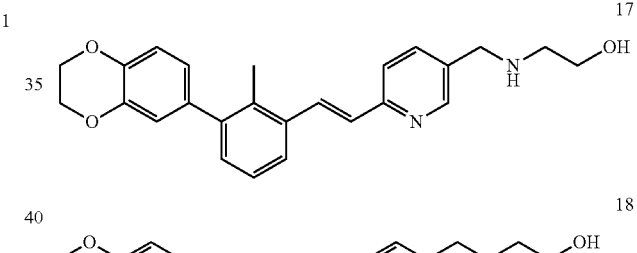
18
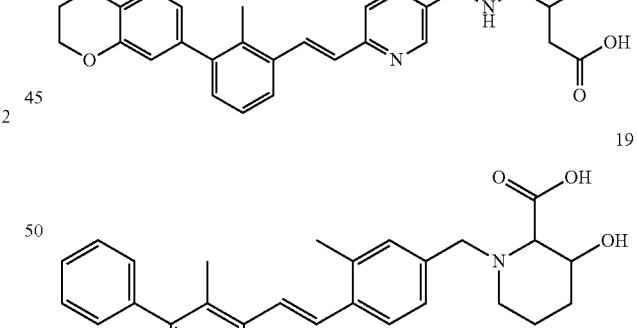
19
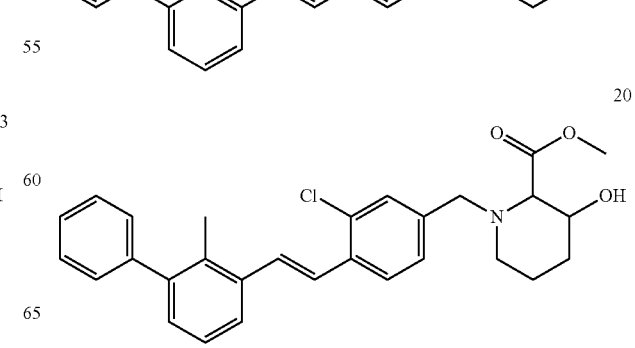
20
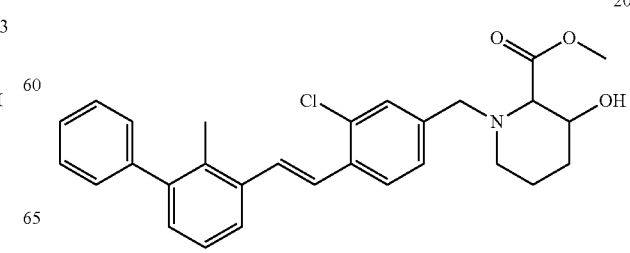

21 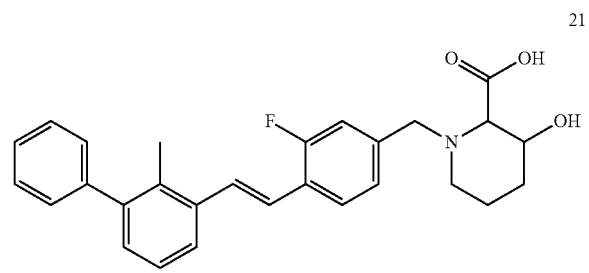
27 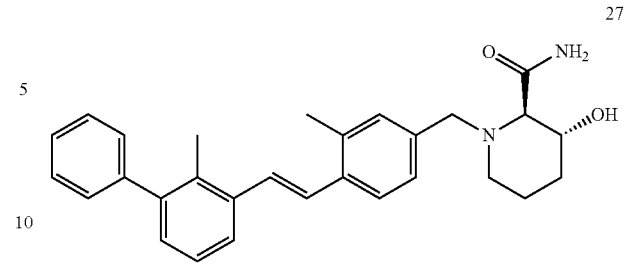
22 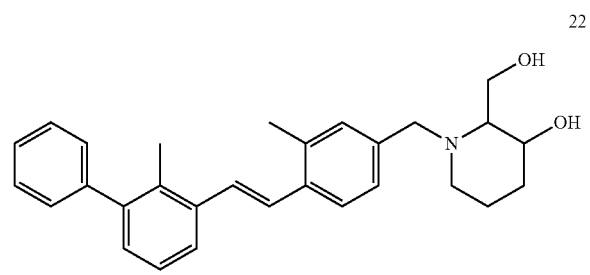
28 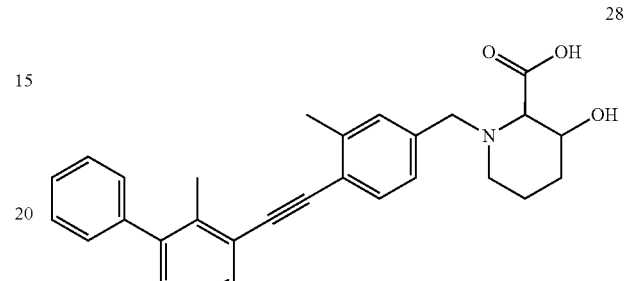
23 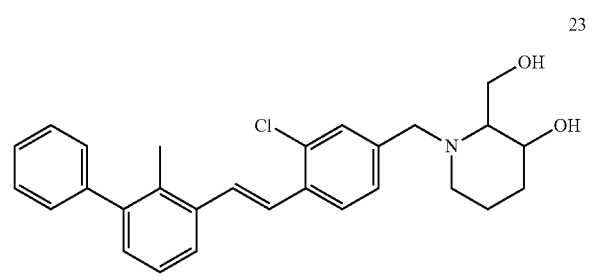
29 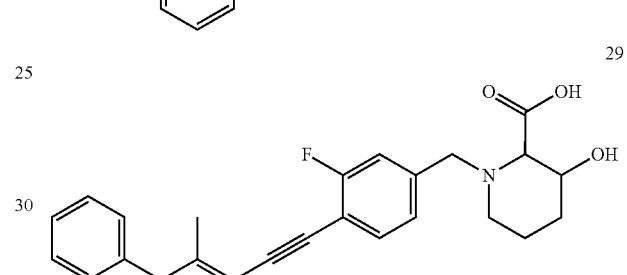
24 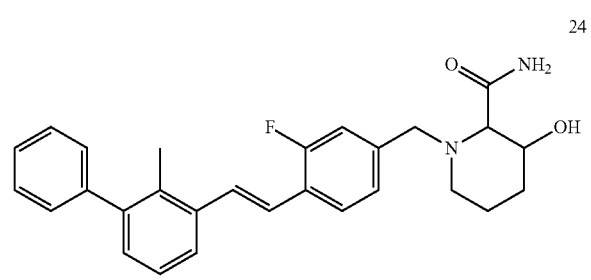
30 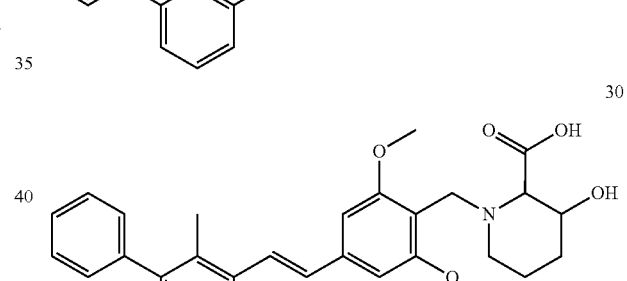
25 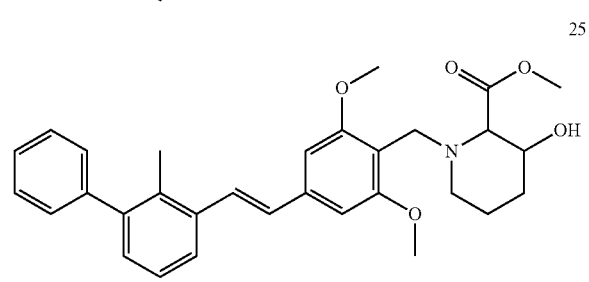
31 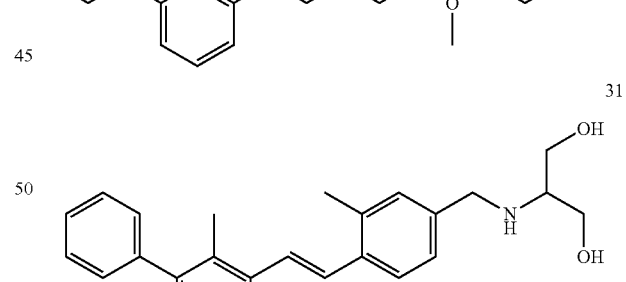
26 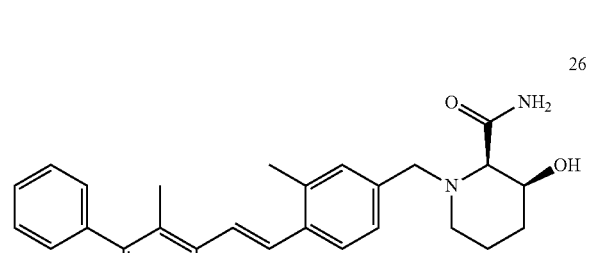
32 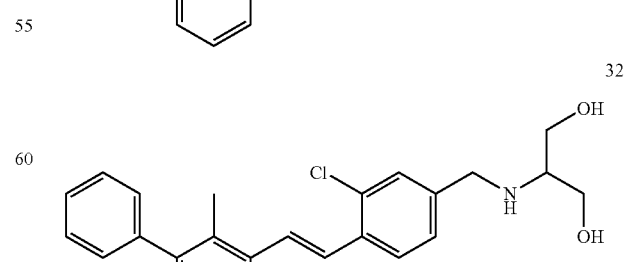

33
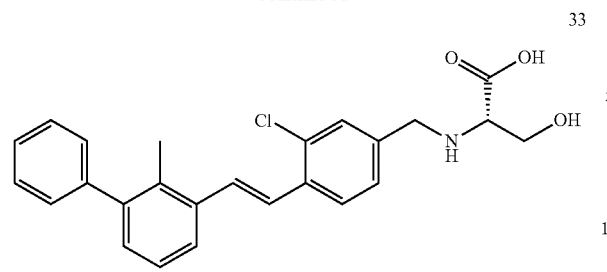
34
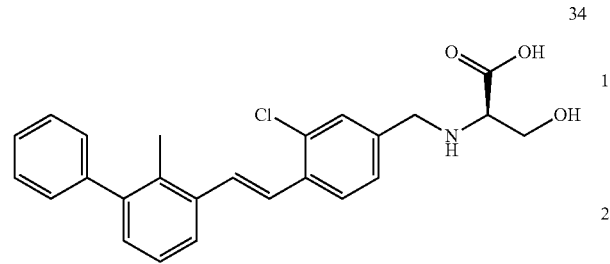
35
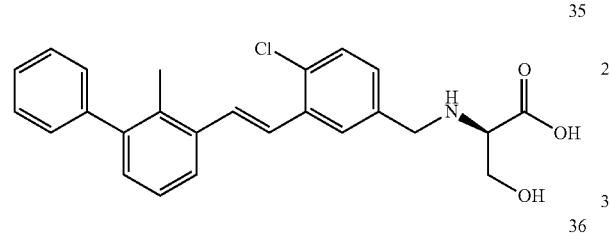
36
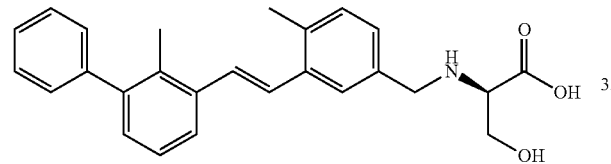
37
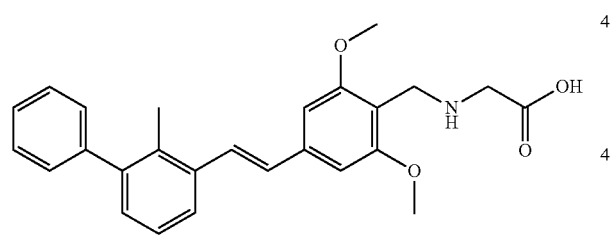
38
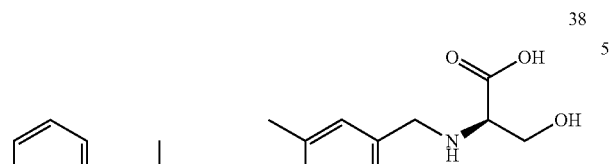
39
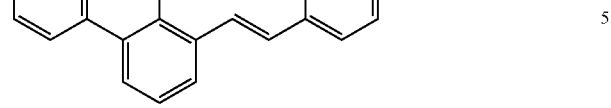
40
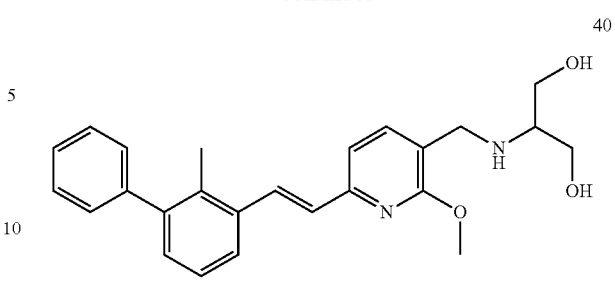
41
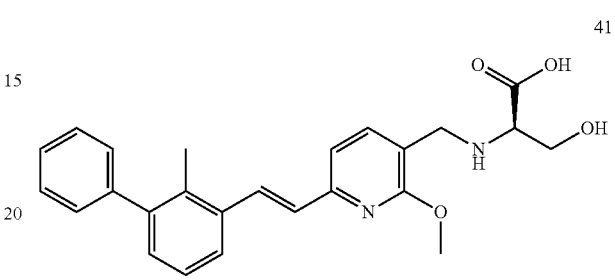
42
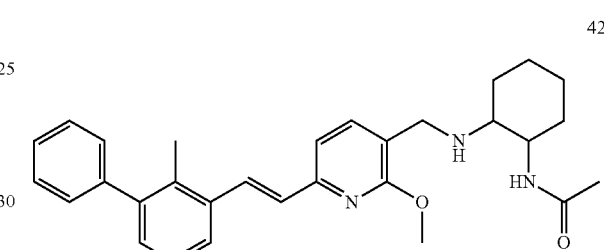
43
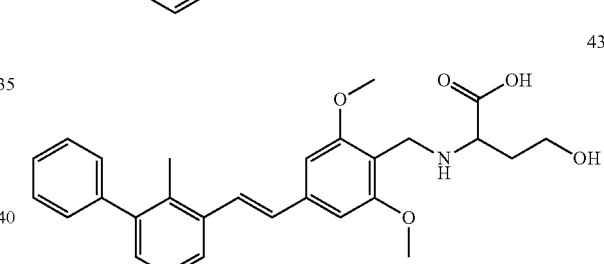
44
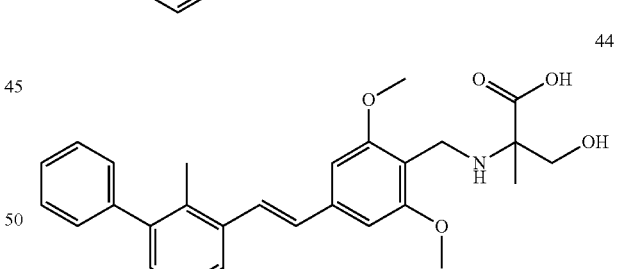
45
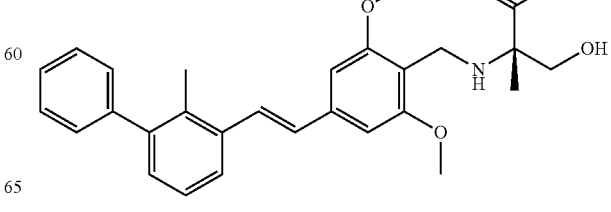

46
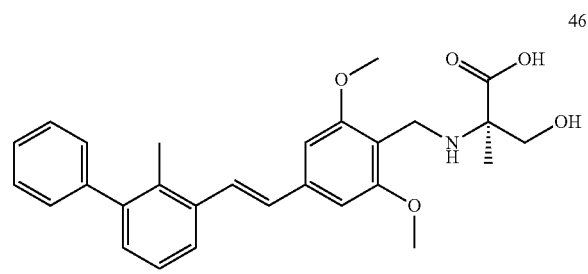
47
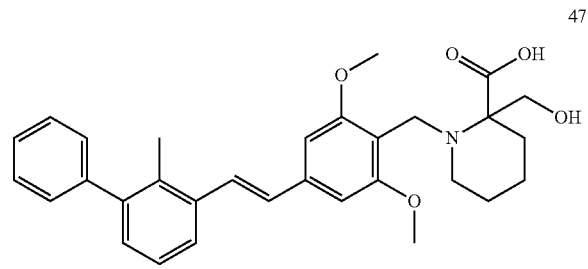
48
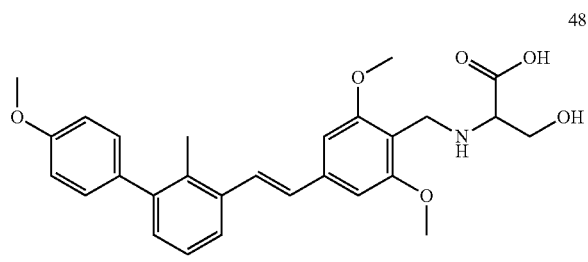
49
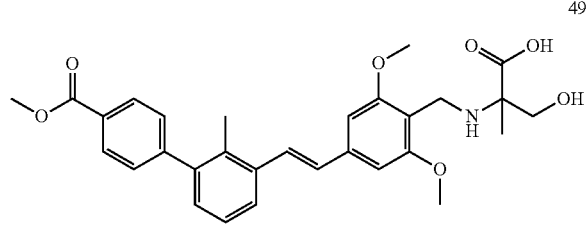
50
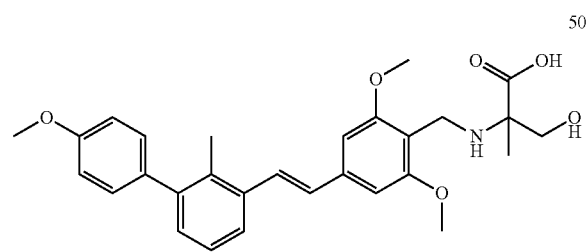
51
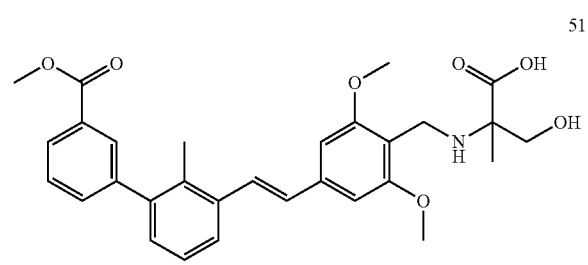
52
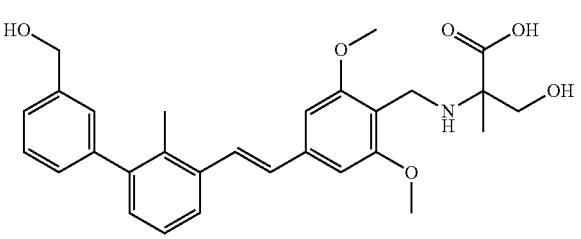
53
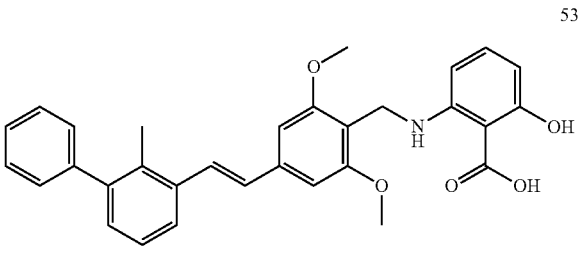
54
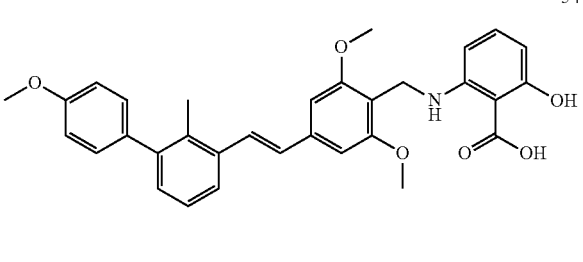
55
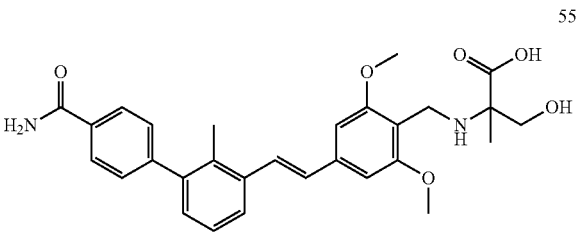
56
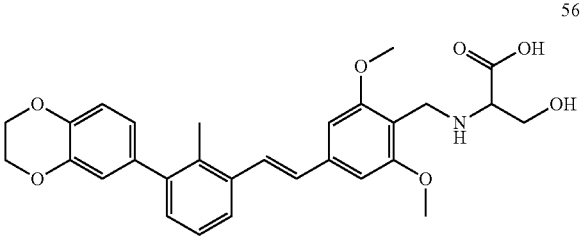
57
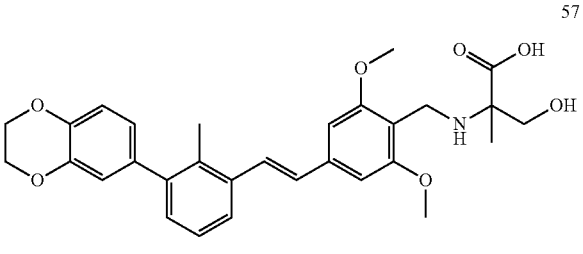

58
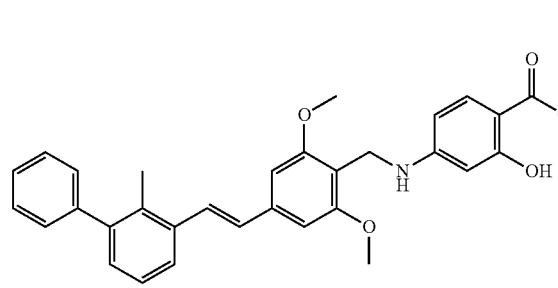
59
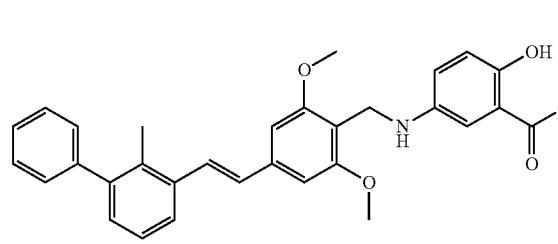
60
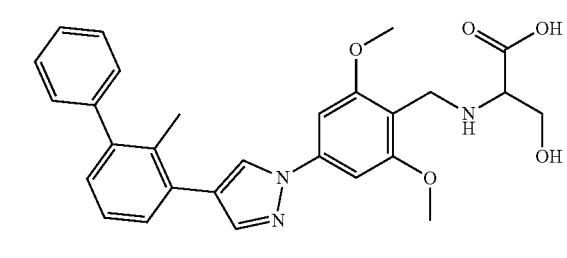
61
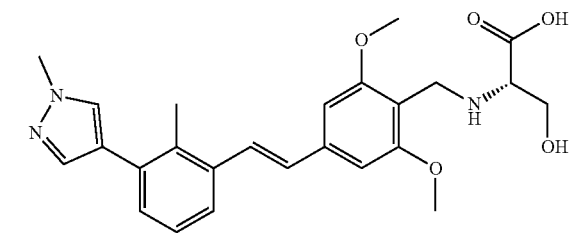
62
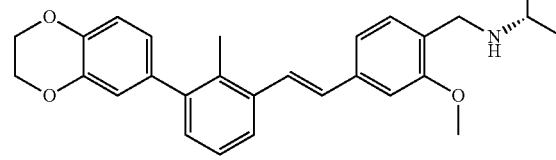
63
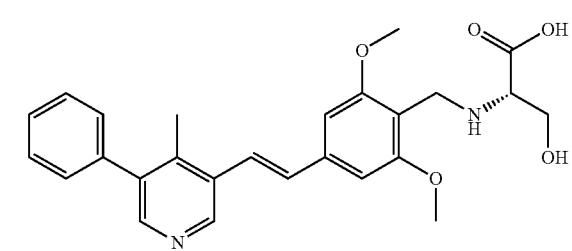
64
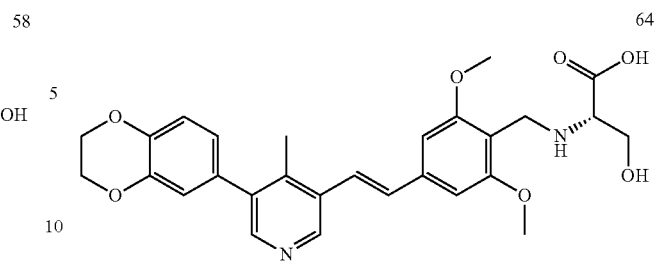
65
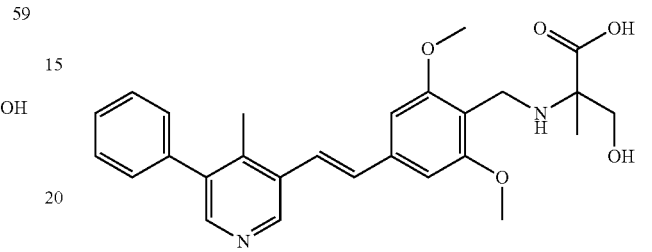
66
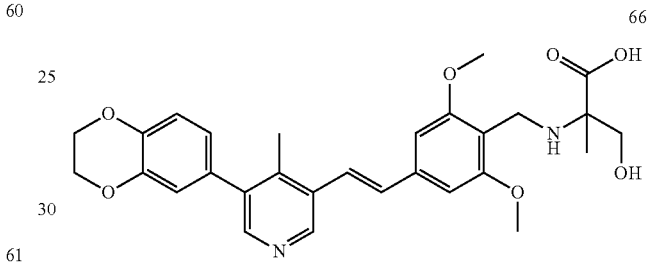
67
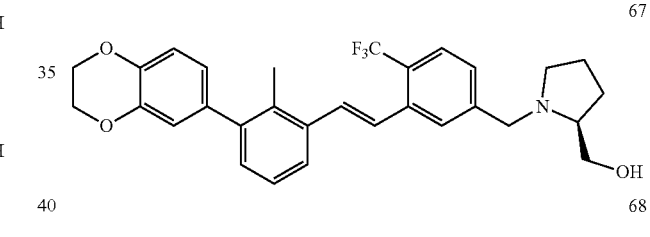
68
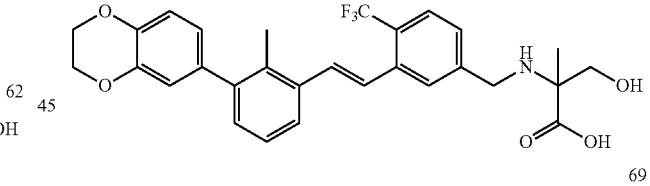
69
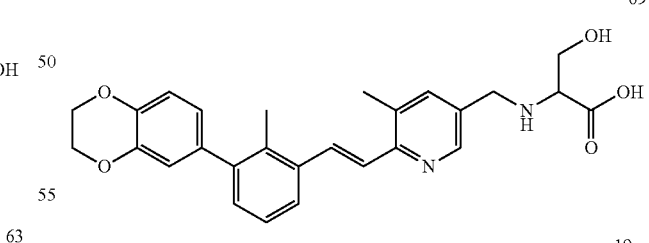
19-a
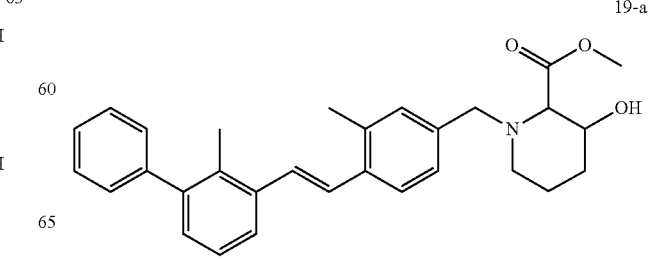

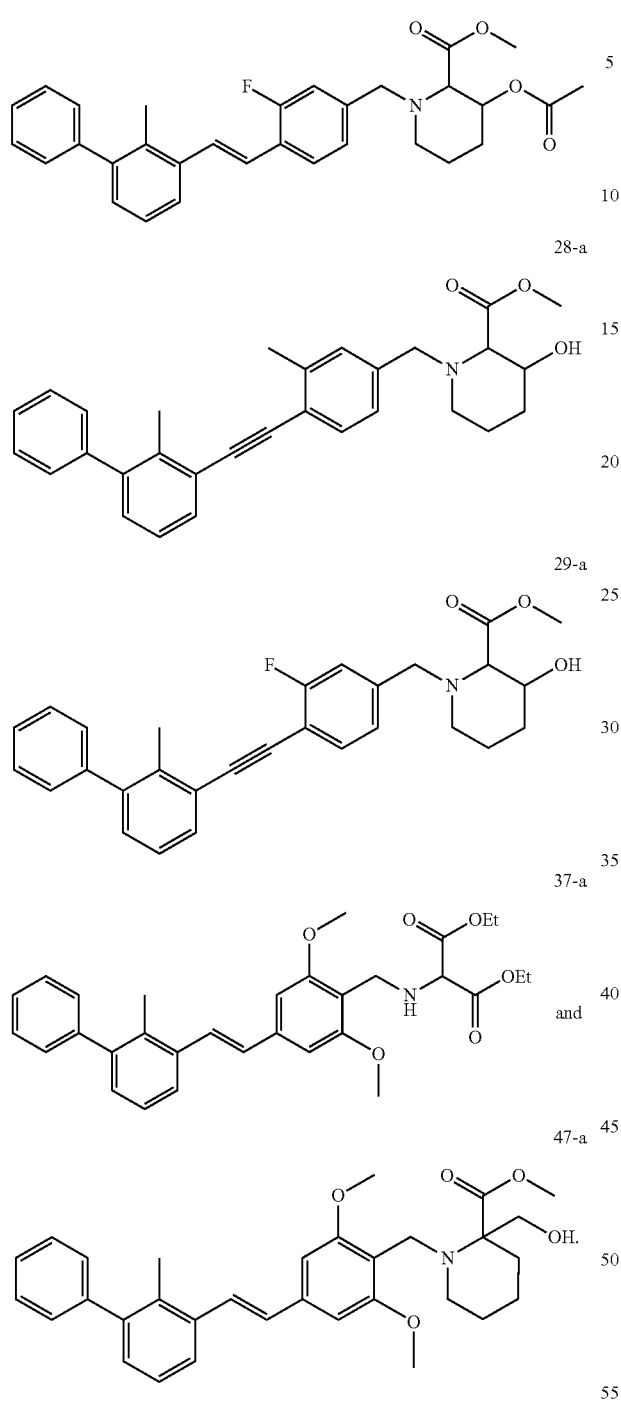

13. A process for preparing the aromatic acetylene or aromatic ethylene compound represented by formula II-0; as defined in claim 1, wherein, the process includes process 1 or process 2:

process 1 comprising conducting a reductive amination reaction of the compound represented by formula I-a with the compound represented by formula I-b as shown below in the presence of a reducing agent in a solvent to give the compound represented by formula II-0;

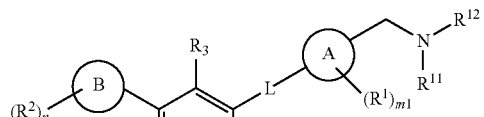

I-a

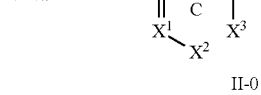

II-0 process 2 comprising conducting a substitution reaction of the compound represented by formula I-a1 and the compound represented by formula I-b as shown below in the presence of a base in a solvent to give the compound represented by formula II-0;

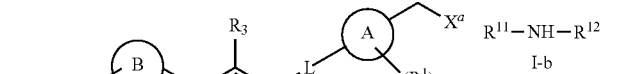

I-a1

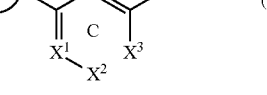

II-0 in formula I-a, formula I-a1, formula I-b and formula II-0, ring A, ring B, $R^1$, $R^2$, $R^3$, $R^{11}$, $R^{12}$, $X^1$, $X^2$, $X^3$, n and m1 are defined as claim 1; in formula I-a1, $X^a$ is halogen.

14. A compound represented by formula I-a or formula I-a1:

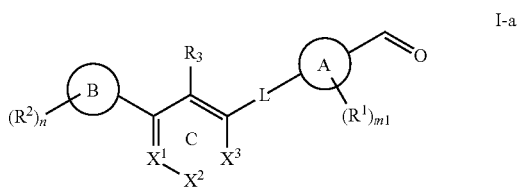

I-a

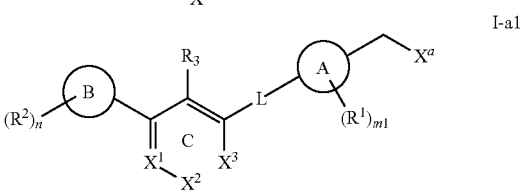

I-a1 in formula I-a, formula I-a1, ring A, ring B, $R^1$, $R^2$, $R^3$, $X^1$, $X^2$, $X^3$, n and m1 are defined as claim 1, $X^a$ is halogen.
15. The compound represented by formula I-a or formula I-a1 as defined in claim 14, which is selected from
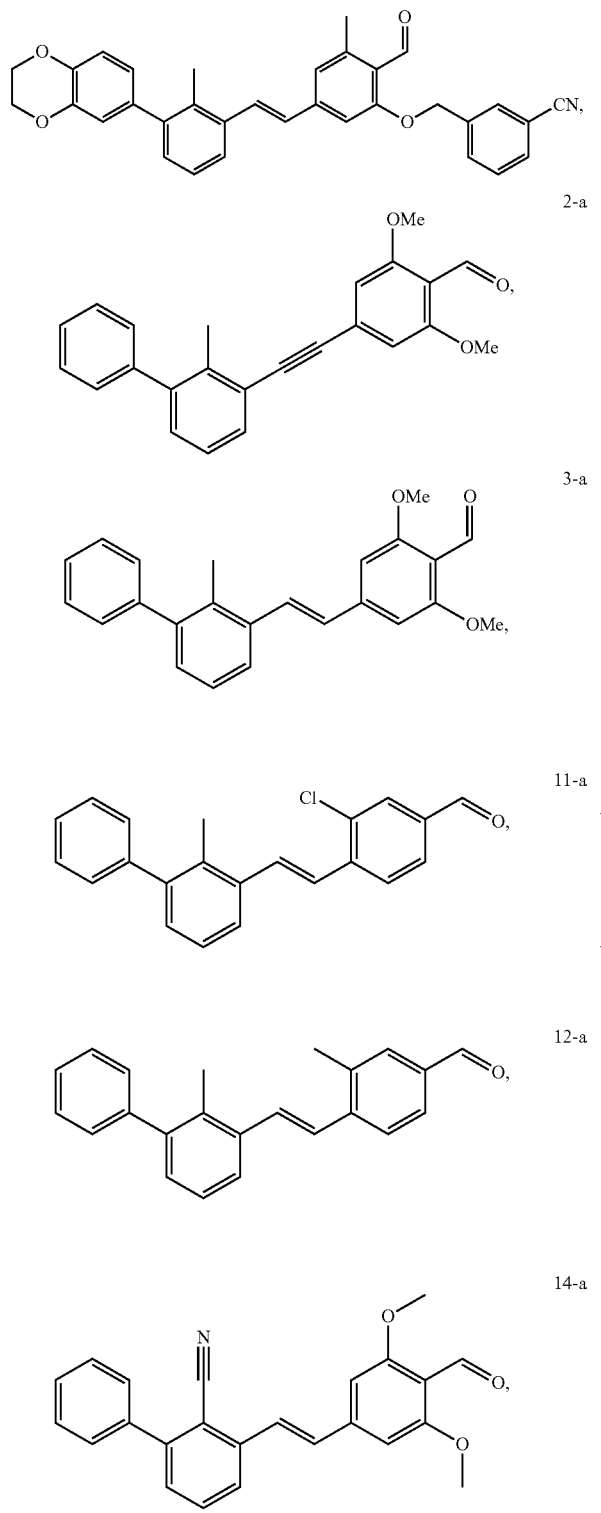
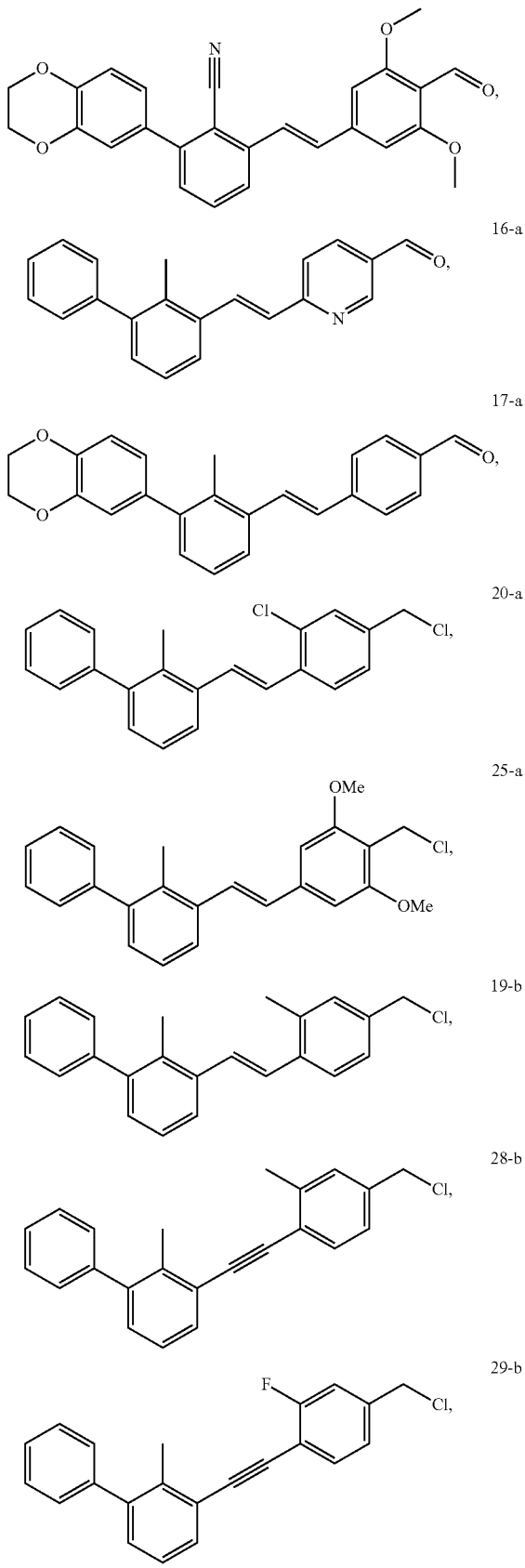

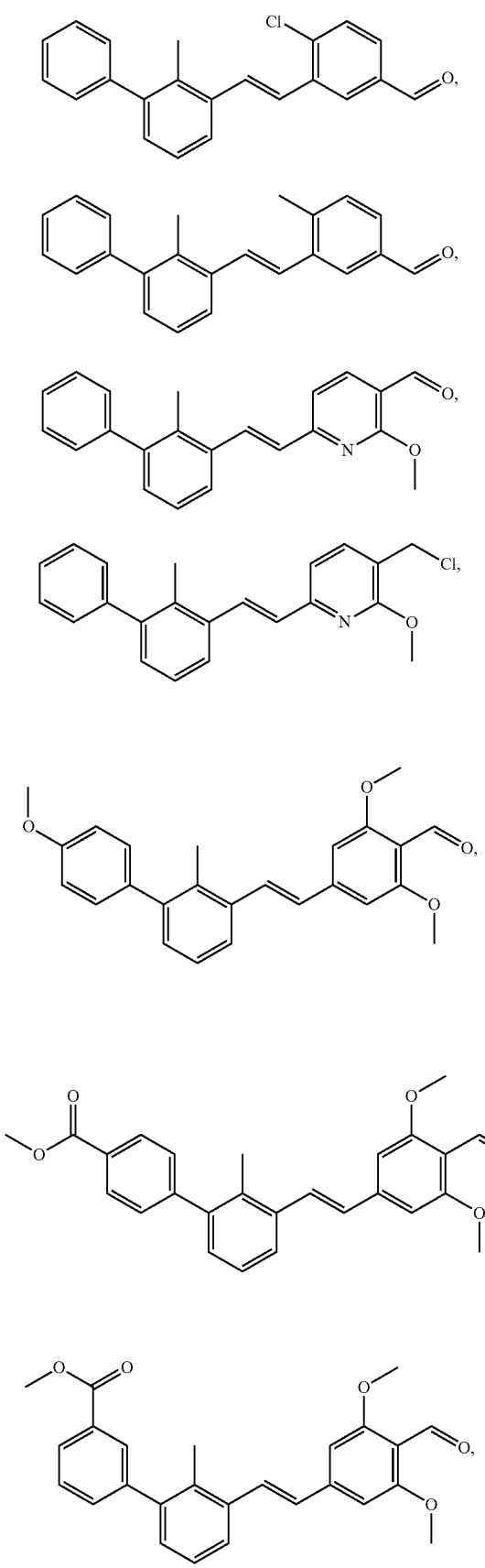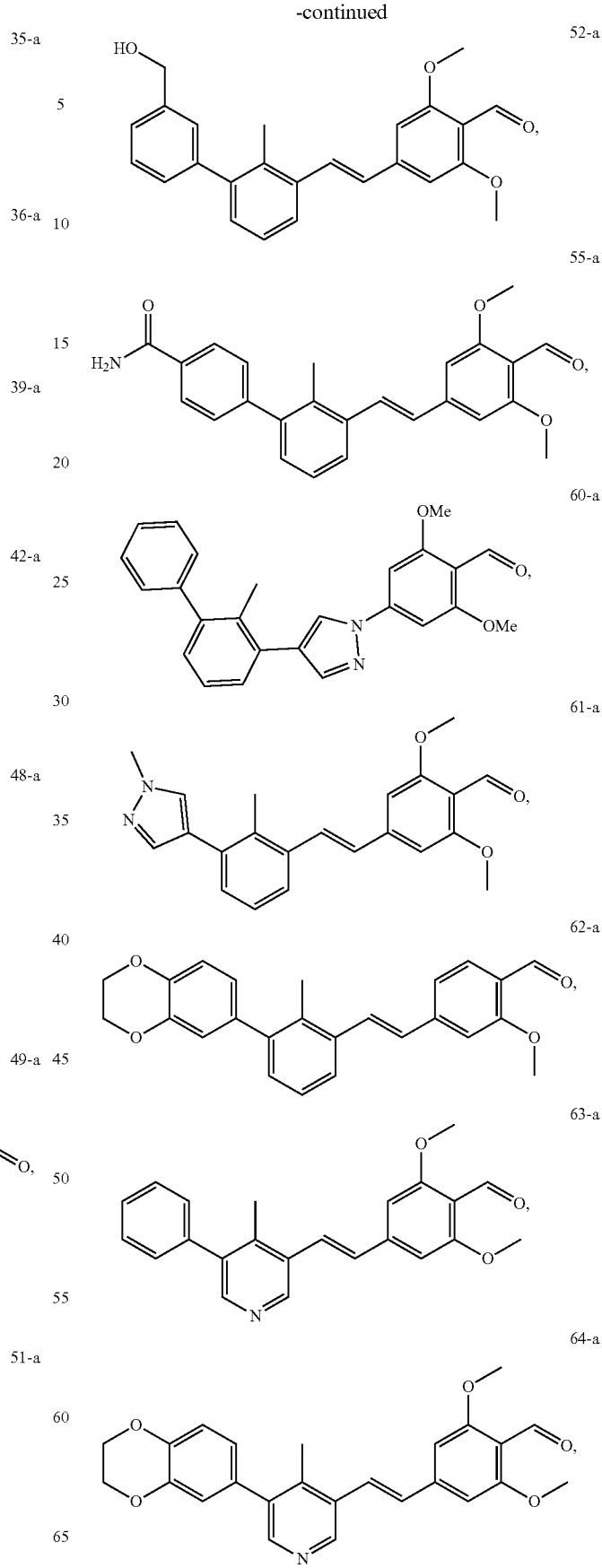

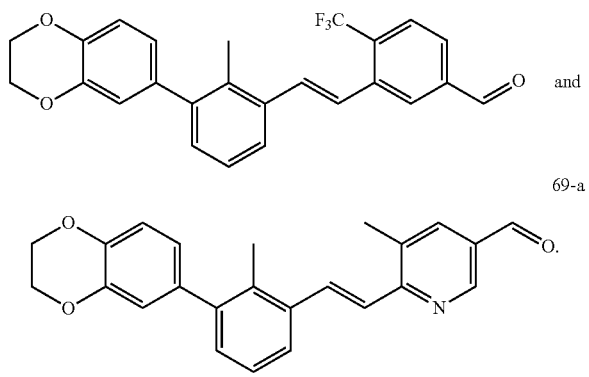

16. A method for treating a cancer, an infection, an autoimmune disease or related diseases in a subject in need thereof, comprising: administering an effective amount of the aromatic acetylene or aromatic ethylene compound represented by formula II-0, the pharmaceutically acceptable salt, the tautomer, the mesomer, the racemate or the stereoisomer thereof as defined in claim 1 to the subject.

17. The method as defined in claim 16, wherein, the cancer is selected from the group consisting of lung cancer, esophageal cancer, gastric cancer, colon cancer, liver cancer, nasopharyngeal cancer, brain tumor, breast cancer, cervical cancer, blood cancer and bone cancer.

18. A method for inhibiting PD-1 and/or PD-L1, comprising: administering to the subject in need thereof a medicament comprising an effective amount of the aromatic acetylene or aromatic ethylene compound represented by formula II-0, the pharmaceutically acceptable salt, the tautomer, the mesomer, the racemate or the stereoisomer thereof as defined in claim 1.

19. A pharmaceutical composition comprising a therapeutically and/or prophylactically effective amount of the aromatic acetylene or aromatic ethylene compound represented by formula II-0, the pharmaceutically acceptable salt, the tautomer, the mesomer, the racemate or the stereoisomer thereof as defined in claim 1, and a pharmaceutically acceptable carrier and/or diluent.

20. A method for treating a cancer, an infection, an autoimmune disease or related diseases in a subject in need thereof, comprising: administering an effective amount of the aromatic acetylene or aromatic ethylene compound represented by formula II-0, the pharmaceutically acceptable salt, the tautomer, the mesomer, the racemate or the stereoisomer thereof as defined in claim 12 to the subject.

21. A pharmaceutical composition comprising a therapeutically and/or prophylactically effective amount of the aromatic acetylene or aromatic ethylene compound represented by formula II-0, the pharmaceutically acceptable salt, the tautomer, the mesomer, the racemate or the stereoisomer thereof as defined in claim 12, and a pharmaceutically acceptable carrier and/or diluent.

* * * * *